United States Patent
Danter

(10) Patent No.: US 9,284,275 B2
(45) Date of Patent: *Mar. 15, 2016

(54) INHIBITOR COMPOUNDS AND CANCER TREATMENT METHODS

(71) Applicant: Critical Outcome Technologies Inc., London (CA)

(72) Inventor: Wayne R. Danter, London (CA)

(73) Assignee: CRITICAL OUTCOME TECHNOLOGIES INC. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/075,597

(22) Filed: Nov. 8, 2013

(65) Prior Publication Data

US 2014/0072555 A1     Mar. 13, 2014

Related U.S. Application Data

(60) Division of application No. 13/636,558, filed on Feb. 1, 2012, now Pat. No. 8,580,792, which is a continuation of application No. 12/505,295, filed on Jul. 17, 2009, now Pat. No. 8,138,191, which is a continuation-in-part of application No. 12/013,079, filed on Jan. 11, 2008, now Pat. No. 8,034,815.

(60) Provisional application No. 61/149,950, filed on Feb. 4, 2009, provisional application No. 61/081,676, filed on Jul. 17, 2008, provisional application No. 60/884,489, filed on Jan. 11, 2007, provisional application No. 60/884,504, filed on Jan. 11, 2007.

(51) Int. Cl.
| | |
|---|---|
| *A61K 45/06* | (2006.01) |
| *A61K 31/704* | (2006.01) |
| *A61K 31/337* | (2006.01) |
| *A61K 31/439* | (2006.01) |
| *A61K 31/555* | (2006.01) |
| *A61K 31/496* | (2006.01) |
| *C07D 215/40* | (2006.01) |
| *C07D 401/12* | (2006.01) |
| *C07D 471/04* | (2006.01) |
| *C07D 471/14* | (2006.01) |
| *A61K 33/24* | (2006.01) |
| *A61K 39/395* | (2006.01) |

(52) U.S. Cl.
CPC ............ *C07D 215/40* (2013.01); *A61K 31/337* (2013.01); *A61K 31/439* (2013.01); *A61K 31/496* (2013.01); *A61K 31/555* (2013.01); *A61K 31/704* (2013.01); *A61K 33/24* (2013.01); *A61K 39/3955* (2013.01); *A61K 45/06* (2013.01); *C07D 401/12* (2013.01); *C07D 471/04* (2013.01); *C07D 471/14* (2013.01)

(58) Field of Classification Search
CPC .. C07D 215/40; C07D 401/12; C07D 471/04; A61K 45/06; A61K 31/704; A61K 31/337; A61K 31/439; A61K 33/24; A61K 31/555; A61K 31/496
USPC ........ 514/253.06, 34, 253.03; 424/133.1, 649
See application file for complete search history.

(56) References Cited

U.S. PATENT DOCUMENTS

| | | |
|---|---|---|
| 3,239,539 A | 3/1966 | Bartlett et al. |
| 3,250,791 A | 5/1966 | Webster et al. |
| 3,671,639 A | 6/1972 | Sasse et al. |
| 4,463,077 A | 7/1984 | Matsuura et al. |
| 4,537,844 A | 8/1985 | Hashimoto |
| 4,593,027 A | 6/1986 | Winklemann et al. |
| 4,619,878 A | 10/1986 | Hashimoto |
| 4,748,160 A | 5/1988 | Bennion et al. |
| 4,927,843 A | 5/1990 | Teitz |
| 4,977,051 A | 12/1990 | Ohno et al. |
| 4,978,670 A | 12/1990 | Rector et al. |
| 4,985,433 A | 1/1991 | Secrist, III et al. |
| 4,985,434 A | 1/1991 | Secrist, III et al. |
| 5,008,265 A | 4/1991 | Secrist, III et al. |
| 5,008,270 A | 4/1991 | Secrist, III et al. |
| 5,023,334 A | 6/1991 | Rector et al. |
| 5,135,928 A | 8/1992 | Reiter et al. |
| 5,155,110 A | 10/1992 | Connor et al. |
| 5,189,039 A | 2/1993 | Niwas et al. |
| 5,196,291 A | 3/1993 | Okada et al. |

(Continued)

FOREIGN PATENT DOCUMENTS

| | | |
|---|---|---|
| CA | 1250292 | 2/1989 |
| CA | 2060843 | 8/1992 |

(Continued)

OTHER PUBLICATIONS

Abad-Zapatero (2010) Drug Discovery Today 00:00 "Ligand efficiency indices for an effective mapping of chemico-biological space: the concept of an atlas-like representation".
Anderson et al. (1996) Cancer Research 56 p. 715-718 "Combination Therapy Including a Gelatinase Inhibitor and Cytotoxic Agent Reduces Local Invasion and Metastasis of Murine Lewis Lung Carcinoma".
Bastian (2006) From Melanocytes to Melanoma: The Progression to Malignancy p. 197-201 "Genetic Progression".

(Continued)

*Primary Examiner* — James O Wilson
*Assistant Examiner* — Ebenezer O Sackey
(74) *Attorney, Agent, or Firm* — Swanson & Bratschun, L.L.C.

(57) ABSTRACT

A synergistically effective combination of an anti-cancer agent and a therapeutic compound, such as an mTOR-Rictor complex inhibitor, a Serine 473 phosphorylation inhibitor, an AKT2 inhibitor, or a combination thereof, for use in the treatment of cancer, and methods and uses thereof. Also included are methods and uses of a thiosemicarbazone for treating a cancer in a mammal in need thereof characterized by over-expression of RAS, by an EGFR mutation, and/or by over-expression of AKT2.

9 Claims, 75 Drawing Sheets

(56) References Cited

U.S. PATENT DOCUMENTS

| | | |
|---|---|---|
| 5,292,756 A | 3/1994 | Duggan et al. |
| 5,328,914 A | 7/1994 | Hocquaux et al. |
| 5,334,748 A | 8/1994 | Buckley et al. |
| 5,344,836 A | 9/1994 | Hamanaka et al. |
| 5,358,946 A | 10/1994 | Wilde |
| 5,409,930 A | 4/1995 | Spada et al. |
| 5,441,847 A | 8/1995 | Fukawa et al. |
| 5,480,883 A | 1/1996 | Spada et al. |
| 5,521,184 A | 5/1996 | Zimmermann |
| 5,543,520 A | 8/1996 | Zimmermann |
| 5,604,210 A | 2/1997 | Nagaoka et al. |
| 5,612,340 A | 3/1997 | Zimmermann |
| 5,618,829 A | 4/1997 | Takayanagi et al. |
| 5,646,153 A | 7/1997 | Spada et al. |
| 5,656,643 A | 8/1997 | Spada et al. |
| 5,710,158 A | 1/1998 | Myers et al. |
| 5,714,493 A | 2/1998 | Myers et al. |
| 5,721,238 A | 2/1998 | Heiker et al. |
| 5,736,534 A | 4/1998 | Arnold |
| 5,750,088 A | 5/1998 | Sworin et al. |
| 5,760,041 A | 6/1998 | Wissner et al. |
| 5,763,470 A | 6/1998 | Tang et al. |
| 5,795,889 A | 8/1998 | Spada et al. |
| 5,798,451 A | 8/1998 | Von Deyn et al. |
| 5,872,272 A | 2/1999 | Yano et al. |
| RE36,256 E | 7/1999 | Spada |
| 5,932,574 A | 8/1999 | Baker |
| 5,948,819 A | 9/1999 | Ohtsuka et al. |
| 5,958,935 A | 9/1999 | Davis et al. |
| 5,977,146 A | 11/1999 | Muller et al. |
| 6,057,320 A | 5/2000 | Spada et al. |
| 6,069,134 A | 5/2000 | Roth et al. |
| 6,103,728 A | 8/2000 | Tang et al. |
| 6,127,374 A | 10/2000 | Bridges |
| 6,153,617 A | 11/2000 | Bridges |
| 6,156,617 A | 12/2000 | Saitoh |
| 6,169,091 B1 | 1/2001 | Cockerill et al. |
| 6,174,889 B1 | 1/2001 | Cockerill et al. |
| 6,180,636 B1 | 1/2001 | Traxler et al. |
| 6,184,377 B1 | 2/2001 | Gao |
| 6,207,669 B1 | 3/2001 | Cockerill et al. |
| 6,235,746 B1 | 5/2001 | Davis et al. |
| 6,251,911 B1 | 6/2001 | Bold et al. |
| 6,268,391 B1 | 7/2001 | Dickerson et al. |
| 6,352,168 B1 | 3/2002 | Lin |
| RE37,650 E | 4/2002 | Myers et al. |
| 6,391,874 B1 | 5/2002 | Cockerill et al. |
| 6,420,560 B1 | 7/2002 | Numerof et al. |
| 6,432,963 B1 | 8/2002 | Hisamichi et al. |
| 6,525,072 B1 | 2/2003 | Tang et al. |
| 6,528,509 B1 | 3/2003 | Hale et al. |
| 6,538,002 B1 | 3/2003 | Finke et al. |
| 6,562,818 B1 | 5/2003 | Bridges |
| 6,600,037 B1 | 7/2003 | Davis et al. |
| 6,635,641 B2 | 10/2003 | Bender et al. |
| 6,723,726 B1 | 4/2004 | Cockerill et al. |
| 6,828,320 B2 | 12/2004 | Cockerill et al. |
| 6,949,639 B1 | 9/2005 | Hovinen et al. |
| 7,052,870 B2 | 5/2006 | Sabatini et al. |
| 7,138,416 B2 | 11/2006 | Sankaranarayanan |
| 7,175,844 B2 | 2/2007 | King |
| 7,202,367 B2 | 4/2007 | Cellier et al. |
| 8,034,815 B2 * | 10/2011 | Danter et al. ............ 514/253.01 |
| 8,138,191 B2 * | 3/2012 | Danter ..................... 514/253.1 |
| 8,367,675 B2 | 2/2013 | Danter et al. |
| 8,420,643 B2 * | 4/2013 | Danter et al. ............. 514/236.8 |
| 8,580,792 B2 * | 11/2013 | Danter ...................... 514/252.13 |
| 2001/0021717 A1 | 9/2001 | Potter et al. |
| 2001/0027205 A1 | 10/2001 | Camden |
| 2001/0041964 A1 | 11/2001 | Grass et al. |
| 2001/0044451 A1 | 11/2001 | Fraley et al. |
| 2001/0047007 A1 | 11/2001 | Fraley et al. |
| 2001/0047364 A1 | 11/2001 | Proctor |
| 2001/0049092 A1 | 12/2001 | Ekins et al. |
| 2001/0051628 A1 | 12/2001 | Huang et al. |
| 2002/0010550 A1 | 1/2002 | Grass et al. |
| 2002/0012641 A1 | 1/2002 | Voorhees et al. |
| 2002/0013334 A1 | 1/2002 | Robl et al. |
| 2002/0013662 A1 | 1/2002 | Grass et al. |
| 2002/0014408 A1 | 2/2002 | Schroeder |
| 2002/0018988 A1 | 2/2002 | Klinck et al. |
| 2002/0028779 A1 | 3/2002 | High et al. |
| 2002/0028826 A1 | 3/2002 | Robl et al. |
| 2002/0042423 A1 | 4/2002 | Richert et al. |
| 2002/0061901 A1 | 5/2002 | Robl et al. |
| 2002/0072526 A1 | 6/2002 | Fraley et al. |
| 2002/0086791 A1 | 7/2002 | Iglesia et al. |
| 2002/0115858 A1 | 8/2002 | Zimmermann et al. |
| 2002/0147214 A1 | 10/2002 | Cockerill et al. |
| 2002/0151540 A1 | 10/2002 | Lai et al. |
| 2003/0087881 A1 | 5/2003 | Bridges |
| 2003/0125343 A1 | 7/2003 | Gambacorti-Passerini et al. |
| 2003/0130286 A1 | 7/2003 | Denny et al. |
| 2003/0153755 A1 | 8/2003 | Moffat et al. |
| 2003/0176396 A1 | 9/2003 | Shea et al. |
| 2003/0181495 A1 | 9/2003 | Lai et al. |
| 2003/0212269 A1 | 11/2003 | Davis et al. |
| 2003/0236413 A1 | 12/2003 | Cellier et al. |
| 2004/0092747 A1 | 5/2004 | Bender et al. |
| 2004/0102453 A1 | 5/2004 | Buerger et al. |
| 2004/0171032 A1 | 9/2004 | Baker et al. |
| 2004/0204477 A1 | 10/2004 | Moll et al. |
| 2004/0224968 A1 | 11/2004 | Seidelmann et al. |
| 2004/0235786 A1 | 11/2004 | Orr |
| 2004/0235798 A1 | 11/2004 | Murthi et al. |
| 2005/0010017 A1 | 1/2005 | Blakely et al. |
| 2005/0014169 A1 | 1/2005 | Latham et al. |
| 2005/0131022 A1 | 6/2005 | Player et al. |
| 2005/0192884 A1 | 9/2005 | Raines |
| 2006/0019831 A1 | 1/2006 | Reinhard et al. |
| 2006/0052361 A1 | 3/2006 | Miyazaki et al. |
| 2006/0217426 A1 | 9/2006 | Eto et al. |
| 2007/0197495 A1 | 8/2007 | Chibale |
| 2007/0280928 A1 | 12/2007 | Buck et al. |
| 2008/0004274 A1 | 1/2008 | Diaz et al. |
| 2008/0171744 A1 | 7/2008 | Danter et al. |
| 2011/0152281 A1 | 6/2011 | Danter et al. |
| 2011/0281887 A1 | 11/2011 | Danter et al. |
| 2012/0077820 A1 | 3/2012 | Danter et al. |
| 2012/0195887 A1 | 8/2012 | Danter |
| 2013/0165449 A1 | 6/2013 | Danter |
| 2013/0231345 A1 | 9/2013 | Danter |
| 2014/0072555 A1 | 3/2014 | Danter |

FOREIGN PATENT DOCUMENTS

| | | |
|---|---|---|
| CA | 2109975 | 5/1994 |
| CA | 2553242 | 8/2005 |
| CA | 2584179 | 4/2006 |
| CN | 1224005 | 7/1999 |
| CN | 1891701 | 1/2007 |
| CN | 1907970 | 2/2007 |
| DE | 3237649 | 4/1984 |
| DE | 4207400 | 9/1993 |
| DE | 04400451 | 7/1994 |
| EP | 0 106 284 | 10/1983 |
| EP | 0 142 740 | 10/1984 |
| EP | 0 225 726 | 11/1986 |
| EP | 00172031 | 5/1988 |
| EP | 0 361 645 | 6/1989 |
| EP | 0329108 | 8/1989 |
| EP | 0 420 005 | 9/1990 |
| EP | 0 452 848 | 4/1991 |
| EP | 0425282 | 5/1991 |
| EP | 0 512 420 | 4/1992 |
| EP | 0 554 856 | 2/1993 |
| EP | 0 580 374 | 7/1993 |
| EP | 00571857 | 12/1993 |
| EP | 0600 832 | 6/1994 |
| EP | 0631179 | 12/1994 |
| EP | 0 722 937 | 1/1996 |
| EP | 0 727 701 | 2/1996 |
| EP | 00727701 | 8/1996 |
| EP | 0 807 580 | 5/1997 |

(56) References Cited

FOREIGN PATENT DOCUMENTS

| | | |
|---|---|---|
| EP | 0 902 028 | 8/1998 |
| EP | 00902028 | 3/1999 |
| EP | 00807850 | 10/2000 |
| EP | 01103549 | 5/2001 |
| EP | 01325921 | 7/2003 |
| FR | 2013371 | 4/1970 |
| FR | 2879194 | 6/2006 |
| GB | 1026401 | 4/1966 |
| GB | 1231783 | 5/1971 |
| GB | 2304471 | 3/1997 |
| GB | 2357971 | 7/2001 |
| JP | 56-095161 | 8/1981 |
| JP | 59088468 | 5/1984 |
| JP | 60184254 | 9/1985 |
| JP | 3093767 | 4/1991 |
| JP | 05058894 | 3/1993 |
| JP | 1993241264 | 9/1993 |
| JP | 06-247990 | 9/1994 |
| JP | 07-072571 | 3/1995 |
| JP | 1995114195 | 5/1995 |
| JP | 7219256 | 8/1995 |
| JP | 9328463 | 12/1997 |
| JP | 11080131 | 3/1999 |
| JP | 11133545 | 5/1999 |
| JP | 2000143636 | 5/2000 |
| JP | 2001172217 | 6/2001 |
| JP | 2006-181940 | 7/2006 |
| JP | 2006181940 | 7/2006 |
| JP | 2008-088107 | 4/2008 |
| WO | WO 86/04582 | 8/1986 |
| WO | WO 91/06548 | 5/1991 |
| WO | WO 92/03421 | 3/1992 |
| WO | WO 92/06076 | 4/1992 |
| WO | WO 92/08464 | 5/1992 |
| WO | WO 93/02091 | 2/1993 |
| WO | WO 93/21187 | 10/1993 |
| WO | WO 94/18959 | 9/1994 |
| WO | WO 95/23796 | 2/1995 |
| WO | WO 95/17423 | 6/1995 |
| WO | WO 95/27693 | 10/1995 |
| WO | WO 96/05818 | 2/1996 |
| WO | WO 96/09294 | 3/1996 |
| WO | WO 96/14295 | 5/1996 |
| WO | WO 96/37472 | 11/1996 |
| WO | WO 97/00894 | 1/1997 |
| WO | WO 97/02238 | 1/1997 |
| WO | WO 97/03069 | 1/1997 |
| WO | WO 97/13760 | 4/1997 |
| WO | WO 98/08492 | 3/1998 |
| WO | WO 98/55448 | 12/1998 |
| WO | WO 99/09016 | 2/1999 |
| WO | WO 99/18102 | 4/1999 |
| WO | WO 99/62486 | 12/1999 |
| WO | WO 00/09126 | 2/2000 |
| WO | WO 00/18737 | 4/2000 |
| WO | WO 00/18740 | 4/2000 |
| WO | WO 00/50032 | 8/2000 |
| WO | WO 00/61186 | 10/2000 |
| WO | WO 00/74702 | 12/2000 |
| WO | WO 00/74742 | 12/2000 |
| WO | WO 01/12227 | 2/2001 |
| WO | WO 01/16271 | 3/2001 |
| WO | WO 01/34585 | 5/2001 |
| WO | WO 01/47899 | 7/2001 |
| WO | WO 01/53274 | 7/2001 |
| WO | WO 01/25220 | 9/2001 |
| WO | WO 01/64650 | 9/2001 |
| WO | WO 01/64825 | 9/2001 |
| WO | WO 01/64828 | 9/2001 |
| WO | WO 01/64994 | 9/2001 |
| WO | WO 01/66709 | 9/2001 |
| WO | WO 01/70741 | 9/2001 |
| WO | WO 02/22597 | 3/2002 |
| WO | WO 02/30931 | 4/2002 |
| WO | WO 02/49413 | 6/2002 |
| WO | WO 02/068574 | 9/2002 |
| WO | WO 02/068577 | 9/2002 |
| WO | WO 02/070541 | 9/2002 |
| WO | WO 02/083126 | 10/2002 |
| WO | WO 03/004489 | 1/2003 |
| WO | WO 03/051276 | 6/2003 |
| WO | WO 03/062204 | 7/2003 |
| WO | WO 03/070241 | 8/2003 |
| WO | WO 03/093297 | 11/2003 |
| WO | WO 2004/004725 | 1/2004 |
| WO | WO 2004/011456 | 2/2004 |
| WO | WO 2004/019933 | 3/2004 |
| WO | WO 2004/063147 | 7/2004 |
| WO | WO 2004/066725 | 8/2004 |
| WO | WO 2004/069801 | 8/2004 |
| WO | WO 2004/076640 | 9/2004 |
| WO | WO 2004/080492 | 9/2004 |
| WO | WO 2004/085382 | 10/2004 |
| WO | WO 2004/099371 | 11/2004 |
| WO | WO 2005/010017 | 2/2005 |
| WO | WO 2005/012252 | 2/2005 |
| WO | WO 2005/023183 | 3/2005 |
| WO | WO 2005/039489 | 5/2005 |
| WO | WO 2005/046604 | 5/2005 |
| WO | WO 2005/073189 | 8/2005 |
| WO | WO 2005/073216 | 8/2005 |
| WO | WO 2005/073217 | 8/2005 |
| WO | WO 2005/087211 | 9/2005 |
| WO | WO 2005/107463 | 11/2005 |
| WO | WO 2005/116039 | 12/2005 |
| WO | WO 2006/009765 | 1/2006 |
| WO | WO 2006/063863 | 6/2006 |
| WO | WO 2006/069080 | 6/2006 |
| WO | WO 2006/069807 | 7/2006 |
| WO | WO 2006/081425 | 8/2006 |
| WO | WO 2006/088919 | 8/2006 |
| WO | WO 2006/095542 | 9/2006 |
| WO | WO 2006/127379 | 11/2006 |
| WO | WO 2006/128129 | 11/2006 |
| WO | WO 2006/128172 | 11/2006 |
| WO | WO 2006/130462 | 12/2006 |
| WO | WO 2007/000432 | 1/2007 |
| WO | WO 2007/037898 | 4/2007 |
| WO | WO 2007/050980 | 5/2007 |
| WO | WO 2007/060404 | 5/2007 |
| WO | WO 2007/106503 | 9/2007 |
| WO | WO 2008/083491 | 7/2008 |
| WO | WO 2008/148074 | 12/2008 |
| WO | WO 2009/079797 | 7/2009 |
| WO | WO 2010/089993 | 8/2010 |

OTHER PUBLICATIONS

Cannistra et al. (2008) Cancer Principles & Practice of Oncology 8 "Fallopian Tube Carcinoma and Peritoneal Carcinoma".
Carling et al. (2008) Cancer Principles & Practice of Oncology 8 p. 1503 "Thyroid Tumors".
Chabner et al. (2006) Goodman & Gilman's: The Pharmacological Basis of Therapeutics 11 p. 1315-1403 "Chemotherapy of Neoplastic Diseases, Neoplastic Agents".
Corrigan (2007) "Salt Forms: Pharmaceutical Aspects".
DeArruda et al. (2006) Int Journal Radiation Oncology Biol Phys 64:2 p. 363-373 "Intensity-Modulated Radiation Therapy for the Treatment of Oropharyngeal Carcinoma".
Druker et al. (2005) Cancer Principles & Practice of Oncology 7 p. 2121 "Chronic Myelogenous Leukemia".
Easmon et al. (1989) Arzneim-Forsch/Drug Res 39:10 "Synthesis and Antiviral Activity of Thiosemicarbazone Derivatives of Pyridazinecarbaldehydes and Alkyl Pyridazinyl Ketones".
Faderi et al. (2005) Cancer Principles & Practice of Oncology 7 p. 2144-2154 "Myelodysplastic Syndromes".
French et al. (1974) Journal of Medicinal Chemistry 17 p. 172-181.
Kobel et al. (2008) PLoS Medicine 5:12 p. 1749-1760 "Ovarian Carcinoma Subtypes Are Different Diseases: Implications for Biomarker Studies".
Libutti (2008) Cancer Principles & Practice of Oncology 8 "Colon Cancer".
Merriman et al. (1989) Cancer Research 49 p. 4509-4516 "Drug Treatments for Metastasis of the Lewis Lung Carcinoma: Lack of Correlation between Inhibition of Lung Metastasis and Survival".

(56) References Cited

OTHER PUBLICATIONS

Montgomery et al. (1977) J Medicinal Chemistry 20:2 p. 291 "Inhibition of Solid Tumors by Nitrosoureas".
O'Brien et al. (2005) Cancer Principles & Practice of Oncology 7 p. 2133-2143 "Chronic Lymphoid Leukemias".
Odunsi et al. (2008) Cancer Principles & Practice of Oncology 8 "Molecular Biology of Gynecological Cancers".
Olive et al. (2006) Clinical Cancer Research 12 p. 5277-5287 "The Use of Targeted Mouse Models for Preclinical Testing of Novel Cancer Therapeutics".
Pusztai (2008) Breast Cancer 2 "Histopathologic and Molecular Markers of Prognosis and Response to Therapy".
Raizer (2005) Journal of Neuro-Oncology 74:1 p. 77-86 "HER1/EGFR tyrosine kinase inhibitors for the treatment of glioblastoma multiforme".
Rustgi (2008) Cancer Principles & Practice of Oncology 8 p. 989-993 "Molecular Biology of the Esophagus and Stomach".
Scheinberg et al. (2005) Cancer Principles & Practice of Oncology p. 2088-2120 "Management of Acute Leukemias".
Smith et al. (2007) Molecular Cancer Therapeutics 6 p. 428-440 "The application of cassette dosing for pharmacokinetic screening in small-molecule cancer drug discovery".
Song et al. (2008) Cancer Principles & Practice of Oncology 8 "Cancer: A Conceptual Framework".
Tiltman (2005) Best Practice & Research Clinical Obstetrics & Gyn 19:4 p. 485-500 "The pathology of cervical tumours".
Traynor et al. (2004) Drugs of Today 40:8 p. 697-710 "Systemic Treatment of Advanced Non-Small Cell Lung Cancer".
Tsai et al. (2008) PNAS 105 p. 3041-3046 "Discovery of a selective inhibitor of oncogenic B-Raf kinase with potent antimelanoma activity".
Verhaak et al. (2010) Cancer Cell 17:1 p. 1-24 "An integrated genomic analysis identifies clinically relevant subtypes of glioblastoma characterized by abnormalities in PDGFRA, IDH1, EGFR and NF1".
Lee et al. (1971) Proc. Nat. Acad. Sci. 68(6):1331-1335 "A Polynucleotide Segment Rich in Adenylic Acid in the Rapidly-Labeled Polyribosomal RNA Component of Mouse Sarcoma 180 Ascites Cells."
Montgomery et al. (1977) Journal of Medicinal Chemistry 20(2) "Inhibition of Solid Tumors by Nitrosoureas. 1. Lewis Lung Carcinoma."
Prakash et al. (1978) Cancer Res. 38:3059-3062 "Effect of α-Difluoromethylornithine, an Enzyme-activated Irreversible Inhibitor of Ornithine Decarboxylase, on L1210 Leukemia in Mice."
Vippagunta et a. (2001) Advanced Drug Delivery Reviews 48:3-26 "Crystalline solids."
Agrawal et al., "Potential Antitumor Agents. 11. Inhibitors of Alkaline Phosphatase, an Enzyme Involved in the Resistance of Neoplastic Cell to 6-Thiopurines", 1974, Journal of Medicinal Chemistry, vol. 17, No. 9, pp. 934-938.
Akashi et al. (2008) Br J Cancer 98: 749-755, "Enhancement of the antitumor activity of ionising radiation by nimotuzumab, a humanized monoclonal antibody to the epidermal growth factor receptor, in non-small cell lung cancer cell lines of differing epidermal growth factor receptor status" abstract.
Akcakanat et al. (2007) Biochem Biophys Res Commun 362: 330-333, "Rapamycin regulates the phosphorylation of rictor." abstract.
Alessi et al. (1997) Curr Biol 7: 261-269, "Characterization of a 3-phosphoinositide-dependent protein kinase which phosphorylates and activates protein kinase Balpha" abstract.
Alessi et al. (1997) Curr Biol 7: 776-789, "3-Phosphoinositide-dependent protein kinase-1 (PDK1): structural and functional homology with the *Drosophila* DSTPK61 kinase" abstract.
Al-Shahrour et al. (2007) Nucleic Acids Research 35:w91-w96, "FatiGO1: a functional profiling tool for genomic data. Integration of functional annotation, regulatory motifs and interaction data with microarray experiments".

Altomare et al. (2004) Oncogene 23: 5853-5857, "AKT and mTOR phosphorylation is frequently detected in ovarian cancer and can be targeted to disrupt ovarian tumor cell growth" abstract.
Altomare et al. (2005) Oncogene 24: 7455-7464, "Perturbations of the AKT signaling pathway in human cancer" abstract.
Ananthanarayanan et al. (2007) J Biol Chem 282: 36634-36641, "Live-cell molecular analysis of Akt activation reveals roles for activation loop phosphorylation" abstract.
Anderson et al., "Some Heterocyclic Thiosemicarbazones", Oct. 1951, Journal of the American Chemical Society, vol. 73, p. 4967-4968.
Andes et al. (2002) International Journal of Antimicrobial Agents, 19:261-268, "Animal model pharmacokinetics and pharmacodynamics: a critical review".
Andrews et al. (1990) Cancer Communications 2(2):93-100, "Rapid emergence of acquired cis-Diamminedichloroplatinum(II) Resistance in an in vivo model of human ovarian carcinoma".
Attoub et al. (2002) Cancer Research 62:4879-4883, "The c-kit tyrosine kinase inhibitor STI571 for colorectal cancer therapy".
Bain et al. (1997) Polyhedron 16(5):855-862, Synthetic and spectroscopic investigations of N(4)-substituted isatin thiosemicarbazones and their copper (II) complexes.
Banker et al. (2002) Journal of Pharmaceutical Sciences 92(5):967-974, "Development and validation of a 96-well equilibrium dialysis apparatus for measuring plasma protein binding".
Bastos et al., (2005) Tetrahedron, vol. 61, p. 7045-7053, "Structural analyses of 4-benzoylpyridine thiosemicarbazone using NMR techniques and theoretical calculations".
Bauer (1963) British Journal of Experimental Pathology, 44, 233-42, "The Chemotherapy of Ectromelia Infection with Isatin β-Dialkylthiosemicarbazones".
Beeram et al. (2005) J Clin Onco 23: 6771-6790, "Raf: a strategic target for therapeutic development against cancer" abstract.
Bellacosa et al. (2005) Adv Cancer Res 94: 29-86, "Activation of AKT kinases in cancer: implications for therapeutic targeting" abstract.
Beraldo et al., (2003) Journal of Molecular Structure, vol. 645, p. 213-220 "Structural studies and spectral characteristics of 4-benzoylpyridine thiosemicarbazone and N(4')-phenyl-4-benzoylpyridine thiosemicarbazone".
Bernhardt et al (2008) Journal of Biological Inorganic Chemistry 13:107-119, "Tuning the antiproliferative activity of biologically active iron chelators: characterization of the coordination chemistry and biological efficacy of 2-acetylpyridine and 2-benzoylpyridine hydrazone ligands".
Bernhardt et al. (2003) Journal of Biological Inorganic Chemistry pp. 866-880, "Cytotoxic iron chelators: characterization of the structure, solution chemistry and redox activity of ligands and iron complexes of the di-2-pyridyl ketone isonicotinoyl hydrazone (HPKIH) analogues" http://dx.doi.org/IO.IOO7/s00775-003-0486-z.
Berns et al. (2007) Cancer Cell 12:395-402, "A Functional Genetic Approach Identifies the PI3K Pathway as a Major Determinant of Trastuzumab Resistance in Breast Cancer".
Bjornsson et al. (2003) Drug Metabolism and Disposition 31:815-832, "The conduct of in vitro and in vivo drug-drug interaction studies: a pharmaceutical research and manufacturers of america (phrma) perspective".
Bjornsti et al. (2004) Nat Rev Cancer 4: 335-348 Ref ID: 154, "The TOR pathway: a target for cancer therapy" abstract.
Bolen (1993) Oncogene 8:2025-2031, "Nonreceptor tyrosine protein kinases".
Bondar et al. (2002) Mol Cancer Ther 1: 989-997, "Inhibition of the phosphatidylinositol 3'-kinase-AKT pathway induces apoptosis in pancreatic carcinoma cells in vitro and in vivo" abstract.
Bose et al. (2009) Exp Cell Res 315: 649-658, "The ErbB kinase domain: structural perspectives into kinase activation and inhibition" abstract.
Bowery et al. (2005) Current Opinion in Pharmacology 5(4):341-448, "Cancer/Immunomodulation".
Braun (1978) Monatshefte fur Chemie 109:63-71, "4,5•Diacylpyidazine: Synthese und Umsetzung zu 1,4-Diaryl- bzw. 1,4-Dialkyl-pyridazino[4,5—d]pyridazinen" English Abstract.

(56) References Cited

OTHER PUBLICATIONS

Braun et al. (2008) Clin Cancer Res 14: 2249-2252, "Targeting Ras in myeloid leukemias" abstract.
Braun et al., "4,5-Diacylpyridazine: Synthese und Umsetzung zu 1,4-Diaryl- bzw. 1,4-Dialkyl-pyridazino [4,5-d] pyridazinen" 1978, Monatshefte fur Chemie 109, pp. 63-71.
Britten et al. (1999) Cancer Research 59:1049-1053, "Enhanced antitumor activity of 6-hydroxymethylacylfulvene in combination with irinotecan and 5-fluorouracil in the HT29 human colon tumor xenograft model".
Brognard et al. (2001) Cancer Res 61: 3986-3997, "Akt/protein kinase B is constitutively active in non-small cell lung cancer cells and promotes cellular survival and resistance to chemotherapy and radiation" abstract.
Brunn et al. (1996) The EMBO Journal 15(19):5256-5267, "Direct inhibition of the signaling functions of the mammalian target of rapamycin by the phosphoinositide 3-kinase inhibitors, wortmannin and LV294002".
Buck et al. (2006) Mol Cancer Ther 5: 2676-2684, "Rapamycin synergizes with the epidermal growth factor receptor inhibitor erlotinib in non-small-cell lung, pancreatic, colon, and breast tumors" abstract.
Byrn et al., Solid-State Chemistry of Drugs, 516 (2nd ed., 1999). "Hydrates are a subset of solvates wherein the solvent is water", id. at 233-247, pp. 233-234.
Canadian Intellectual Property Office acting as International Searching Authority, International Search Report and Written Opinion prepared Mar. 2, 2009 for International Application No. PCT/CA2008/002293, 12 pages.
Canadian Intellectual Property Office acting as International Searching Authority, International Search Report prepared Apr. 28, 2008 for International Application No. PCT/CA2008/000045, 5 pages.
Canadian Intellectual Property Office acting as International Searching Authority, International Search Report prepared Sep. 22, 2009 and Written Opinion prepared Oct. 28, 2009 for International Application No. PCT/CA2009/001004, 15 pages.
Canadian Intellectual Property Office acting as International Searching Authority, Written Opinion of the International Searching Authority prepared Apr. 28, 2008 for International Application No. PCT/CA2008/000045, 6 pages.
Caron et al. (2005) Mol Cancer Ther 4: 257-270, "Activated forms of H-RAS and K-RAS differentially regulate membrane association of PI3K, PDK-1, and AKT and the effect of therapeutic kinase inhibitors on cell survival" abstract.
CAS Registry No. 76780-41-1, 2 pages.
CAS Registry No. 868364-38-9, Nov. 18, 2005.
CAS Registry No. 868364-43-6, Nov. 18, 2005.
CAS Registry No. 901285-15-2, Aug. 15, 2006.
CAS Registry No. 901329-97-3, Aug. 15, 2006.
CAS Registry No. 901348-18-3, Aug. 15, 2006.
CAS Registry No. 901349-50-6, Aug. 15, 2006.
CAS Registry No. 901360-08-5, Aug. 15, 2006.
CAS Registry No. 901391-84-2, Aug. 15, 2006.
CAS Registry No. 903180-32-5, Aug. 22, 2006.
CAS Registry No. 903274-24-8, Aug. 26, 2006.
CAS Registry No. 91189-95-6, Nov. 16, 1984.
CAS Registry No. 500300-93-6, Mar. 24, 2003.
CAS Registry No. 518299-22-4, May 21, 2003.
CAS Registry No. 519151-42-9, May 23, 2003.
CAS Registry No. 549530-64-5, Jul. 17, 2003.
CAS Registry No. 732257-35-1, Aug. 25, 2004.
CAS Registry No. 732992-68-6, Aug. 26, 2004.
CAS Registry No. 733793-43-6, Aug. 27, 2004.
CAS Registry No. 802269-45-0, Dec. 23, 2004.
CAS Registry No. 847046-07-5, Mar. 23, 2005.
CAS Registry No. 852401-92-4, Jun. 16, 2005.
CAS Registry No. 852401-95-7, Jun. 16, 2005.
Castagnola et al. (2005) Biochim Biophys Acta 1756: 115-125, "Mutant KRAS, chromosomal instability and prognosis in colorectal cancer" abstract.
Castillo et al. (2004) Cancer Res 64: 2782-2792, "Preferential inhibition of Akt and killing of Akt-dependent cancer cells by rationally designed phosphatidylinositol ether lipid analogues."
Castro-Carpeno et al. (2008) Clin Transl Onco/1 0: 6-13, "EGFR and colon cancer: a clinical view" abstract.
Cespedes et al. (2006) Carcinogenesis 27: 2190-2200, "K-ras Asp12 mutant neither interacts with Raf, nor signals through Erk and is less tumorigenic than K-ras Val 12" abstract.
Chadha et al. (2006) Ann Surg Oncol 13: 933-939, "Activated Akt and Erk expression and survival after surgery in pancreatic carcinoma" abstract.
Chau et al. (2009) Br J Cancer 100:1704-1719, "Treatment in advanced colorectal cancer: what, when and how?" abstract.
ChemCats record, CAS Registry No. 903274-24-8, 903180-32-5, 901391-84-2, 901360-35-8, 901360-08-5, 901349-50-6, 901348-18-3, 901329-97-3, 901285-15-2, 847046-07-5, 802269-45-0, 733793-43-6, 732992-68-6, 732257-35-1, 519151-42-9, 501650-12-0, 500300-93-6 (10 pages).
Chen et al. (2001) J Biol Chem 276: 31858-31862, "Regulation of Akt/PKB activation by tyrosine phosphorylation" abstract.
Cheng et al. (1992) Proc Natl Acad Sci U S A 89: 9267-9271, "AKT2, a putative oncogene encoding a member of a subfamily of protein-serine/threonine kinases, is amplified in human ovarian carcinomas" abstract.
Cheng et al. (1996) Proc Natl Acad Sci U S A 93: 3636-3641, "Amplification of AKT2 in human pancreatic cells and inhibition of AKT2 expression and tumorigenicity by antisense RNA" abstract.
Cheng et al. (2005) Oncogene 24: 7482-7492, "The Akt/PKB pathway: molecular target for cancer drug discovery" abstract.
Chiang et al. (2007) Trends in Molecular Medicine 13:433-442, "Targeting the mTOR signaling network in cancer".
Chiang et al. (2007) Trends in Molecular Medicine 13:433-442, "Targeting the mTOR signaling network in cancer" abstract.
Chou (2006) Pharmacol Rev 58:621-681, "Theoretical Basis, Experimental Design, and Computerized Simulation of Synergism and Antagonism in Drug Combination Studies".
Chou et al. (1983) Trends in Pharm Sci 4:450-454, "Analysis of combined drug effects: a new look at a very old problem".
Choudhary et al. (1998) Journal of the Indian Chemical Society, 75, 392-394, "Structural Aspects of Morpholine-N-thiohydrazone Complexes with some Bivalent Metals".
Clark et al. (2002) Mol Cancer Ther 1: 707-717, "Constitutive and inducible Akt activity promotes resistance to chemotherapy, trastuzumab, or tamoxifen in breast cancer cells" abstract.
Copp et al. (2009) Cancer Res 69: 1821-1827, "TORC-specific phosphorylation of mammalian target of rapamycin (mTOR): phospho-Ser2481 is a marker for intact mTOR signaling complex 2" abstract.
Cully et al. (2006) Nature 6:184-192, "Beyond PTEN mutations: the PI3K pathway as an integrator of multiple inputs during tumorigenesis".
Dacic, S. (2008) Adv Anat Pathol 15: 241-247, "EGFR assays in lung cancer" abstract.
Datta et al. (1999) Genes Dev 13: 2905-2927, "Cellular survival: a play in three Akts" abstract.
Daunis et al. (1970) Bull. Soc. Chim. Fr., No. 6:2289-2291, "Semicarbazones et thiosemicarbazones N-4 substituees de l'isatine".
de Gunzburg, J. (1999) Cell Bioi Toxicol 15: 345-358, "Proteins of the Ras pathway as novel potential anticancer therapeutic targets" abstract.
Decaudin (2005) Int. J. Cancer 113:849-856, "In vivo efficacy of STI571 in xenografted human small cell lung cancer alone or combined with chemotherapy".
Defeo-Jones et al. (2005) Mol Cancer Ther 4:271-279, "Tumor cell sensitization to apoptotic stimuli by selective inhibition of specific Akt/PKB family members" abstract.
DeGraffenried et al. M (2004) Ann Oncol 15: 1510-1516, "Reduced PTEN expression in breast cancer cells confers susceptibility to inhibitors of the PI3 kinase/Akt pathway" abstract.
Deramaudt T, Rustgi AK (2005) Biochim Biophys Acta 1756:97-101, "Mutant KRAS in the initiation of pancreatic cancer".

(56) References Cited

OTHER PUBLICATIONS

Dierks et al. (2001) Drug Metabolism and Disposition 29:23-29, "A method for the simultaneous evaluation of the activities of seven major human drug-metabolizing cytochrome P450S using an in vitro cocktail of probe substrates and fast gradient liquid chromatography tandem mass spectrometry".
Dobashi et al. (2009) Cancer 115: 107-118, "Critical and diverse involvement of Akt/mammalian target of rapamycin signaling in human lung carcinomas" abstract.
Doody et al. (2007) Mol Cancer Ther 6: 2642-2651, "Inhibitory activity of cetuximab on epidermal growth factor receptor mutations in non small cell lung cancers" abstract.
Dowling et al. (2009) BioDrugs 23: 77-91, "Current status and challenges associated with targeting mTOR for cancer therapy" abstract.
Downward, J. (2003) Nat Rev Cancer 3: 11-22, "Targeting RAS signalling pathways in cancer therapy" abstract.
Du K, Tsichlis PN (2005) Oncogene 24: 7401-7409, "Regulation of the Akt kinase by interacting proteins" abstract.
Duca et al., (1952) Antibiotics and Chemotherapy, II(1):16-20, "Studies in Experimental Tuberculosis In Vitro and In Vivo Activities of Thiosemicarbazones".
Dwivedi et al. (1995) J. Indian Chem. Soc. 72:403-405, "Donor Behaviour of some Motpholine-N-thiohydrazoneswith some Bivalent Metal 'Ions".
Dziadulewicz et al. (2001) Bioorganic and Medicinal Organic Letters, 11, 705-709, "Design of Non-Peptide CCK2 and NK1 Peptidomimetics Using 1-(2-Nitrophenyl)thiosemicarbazide as a Novel Common Scaffold".
Easmon et al., "Pyridazines 47,1 The Configuration of Novel Thiosemicarbazone Derivatives of Pyridazinecarbaldehydes and Alkyl Pyridazinyl Ketones", 1989, Heterocycles, vol. 29, No. 7, pp. 1399-1408.
Easmon et al., "Synthesis and Antiviral Activity of Thiosemicarbazone Derivatives of Pyridazinecarbaldehydes and Alkyl Pyridazinyl Ketones", 1989, Arzneim-Forsch/Drug Res. 39 (II), No. 10.
El Rayes et al. (2006) Cancer Res 66: 10553-10559, "Potentiation of the effect of erlotinib by genistein in pancreatic cancer: the role of Akt and nuclear factor-kappaB" abstract.
Eliel et al. (1994) A Wiley-Interscience Publication: Stereochemistry of Organic Compounds, ch.14:1119-1190. "Chirality in molecilles devoid of chiral centers".
Ellis et al. (2000) Cell Signal 12: 425-434, "The importance of being K-Ras" abstract.
Engelman et al. (2008) Clin Cancer Res 14: 2895-2899, "Mechanisms of acquired resistance to epidermal growth factor receptor tyrosine kinase inhibitors in non-small cell lung cancer" abstract.
Engelman et al. (2008) Nat Med 14: 1351-1356, "Effective use of PI3K and MEK inhibitors to treat mutant Kras G12D and PIK3CA H1047R murine lung cancers" abstract.
Engelman, JA (2009) Nat Rev Cancer 9: 550-562, "Targeting PI3K signalling in cancer: opportunities, challenges and limitations" abstract.
Europe Application No. 08700510.4.2117 Examination Report mailed Feb. 22, 2012.
EP Examination for EP Application No. 09797322.6 dated Sep. 10, 2012, 7 pages.
EP Examination for EP Application No. 08700510.4 dated Jan. 16, 2013, 5 pages.
European Supplemental Search Report for EP Application No. 09797322 mailed Dec. 20, 2011.
Fakih M (2008) Curr Treat Options Oncol 9: 357-374, "The role of targeted therapy in the treatment of advanced colorectal cancer" abstract.
Feldman et al. (2009) PLoS Biol 7:e38, "Active-site inhibitors of mTOR target rapamycin-resistant outputs of mTORC1 and mTORC2" abstract.
Fischer et al. (2007) Cancer Treat Rev 33: 391-406, "Targeting receptor tyrosine kinase signalling in small cell lung cancer (SCLC): what have we learned so far?" abstract.
Fotiadou et al. (2007) Mol Cell Biol 27: 6742-6755, "Wild-type NRas and KRas perform distinct functions during transformation" abstract.
Franke et al. (2003) Oncogene 22: 8983-8998, "PI3K/Akt and apoptosis: size matters" abstract.
Franke et al. (2006) The American Journal of Human Genetics 78:1011-1025, "Reconstruction of a functional human gene network, with an application for prioritizing positional candidate genes".
French et al. (1966) J Med Chem 9(4):585-589, "The carcinostatic activity of thiosemicarhazones of formyl heteroaromatic compounds. III. Primary correlation".
Friday et al. (2005) Biochim Biophys Acta 1756: 127-144, "K-ras as a target for cancer therapy" abstract.
Fukui et al. (2008) Gen Thorac Cardiovasc Surg 56: 97-103, "Mutations in the epidermal growth factor receptor gene and effects of EGFR-tyrosine kinase inhibitors on lung cancers" abstract.
Furukawa, T. (2008) J Gastroenterol 43: 905-911, "Molecular targeting therapy for pancreatic cancer: current knowledge and perspectives from bench to bedside".
Gadducci et al. (2008) Gynecol Endocrinol 24: 239-249, "Molecular target therapies in endometrial cancer: from the basic research to the clinic" abstract.
Garassino et al. (2009) Anticancer Res 29: 2691-2701, "Biological and clinical features in predicting efficacy of epidermal growth factor receptor tyrosine kinase inhibitors: a systematic review and meta-analysis" abstract.
Gazdar, AF (2009) Oncogene 28 Suppll: S24-S31, "Activating and resistance mutations of EGFR in non-small-cell lung cancer: role in clinical response to EGFR tyrosine kinase inhibitors" abstract.
Granville et al. (2006) Clin Cancer Res 12(3):679-689, "Handicapping the race to develop inhibitors of the phosphoinositide 3-Kinase/Akt/Mammalian target of rapamycin pathway".
Gres et al. (1998) Pharmaceutical Research 15(5):726-733, "Correlation between oral drug absorption in humans, and apparent drug permeability in TC-7 cells, a human epithelial intestinal cell line: comparison with the parental caco-2 cell line".
Gridelli et al. (2008) Oncologist 13: 139-147, "The potential role of mTOR inhibitors in non-small cell lung cancer".
Guerrero et al. (2002) FASEB J 16: 1642-1644, "Codon 12 and codon 13 mutations at the K-ras gene induce different soft tissue sarcoma types in nude mice" abstract.
Guertin et al. (2007) Cancer Cell 12: 9-22, "Defining the role of mTOR in cancer" abstract.
Gururaja et al. (2006) Clin Cancer Res 12(12)3831-3842, "R-253 disrupts microtubule networks in multiple tumor cell lines".
Guzeloglu et al. (2004) Biol Reprod 71: 714-721, "In vivo and in vitro regulation of Akt activation in human endometrial cells is estrogen dependent" abstract.
Hartmann et al. (2006) Clin Cancer Res 12: 3019-3027, "Phosphatidylinositol 3'-kinase/AKT signaling is activated in medulloblastoma cell proliferation and is associated with reduced expression of PTEN" abstract.
Hay, N. (2005) Cancer Cell 8: 179-183, "The Akt-mTOR tango and its relevance to cancer".
Heinemann et al. (2009) Cancer Treat Rev 35:262-271, "Clinical relevance of EGFR-and KRAS-status in colorectal cancer patients treated with monoclonal antibodies directed against the EGFR" abstract.
Heinisch et al. (1972) Journal fur Prakt. Chemie. Band 314, 682-698, "Synthesis und Struktur substituierter Isatinthiosemicarbazone und—isothiosemicarbazone".
Heinisch et al., "Synthesen and Reaktionen von Pyridazinderviaten", 1973, Monatshefte fur Chemie 104, pp. 1372-1382.
Helfrich et al. (2006) Clin Cancer Res 12: 7117-7125, "Antitumor activity of the epidermal growth factor receptor (EGFR) tyrosine kinase inhibitor gefitinib (ZD1839, Iressa) in non-small cell lung cancer cell lines correlates with gene copy number and EGFR mutations but not EGFR protein levels" abstract.
Hennessy et al. (2005) Nat Rev Drug Discov 4: 988-1004, "Exploiting the PI3K/AKT pathway for cancer drug discovery".
Hennessy et al. (2005) Nat Rev Drug Discov 4: 988-1004, "Exploiting the PI3K/AKT pathway for cancer drug discovery" abstract.

(56) References Cited

OTHER PUBLICATIONS

Hirsch et al. (2006) J Clin Oncol 24: 5034-5042, "Molecular predictors of outcome with gefitinib in a phase III placebo-controlled study in advanced non-small-cell lung cancer" abstract.
Ho Sui et al. (2005) Nucleic Acids Research 33(10)3154-3164, "oPOSSUM: identification of over-represented transcription factor binding sites in co-expressed genes".
Holland et al. (2000) Nat Genet 25: 55-57, "Combined activation of Ras and Akt in neural progenitors induces glioblastoma formation in mice" abstract.
Houlston, RS (2001) Mol Pathol 54: 206-214, "What we could do now: molecular pathology of colorectal cancer" abstract.
Huang et al. (2004) Cancer Res 64: 5355-5362, "Dual-agent molecular targeting of the epidermal growth factor receptor (EGFR): combining anti-EGFR antibody with tyrosine kinase inhibitor" abstract.
Huang et al. (2006) Mol Cell Proteomics 5: 1045-1053, "Interdomain conformational changes in Akt activation revealed by chemical cross-linking and tandem mass spectrometry" abstract.
Huang et al. (2009) Biochem Soc Trans 37: 217-222, "A complex interplay between Akt, TSC2 and the two mTOR complexes" abstract.
Huang et al. (2009) J Formos Med Assoc 108: 180-194, "Induction of Akt activity by chemotherapy confers acquired resistance" abstract.
Hynes et al. (2009) Curr Opin Cell Biol 21: 177-184, "ErbB receptors and signaling pathways in cancer" abstract.
Ikeda et al. (2007) Pathol Int 57: 268-275, "Correlation between EGFR gene mutation pattern and Akt phosphorylation in pulmonary adenocarcinomas" abstract.
International Search Report for International Application No. PCT/US2005/021253 mailed Mar. 29, 2006.
Itoh et al. (2002) Cancer 94: 3127-3134, "Phosphorylation of Akt/PKB is required for suppression of cancer cell apoptosis and tumor progression in human colorectal carcinoma" abstract.
Izzard et al. (1999) Cancer Research 59:2581-2586, "Competitive and noncompetitive inhibition of the DNA-dependent protein kinase".
Jacinto et al. (2006) Cell 127: 125-137, "SIN1/MIP1 maintains rictor-mTOR complex integrity and regulates Akt phosphorylation and substrate specificity" abstract.
Janmaat et al. (2003) Clin Cancer Res 9: 2316-2326, "Response to epidermal growth factor receptor inhibitors in non-small cell lung cancer cells: limited antiproliferative effects and absence of apoptosis associated with persistent activity of extracellular signal-regulated kinase or Akt kinase pathways" abstract.
Janmaat et al. (2006) Int J Cancer 118: 209-214, "Enhanced cytotoxicity induced by gefitinib and specific inhibitors of the Ras or phosphatidyl inositol-3 kinase pathways in non-small cell lung cancer cells" abstract.
Janne, PA (2008) Lung Cancer 60 Suppl 2: S3-S9, "Challenges of detecting EGFR T790M in gefitinib/erlotinib-resistant tumours" abstract.
Jetzt et al. (2003) Cancer Res 63: 6697-6706, "Adenoviral-mediated expression of a kinase-dead mutant of Akt induces apoptosis selectively in tumor cells and suppresses tumor growth in mice" abstract.
Ji et al. (2007) J Biol Chem 282: 14048-14055, "Oncogenic KRAS activates hedgehog signaling pathway in pancreatic cancer cells" abstract.
Jiang et al. (2000) Mol Cell Biol 20: 139-148, "The phosphoinositide 3-OH kinase/AKT2 pathway as a critical target for farnesyltransferase inhibitor-induced apoptosis" abstract.
Jiang et al. (2008) Drug Resist Updat 11: 63-76, "Role of mTOR in anticancer drug resistance: perspectives for improved drug treatment" abstract.
Jiang et al. (2009) Adv Cancer Res 102: 19-65, "PI3K/PTEN signaling in angiogenesis and tumorigenesis" abstract.
Jiang et al. (2009) Cancer 115: 3609-3617, "Assessment of K-ras mutation: a step toward personalized medicine for patients with colorectal cancer" abstract.
Jimeno et al. (2009) Cancer J 15: 110-113, "KRAS mutations and susceptibility to cetuximab and panitumumab in colorectal cancer" abstract.
Jimeno et al. (2009) J Clin Oncol 27: 1130-1136, "KRAS mutations and sensitivity to epidermal growth factor receptor inhibitors in colorectal cancer: practical application of patient selection" abstract.
John et al. (2009) Oncogene 28 Suppl 1: S14-S23, "Overview of molecular testing in non-small-cell lung cancer: mutational analysis, gene copy number, protein expression and other biomarkers of EGFR for the prediction of response to tyrosine kinase inhibitors" abstract.
Joshi et al., "Organic Pesticides. Part XIII. Synthesis of Some New Fluoro-ketones and their Thiosemicarbazones", 1963, Journal of Indian Chemical Society, vol. 40, No. 1, p. 42-44.
Kalinowski et al., "Design, Synthesis, and Characterization of Novel Iron Chelators: Structure-Activity Relationships of the 2-Benzoylpyridine Thiosemicarbazone Series and Their 3-Nitrobenzoyl Analogues as Potent Antitumor Agents", 2007, J. Med. Chem., 50, pp. 3716-3729.
Kandasamy et al. (2002) Cancer Res 62: 4929-4937, "Role of the phosphatidylinositol 3'-kinase/PTEN/Akt kinase pathway in tumor necrosis factor-related apoptosis-inducing ligand-induced apoptosis in non-small cell lung cancer cells" abstract.
Kang et al. (2008) Int J Gynecol Cancer 18: 1339-1343, "Mutual exclusiveness between PIK3CA and KRAS mutations in endometrial carcinoma" abstract.
Kim et al. (2002) J Biochem Mol Biol 35: 106-115, "Akt: versatile mediator of cell survival and beyond" abstract.
Kimura et al. (2007) Cancer Sci 98: 12751280, "Antibody-dependent cellular cytotoxicity of cetuximab against tumor cells with wild-type or mutant epidermal growth factor receptor" abstract.
Klein et al. (2009) Curr Opin Cell Bioi 21 : 185-193, "Targeting the EGFR and the PKB pathway in cancer" abstract.
Kobayashi et al. (2005) N Engl J Med 352: 786792, "EGFR mutation and resistance of non-small-cell lung cancer to gefitinib" abstract.
Konstantinopoulos et al. (2007) Nat Rev Drug Discov 6: 541-555, "Post-translational modifications and regulation of the RAS superfamily of GTPases as anticancer targets" abstract.
Krause et al (2005) New England Journal of Medicine 353(2):172-187 "Tyrosine kinases as targets for cancer therapy".
Kurman et al. (2008) Int J Gynecol Pathol 27: 151-160, "Pathogenesis of ovarian cancer: lessons from morphology and molecular biology and their clinical implications" abstract.
Labisbal et al. (2000) Polyhedron, 19, 1255-1262, "Spectral and structural studies of metal complexes of isatin 3-hexamethyleneiminylthiosemicarbazone prepared electrochemically".
Ladanyi et al. (2008) Mod Pathol 21 Suppl 2: S16-S22, "Lung adenocarcinoma: guiding EGFR-targeted therapy and beyond" abstract.
Laurent-Puig et al. (2008) Curr Opin Onco/20: 454-458, "Lessons from Tarceva in pancreatic cancer: where are we now, and how should future trials be designed in pancreatic cancer?" abstract.
Laurent-Puig et al. (2009) Clin Cancer Res 15: 1133-1139, "Mutations and response to epidermal growth factor receptor inhibitors" abstract.
le Coutre et al. (1999) Jrnl National Cancer Institute 91(2):163-168, In vivo eradication of human BCR/ABL-Positive leukemia cells with an ABL kinase inhibitor.
Lee et al. (2005) Clin Cancer Res 11: 6065-6074, "Response of non-small cell lung cancer cells to the inhibitors of phosphatidylinositol 3-kinase/Akt- and MAPK kinase 4/c-Jun NH2-terminal kinase pathways: an effective therapeutic strategy for lung cancer" abstract.
Lee et al. (2008) Int J Cancer 122: 2380-2384, "Akt1 inhibition by RNA interference sensitizes human non-small cell lung cancer cells to cisplatin" abstract.
Legrier et al. (2007) Cancer Res 67: 11300-11308, "Targeting protein translation in human non small cell lung cancer via combined MEK and mammalian target of rapamycin suppression" abstract.
Lev et al. (2005) Clinical Cancer Research 11:306-314, "Inhibition of platelet-derived growth factor receptor signaling restricts the growth of human breast cancer in the bone of nude mice".

(56) References Cited

OTHER PUBLICATIONS

Lievre et al. (2006) Cancer Res 66(8):3992-3995, "KRAS mutation status is predictive of response to cetuximab therapy in colorectal cancer".
Lin et al. (2005) Br J Cancer 93: 1372-1381, "Elevated phosphorylation and activation of PDK-1/AKT pathway in human breast cancer" abstract.
Linardou et al. (2008) Lancet Oneol 9: 962-972, "Assessment of somatic k-RAS mutations as a mechanism associated with resistance to EGFR-targeted agents: a systematic review and meta-analysis of studies in advanced non-small-cell lung cancer and metastatic colorectal cancer" abstract.
Liscovitch et al. (2002) IDrugs 5(4):349-355, "Cancer multidrug resistance: A review of recent drug discovery research".
Lister et al. (1970) Journal of the Chemical Society, 1313-1315, "Potentially Chemotherapeutic Purine Analogues, Part V. Some Hydrazone Derivatives of Pyrazole-4,5-diones and their Cyclisation to Pyrazolo [3,4-e][1,2,4]triazines".
Liu et al. (2007) Clin Cancer Res 13: 67886795, "Relationship of EGFR mutations, expression, amplification, and polymorphisms to epidermal growth factor receptor inhibitors in the NCI60 cell lines." abstract.
Liu et al. (2008) PLoS One 3: e2850, "K-ras/PI3K-Akt signaling is essential for zebrafish hematopoiesis and angiogenesis" abstract.
Liu et al. (2009) Nat Rev Drug Discov 8: 627-644, "Targeting the phosphoinositide 3-kinase pathway in cancer" abstract.
LoPiccolo et al. (2008) Drug Resist Updat 11: 32-50, "Targeting the PI3K/Akt/mTOR pathway: effective combinations and clinical considerations".
LoPiccolo et al. (2008) Drug Resist Updat 11: 32-50, "Targeting the PI3K/Akt/mTOR pathway: effective combinations and clinical considerations" abstract.
Mahoney et al. (2009) Br J Cancer 100: 370-375, "LKB1/KRAS mutant lung cancers constitute a genetic subset of NSCLC with increased sensitivity to MAPK and mTOR signalling inhibition" abstract.
Manning (2009) Biochem Soc Trans 37:217-222, "A complex interplay between Akt, TSC2 and the two mTOR complexes" abstract.
Manning et al. (2007) Cell 129: 1261-1274 Ref ID: 125, "AKT/PKB signaling: navigating downstream" abstract.
MAPK Antibody is used to control for loading and specificity of PTEN siRNA (data obtained from Cell Signaling Technology website, http://www.eellsignal.eom/produets/6251.html) 3 pages.
Martelli et al. (2006) Leukemia 20: 911-928, "Phosphoinositide 3-kinase/Akt signaling pathway and its therapeutical complications for human acute myeloid leukemia" abstract.
Massion et al. (2004) Am J Respir Crit Care Med 170: 1088-1094, "Early involvement of the phosphatidylinositol 3-kinase/Akt pathway in lung cancer progression" abstract.
Masure et al. (1999) Eur J Biochem 265: 353-360, "Molecular cloning, expression and characterization of the human serine/threonine kinase Akt-3" abstract.
McCubrey et al. (2008) Adv Enzyme Regul 48: 113-135, "Alteration of Akt activity increases chemotherapeutic drug and hormonal resistance in breast cancer yet confers an achilles heel by sensitization to targeted therapy" abstract.
McNeill (1973) Antimicrobial Agents and Chemotherapy 4(2):105-108, "Inhibition of granulocyte-macrophage colony formation in vitro by substituted isatin thiosemicarbazones".
Memmott (2009) Cell Signal 21: 656-664, "Akt-dependent and -independent mechanisms of mTOR regulation in cancer" abstract.
Meric-Bernstam et al. (2009) J Clin Oncol 27: 2278-2287, "Targeting the mTOR signaling network for cancer therapy" abstract.
Miller III, et al., "The Cytotoxicity of Copper(II) Complexes of 2-Acetyl-Pyridyl-N-Substituted Thiosemicarbazones", 1998, Anticancer Research 18, pp. 4131-4140.
Minaguchi et al. (2007) Cancer Lett 248: 112-122, "Combined phospho-Akt and PTEN expressions associated with post-treatment hysterectomy after conservative progestin therapy in complex atypical hyperplasia and stage Ia, G1 adenocarcinoma of the endometrium" abstract.
Missbach (1996) Journal of Biological Chemistry 271, 13515-13522, "Thiazolidine Diones, Specific Ligands of the Nuclear Receptor Retinoid Z Receptor/Retinoid Acid Receptor-related Orphan Receptor a with Potent Antiarthritic Activity".
Monks et al. (1991) National Cancer Institute 83(11)757-766, "Feasibility of a high-flux anticancer drug screen using a diverse panel of cultured human tumor cell lines".
Morgan et al. (1983), International Journal of Applied Radiation and Isotopes, 34(11), 1501-1504, "Synthesis of [1-14C]1,2-Cyclohexanedione bis(4-diethylenoxythiosemicarbazone) and Preliminary Biodistribution Studies of this Potential Antitumor Agent".
Morgensztern et al. (2005) Anticancer Drugs 16: 797-803, "PI3K/Akt/mTOR pathway as a target for cancer therapy" abstract.
Nelson et al. (2007) Prostate Cancer Prostatic Dis 10: 331-339, "Inhibition of Akt pathways in the treatment of prostate cancer".
Normanno et al. (2006) Gene 366: 2-16, "Epidermal growth factor receptor (EGFR) signaling in cancer" abstract.
Noske et al. (2007) Cancer Lett 246: 190-200, "Specific inhibition of AKT2 by RNA interference results in reduction of ovarian cancer cell proliferation: increased expression of AKT in advanced ovarian cancer" abstract.
NSC No. 84442-R, National Cancer Institute, 5 pages.
O'Sullivan et al. (1963), Chemotherapia, 7, 17-26, "A Study of the Chemotherapeutic Activity of Isatin β-4',4'-Dialkylthiosemicarbazones against Ectromelia Infection".
O'Sullivan et al. (1963), International Congress of chemotherapy, (1), 879-883, "A Study of Isatin β-Thiosemicarbazone Derivatives in Relation to the Cytopathic Changes Produced by Type 1 and Type 2 Poliovirus on Embryonic Rabbit Kidney Cells in Tissue-Culture".
Oehler-Janne et al. (2008) Biochem Biophys Res Commun 375: 399-404, "Temperature sensitivity of phospho-Ser(473)-PKB/AKT" abstract.
Office Action for CA 2,673,683 mailed Jan. 28, 2013, 8 pages.
Office Action for JP 2009-545043, mailed Mar. 12, 2013, with English Translation, 10 pages.
Okudela et al. (2004) Am J Pathol 164: 91-100, "K-ras gene mutation enhances motility of immortalized airway cells and lung adenocarcinoma cells via Akt activation: possible contribution to non-invasive expansion of lung adenocarcinoma" abstract.
Ono et al. (2006) Clin Cancer Res 12: 7242-7251, "Molecular mechanisms of epidermal growth factor receptor (EGFR) activation and response to gefitinib and other EGFR-targeting drugs" abstract.
Pacifici et al. (1992) Clin Pharmacokinetics 23(6):449-468, "Methods of determining plasma and tissue binding of drugs. Pharmacokinetic consequences" abstract.
Pandyra et al. (2007) Jrnl Pharmacology and Experimental Therapeutics 322(1):123-132, "Combination silencer RNA (siRNA) targeting Bcl-2 antagonizes siRNA against thymidylate synthase in human tumor cell lines".
Pao et al. (2005) PLoS Med 2: e73, "Acquired resistance of lung adenocarcinomas to gefitinib or erlotinib is associated with a second mutation in the EGFR kinase domain" abstract.
Pao, W (2006) Cancer Chemother Pharmacol 58 Suppl: s11-s15, "Defining clinically relevant molecular subsets of lung cancer" abstract.
Papadimitrakopoulou et al. (2006) J Thorac Oncol 1: 749-751, "The Akt/mTOR and mitogen-activated protein kinase pathways in lung cancer therapy" abstract.
Parikh et al. (2007) Cancer Res 67: 7139-7146, "Oncogenic NRAS, KRAS, and HRAS exhibit different leukemogenic potentials in mice" abstract.
Pectasides, et al., "Systemic therapy in metastatic or recurrent endometrial cancer", Mar. 3, 2007, Cancer Treatment Reviews, Saunders, US, vol. 33, No. 2, pp. 177-190.
Peterson et al. (2000) Jrnl Biological Chemistry 275(10):7416-7423, FKBP12-Rapamycin-associated protein (FRAP) autophosphorylates at serine 2481 under translationally repressive conditions.
Plesec et al. (2009) Adv Anat Pathol 16: 196-203, "KRAS mutation testing in colorectal cancer" abstract.

(56) References Cited

OTHER PUBLICATIONS

Plowman et al. (1994) DN&P 7(6):334-339, "Receptor tyrosine kinases as targets for drug intervention".
Prakash et al. (1989) Indian Drugs 27(2), 106-110, "Synthesis and Screening of N-Morpholino/Piperidino Thiosemicarbazones as Potential Anitmicrobial Agents".
Pretlow et al. (2005) Biochim Biophys Acta 1756: 83-96, "Mutant KRAS in aberrant crypt foci (ACF): initiation of colorectal cancer?" abstract.
Raponi et al. (2008) Curr Opin Pharmacol 8: 413-418, "KRAS mutations predict response to EGFR inhibitors" abstract.
Rhodes et al. (2005) Nature Biotechnology 23(8):951-959, "Probabilistic model of the human protein-protein interaction network".
Riely et al. (2009) Proc Am Thorac Soc 6: 201-205, "KRAS mutations in non-small cell lung cancer" abstract.
Riely, GJ (2008) J Thorac Oncol 3: S146-S149, "Second-generation epidermal growth factor receptor tyrosine kinase inhibitors in non-small cell lung cancer" abstract.
Riely, GJ (2008) Lung Cancer 60 Suppl 2: S19-S22, "The use of first-generation tyrosine kinase inhibitors in patients with NSCLC and somatic EGFR mutations" abstract.
Riondel et al. (1988) Anticancer Research 8:387-390, "Antineoplastic activity of two taxol derivatives on an ovarian tumor xenografted into nude mice".
Rong et al. (2001) J Med Chem 44: 898-908, "Molecular modeling studies of the Akt PH domain and its interaction with phosphoinositides" abstract.
Rosner et al. (2008) Mutat Res 659: 284-292, "The mTOR pathway and its role in human genetic diseases" abstract.
Rosti et al. (2006) Ann Oncol 17 Suppl 5: v99-102, "Chemotherapy advances in small cell lung cancer" abstract.
Ruggeri et al. (1998) Mol Carcinog 21: 81-86, "Amplification and overexpression of the AKT2 oncogene in a subset of human pancreatic ductal adenocarcinomas" abstract.
Ruggero et al. (2005) Oncogene 24: 7426-7434, "The Akt of translational control" abstract.
Rusinov et al., "New reaction of 3,6-bis(2-pyridyl)-1,2,4,5-tetrazine with anhydro base of 1,2,3-trimethylquinoxalinium and intramolecular aminolysis of the resulting azomethine", 1981, (abstract).
Sabatini, DM (2006) Nat Rev Cancer 6: 729-734, "mTOR and cancer: insights into a complex relationship" abstract.
Saif et al. (2009) Clin Adv Hematol Oncol/7: 45-53, 64, "K-ras mutations in colorectal cancer: a practice changing discovery" abstract.
Sambuy et al. (2005) Cell Biology and Toxicology 21:1-26, "The Caco-2 cell line as a model of the intestinal barrier: infuence of cell and culture-related factors on Caco-2 cell functional characteristics".
Sarbassov et al. (2004) Current Biology 14:1296-1302, "Rictor, a novel binding partner of mTOR, defines a rapamycin-insensitive and raptor-independent pathway that regulates the cytoskeleton".
Sarbassov et al. (2005) Science 307: 1098-1101, "Phosphorylation and regulation of Akt/PKB by the rictor-mTOR complex" abstract.
Schneider et al. (2003) Mol Cancer 2: 15, "Genetic alterations in pancreatic carcinoma" abstract.
Schubbert et al. (2007) Nat Rev Cancer 7: 295-308, "Hyperactive Ras in developmental disorders and cancer" abstract.
Scripture et al. (2006) Nature 6:546-558, "Drug interactions in cancer therapy".
Sebille (1990) Fundam Clin Pharmacol 4(S2):151s-161s, "Methods of drug protein binding determinations".
Seeliger et al. (2007) Cancer Metastasis Rev 26: 611-621, "Role of mTOR in solid tumor systems: a therapeutical target against primary tumor growth, metastases, and angiogenesis" abstract.
Seleem et al. (2002) Journal of the Serbian Chemical Society, 67(4), 243-256, "Thermodynamics of complexation of isatin-3-thiosemicarbazone (HIT) and other related derivatives with some metal ions".
Sequence Listing for International Application No. PCT/US2005/021253.

Sequist et al. (2008) Annu Rev Med 59:429-442, "EGFR tyrosine kinase inhibitors in lung cancer: an evolving story" abstract.
Sequist, LV (2008) J Thorac Oncol 3: S143-S145, "First-generation epidermal growth factor receptor tyrosine kinase inhibitors in EGFR mutation: positive non-small cell lung cancer patients" abstract.
Several mutations that abolish PI3-K activity have been described and are catalogued in the human protein mutation database MutDB (http://mutdb.org/) 1 page.
Shaw et al. (2006) Nature 441: 424-430, "Ras, PI(3)K and mTOR signalling controls tumour cell growth" abstract.
She et al. (2008) PLoS One 3: e3065, "Breast tumor cells with PI3K mutation or HER2 amplification are selectively addicted to Akt signaling" abstract.
Sherman et al. (2007) BMC Bioinformatics 8:426-436, "DAVID Knowledgebase: a gene-centered database integrating heterogeneous gene annotation resources to facilitate high-throughput gene functional analysis".
Shridhar et al. (1987) Indian Journal of Chemistry 26B:596-598, "Synthesis & antiparasitic activity of some new 1-(6/7-Nitrobenzoxazin-3-yl)-4-substituted-3-thiosemicarbazides & 4-Disubstituted 3-(6-Acetylbenzoxazin3-one)thiosemicarbazones".
Shtilbans et al. (2008) Ann Diagn Pathol 12: 153-160, "Current overview of the role of Akt in cancer studies via applied immunohistochemistry" abstract.
Siegel-Lakhai et al. (2005) Oncologist 10: 579-589, "Current knowledge and future directions of the selective epidermal growth factor receptor inhibitors erlotinib (Tarceva) and gefitinib (Iressa)" abstract.
Simone (1996) Cecil Textbook of Medicine, 20th Edition 1:1004-1010, "Part XIV Oncology: 154 Introduction".
Smakman et al. (2005) Biochim Biophys Acta 1756: 103-114, "Control of colorectal metastasis formation by K-Ras" abstract.
Spano et al. (2008) Crit Rev Oncol Hematol 66: 21-30, "Potential predictive markers of response to EGFR-targeted therapies in colorectal cancer" abstract.
Steelman et al. (2008) Leukemia 22: 686-707, "Contributions of the Raf/MEK/ERK, PI3K/PTEN/Akt/mTOR and Jak/STAT pathways to leukemia" abstract.
Steiner et al. (2007) Clin Cancer Res 13: 1540-1551, "Tumor growth inhibition with cetuximab and chemotherapy in non-small cell lung cancer xenografts expressing Wild-type and mutated epidermal growth factor receptor" abstract.
Stintzing et al. (2009) Dtsch Arztebllnt 106: 202-206, "The treatment of colorectal carcinoma with monoclonal antibodies: the importance of KRAS mutation analysis and EGFR status" abstract.
Strimpakos et al. (2009) Cancer Treat Rev 35: 148-159, "The role of mTOR in the management of solid tumors: an overview" abstract.
Suda et al. (2009) J Thorac Oncol 4: 1-4, "N(4)-substituted isatin thiosemicarbazones and their copper(II) complexes EGFR T790M mutation: a double role in lung cancer cell survival?" abstract.
Sugimoto et al., "Activation of Dithiocarbamate by 2-Halothiazolium Salts", 1988, J. Org. Chem., 53, pp. 2263-2267.
Suzuki et al., Preparation of diphenylmethylimine derivatives as antiinflammatories, *antitumors, and lipoxygenase and cyclooxygenase inhibitors, 1987 (abstract).
Szakács et al. (2006) Nature Reviews Drug Discovery 5:219-234, "Targeting multidrug resistance in cancer".
Szakács et al. (2008) Drug Discovery Today 13(9/10):379-393, "The role of ABC transporters in drug absorption, distribution, metabolism, excretion and toxicity (ADME—Tox)".
Tang et al. (2006) Oncol Rep 15: 855-859, "PTEN sensitizes epidermal growth factor-mediated proliferation in endometrial carcinoma cells" abstract.
Teachey et al. (2009) Br J Haematol 145: 569-580, "Mammalian target of rapamycin inhibitors and their potential role in therapy in leukaemia and other haematological malignancies" abstract.
Testa et al. (2005) Oncogene 24: 7391-7393, "AKT signaling in normal and malignant cells" abstract.
The intersection of common genes was determined using GeneVenn (http://mcbc.usm.edu/genevenn/genevenn.htm) 1 page.
Tomida et al. (2005) Cancer Sci 96: 63-68, "Throwing new light on lung cancer pathogenesis: updates on three recent topics" abstract.
Tzeng et al. (2007) J Surg Res 143: 20-26, "EGFR genomic gain and aberrant pathway signaling in pancreatic cancer patients" abstract.

(56) References Cited

OTHER PUBLICATIONS

Undevia et al. (2005) Nature Reviews 5:447-458, "Pharmacokinetic variability of anticancer agents".
Uramoto et al. (2007) Br J Cancer 96: 857-863, "Which biomarker predicts benefit from EGFR-TKI treatment for patients with lung cancer?" abstract.
Van den Bongard et al. (2000) Clinical Pharmacokinetics 39(5):345-367, "Pharmacokinetically Guided Administration of Chemotherapeutic Agents" abstract.
Vanhaesebroeck et al. (2000) Biochem J 346 Pt 3: 561-576, "The PI3K-PDK1 connection: more than just a road to PKB" abstract.
Varughese et al. (1984) Drugs under Experimental and Clinical Research 10(2), 67-74, "A Biodistribution Study of 1-14C-1,2-Cyclohexanedione Bis(4-Diethylenoxythiosemicarbazone), A Potential Antitumour Agent".
Venkatakrishnan et al. (2001) J Clin Pharmacol 41:1149-1179, "Human drug metabolism and the cytochromes P450: application and relevance of in vitro models".
Vivanco et al. (2002) Nat Rev Cancer 2: 489-501, "The phosphatidylinositol 3-Kinase AKT pathway in human cancer" abstract.
Walther et al. (2009) Nat Rev Cancer 9: 489-499, "Genetic prognostic and predictive markers in colorectal cancer" abstract.
Wang et al. (2008) Cancer Res 68: 7409-7418, "Enhancing mammalian target of rapamycin (mTOR)-targeted cancer therapy by preventing mTOR/raptor inhibition-initiated, mTOR/rictor-independent Akt activation" abstract.
Wang et al., "Preparation of heteroaryl substituted hydrazinecarbothioamide compounds for treatment of cancer", 2007 (abstract).
Weng et al. (2009) Cancer Lett 273: 257-265, "Implication of the Akt2/survivin pathway as a critical target in paclitaxel treatment in human ovarian cancer cells" abstract.
West et al., "Copper(II) complexes of 2-formyl-, 2-acetyl- and 2-benzoylpyridine N(4)-o-, N(4)-m-, N(4)-p-chlorophenylthiosemicarbazones", 1996, Transition Met. Chem., 21, pp. 52-57.
West et al., "Copper(II) complexes of 2-formyl-, 2-acetyl- and 2-benzoy-pyridine N(4)-phenyl-, N(4)-o-methoxyphenyl-, N(4)-p-methoxy-phenyl-and N(4)-p-nitrophenylthiosemicarbazones", 1996, Transition Met. Chem., 21, pp. 213-218.
West et al., "Copper(II) complexes of 2-formyl-, 6-methyl-2-formyl- and 2-benzoylpyridine N(4)-(2-methylpyridinyl)-,N(4)-(2-ethylpyridinyl)-and N(4)-methyl(2-ethylpyridinyl) thiosemicarbazones", 1996, Transition Met. Chem., 21, pp. 289-295.
Winkelmann et al. (1987) Drug Res 37(1):647-661, "Antimalarial and Anticoccidial Activity of 3-Aryl-7-chloro-3,4-dihydroacridine-1,9-(2H, 1OH)-diones".
Wolber et al. (2006) Methods in Enzymology 410:28-57, "The agilent in situ-synthesized microarray platform".
Wong, KK (2008) Lung Cancer 60 Suppl 2: S10-S18, "Searching for a magic bullet in NSCLC: the role of epidermal growth factor receptor mutations and tyrosine kinase inhibitors".
Yamamoto et al. (2008) Cancer Res 68: 6913-6921, "PIK3CA mutations and copy number gains in human lung cancers" abstract.
Yang et al. (2002) Nat Struct Biol 9: 940-944, "Crystal structure of an activated Akt/protein kinase B ternary complex with GSK3-peptide and AMP-PNP" abstract.
Yap et al. (2008) Curr Opin Pharmacol 8: 393-412, "Targeting the PI3K-AKT-mTOR pathway: progress, pitfalls, and promises" abstract.
Yuan et al. (2000) Oncogene 19: 2324-2330, "Frequent activation of AKT2 and induction of apoptosis by inhibition of phosphoinositide-3-OH kinase/Akt pathway in human ovarian cancer" abstract.
Yuan et al. (2004) Blood 104:1450-1458, "Novel di-2-pyridyl-derived iron chelators with marked and selective antitumor activity: in vitro and in vivo assessment".
Zhang et al. (2005) Proc Natl Acad Sci U S A 102: 14605-14610, "Identification of K-ras as the major regulator for cytokine-dependent Akt activation in erythroid progenitors in vivo" abstract.
Zhang et al. (2007) J Med Genet 44: 166-172, "Somatic mutations of the epidermal growth factor receptor and non-small-cell lung cancer" abstract.
Zhang et al. (2007) Nat Med 13: 1114-1119, "Molecular imaging of Akt kinase activity" abstract.
Zhou (2008) Xenobiotica 38(7-8):802-832, "Structure, function and regulation of P-glycoprotein and its clinical relevance in drug disposition".
Zwick et al (2002) Trends in Molecular Medicine 8(1):17-23, "Receptor tyrosine kinases as targets for anticancer drugs" abstract.
European Search Report for Application No. 11761876.9 dated Jul. 15, 2014.

* cited by examiner

INHIBITOR COMPOUNDS AND CANCER TREATMENT METHODS

RELATED APPLICATIONS

This application is a division of U.S. patent application Ser. No. 13/363,558, filed Feb. 1, 2012, entitled "Inhibitor Compounds and Cancer Treatment Methods," which is a continuation of U.S. patent application Ser. No. 12/505,295 (now U.S. Pat. No. 8,138,191), filed Jul. 17, 2009, entitled "Inhibitor Compounds and Cancer Treatment Methods," which is a continuation-in-part of U.S. patent application Ser. No. 12/013,079 (now U.S. Pat. No. 8,034,815), filed Jan. 11, 2008, which claims the benefit of U.S. Provisional Application No. 60/884,489, filed Jan. 11, 2007, which also claims priority to U.S. Provisional Application No. 60/884,504, filed Jan. 11, 2007. In addition, U.S. patent application Ser. No. 12/505,295, filed Jul. 17, 2009 also claims priority from U.S. Provisional Application No. 61/081,679, filed Jul. 17, 2008, which also claims priority from U.S. Provisional Application No. 61/149,950, filed Feb. 4, 2009, which are each incorporated herein in their entirety by reference.

FIELD OF THE INVENTION

The present invention relates generally to inhibitor compounds, compositions and cancer treatment methods.

BACKGROUND OF THE INVENTION

Cancer, irrespective of its pathogenesis, is characterized by uncontrolled growth and survival of cells. Common to most forms of cancer is an error in the cellular mechanism responsible for balancing cell survival and cell death.

According to the American Cancer Society, lung cancer is the leading cause of cancer death for both men and women. Small cell lung cancer (SCLC) accounts for approximately 20% of all lung cancers. The 5-year survival rate for small cell lung cancer is about 15%.

Certain thiosemicarbazones, such as those disclosed in British Patent No. 1,026,401, International Patent Application No. WO2004/066725, Japanese Patent No. 56-95161 and U.S. Pat. No. 4,927,843, have been used to treat, for example, a variety of viruses. Other thiosemicarbazones, however, may be used to treat cancer. French Patent No. 2,879,194 is directed to certain thiosemicarbazones that may be used in the treatment or prevention of cancer, in dermatological treatment, in the treatment of cardiovascular and immune diseases, lipid-metabolism related diseases and modulate PPAR's. International Patent Application No. WO 2006/009765 is directed to specific thiosemicarbazones that may be used in anti-cancer therapy that mitigates the development of drug resistance. U.S. Pat. No. 4,593,027 is directed to hydrazone derivatives that may be used as a chemotherapeutic.

There is a need, however, for new therapeutic drug treatments to treat cancers more efficiently, and lung cancer in particular. Current treatment regimes for small cell lung cancer involve surgery, radiation and chemotherapy. While timely surgery can be curative, new therapies are necessary when timely surgery is not an option.

SUMMARY OF THE INVENTION

In an aspect, there is provided a therapeutically effective composition for use in the treatment of cancer comprising an anti-cancer agent and a therapeutically effective amount of a compound comprising a compound of Formula I:

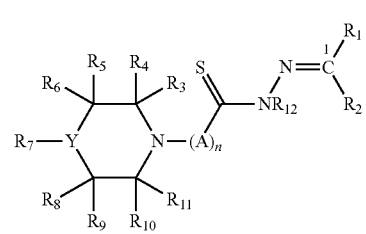

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

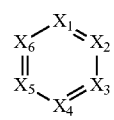

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

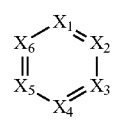

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group;

$R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer;

wherein the composition produces a synergistic therapeutic effect as compared to sole administration of either the anti-cancer agent or the compound.

With respect to the above aspect, in another aspect, the compound is an mTOR-Rictor complex inhibitor, a Serine 473 phosphorylation inhibitor, an AKT2 inhibitor, or a combination thereof. In a further aspect, the compound is an mTOR-Rictor complex inhibitor, a Serine 473 phosphorylation inhibitor, or a combination thereof. In another aspect, the compound is both an mTOR-Rictor complex inhibitor and a Serine 473 phosphorylation inhibitor. In another aspect, the compound is an mTOR-Rictor complex inhibitor. In another aspect, the anti-cancer agent is an mTOR-Raptor complex inhibitor. In another aspect, the anticancer agent is a cytotoxic agent. In another aspect, the synergistic effect is reduction or prevention of resistance to the cytotoxic agent. In another aspect, the anti-cancer agent is selected from the group consisting of cisplatin, rapamycin, tecrolimus, temsirolimus, paclitaxel, erlotinib, cetuximab and doxorubicin. In another aspect, the cancer is treatable by inhibition of mTOR. In another aspect, the cancer is selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial cancer, and kidney cancer. In a further aspect, the cancer is selected from the group consisting of small cell lung cancer, breast cancer, acute leukemia, chronic leukemia, colorectal cancer, colon cancer, brain cancer, carcinoma, ovarian cancer, endometrial cancer, carcinoid tumors, metastatic colorectal cancer, islet cell carcinoma, metastatic renal con carcinoma, adenocarcinomas, glioblastoma multiforme, bronchoalveolar lung cancers, non-Hodgkin's lymphoma, neuroendocrine tumors, and neuroblastoma. In another aspect, the cancer is ovarian, colon, colorectal or endometrial cancer. In another aspect, the amount of the anti-cancer agent is selected to lower overall toxicity as compared to administration of the anti-cancer agent alone in an amount sufficient to achieve substantially the same treatment effect on cancerous cells. In another aspect, the dose of at least one of the anti-cancer agent or the compound is selected to increase the overall treatment effect on cancerous cells as compared to administration of the anti-cancer agent alone in an amount producing substantially the same toxicity. In a further aspect, the amount of the compound is less than an amount of the anti-cancer agent. In another aspect, the amount of the compound is at most about 80%, about 50%, about 40%, about 30%, about 20%, about 10%, about 5%, about 3%, about 2%, about 1%, about 0.75%, about 0.5%, about 0.25%, or about 0.1% of the amount of the anti-cancer agent. In another aspect, the first ring system is a substituted or unsubstituted heterocyclic group, the second ring system is a substituted or unsubstituted heteroaromatic group, a substituted or unsubstituted carbocyclic group, or a substituted or unsubstituted heterocyclic group. In another aspect, the substituted or unsubstituted polycyclic ring further comprises a third ring system fused to the first ring system. In another aspect, the third ring system is a substituted or unsubstituted aromatic group, a substituted or unsubstituted heteroaromatic group, a substituted or unsubstituted carbocyclic group, or a substituted or unsubstituted heterocyclic group. In another aspect, n is 0. In another aspect, n is 1 and A is a substituted or unsubstituted heteroaromatic group. In another aspect, A is a pyridinyl group. In another aspect, Y is a nitrogen atom. In another aspect, $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group. In another aspect, $R_7$ is the substituted or unsubstituted alkyl group or a substituted or unsubstituted pyridyl group and $R_3$ to $R_6$ and $R_8$ to $R_{12}$ are each H. In another aspect, the compound is selected from:

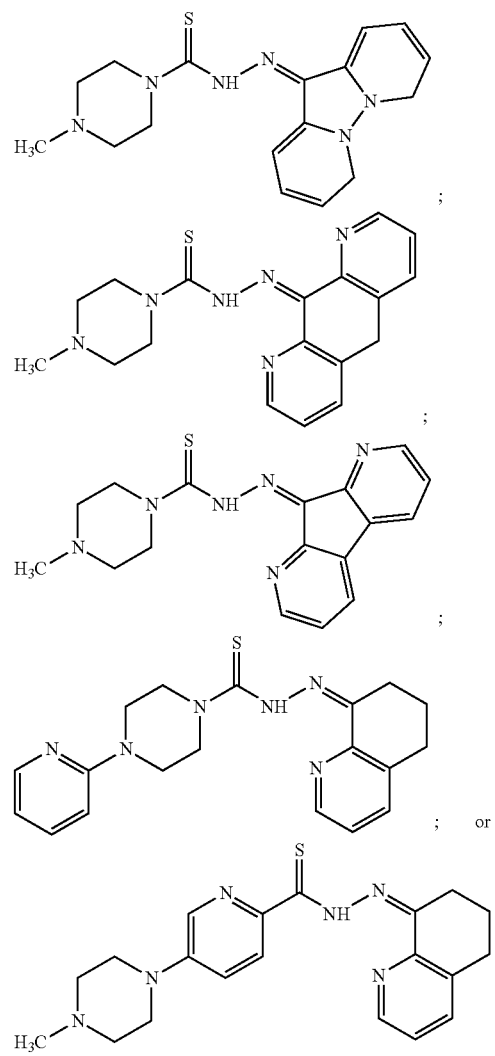

and/or a pharmaceutically-acceptable salt, hydrate, solvate or combination thereof. In another aspect, the compound of Formula I is:

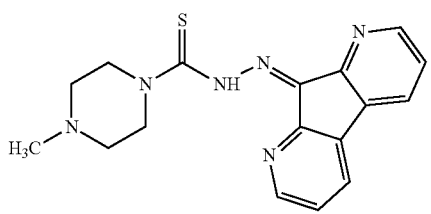 [SMILES: CN1CCN(C(=S)NN=C2c3ncccc3-c3cccnc32)CC1]

and/or a pharmaceutically-acceptable salt, hydrate, solvate or combination thereof. In another aspect, the compound of Formula I is:

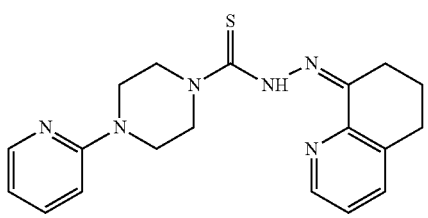 [SMILES: S=C(N/N=C1/CCCc2cccnc21)N1CCN(c2ccccn2)CC1]

and/or a pharmaceutically-acceptable salt, hydrate, solvate or combination thereof. In another aspect, the composition further comprising at least one pharmaceutically acceptable carrier and/or diluent. In another aspect, the compound is a pharmaceutically-acceptable salt of Formula I. In another aspect, the salt is an oxalate or tartrate.

In yet another aspect, there is provided a pharmaceutically-acceptable salt of a compound of Formula I:

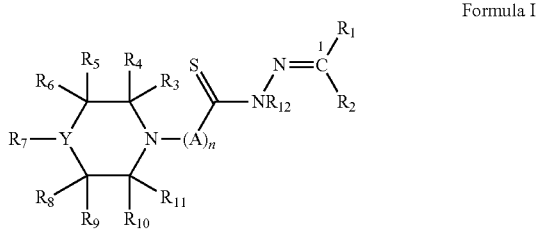

Formula I and/or optical isomer thereof;
wherein:
$R_1$ and $R_2$ together form a substituted or unsubstituted polycyclic ring comprising at least two ring systems, said at least two ring systems comprising a first ring system bonded to C1 and a second ring system fused to the first ring system, wherein:
the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or
the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or
the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

Ring B wherein $X_1$ to $X_6$ are each independently selected from carbon or a heteroatom; or
the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

Ring B wherein $X_1$ to $X_6$ are each independently selected from carbon or a heteroatom; or
the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and
$R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;
$R_{12}$ is selected from H or a hydrocarbyl group;
Y is selected from a heteroatom or a carbon atom;
A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and
n is an integer.

In a further aspect, there is provided a pharmaceutically-acceptable oxalate or tartrate salt of a compound of Formula I:

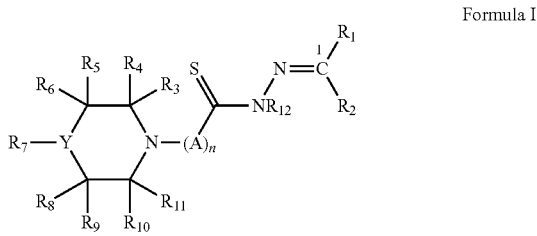

Formula I and/or optical isomer thereof;

wherein:

R₁ and R₂ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

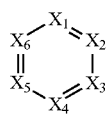

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

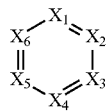

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer.

With respect to the above aspects, in another aspect, the first ring system is a substituted or unsubstituted heterocyclic group, the second ring system is a substituted or unsubstituted heteroaromatic group, a substituted or unsubstituted carbocyclic group, or a substituted or unsubstituted heterocyclic group. In another aspect, the substituted or unsubstituted polycyclic ring further comprises a third ring system fused to the first ring system. In another aspect, the third ring system is a substituted or unsubstituted aromatic group, a substituted or unsubstituted heteroaromatic group, a substituted or unsubstituted carbocyclic group, or a substituted or unsubstituted heterocyclic group. In another aspect, n is 0. In another aspect, n is 1 and A is a substituted or unsubstituted heteroaromatic group. In another aspect, A is a pyridinyl group. In another aspect, Y is a nitrogen atom. In another aspect, $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group. In another aspect, $R_7$ is the substituted or unsubstituted alkyl group or a substituted or unsubstituted pyridyl group and $R_3$ to $R_6$ and $R_8$ to $R_{12}$ are each H. In another aspect, the compound is selected from the salt of:

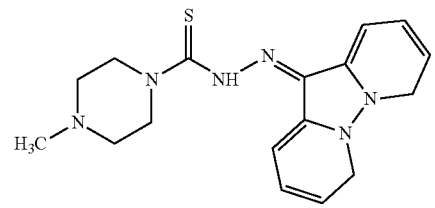

;

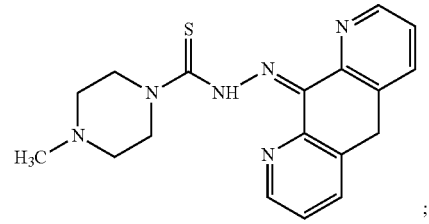

;

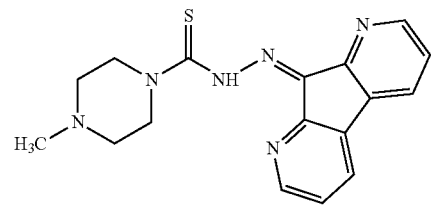

;

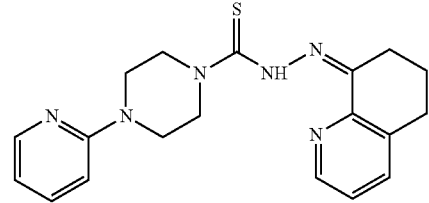

; or

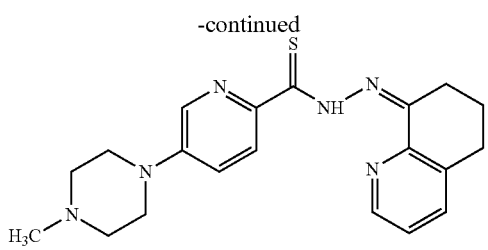

In another aspect, the compound of Formula I is the salt of:

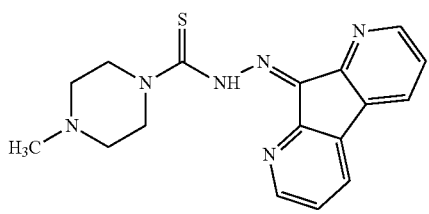

In another aspect, the compound of Formula I is the salt of:

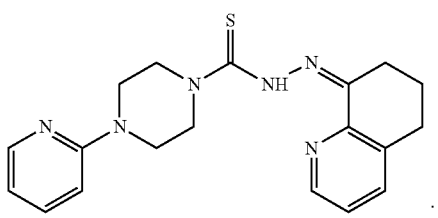 [SMILES: S=C(N/N=C1/CCCc2cccnc21)N1CCN(c2ccccn2)CC1]

In a further aspect, there is provided a method of treating a cancer in a mammal in need thereof comprising simultaneously or sequentially administering an anti-cancer agent in combination with a therapeutically effective amount of a compound that is an mTOR-Rictor complex inhibitor, a Serine 473 phosphorylation inhibitor, an AKT2 inhibitor, or a combination thereof, the combination providing a synergistic therapeutic effect as compared to sole administration of either the anti-cancer agent or the compound.

With respect to the above aspects, in another aspect, the cancer is treatable by inhibition of mTOR. In another aspect, the anti-cancer agent is an mTOR-Raptor complex inhibitor. In another aspect, the anticancer agent is a cytotoxic agent. In another aspect, the synergistic effect is reduction or prevention of resistance to the cytotoxic agent. In another aspect, the anti-cancer agent is selected from the group consisting of cisplatin, rapamycin, tecrolimus, temsirolimus, paclitaxel, erlotinib, cetuximab and doxorubicin. In another aspect, the dose of the anti-cancer agent is selected to lower overall toxicity as compared to administration of the anti-cancer agent alone in an amount sufficient to achieve substantially the same treatment effect on cancerous cells. In another aspect, the dose of at least one of the anti-cancer agent or the compound is selected to increase the overall treatment effect on cancerous cells as compared to administration of the anti-cancer agent alone in an amount producing substantially the same toxicity. In another aspect, the anti-cancer agent is administered at a sub-therapeutic dose without substantially reducing the efficacy of the cancer treatment. In another aspect, the dose of the compound is less than the dose of the anti-cancer agent. In another aspect, the dose of the compound is at most about 80%, about 50%, about 40%, about 30%, about 20%, about 10%, about 5%, about 3%, about 2%, about 1%, about 0.75%, about 0.5%, about 0.25%, or about 0.1% of the dose of the anti-cancer agent. In another aspect, the compound is an mTOR-Rictor complex inhibitor.

In another aspect, the cancer is selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In another aspect, the cancer is selected from the group consisting of small cell lung cancer, breast cancer, acute leukemia, chronic leukemia, colorectal cancer, colon cancer, brain cancer, carcinoma, ovarian cancer, or endometrial cancer, carcinoid tumors, metastatic colorectal cancer, islet cell carcinoma, metastatic renal cell carcinoma, adenocarcinomas, glioblastoma multiforme, bronchoalveolar lung cancers, non-Hodgkin's lymphoma, neuroendocrine tumors, and neuroblastoma. In another aspect, the cancer is ovarian, colon, colorectal or endometrial cancer. In another aspect, the compound comprises a compound of Formula I:

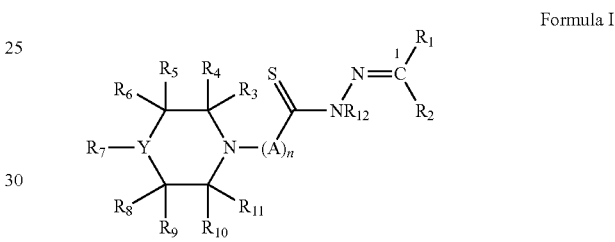

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

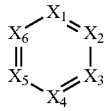

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer.

In another aspect, there is provided a method of treating a cancer in a mammal in need thereof comprising simultaneously or sequentially administering an anti-cancer agent in combination with a therapeutically effective amount of a compound comprising a compound of Formula I:

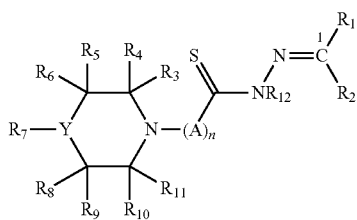

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

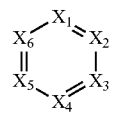

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

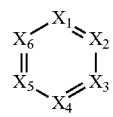

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer;

the combination providing a synergistic therapeutic effect as compared to sole administration of either the anti-cancer agent or the compound.

With respect to the above aspects, in another aspect, the cancer is selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In another aspect, the cancer is selected from the group consisting of small cell lung cancer, breast cancer, acute leukemia, chronic leukemia, colorectal cancer, colon cancer, brain cancer, carcinoma, ovarian cancer, or endometrial cancer, carcinoid tumors, metastatic colorectal cancer, islet cell carcinoma, metastatic renal cell carcinoma, adenocarcinomas, glioblastoma multiforme, bronchoalveolar lung cancers, non-Hodgkin's lymphoma, neuroendocrine tumors, and neuroblastoma. In another aspect, the cancer is ovarian, colon, colorectal or endometrial cancer. In another aspect, there is provided a method of treating endometrial cancer in a mammal in need thereof comprising administering a therapeutically effective amount of a compound comprising a compound of Formula I:

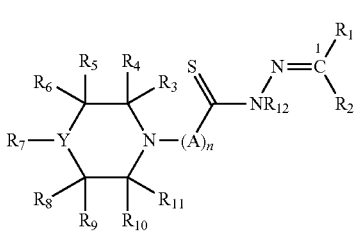

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

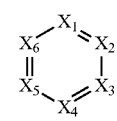

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

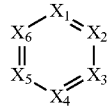

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer.

With respect to the above aspects, in another aspect, the cancer is characterized by a KRAS mutation. In another aspect, the cancer is characterized by an EGFR mutation.

In another aspect, there is provided a method of treating a cancer in a mammal in need thereof characterized by overexpression of RAS, by an EGFR mutation, and/or by overexpression of AKT2, comprising administering a therapeutically effective amount of a compound comprising a compound of Formula I:

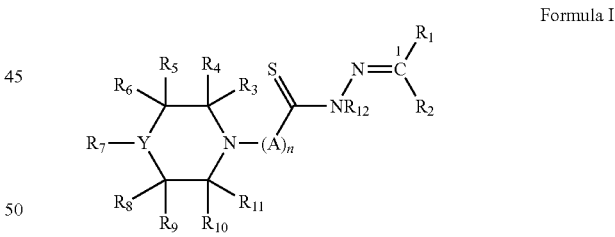

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

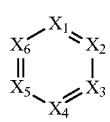

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

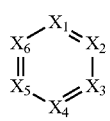

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer.

With respect to the above aspects, in another aspect, the cancer is characterized by a KRAS mutation. In another aspect, the cancer is selected from the group consisting of leukemia, colon cancer, colorectal cancer, pancreatic cancer, lung cancer, multiple myeloma, endometrial cancer, and ovarian cancer. In another aspect, the cancer is colorectal cancer. In another aspect, the cancer is characterized by an EGFR mutation. In another aspect, the cancer is selected from the group consisting of lung cancer, glioblastoma, colon cancer, gastric cancer, renal cancer, prostate cancer, breast cancer, and ovarian cancer. In another aspect, the cancer is non-small cell lung cancer. In another aspect, the cancer is characterized by over-expression of AKT2. In another aspect, the cancer is selected from the group consisting of breast cancer, ovarian cancer, colon cancer, pancreatic cancer, glioma, glioblastoma, lung cancer, and prostate cancer. In another aspect, the cancer is treatable by inhibition of mTOR. In another aspect, the method further comprises simultaneously or sequentially administering an anti-cancer agent in combination with the compound. In another aspect, the combination produces a synergistic therapeutic effect as compared to sole administration of either the anti-cancer agent or the compound. In another aspect, the anti-cancer agent is an mTOR-Raptor complex inhibitor. In another aspect, the anticancer agent is a cytotoxic agent. In another aspect, the synergistic effect is reduction or prevention of resistance to the cytotoxic agent. In another aspect, the anti-cancer agent is selected from the group consisting of cisplatin, rapamycin, tecrolimus, temsirolimus, paclitaxel, erlotinib, cetuximab and doxorubicin. In another aspect, the dose of the anti-cancer agent is selected to lower overall toxicity as compared to administration of the anti-cancer agent alone in an amount sufficient to achieve substantially the same treatment effect on cancerous cells. In another aspect, the dose of at least one of the anti-cancer agent or the compound is selected to increase the overall treatment effect on cancerous cells as compared to administration of the anti-cancer agent alone in an amount producing substantially the same toxicity. In another aspect, the anti-cancer agent is administered at a sub-therapeutic dose without substantially reducing the efficacy of the cancer treatment. In another aspect, the dose of the compound is less than the dose of the anti-cancer agent. In another aspect, the dose of the compound is at most about 80%, about 50%, about 40%, about 30%, about 20%, about 10%, about 5%, about 3%, about 2%, about 1%, about 0.75%, about 0.5%, about 0.25%, or about 0.1% of the dose of the anti-cancer agent. In another aspect, the first ring system is a substituted or unsubstituted heterocyclic group, the second ring system is a substituted or unsubstituted heteroaromatic group, a substituted or unsubstituted carbocyclic group, or a substituted or unsubstituted heterocyclic group. In another aspect, the substituted or unsubstituted polycyclic ring further comprises a third ring system fused to the first ring system. In another aspect, the third ring system is a substituted or unsubstituted aromatic group, a substituted or unsubstituted heteroaromatic group, a substituted or unsubstituted carbocyclic group, or a substituted or unsubstituted heterocyclic group. In another aspect, n is 0. In another aspect, n is 1 and A is a substituted or unsubstituted heteroaromatic group. In another aspect, A is a pyridinyl group. In another aspect, Y is a nitrogen atom. In another aspect, $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group. In another aspect, $R_7$ is the substituted or unsubstituted alkyl group or a substituted or unsubstituted pyridyl group and $R_3$ to $R_6$ and $R_8$ to $R_{12}$ are each H. In another aspect, the compound is selected from:

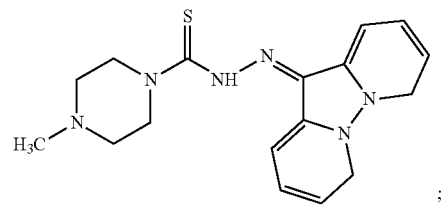

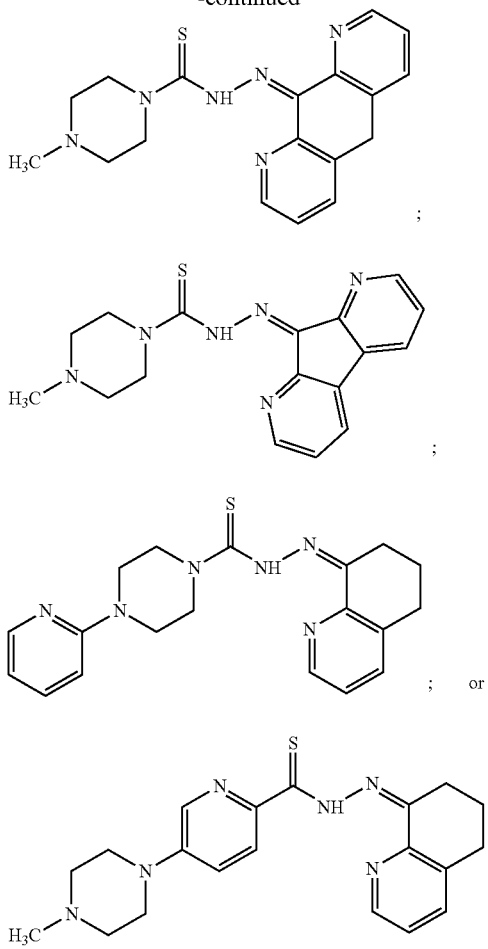

and/or a pharmaceutically-acceptable salt, hydrate, solvate or combination thereof. In another aspect, the compound of Formula I is:

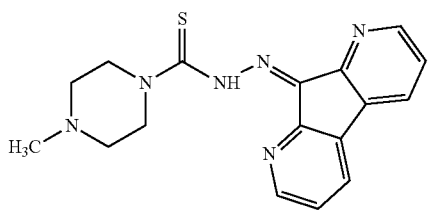 [SMILES: CN1CCN(C(=S)NN=C2c3ncccc3-c3cccnc32)CC1]

and/or a pharmaceutically-acceptable salt, hydrate, solvate or combination thereof. In another aspect, the compound of Formula I is:

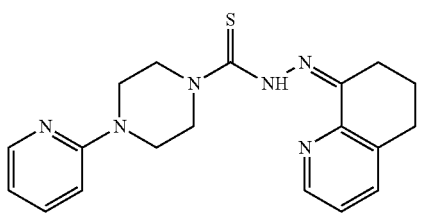 [SMILES: S=C(N/N=C1/CCCc2cccnc21)N1CCN(c2ccccn2)CC1]

and/or a pharmaceutically-acceptable salt, hydrate, solvate or combination thereof. In another aspect, the compound is a pharmaceutically-acceptable salt of Formula I. In another aspect, the salt is an oxalate or tartrate.

In another aspect, there is provided use of an anti-cancer agent in combination with a therapeutically effective amount of a compound that is an mTOR-Rictor complex inhibitor, a Serine 473 phosphorylation inhibitor, an AKT2 inhibitor, or a combination thereof for treating a cancer in a mammal in need thereof, wherein the combination provides a synergistic therapeutic effect as compared to sole administration of either the anti-cancer agent or the compound.

In another aspect, there is provided use of an anti-cancer agent in combination with a therapeutically effective amount of a compound that is an mTOR-Rictor complex inhibitor, a Serine 473 phosphorylation inhibitor, an AKT2 inhibitor, or a combination thereof in the manufacture of a medicament for treating a cancer in a mammal in need thereof, wherein the combination provides a synergistic therapeutic effect as compared to sole administration of either the anti-cancer agent or the compound.

With respect to the above aspects, in another aspect, the cancer is treatable by inhibition of mTOR. In another aspect, the anti-cancer agent is an mTOR-Raptor complex inhibitor. In another aspect, the anticancer agent is a cytotoxic agent. In another aspect, the synergistic effect is reduction or prevention of resistance to the cytotoxic agent. In another aspect, the anti-cancer agent is selected from the group consisting of cisplatin, rapamycin, tecrolimus, temsirolimus, paclitaxel, erlotinib, cetuximab and doxorubicin. In another aspect, the dose of the anti-cancer agent is selected to lower overall toxicity as compared to administration of the anti-cancer agent alone in an amount sufficient to achieve substantially the same treatment effect on cancerous cells. In another aspect, the dose of at least one of the anti-cancer agent or the compound is selected to increase the overall treatment effect on cancerous cells as compared to administration of the anti-cancer agent alone in an amount producing substantially the same toxicity. In another aspect, the anti-cancer agent is administered at a sub-therapeutic dose without substantially reducing the efficacy of the cancer treatment. In another aspect, the dose of the compound is less than the dose of the anti-cancer agent. In another aspect, the dose of the compound is at most about 80%, about 50%, about 40%, about 30%, about 20%, about 10%, about 5%, about 3%, about 2%, about 1%, about 0.75%, about 0.5%, about 0.25%, or about 0.1% of the dose of the anti-cancer agent. In another aspect, the compound is an mTOR-Rictor complex inhibitor. In another aspect, the cancer is selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In another aspect, the cancer is selected from the group consisting of small cell lung cancer, breast cancer, acute leukemia, chronic leukemia, colorectal cancer, colon cancer, brain cancer, carcinoma, ovarian cancer, or endometrial cancer, carcinoid tumors, metastatic; colorectal cancer, islet cell carcinoma, metastatic renal cell carcinoma, adenocarcinomas, glioblastoma multiforme, bronchoalveolar lung cancers, non-Hodgkin's lymphoma, neuroendocrine tumors, and neuroblastoma. In another aspect, the cancer is ovarian, colon, colorectal or endometrial cancer. In another aspect, the compound comprises a compound of Formula I:

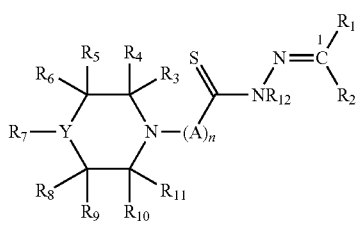

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

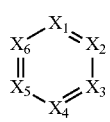

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

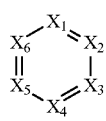

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer.

In another aspect, there is provided use of an anti-cancer agent in combination with a therapeutically effective amount of a compound comprising a compound of Formula I:

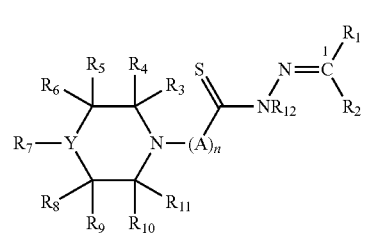

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

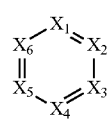

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

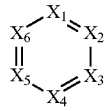

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer;

for treating a cancer in a mammal in need thereof, wherein the combination provides a synergistic therapeutic effect as compared to sole administration of either the anti-cancer agent or the compound.

In another aspect, there is provided use of an anti-cancer agent in combination with a therapeutically effective amount of a compound comprising a compound of Formula I:

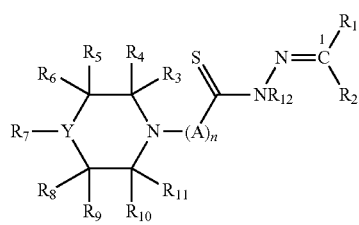

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

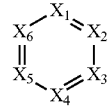

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

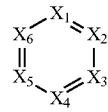

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer;

in the manufacture of a medicament for treating a cancer in a mammal in need thereof, wherein the combination provides a synergistic therapeutic effect as compared to sole administration of either the anti-cancer agent or the compound.

With respect to the above aspects, in another aspect, the cancer is selected from the group consisting of lung cancer, cervical cancer, ovarian cancer, cancer of CNS, skin cancer, prostate cancer, sarcoma, breast cancer, leukemia, colorectal cancer, colon cancer, head cancer, neck cancer, endometrial and kidney cancer. In another aspect, the cancer is selected from the group consisting of small cell lung cancer, breast cancer, acute leukemia, chronic leukemia, colorectal cancer, colon cancer, brain cancer, carcinoma, ovarian cancer, or endometrial cancer, carcinoid tumors, metastatic colorectal cancer, islet cell carcinoma, metastatic renal cell carcinoma, adenocarcinomas, glioblastoma multiforme, bronchoalveolar lung cancers, non-Hodgkin's lymphoma, neuroendocrine tumors, and neuroblastoma. In another aspect, the cancer is ovarian, colon, colorectal or endometrial cancer.

In another aspect, there is provided use of a therapeutically effective amount of a compound comprising a compound of Formula I:

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

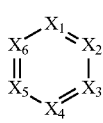

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer, for treating endometrial cancer in a mammal in need thereof.

In another aspect, there is provided use of a therapeutically effective amount of a compound comprising a compound of Formula I:

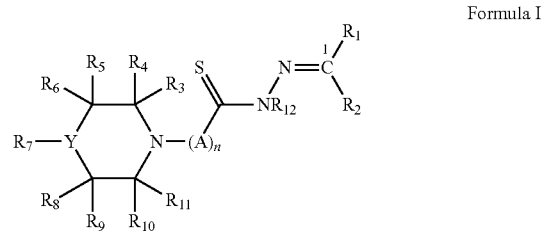

Formula I and/or a pharmaceutically-acceptable salt, hydrate, solvate, tautomer, optical isomer, or combination thereof; wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

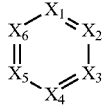

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

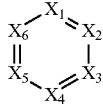

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer, in the manufacture of a medicament for treating endometrial cancer in a mammal in need thereof.

With respect to the above aspects, in another aspect, the cancer is characterized by a KRAS mutation. In another aspect, the cancer is characterized by an EGFR mutation.

In another aspect, there is provided use of a therapeutically effective amount of a compound comprising a compound of Formula I:

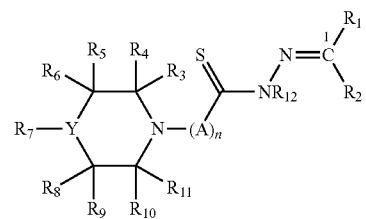

Formula I and/or a pharmaceutically-acceptable salt, hydrate, solvate, tautomer, optical isomer, or combination thereof;

wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer, for treating a cancer in a mammal in need thereof, the cancer characterized by over-expression of RAS, by an EGFR mutation, and/or by over-expression of AKT2.

In another aspect, there is provided use of a therapeutically effective amount of a compound comprising a compound of Formula I:

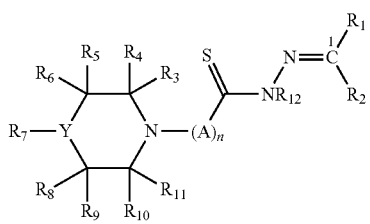

Formula I and/or a pharmaceutically-acceptable salt, hydrate, solvate, tautomer, optical isomer, or combination thereof;

wherein:

$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

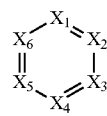

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

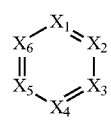

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom or a carbon atom;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is an integer, in the manufacture of a medicament for treating a cancer in a mammal in need thereof, the cancer characterized by over-expression of RAS, by an EGFR mutation, and/or by over-expression of AKT2.

With respect to the above aspects, in another aspect, the cancer is characterized by a KRAS mutation. In another aspect, the cancer is selected from the group consisting of leukemia, colon cancer, colorectal cancer, pancreatic cancer, lung cancer, multiple myeloma, endometrial cancer, and ovarian cancer. In another aspect, the cancer is colorectal cancer. In another aspect, the cancer is characterized by an EGFR mutation. In another aspect, the cancer is selected from the group consisting of lung cancer, glioblastoma, colon cancer, gastric cancer, renal cancer, prostate cancer, breast cancer, and ovarian cancer. In another aspect, the cancer is non-small cell lung cancer. In another aspect, the cancer is characterized by over-expression of AKT2. In another aspect, the cancer is selected from the group consisting of breast cancer, ovarian cancer, colon cancer, pancreatic cancer, glioma, glioblastoma, lung cancer, and prostate cancer. In another aspect, the cancer is treatable by inhibition of mTOR. In another aspect, the use further comprises an anti-cancer agent in combination with the compound. In another aspect, the combination produces a synergistic therapeutic effect as compared to sole administration of either the anti-cancer agent or the compound. In another aspect, the anti-cancer agent is an mTOR-Raptor complex inhibitor. In another aspect, the anticancer agent is a cytotoxic agent. In another aspect, the synergistic effect is reduction or prevention of resistance to the cytotoxic agent. In another aspect, the anti-cancer agent is selected from the group consisting of cisplatin, rapamycin, tecrolimus, temsirolimus, paclitaxel, erlotinib, cetuximab and doxorubicin. In another aspect, the amount of the anti-cancer agent is selected to lower overall toxicity as compared to administration of the anti-cancer agent alone in an amount sufficient to achieve substantially the same treatment effect on cancerous cells. In another aspect, the amount of at least one of the anti-cancer agent or the compound is selected to increase the overall treatment effect on cancerous cells as compared to administration of the anti-cancer agent alone in an amount producing substantially the same toxicity. In another aspect, the anti-cancer agent is present at a sub-therapeutic amount without substantially reducing the efficacy of the cancer treatment. In another aspect, the amount of the compound is less than the amount of the anti-cancer agent. In another aspect, the amount of the compound is at most about 80%, about 50%, about 40%, about 30%, about 20%, about 10%, about 5%, about 3%, about 2%, about 1%, about 0.75%, about 0.5%, about 0.25%, or about 0.1% of the amount of the anti-cancer agent. In another aspect, the first ring system is a substituted or unsubstituted heterocyclic group, the second ring system is a substituted or unsubstituted heteroaromatic group, a substituted or unsubstituted carbocyclic group, or a substituted or unsubstituted heterocyclic group. In another aspect, the substituted or unsubstituted polycyclic ring further comprises a third ring system fused to the first ring system. In another aspect, the third ring system is a substituted or unsubstituted aromatic group, a substituted or unsubstituted heteroaromatic group, a substituted or unsubstituted carbocyclic group, or a substituted or unsubstituted heterocyclic group. In another aspect, n is 0. In another aspect, n is 1 and A is a substituted or unsubstituted heteroaromatic group. In another aspect, A is a pyridinyl group. In another aspect, Y is a nitrogen atom. In another aspect, $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group. In another aspect, $R_7$ is the substituted or unsubstituted alkyl group or a substituted or unsubstituted pyridyl group and $R_3$ to $R_6$ and $R_8$ to $R_{12}$ are each H. In another aspect, the compound is selected from:

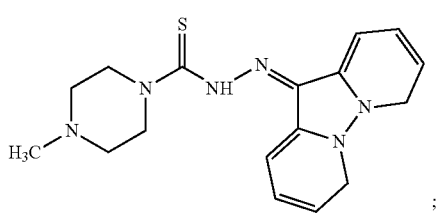
;

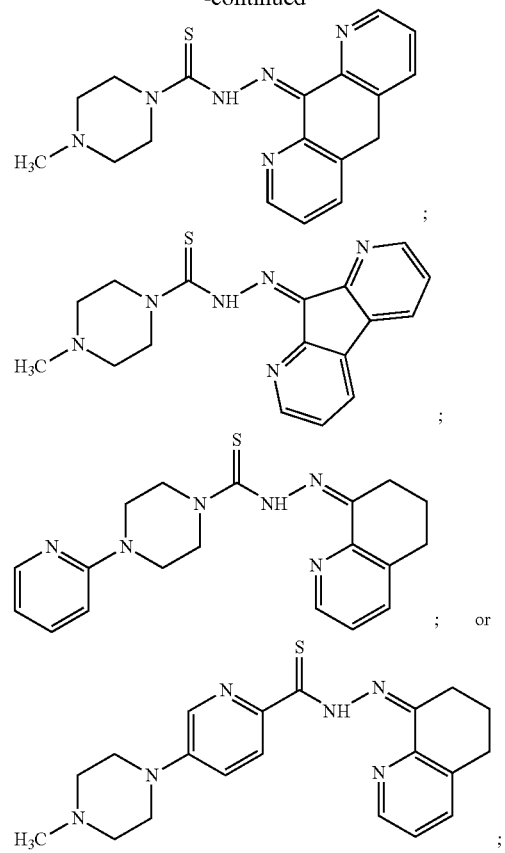

and/or a pharmaceutically-acceptable salt, hydrate, solvate or combination thereof. In another aspect, the compound of Formula I is:

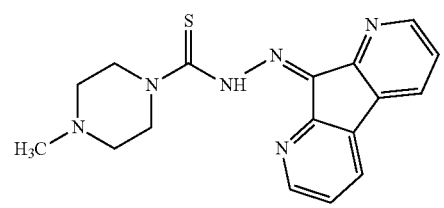 [SMILES: CN1CCN(C(=S)NN=C2c3ncccc3-c3cccnc32)CC1]

and/or a pharmaceutically-acceptable salt, hydrate, solvate or combination thereof. In another aspect, the compound of Formula I is:

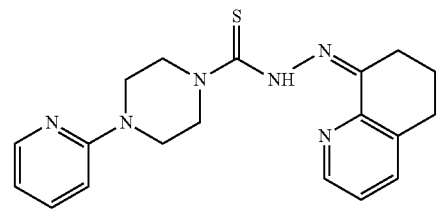 [SMILES: S=C(N/N=C1/CCCc2cccnc21)N1CCN(c2ccccn2)CC1]

and/or a pharmaceutically-acceptable salt, hydrate, solvate or combination thereof. In another aspect, the compound is a pharmaceutically-acceptable salt of Formula I. In another aspect, the salt is an oxalate or tartrate.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

BRIEF DESCRIPTION OF THE DRAWINGS

Embodiments of the present invention will now be described, by way of example only, with reference to the attached Figures.

FIGS. 43A and 43B show down-regulation of FOXO transcription factors, phospho-FOXO1 and phosphor-FOXO3a levels were measured by densitometry analysis and corrected for total protein levels, as described in the legend to FIG. 42;

DETAILED DESCRIPTION

Definitions

Figure 1:
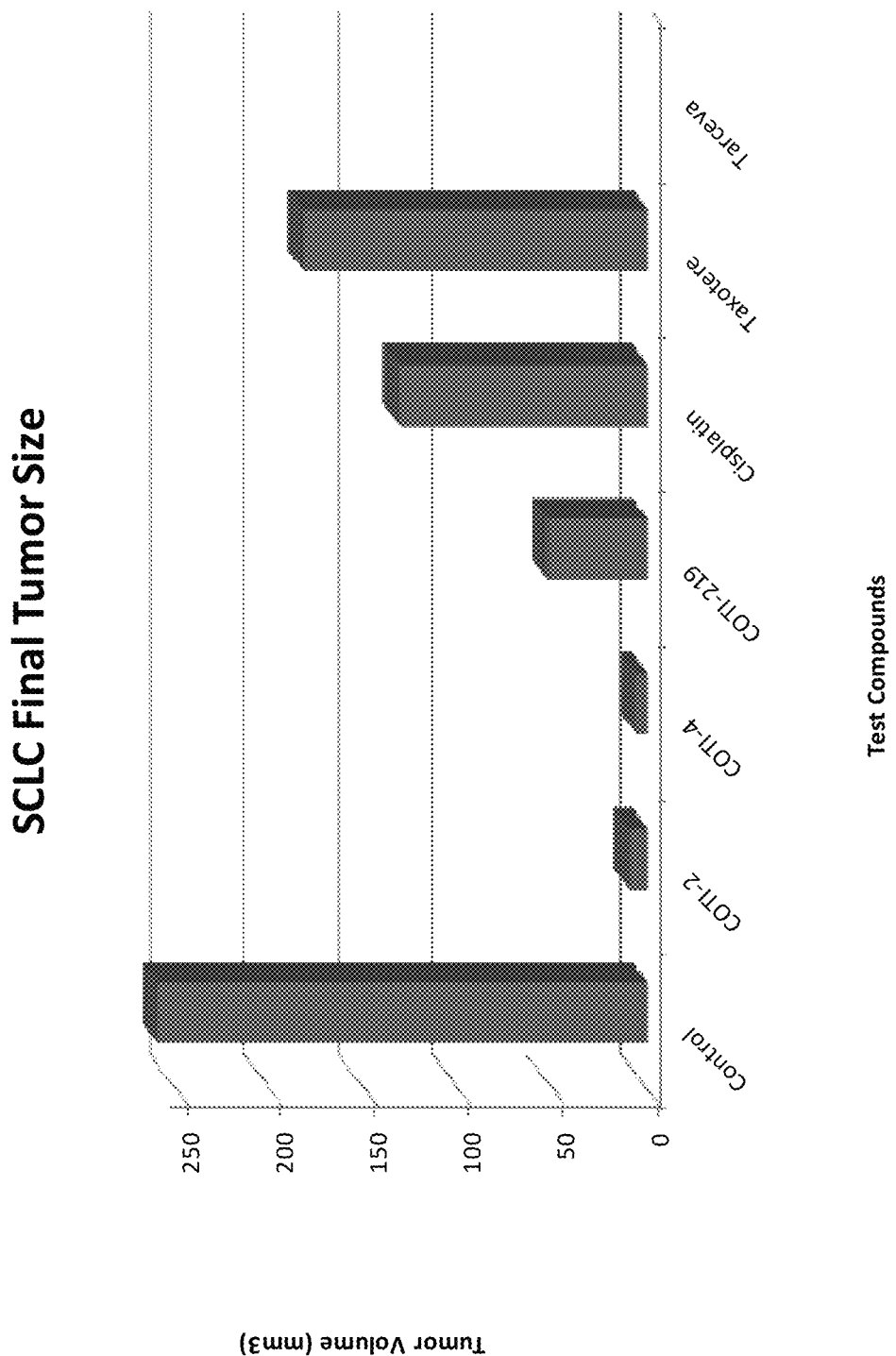
FIG. 1 shows the volume of SHP77 human SCLC tumour in nude mice treated with test compounds.

When describing the compounds, compositions, methods and uses of this invention, the following terms have the following meanings, unless otherwise indicated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The compounds of the present invention may have asymmetric centers, chiral axes, and chiral planes (as described, for example, in: E. L. Eliel and S. H. Wilen, Stereo-chemistry of Carbon Compounds, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, preferably 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O—.

The term "carbonyl group", whether used alone or with other terms, such as "aminocarbonyl group", denotes —(C=O)—.

The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N,N-dimethyl-aminoethyl, N,N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

The pharmaceutically acceptable salts of the compounds of this invention include the conventional non-toxic salts of the compounds of this invention as formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Preferred salts include oxalate and tartrate salts.

The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

The present invention includes pharmaceutically acceptable salts, solvates and prodrugs of the compounds of the invention and mixtures thereof.

The terms "comprising", "having" and "including", and various endings thereof, are meant to be open ended, including the indicated component but not excluding other elements.

Therapeutically active compounds of the present invention comprise thiosemicarbazones, in particular thiosemicarbazones represented by Formula I:

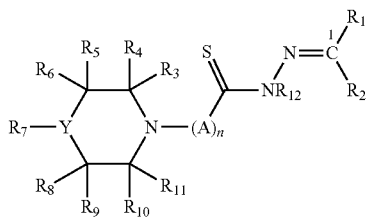

Formula I wherein:

$R_1$ and $R_2$ together form a substituted or unsubstituted polycyclic ring. The ring has at least two ring systems. The two ring systems have a first ring system that is bonded to C1 and a second ring system that is fused to the first ring system.

In one embodiment, the first ring system is a substituted or unsubstituted aromatic group and the second ring system is a substituted or unsubstituted aromatic group, a substituted or unsubstituted heteroaromatic group, a substituted or unsubstituted carbocyclic group, or a substituted or unsubstituted heterocyclic group.

In a second embodiment, the first ring system is a substituted or unsubstituted heteroaromatic group and the second ring system is a substituted or unsubstituted aromatic group, a substituted or unsubstituted heteroaromatic group, a substituted or unsubstituted carbocyclic group, a substituted or unsubstituted heterocyclic group.

In a further embodiment, the first ring system is a substituted or unsubstituted saturated carbocyclic group and the second ring system is a substituted or unsubstituted aromatic group, a substituted or unsubstituted unsaturated carbocyclic group, a substituted or unsubstituted heterocyclic group, or a substituted or unsubstituted ring B:

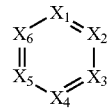

Ring B wherein $X_1$ to $X_6$ are each independently selected from carbon or a heteroatom.

In another embodiment, the first ring system is a substituted or unsubstituted unsaturated carbocyclic group and the second ring system is a substituted or unsubstituted aromatic group, a substituted or unsubstituted carbocyclic group, a substituted or unsubstituted heterocyclic group, or a substituted or unsubstituted ring B:

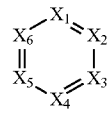

Ring B wherein $X_1$ to $X_6$ are each independently selected from carbon or a heteroatom.

In yet another embodiment, the first ring system is a substituted or unsubstituted heterocyclic group, the second ring system is a substituted or unsubstituted heteroaromatic group, a substituted or unsubstituted carbocyclic group, or a substituted or unsubstituted heterocyclic group.

In another embodiment relating to the above-identified embodiments, the first ring system is a five- or six-membered ring.

In embodiments, the $R_3$ to $R_{11}$ groups are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic. The $R_{12}$ group is selected from H or a hydrocarbyl group and Y is selected from a heteroatom or a carbon atom. "A" is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic and "n" is an integer.

Therapeutically active compounds described herein can be the thiosemicarbazone compounds of Formula I, pharmaceutically-acceptable salts thereof, hydrates thereof, solvates thereof, tautomers thereof, optical isomers thereof, or a combination thereof.

In a specific embodiment, the first ring system of the compound of Formula I is a substituted or unsubstituted carbocyclic group and the second ring system is a substituted or unsubstituted ring B:

Ring B

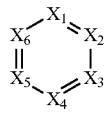

wherein $X_1$ to $X_6$ are each independently selected from carbon or a heteroatom. In a more specific embodiment, ring B is a pyridine ring, typically fused to the first ring at C2 and C3 of the pyridine ring.

Although a first and second ring system is described herein, the substituted or unsubstituted polycyclic ring may further comprise other ring systems other than the first and second ring systems. For example, a third ring system may also be fused to the first ring system. The third ring system can be, for instance, a substituted or unsubstituted aromatic group, a substituted or unsubstituted heteroaromatic group, a substituted or unsubstituted carbocyclic group, or a substituted or unsubstituted heterocyclic group. Typically, the third ring system is a substituted or unsubstituted heteroaromatic group or a substituted or unsubstituted heterocyclic group.

With respect to the embodiments described above with respect to Formula I, typically "n" is 0 or 1. If "n" is 1, "A" is typically a substituted or unsubstituted heteroaromatic group, in particular, a pyridinyl group.

Also, with respect to the embodiments of Formula I, Y is typically a nitrogen atom. The ring:

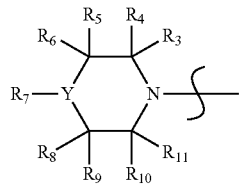

can be a variety of rings. The ring can be a substituted or unsubstituted thiomorpholinyl group, a substituted or unsubstituted morpholinyl group, a substituted or unsubstituted piperidinyl group, or a substituted or unsubstituted piperazinyl group.

In specific embodiments of Formula I, $R_7$ is a substituted or unsubstituted alkyl group or a substituted or unsubstituted heteroaromatic group and $R_3$ to $R_6$ and $R_8$ to $R_{12}$ are each independently selected from H or a substituted or unsubstituted hydrocarbon group. More specifically, $R_7$ can be the substituted or unsubstituted alkyl group or a substituted or unsubstituted pyridyl group and $R_3$ to $R_6$ and $R_8$ to $R_{12}$ are each H.

In specific embodiments, the compound of Formula I can be:

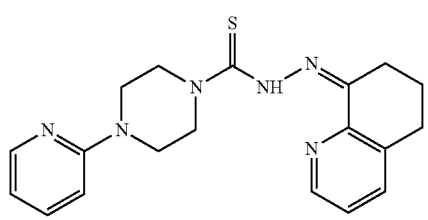

COTI-2

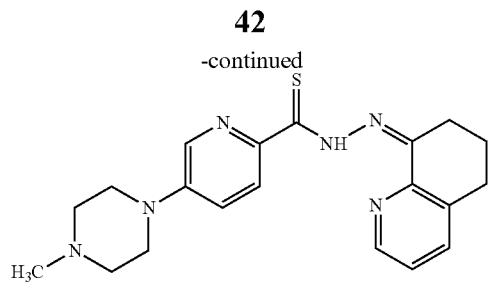

COTI-5

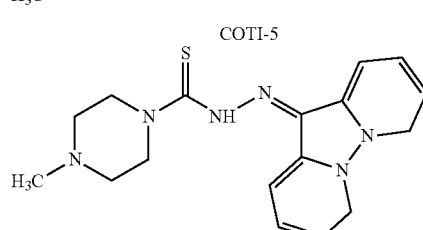

COTI-217

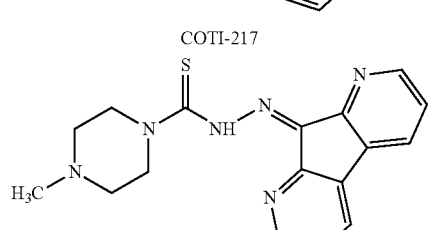

COTI-219

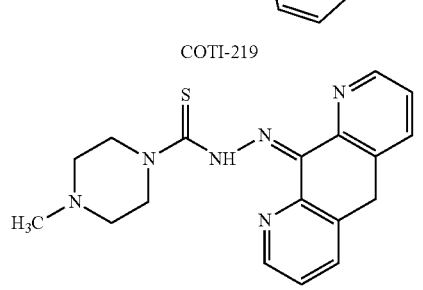

COTI-220

Such compounds may be used and/or in the form of a pharmaceutically-acceptable salt, hydrate, solvate or any combination thereof.

The compounds of Formula I described herein can be prepared as follows:

a) reacting a compound of Formula II:

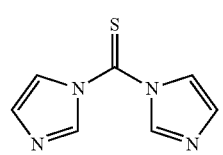

Formula II with a compound of Formula IIA:

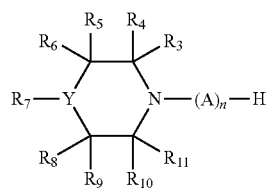

Formula IIA to form an intermediate of Formula III:

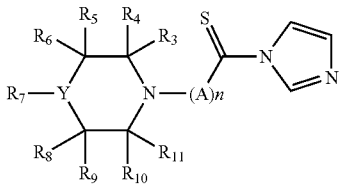

Formula III b) reacting the Intermediate of Formula III with $R_{12}NHNH_2$ to form an Intermediate of Formula IV:

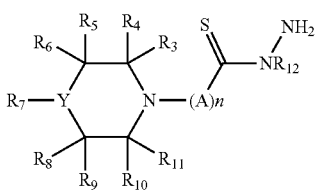

Formula IV c) reacting the Intermediate of Formula IV with a ketone:

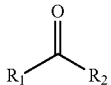

under condensation conditions, to form the compound of Formula I. In specific embodiments, the above-identified synthetic method can be used when "n" is 0 or 1; more typically, when "n" is 0.

The compounds of Formula I described herein can also be prepared as follows:

a) dithioesterifying a halo compound of Formula V:

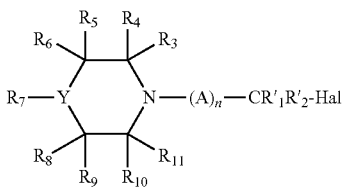

Formula V to form an intermediate of Formula VI, wherein R, R'$_1$, or R'$_2$ is substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic:

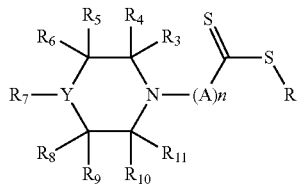

Formula VI b) reacting the Intermediate of Formula VI with $R_{12}NHNH_2$ to form an Intermediate of Formula IV:

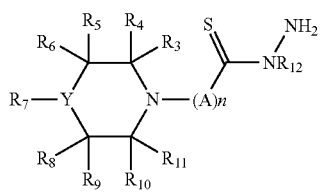

Formula IV c) reacting the Intermediate of Formula IV with a ketone:

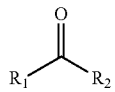

under condensation conditions, to form the compound of Formula I. In specific embodiments, the above-identified synthetic method can be used when "n" is 0 or 1; more typically, when "n" is 1.

The compounds of Formula I described herein can also be prepared as follows:

a) esterifying compound of Formula IIA:

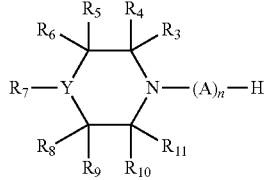

Formula IIA to form an intermediate of Formula VII, wherein R is substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic:

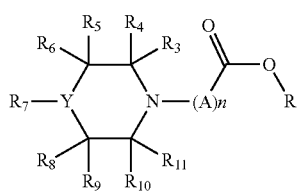

Formula VII b) reacting the Intermediate of Formula VII with $R_{12}NHNH_2$ to form an Intermediate of Formula VIII:

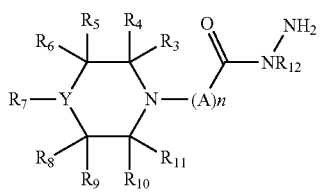

Formula VIII c) reacting the Intermediate of Formula VIII with a thiation agent to form an Intermediate of Formula IV:

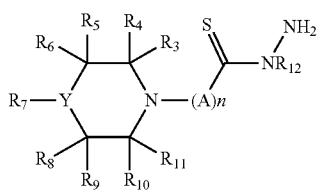

Formula IV c) reacting the Intermediate of Formula IV with a ketone:

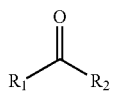

under condensation conditions, to form the compound of Formula I. Examples of a thiation agent include, but are not limited to, phosphorus pentasulfide or Lawesson's reagent. In specific embodiments, the above-identified synthetic method can be used when "n" is 0 or 1; more typically, when "n" is 1.

The compounds described herein are useful in the treatment of cancer. High levels of activity for in vitro and in vivo testing have been observed against cancers and cancer models using the compounds of the present invention. This may lead to reduced dosages as compared with conventional therapeutic dosages of known agents.

The cancer treated may be, for example, lung cancer, cervical cancer, ovarian cancer, cancer of CNS, skin cancer, prostate cancer, sarcoma, breast cancer, leukemia, colorectal cancer, endometrial cancer, head cancer, neck cancer or kidney cancer. More typically, the cancer may be small cell lung cancer, breast cancer, acute leukemia, chronic leukemia, colorectal cancer, ovarian cancer, endometrial cancer or brain cancer. The cancer may be a carcinoma. The carcinoma may be selected from small cell carcinomas, cervical carcinomas, glioma, astrocytoma, prostate carcinomas, ovarian carcinomas, melanoma, breast carcinomas, endometrial carcinomas or colorectal carcinomas. Compounds of the present invention may be even more particularly useful in the treatment of small cell lung cancer (SCLC) carcinomas.

Compounds useful according to the present invention can have an $IC_{50}$ for a cancer cell population when administered as single agents of less than about 1000 nM. In specific embodiments, compounds of the present invention show efficacy against SHP77 cells when administered as single agents at IC50's of less than about 1000 nM, typically less than about 800 nM, more typically less than about 500 nM, even more typically less than about 200 nM.

Compounds useful according to the present invention show efficacy against DMS144 cells when administered as single agents at IC50's of less than about 1000 nM, typically less than about 750 nM, more typically less than about 500 nM, even more typically less than about 300 nM, yet more typically less than about 100 nM.

Compounds useful according to the present invention show efficacy against U87 cells when administered as single agents at IC50's of less than about 2500 nM, typically less than about 1000 nM, more typically less than about 480 nM, even more typically less than about 200 nM, yet more typically less than about 75 nM.

Compounds useful according to the present invention show efficacy against SNB-19 cells when administered as single agents at IC50's of less than about 2150 nM, typically less than about 1500 nM, more typically less than about 800 nM, even more typically less than about 100 nM, yet more typically less than about 50 nM, still more typically less than about 15 nM.

Compounds useful according to the present invention are effective in reducing the size of malignant human cancer tumors created from SHP77, DMS114, N417 and/or U87 cell lines.

Compounds useful according to the present invention can penetrate the blood brain bather of a mammal, typically, a human.

Compounds useful according to the present invention may exhibit a reduced tendency to induce cellular resistance to either their own anti-cancer effects or the effects of other anti-cancer agents. Therefore, use of the compounds of the present invention to treat a cancer, as single agents or as part of a combination, may inhibit development of a drug resistant form of that cancer. Without wishing to be limited by theory, it is believed that the compounds of the present invention may inhibit development of P-glycoprotein mediated drug resistance and/or function as weak substrates of P-glycoprotein.

Certain compounds useful according to the present invention may exhibit reduced toxicity as compared with conventionally administered agents.

The compounds of this invention may be administered to mammals, typically humans, either alone or, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, and subcutaneous routes of administration.

As noted, compounds useful according to the present invention may be administered orally, unlike most current cancer therapies, which are administered intravenously. For oral use of a compound or composition in this invention, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

At least about 50% of compounds useful according to the present invention can be orally absorbed by a mammal. In specific embodiments, at least about 60%; about 60% to about 85%; about 65%; about 70%; about 72%; about 73%, about 75%; about 80%; about 82%; or about 85% of the compound can be orally absorbed by a mammal, more typically, a human. "Oral absorption" is used in the context of how the compound/composition is delivered and absorbed into the blood. Typically, the compound/composition is administered orally and crosses a mucosal membrane of the gastro-intestinal tract, typically in the intestines. However, other methods of contacting the compounds/compositions of the present invention with the mucosal membrane of the gastro-intestinal tract may also be used.

The compounds of the present invention may also be combined and/or co-administered with other therapeutic agents that are selected for their particular usefulness against the cancer that is being treated. For example, the compounds of the present invention may be combined and/or co-administered with anti-cancer agent(s).

Examples of anti-cancer agents include, without being limited thereto, the following: estrogen receptor modulators, androgen receptor modulators, retinoid receptor modulators, cytotoxic agents, mTOR inhibitors, particularly mTOR-Raptor complex inhibitors, antiproliferative agents, tyrosine kinase inhibitors, prenyl-protein transferase inhibitors, HMG-CoA reductase inhibitors, HIV protease inhibitors, reverse transcriptase inhibitors, other angiogenesis inhibitors and combinations thereof. The present compounds may also be useful with other therapies such as when co-administered with radiation therapy.

"Estrogen receptor modulators" refers to compounds which interfere or inhibit the binding of estrogen to the receptor, regardless of mechanism. Examples of estrogen receptor modulators include, but are not limited thereto, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide and N-4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited thereto, cyclophosphamide ifosfamide, hexamethylmelamine, tirapazimine, sertenef, cachectin, ifosfamide, tasonermin, lonidamine, carboplatin, mitomycin, altretamine, prednimustine, dibromodulcitol, ranimustine, fotemustine, nedaplatin, oxaliplatin, temozolomide, doxorubicin (Doxil™), heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum (II)]bis[diamine(chloro)-platinum (II)]tetrachloride, diariz-idinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycaminomycin, annamycin, galarubicin, elinafide, MEN10755, and 4-demethoxy-3-deamino-3-aziridinyl-4-methylsulphonyl-daunor-ubicin (see International Patent Application No. WO 00/50032).

"mTOR inhibitors" are a subset of the cytotoxic agents and refer particularly to inhibitors of the mTOR-Raptor complex. Included in the definition of mTOR inhibitors are anti-cancer agents such as rapamycin and its derivatives, sirolimus, temsirolimus, everolimus, zotarolimus and deforolimus.

Examples of microtubulin inhibitors include paclitaxel (Taxol®), vindesine sulfate, 3',4'-didehydro-4'-deoxy-8'-norvincaleukoblastine, docetaxel, rhizoxin, dolastatin, mivobulin isethionate, auristatin, cemadotin, RPR109881, BMS184476, vinflunine, cryptophycin, 2,3,4,5,6-pentafluoro-N-(-3-fluoro-4-methoxyphenyl)benzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H,12H benzo[de]pyrano[3',4':b,7]indolizino[1,2b]quinoline-10,13(9H,15H) dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazo-1e-1-carboxamide, asulacrine, (5a, 5aB, 8aa,9b)-9-[2-[N-[2-(dimethylamino)-ethyl]-N-methylamino]ethyl]-5-[4-Hydroxy-3,5-dimethoxyphenyl]-5,5a,6,8,8a,-9-hexohydrofuro(3',':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl) amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acrid-ine-4-carboxamide, 6-[[2-(dimethylamino)ethyl]amino]-3-hydroxy-7H-indeno[2-,1-c]quinolin-7-one, and dimesna.

"Antiproliferative agents" includes BCNU, antisense RNA and DNA oligonucleotides such as G3139, ODN698, RVASKRAS, GEM231, and INX3001, and antimetabolites such as floxuridine, enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxy-cytidine, N-[5-(2,3-dihydro-benzofuryl)sulfonyl]-N'-(3,4-dichlorophenyl) urea, N6-[4-deoxy-4-[N2-[2(E),4(E)-tetradecadienoyl]glycylamino]-L-glycer-o-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4] thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone.

"Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

Some specific examples of tyrosine kinase inhibitors include N-(trifluoromethylphenyl)-5-methylisoxazol-4-carboxamide, 3-[(2,4-dimethylpyrrol-5-yl)-methylidenyl]indolin-2-one, 17-(allylamino)-17-demethoxygeldanamycin, 4-(3-chloro-4-fluorophenylamino-)-7-methoxy-6-[3-(4-morpholinyl)propoxyl]-quinazoline, N-(3-ethynylphenyl)-6,7-bis(2-methoxyethoxy)-4-quinazolinamine, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH1382, genistein, 4-(3-chlorophenylamino)-5,6-dimethyl-7H-pyrrolo[2,3-d]pyrimidinemethane sulfonate, 4-(3-bromo-4-hydroxyphenyl)-amino-6,7-dimethoxyquinazoline, 4-(4'-hydroxyphenyl)amino-6,7-dimethoxyquinazoline, N-4-chlorophenyl-4-(4-pyridylmethyl)-1-phthalazinamine, and Tarceva® (erlotinib).

Typical examples of anti-cancer agents suitable for use in combination therapies or compositions according to the invention include cisplatin, rapamycin, tecrolimus, temsirolimus, paclitaxel, erlotinib, cetuximab and doxorubicin.

If formulated as a fixed dose, such combination products employ the compounds of this invention within the dosage range described below and the other pharmaceutically active agent(s) within its approved dosage range. Compounds of the present invention may alternatively be used sequentially with known pharmaceutically acceptable agent(s) when a combination formulation is inappropriate.

The term "administration" (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount from about 0.01 mg/kg of body weight to greater than about 100 mg/kg of body weight per day; from about 0.01 mg/kg of body weight to about 500 mg/kg of body weight per day; from about 0.01 mg/kg of body weight to about 250 mg/kg of body weight per day; or 0.01 mg/kg of body weight to about 100 mg/kg of body weight per day. These dosages can be more particularly used orally.

The compounds of this invention may be prepared by employing reactions and standard manipulations that are known in the literature or exemplified herein.

Without wishing to be limited by theory, it is believed that the therapeutic compounds described herein, especially those compounds according to Formula I, function by reducing or preventing activity of Akt, particularly Akt2, via inhibition of Serine 473 ("Ser 473") phosphorylation. Akt (also known as protein kinase B) is a serine/threonine kinase, which in mammals comprises three isoforms known as Akt1, Akt2, and Akt3. Cancerous cells often auto-phosphorylate Akt and an interruption in this cycle is useful in preventing tumour growth Inhibition of Ser 473 phosphorylation may decrease phosphorylation of Caspase 9, which may have the effect of increasing active Caspase 9 and inducing apoptosis via Caspase 3.

Again, without wishing to be limited by theory, it is believed that the Mamallian Targets of Rapamycin (mTOR) cell signaling pathway may be involved in a compound's ability to inhibit Akt phosphorylation at Ser 473. The preponderance of the available evidence supports the contention that the mTOR-Rictor complex is the agent responsible for the phosphorylation event at Ser 473 of Akt. At present two major components of mTOR, namely mTOR-Raptor complex and mTOR-Rictor complex, have been identified. mTOR-Raptor complex is centrally involved in cellular immunity and organ rejection. mTOR-Raptor complex inhibitors have also demonstrated both in vitro and in vivo anti-neoplastic properties.

Conventional mTOR inhibitors are thought to interfere with the mTOR-Raptor complex. Prior to this disclosure, there were no recognized therapeutic agents shown to inhibit the mTOR-Rictor complex. The compounds described herein according to Formula I include examples of mTOR-Rictor complex inhibitors, particularly the compound designated as COTI-2. By inhibiting Ser 473 phosphorylation of Akt2, the compounds described herein implicate the mTOR-Rictor complex and therefore provide a novel mechanistic pathway for anti-cancer therapy.

It has been shown herein that there is a synergistic effect, defined as a greater than additive benefit, provided by co-administration of an mTOR-Raptor complex inhibitor and an mTOR-Rictor complex inhibitor in the treatment of cancer. It is believed that, by acting simultaneously on both the Raptor and Rictor components of mTOR, superior inhibiton of mTOR can be achieved leading to improved cancer treatment outcomes, at least for cancers normally susceptible to treatment by conventional mTOR inhibitors. In particular, those cancers that are treatable by inhibition of Akt and particularly Akt2, for example via inhibition of Ser473 phosphorylation, are believed to be especially good candidates for exhibiting synergistic improvements in treatment outcome when exposed to co-administration of mTOR-Raptor and mTOR-Rictor complex inhibitors.

However, the synergistic improvement in treatment outcome is not only limited to combinations of the therapeutic compounds of the invention and mTOR inhibitors. Synergy has also been observed with other anti-cancer agents, for example the cytotoxic agents cisplatin, paclitaxel, erlotinib, cetuximab and doxorubicin. Therefore, there are numerous anti-cancer agents that exhibit synergistic improvements in treatment outcome when co-administered with the therapeutic compounds of the invention, especially those according to Formula I.

These methods and uses are applicable to cancers characterized by expression of Akt, particularly cancers characterized by auto-phosphorylation of Akt. Cancers wherein the mTOR cell signaling pathway has been implicated or where administration of mTOR-Raptor complex inhibitors are part of accepted treatment practices, for example, small cell lung cancer, carcinoid tumors, metastatic colorectal cancer, islet cell carcinoma, metastatic renal cell carcinoma, breast cancer, ovarian cancer or endometrial cancer, adenocarcinomas, glioblastoma multiforme, bronchoalveolar lung cancers, sarcomas (including leiomyosarcomas), non-Hodgkin's lymphoma, neuroendocrine tumors, and neuroblastoma are particularly suitable examples.

Although any combination of doses may be used, typically doses of the anti-cancer agent and/or the therapeutic compound that provide a synergistic effect, or greater than additive benefit, are used. For example, doses of the anti-cancer agent and/or the therapeutic compound may be selected to synergistically lower overall toxicity while maintaining substantially the same overall treatment effect on cancerous cells as observed when the anti-cancer agent is administered alone. In another example, doses of the anti-cancer agent and/or the therapeutic compound may be selected to produce substantially the same overall toxicity while synergistically increasing the treatment effect on cancerous cells as observed when the anti-cancer agent is administered alone.

Due to this synergistic behaviour, anti-cancer agents, particularly mTOR-Raptor complex inhibitors, may be advantageously administered at doses lower than currently approved doses by co-administration with therapeutic compounds according to the invention without substantially reducing the efficacy of the cancer treatment. This has the benefit of reducing toxicity of the combination. In addition, the toxicity of the therapeutic compound being co-administered may be less due to either a lower required dose or improved toxicological properties; this has the effect of further lowering overall toxicity of the combination without compromising the overall treatment effect.

The use of the therapeutic compound at a lower dose than the anti-cancer agent includes doses that are, for example, at most about 80%, about 50%, about 40%, about 30%, about 20%, about 10%, about 5%, about 3%, about 2%, about 1%, about 0.75%, about 0.5%, about 0.25%, or about 0.1%, etc. of the dose of the anti-cancer compound. At these doses, a synergistic effect in the treatment of cancerous cells may be observed.

Without wishing to be limited by theory, compounds described herein may also function by interrupting cellular metabolic cycles in which p-glycoprotein (Pgp) participates. These cellular cycles are known to "pump" cellular toxins such as some chemotherapeutic agents across the cellular membrane out of the cell and serve to lower the concentration of therapeutic agents within cancerous cells. By interrupting this process, the compounds described herein are allowed to accumulate to higher concentrations within cancerous cells, thereby providing them with substantially increased efficacy in the treatment of cancer. The compounds are characterized in that they inhibit p-glycoprotein and/or are weak substrates for p-glycoprotein.

The effect on P-glycoprotein of compounds described herein makes them particularly suitable for use in combination therapy with other anti-cancer agents, in particular cytotoxic agents such as cisplatin and paclitaxel (Taxol™), since these agents are thereby allowed to accumulate to higher levels within the cancerous cells. A synergistic effect or greater than additive benefit may therefore be observed when compounds described herein are administered in combination with other anti-cancer agents, in particular cytotoxic agents such as cisplatin and paclitaxel (see FIGS. 19-22).

Also provided herein is a therapeutic method or use for the treatment of cancer comprising potentiating an anti-cancer agent, particularly a cytotoxic agent, by co-administering a therapeutic compound as described herein that is a p-glycoprotein inhibitor and/or weak p-glycoprotein substrate, preferably in a manner producing a synergistic therapeutic effect.

Without wishing to be limited by theory, compounds described herein may work by preventing activity of Akt via inhibition of Ser 473 phosphorylation, and also by interrupting cellular metabolic cycles in which P-glycoprotein (Pgp) participates This defines a further novel sub-class of therapeutic compounds; compounds that are both Ser 473 phosphorylation inhibitors and P-glycoprotein inhibitors. Although applicable to a wide variety of cancers, this novel sub-class of therapeutic compounds is particularly useful in the treatment of cancers wherein administration of mTOR-Raptor complex inhibitors and/or cytotoxic agents is/are part of accepted treatment practices.

The synergistic improvement in treatment outcome may be a greater than additive improvement in overall efficacy obtained by co-administration as compared with administration of either agent alone. This may be illustrated through obtaining a "combination index" (CI) value of less than 1, as is described in detail in Example 18, hereinafter.

It has also been shown that therapeutic compounds according to Formula I exhibit improved efficacy in treatment of cancers characterized by over-expression of RAS, by an EGFR mutation, and/or by over-expression of AKT2. Such compounds are beneficial as many anti-cancer agents are known to have difficulty in obtaining efficacy in the treatment of these types of cancers. In particular, compounds of Formula I have been shown efficacious in treatment of cancers characterized by the KRAS mutation. Exemplary forms of this cancer include leukemia, colon cancer, colorectal cancer, pancreatic cancer, lung cancer, multiple myeloma, endometrial cancer, and ovarian cancer. Cancers characterized by the EGFR mutation include lung cancer, glioblastoma, colon cancer, gastric cancer, renal cancer, prostate cancer, breast cancer, and ovarian cancer. In particular, compounds according to formula I have shown efficacy in the treatment of non-small cell lung cancer cell lines, particularly those with the EGFR mutation. The compounds of Formula I may be advantageously co-administered with other anti-cancer agents in the treatment of cancers characterized by over-expression of RAS, by an EGFR mutation, and/or by over-expression of AKT2. This co-administration may produce an improved treatment outcome as compared with sole administration. This co-administration may even produce a synergistic benefit, as previously defined, in treatment outcome as compared with sole administration.

COTI-2 and COTI-2MO5 are one and the same. COTI-2 and COTI-2MO5 are used interchangeably throughout the specification.

When introducing elements disclosed herein, the articles "a", "an", "the", and "said" are intended to mean that there are one or more of the elements.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Synthesis of COTI-2

The synthesis of COTI-2, as depicted above, was conducted according to the following synthetic methodology:

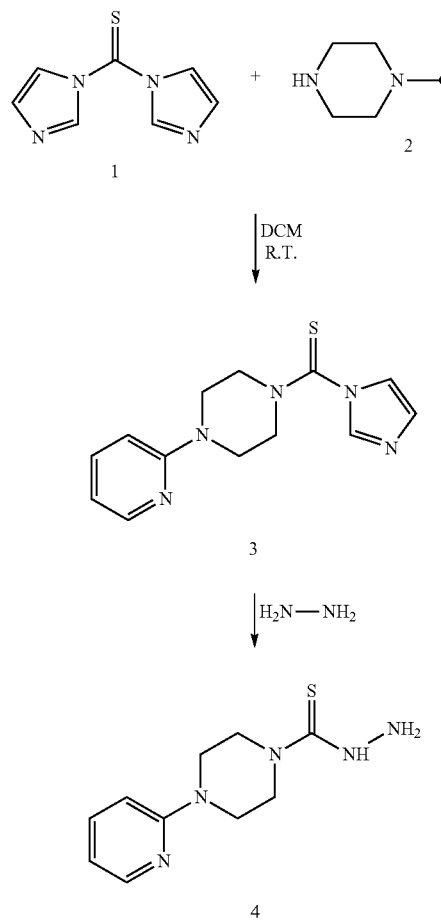

Imidazol-1-yl-(4-pyridin-2-yl-piperazin-1-yl)-methanethione (or intermediate 3 above) was formed as follows. N-(2-pyridyl) piperazine (MW 163.22, 0.91 ml, 6.0 mmoles, 1 eq) 2 was added to a solution of 1,1'-thiocarbonyldiimidazole (MW 178.22, 1.069 g, 6.0 mmoles, 1 eq) 1 in 50 ml of dichloromethane at room temperature. The reaction mixture was stirred overnight at room temperature. The mixture was washed with water, dried over sodium sulfate, filtered and concentrated to provide imidazol-1-yl-(4-pyridin-2-yl-piperazin-1-yl)-methanethione (MW 273.36, 1.354 g, 4.95 mmol, 83% yield)3, which was used without further purification. TLC(CH$_2$Cl$_2$/MeOH: 95/5): Rf=0.60, Product UV and Ninhydrin stain active. $^1$H-NMR (400 MHz, CDCl$_3$), δ ppm: 3.72 (s, 4H), 4.02 (s, 4H), 6.67 (d, 1H, J=7 Hz), 6.72 (dd, 1H, J=7 and 5 Hz), 7.11 (s, 1H), 7.24 (s, 1H), 7.54 (t, 1H, J=7 Hz), 7.91 (s, 1H), 8.20 (d, 1H, J=5 Hz).

Hydrazine hydrate (MW 50.06, 0.26 ml, 5.44 mmoles, 1.1 eq) was added to a solution of imidazol-1-yl-(4-pyridin-2-yl-piperazin-1-yl)-methanethione 3 (MW 210.30, 1.040 g, 4.95 mmol, 1 eq) in 30 ml of ethanol at room temperature. The reaction mixture was stirred under reflux for 2 hours. A white precipitate formed. This white solid was filtered off and rinsed with diethyl ether to yield 1-[N-(2-pyridyl)-piperazine)-carbothioic acid hydrazide (MW 237.33, 0.86 g, 3.62 mmol, 73% yield) 4 as a white solid, and used without further purification. TLC(CH$_2$Cl$_2$/MeOH: 95/5): Rf=0.20, Product UV and Ninhydrin stain active. $^1$H-NMR (400 MHz, DMSO-d$_6$), δ? ppm: 3.53 (s, 4H), 3.85 (s, 4H), 6.66 (dd, 1H, J=8 and 5 Hz), 6.82 (d, 1H, J=8 Hz), 7.55 (t, 1H, J=8 Hz), 8.12 (d, 1H, J=5 Hz).

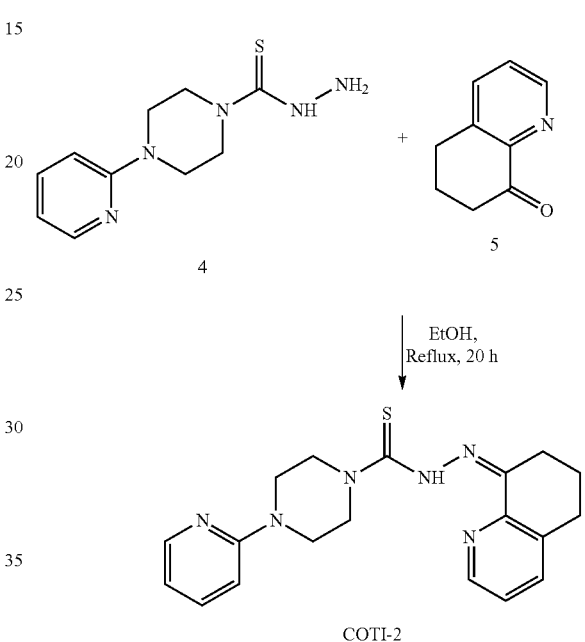

Finally, COTI-2 was formed as follows. 1-[N-(2-pyridyl)-piperazine)-carbothioic acid hydrazide (MW 237.33, 0.475 g, 2.0 mmol, 1 eq) 4 and 6,7-dihydro-5H-quinolin-8-one (MW 147.18, 0.306 g, 2.0 mmol, 1 eq) 5 was dissolved in 15 ml of ethanol at room temperature. The mixture was then stirred under reflux for 20 hours. A yellow solid precipitated out of the solution. This solid was filtered off then rinsed with methanol and diethyl ether to yield COTI-2 (MW 366.48, 0.60 g, 1.64 mmol, 82% yield) as a yellow solid. TLC (CH$_2$Cl$_2$/MeOH: 95/5): Rf=0.75, Product UV and Ninhydrine stain active. HPLC analysis showed a mixture of isomers (approximately in 80/20 ratio), and >98% purity. During the HPLC Method Development, as expected, this product tends to be hydrolyzed in presence of TFA in mobile phase solution. MS (ESI+, 0.025% TFA in 50/50 MeOH/H$_2$O): [M+H]$^+$=367.1, [M+Na]$^+$=389.1; $^1$H-NMR (400 MHz, CDCl$_3$), δ? ppm (Major isomer): 2.09 (m, 2H), 2.92 (m, 4H), 3.67 (m, 4H), 4.27 (m, 4H), 6.69 (dd, 1H, J=8 and 5 Hz), 7.25 (dd, 1H, J=8 and 5 Hz), 7.55 (d, 2H, J=8 Hz), 8.23 (d, 1H, J=5 Hz), 8.63 (d, 1H, J=5 Hz), 14.76 (s, 1H). δ ppm (Minor isomer): 2.09 (m, 2H), 3.14 (t, 4H, J=6 Hz), 3.80 (m, 4H), 4.27 (m, 4H), 6.66 (m, 1H), 7.31 (dd, 1H, J=8 and 5 Hz), 7.52 (m, 1H), 7.70 (d, 1H, J=8 Hz), 8.23 (d, 1H, J=5 Hz), 8.53 (d, 1H, J=5 Hz), 15.65 (s, 1H).

Synthesis of COTI-219

The synthesis of COTI-219, as depicted above, was conducted according to the following synthetic methodology:

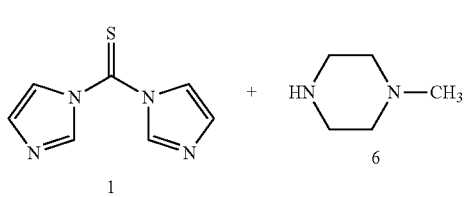

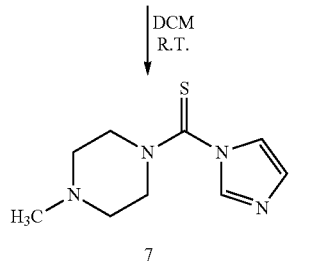

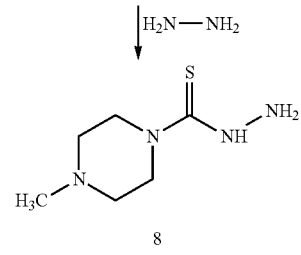

Imidazol-1-yl-(4-methyl-piperazin-1-yl)-methanethione (or intermediate 7 above) was formed as follows. N-Methyl piperazine (MW 100.16, 0.67 ml, 6.0 mmol, 1 eq) 6 was added to a solution of 1,1'-thiocarbonyldiimidazole (MW 178.22, 1.069 g, 6.0 mmol, 1 eq) 1 in 50 ml of dichloromethane at room temperature. The reaction mixture was stirred overnight at room temperature. This mixture was washed with water, dried over sodium sulfate, filtered and concentrated to provide imidazol-1-yl-(4-methyl-piperazin-1-yl)-methanethione (MW 210.30, 1.040 g, 4.95 mmol, 82% yield) 7 and used without further purification. TLC (CH$_2$Cl$_2$/MeOH: 95/5): Rf=0.35, Product UV and Ninhydrine stain active. $^1$H-NMR (400 MHz, CDCl$_3$), δ ppm: 2.37 (s, 3H), 2.56 (s, 4H), 3.94 (s, 4H), 7.11 (s, 1H), 7.21 (s, 1H), 7.88 (s, 1H).

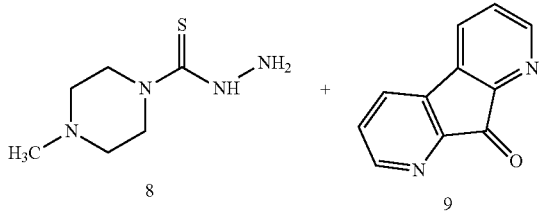

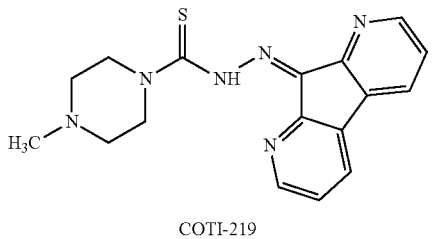

COTI-219

1-(N-Methyl piperazine)-carbothioic acid hydrazide (or intermediate 8 above) was formed as follows. Hydrazine hydrate (MW 50.06, 0.26 ml, 5.44 mmol, 1.1 eq) was added to a solution of imidazol-1-yl-(4-methyl-piperazin-1-yl)-methanethione 7 (MW 210.30, 1.040 g, 4.95 mmol, 1 eq) in 30 ml of ethanol at room temperature. The reaction mixture was stirred under reflux for 2 hours. This mixture was concentrated. The solid thus obtained was triturated with diethyl ether and filtered to yield 1-(N-Methyl piperazine)-carbothioic acid hydrazide (MW 174.27, 0.53 g, 3.04 mmol, 61% yield) 8 as a white solid which was used without further purification. TLC(CH$_2$Cl$_2$/MeOH: 90/10): Rf=0.15, Product UV and Ninhydrin stain active. $^1$H-NMR (400 MHz, DMSO-d$_6$), δ ppm: 2.17 (s, 3H), 2.28 (t, 4H, J=5 Hz), 3.69 (t, 4H, J=5 Hz).

Finally, COTI-219 was made as follows. 1-(N-Methyl piperazine)-carbothioic acid hydrazide (MW 174.27, 0.174 g, 1.0 mmol, 1 eq) 8 and 1,8-diazafluoren-9-one (MW 182.18, 0.182 g, 1.0 mmol, 1 eq) 9 was dissolved in 15 ml of ethanol at room temperature, in the presence of 1% glacial acetic acid (MW 60.05, 0.15 ml, 2.6 mmol, 2.6 eq). The mixture was stirred under reflux for 6 hours. After concentration, the crude thus obtained was taken up in dichloromethane, washed with a potassium carbonate aqueous solution then with water. The organic layer was dried over sodium sulfate, filtered and concentrated. The crude was purified by ISCO CombiFlash™ Companion (Redisep™ cartridge 12 g, Normal phase, Gradient DCM/MeOH:10/0 to 9/1) and provided COTI-219 (MW 338.43, 0.330 g, 0.975 mmol, 98% yield) as a rust red solid. >95% purity by $^1$H-NMR. MS [ESI+, 90/10 MeOH/H$_2$O (5 mM NH$_4$OAc, 0.2% Acetic acid)]: [M+H]$^+$=339.1, [M+Na]$^+$=361.1; $^1$H-NMR (400 MHz, CDCl$_3$), δ ppm: 2.31 (s, 3H), 2.56 (t, 4H, J=5 Hz), 4.17 (t, 4H, J=5 Hz), 7.23 (dd, 1H, J=8 and 5 Hz), 7.31 (dd, 1H, J=8 and 5 Hz), 7.86 (d, 1H, J=8 Hz), 7.97 (d, 1H, J=8 Hz), 8.47 (d, 1H, J=5 Hz), 8.51 (d, 1H, J=5 Hz), 13.53 (s, 1H).

Synthesis of COTI-5

The synthesis of COTI-5, as depicted above, is conducted according to the following synthetic methodology:

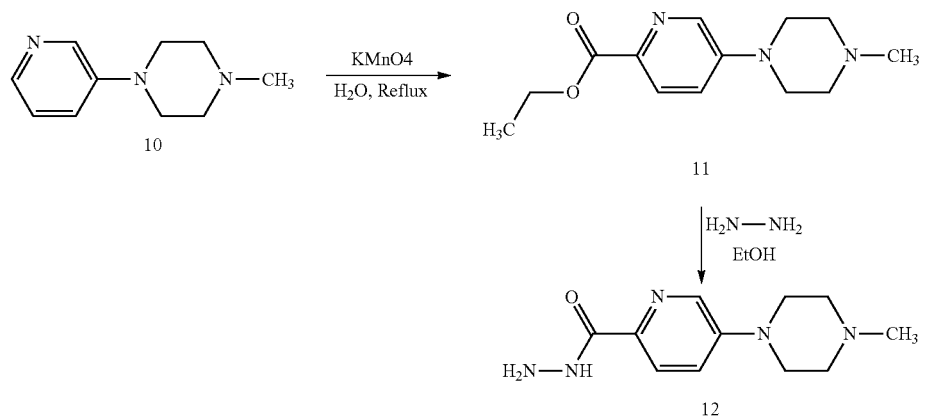

Intermediate 11 is formed by reacting compound 10 with potassium, permanganate under reflux conditions. Intermediate 11 is reacted with hydrazine hydrate in ethanol to form intermediate 12.

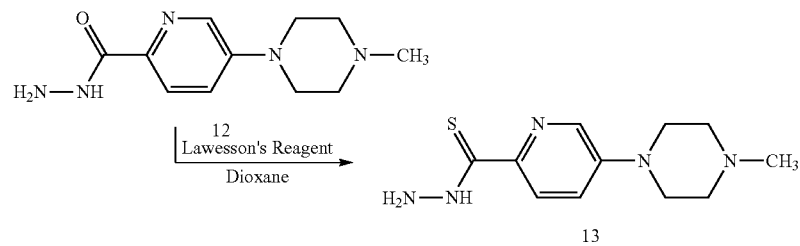

Intermediate 12 is reacted with Lawesson's reagent in dioxane to form intermediate 13.

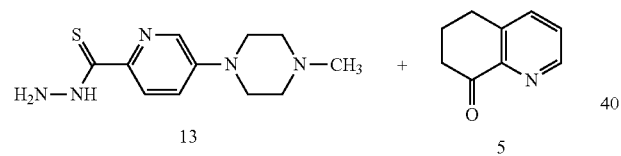

Finally, COTI-5 is formed as follows. Intermediate 13 and 6,7-dihydro-5H-quinolin-8-one 5 is dissolved in ethanol at room temperature to yield COTI-5.

Synthesis of COTI-5

The synthesis of COTI-5, as depicted above, is conducted according to the following synthetic methodology:

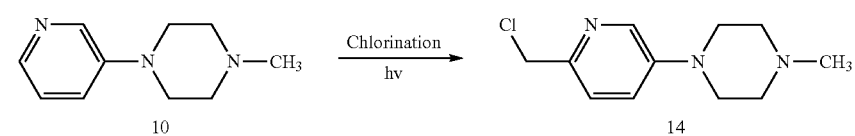

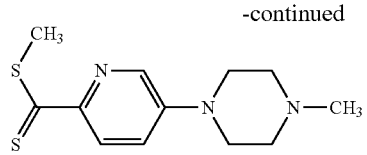

15

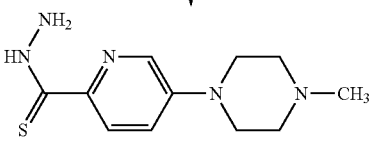

13

Intermediate 14 is formed by irradiating compound 10 in the presence of chlorine (the corresponding bromo compound of intermediate 14 can be formed using N-bromosuccinimide, benzyl peroxide in benzene). Intermediate 14 is reacted with $S_8$ and methyl iodide in TEA and DMF ($PhSO_2Na$, acetonitrile, $Pr_4NBr$ at 80° C. for 24 h or $S_8$, t-BuOK at R.T., THF then methyl iodide may also be used) to yield intermediate 15. Intermediate 15 is reacted with hydrazine hydrate in ethanol to form intermediate 13.

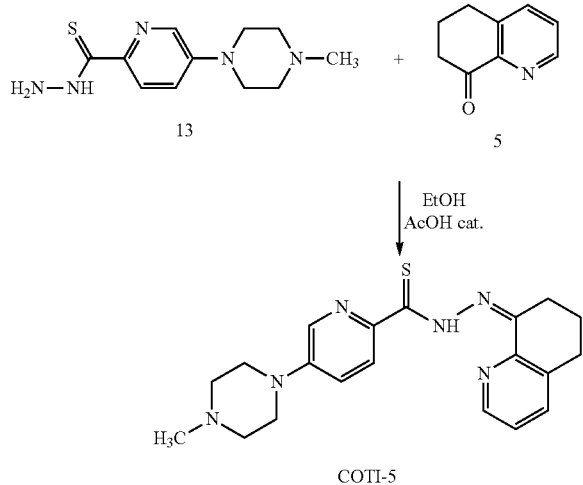

COTI-5

Finally, COTI-5 is formed as follows. Intermediate 13 and 6,7-dihydro-5H-quinolin-8-one 5 is dissolved in ethanol at room temperature to yield COTI-5.

Example 1

In-Silico Assessment of Properties

An in-silico assessment of the properties of compounds according to the present invention was performed using the CHEMSAS® computational platform. CHEMSAS® is a robust proprietary computational platform for accelerated drug discovery, optimization and lead selection based upon a unique combination of traditional and modern pharmacology principles, statistical modeling and machine learning technologies. At the centre of the CHEMSAS® platform is a hybrid machine learning technology that may be used to: find, profile and optimize new targeted lead compounds; find novel uses for known compounds; and, solve problems with existing or potential drugs. In using the CHEMSAS® platform, first a therapeutic target was selected, in this case cancer and more particularly Small Cell Lung Cancer. The second step involved the design of a candidate molecule library containing thousands of potential compounds through the assembly of privileged molecular fragments. Thirdly, the candidate library was profiled and optimized using a combination of validated computational models and traditional expert medicinal chemistry. In this step, the CHEMSAS® platform developed 244 molecular descriptors for each candidate therapeutic compound. For example, molecular properties relating to a candidate compound's therapeutic efficacy, expected human toxicity, oral absorption, cumulative cellular resistance and/or kinetics were assessed. In some instances, comparative properties relating to commercially relevant benchmark compounds were also assessed. Potential lead compounds were then selected from the candidate library using a proprietary decision making tool designed to identify candidates with the optimal physical chemical properties, efficacy, ADME/Toxicity profile, etc. according to a pre-determined set of design criteria. The lead compounds selected from the candidate library were then synthesized for further pre-clinical development.

The properties of certain compounds according to the present invention, specifically COTI-217, COTI-220, COTI-219, COTI-2 and COTI-5, that were assessed in-silico using the CHEMSAS® computational platform are shown in Tables 1 to 13. Some of the predicted properties are validated by the experimental data provided herein, while other properties have been validated elsewhere during the development of other clinical candidates. The CHEMSAS® platform therefore provides a means of determining, predicting and/or testing the properties of a compound, particularly when used to determine the properties of compounds according to the present invention. The CHEMSAS® platform is also particularly useful in comparing the properties of compounds according to the invention with prior art compounds on a relative basis in silico.

Tables 1A and 1B: Physical Chemical Properties

Tables 1A and 1B shows that COTI-217, COTI-220, COTI-219, COTI-2 and COTI-5 are "drug-like" with good drug like physical properties.

TABLE 1A

| MolID | FORMULA | MolWeight | MnLogP | HBndDon | HBndAcc |
|---|---|---|---|---|---|
| COTI217 | C17H22N6S | 342.469 | 1.859199 | 1 | 6 |
| 220 | C18H20N6S | 352.464 | 2.078432 | 1 | 6 |
| COTI219 | C17H18N6S | 338.437 | 1.7646 | 1 | 6 |
| COTI2 | C19H22N6S | 366.491 | 3.041311 | 1 | 6 |
| COTI5 | C20H24N6S | 380.518 | 2.22023 | 1 | 6 |

TABLE 1B

| MolID | TPSA | RotBnds | LipinskiAlerts | Veber |
|---|---|---|---|---|
| COTI217 | 37.5435 | 3 | 0 | 0 |
| COTI220 | 53.3605 | 3 | 0 | 0 |
| COTI219 | 53.3605 | 3 | 0 | 0 |
| COTI2 | 53.3605 | 4 | 0 | 0 |
| COTI5 | 53.3605 | 4 | 0 | 0 |

Legend for Table 1:

MolWeight stands for Molecular Weight measured in Daltons and is a size descriptor; MnLogP is an average of MLogP, ALogP98 and CLogP, all of which are calculated lipophilicity/solubility estimates;

HBndDon stands for Hydrogen Bond Donor and refers to the number of atoms able to donate electrons to potentially form Hydrogen bonds;

HBndAcc stands for Hydrogen Bond Acceptor and refers to the number of atoms able to accept electrons to potentially form Hydrogen bonds;

TPSA stands for Topological Polar Surface Area and is a measure of Molecular Surface Charge/Polarity;

RotBnds stands for Rotatable Bonds which is a count of freely rotatable single bonds in the molecule;

Lipinski Alerts: If any 2 of (Molecular weight >500 Daltons, Hydrogen Bond Donors >5, Hydrogen Bond Acceptors >10, MLogP >4.15) are true, then a molecule is likely to have poor bioavailability;

Veber Alerts: If TPSA >140 or number of Rotatable Bonds is >10, then bioavailability is likely to be poor.

Tables 2A and 2B: Solubility Properties

Tables 2A and 2B shows that COTI-217, COTI-220, COTI-219, COTI-2 and COTI-5 are expected to have acceptable solubility values for drug-like compounds.

TABLE 2A

| MolID | FORMULA | MnLogP | LogD(pH 7) | LogS |
|---|---|---|---|---|
| COTI217 | C17H22N6S | 1.859199 | 0.309304 | −3.09009 |
| COTI220 | C18H20N6S | 2.078432 | 0.992417 | −4.20136 |
| COTI219 | C17H18N6S | 1.7646 | 1.067558 | −3.78407 |
| COTI2 | C19H22N6S | 3.041311 | 2.380243 | −4.52904 |
| COTI5 | C20H24N6S | 2.22023 | 1.019701 | −4.49499 |

TABLE 2B

| MolID | FORMULA | Acid pKa 2 | Base pKa 1 | Base pKa 2 |
|---|---|---|---|---|
| COTI217 | C17H22N6S | None | 7.65056 | None |
| COTI220 | C18H20N6S | None | 7.65056 | 4.71559 |
| COTI219 | C17H18N6S | None | 7.65056 | 3.90139 |
| COTI2 | C19H22N6S | None | 5.65356 | 4.882592 |
| COTI5 | C20H24N6S | None | 7.870707 | 5.617688 |

Legend for Table 2:

MnLogP is an average of MLogP, ALogP98 and CLogP, all of which are calculated lipophilicity/solubilty estimates;

LogD(7.4) is a measure of relative solubility in octanol vs water at a specific pH, in this case pH=7.4;

LogS is the logarithm of the calculated solubility in pure water usually measured at 25 degrees centigrade;

pKa is a calculated estimate of the pH at which the drug or substructures of the drug is 50% ionized and 50% is unionized.

Table 3: Efficacy (LogGI50)

Table 3 shows that COTI-217, COTI-220, COTI-219, COTI-2 and COTI-5 are predicted to have sub-micromolar in vitro activity vs human SCLC cell lines. Actual measurements obtained in vitro confirm the prediction of activity at sub-micromolar levels for COTI-2 and COTI-219.

| MolID | FORMULA | DMS114 | SHP-77 | Predicted | Actual |
|---|---|---|---|---|---|
| COTI217 | C17H22N6S | <−6 | <−6 | Active | ND |
| COTI220 | C18H20N6S | <−6 | <−6 | Active | ND |
| COTI219 | C17H18N6S | <−6 | <−6 | Active | Active |
| COTI2 | C19H22N6S | <−6 | <−6 | Active | Active |
| COTI5 | C20H24N6S | <−6 | <−6 | Active | ND |

Legend for Table 3:

DMS114 is a "classical" human small cell lung cancer line that is maintained by the National Cancer Institute in the United States;

SHP-77 is a "variant" human small cell lung cancer line that is maintained by the National Cancer Institute in the United States;

Predicted is the predicted in vitro Activity of the drug;

Actual is the actual outcome of in vitro testing in both of the reference human small cell lung cancer lines;

"Active" refers to drugs with predicted or measured GI50 <1 μmol/L;

ND means that the drug has not yet been tested in vitro.

Tables 4A and 4B: Oral Absorption and BBB Penetration

Tables 4A and 4B shows that COTI-217, COTI-220, COTI-219, COTI-2 and COTI-5 are expected to be absorbed orally.

TABLE 4A

| MolID | FORMULA | Mn % OrlAbs | Min % Abs | HIA-T2(MD) |
|---|---|---|---|---|
| COTI217 | C17H22N6S | 82.67412 | 67.67412 | 2.16777 |
| COTI220 | C18H20N6S | 88.79283 | 73.79283 | 0.144973 |
| COTI219 | C17H18N6S | 85.52785 | 70.52785 | 0.314455 |
| COTI2 | C19H22N6S | 87.02755 | 72.02755 | 0.38029 |
| COTI5 | C20H24N6S | 88.43881 | 73.43881 | 0.277855 |

TABLE 4B

| MolID | ProbBBB Pene | LogBBB | BBB-T2(MD) | Clark LogBBB | SubKit LogBB |
|---|---|---|---|---|---|
| COTI217 | 0.918625 | −0.32584 | 2.280528 | −0.09599 | −0.22923 |
| COTI220 | 0.26949 | −0.24921 | 0.254967 | −0.36111 | −0.20053 |
| COTI219 | 0.331 | −0.39022 | 0.551314 | −0.39876 | −0.31048 |
| COTI2 | 0.710661 | −0.01576 | 0.416152 | −0.19558 | −0.0185 |
| COTI5 | 0.089884 | −0.0646 | 0.315208 | −0.37444 | −0.05658 |

Legend for Table 4:

Mn % OrlAbs is the prediction of the mean percent oral absorption of the drug from an ensemble of 5-7 different models;

Min % Abs is the minimum value for the Mn % OrlAbs at the lower 95% Confidence Interval;

HIA-T2(MD) is the Malanabois distance, which is a measure of the calculated statistical distance from the centre of a population of drugs with optimal oral absorption;

ProbBBBPene is an estimate of the probability that the drug will penetrate the blood brain barrier and enter the central nervous system (CNS);

BBB-T2(MD) is the Malanabois distance, which is a measure of the calculated statistical distance from the centre of a population of drugs with optimal blood brain barrier penetration;

ClarkLogBBB is an estimate of a drugs penetration of the blood brain bather based on the drugs LogP and TPSA;

SubKitLogBB is another estimate of a drugs penetration of the blood brain barrier based on the drugs LogP and TPSA;

LogBB: if LogBB <=−1 the drug does not pentrate the BBB; if Log BB>0 there is likely to be good BB penetration; if −1<logBB<0 then BBB penetration is likely to be variable and may be poor.

Table 5: Metabolic Stability (Percent Remaining at 60 Minutes and Calculated Half Life in Hours)

Table 5 shows that in vitro metabolic stability is expected to be adequate for COTI-217, COTI-220, COTI-219, COTI-2 and COTI-5. COTI-2 is expected to be metabolized more quickly in human liver microsomes than the other COTI compounds. Both the estimated T1/2 and the T1/2 measured in vitro for COTI-2 and 219 are good.

| MolID | Liver Microsomes | Hepatocytes | T½ hrs | 95% CI in Hrs | In vitro T½ (Hrs) |
|---|---|---|---|---|---|
| COTI217 | 54 | 66.4 | 5.3 | 1.9-8.7 | ND |
| COTI220 | 64.1 | 72.5 | 3.9 | 1.4-6.4 | ND |
| COTI219 | 66.7 | 74.18 | 4 | 1.4-6.6 | ~6.8 (5.0, 7.0, 8.5) |
| COTI2 | 23.7 | 55.94 | 8.7 | 3.1-14.3 | ~6.0 (1.7, 4.8, 11.4) |
| COTI5 | 50.9 | 64.42 | 6.1 | 2.2-10 | ND |

Legend for Table 5:

Liver Microsomes is the estimated percent remaining at 60 minutes after introduction of a dose of the drug into an in vitro/human liver microsomal enzyme system;

Hepatocytes is the estimated percent remaining at 60 minutes after introduction of a dose of the drug into an in vitro/human hepatocyte cellular system;

T1/2 hrs is a calculated estimate of the half life of the drug measured in hours; 95% CI in Hrs is the calculated 95% confidence interval estimate of the half life of the drug measured in hours;

In vitro T1/2(Hrs) is the actual half life in hours obtained from 3 in vitro experiments carried out at doses of 1 µmol, 10 µmol and 100 µmol (in brackets).

Table 6: Probability (CYP450 Isoenzyme Substrate)

Table 6 shows that COTI-217, COTI-220, COTI-219, COTI-2 and COTI-5 are likely to be metabolized by the CYP450 enzyme system. COTI-217, COTI-220, COTI-219, COTI-2 and COTI-5 are expected to undergo at least some CYP3A457 metabolism and COTI-2 may also undergo some CYP2D6 metabolism.

| MolID | FORMULA | CYP1A2 | CYP2B6 | CYP2C8/9 | CYP2C19 | CYP2D6 | CYP2E1 | CYP3A457 |
|---|---|---|---|---|---|---|---|---|
| COTI217 | C17H22N6S | 0.57 | 0.03 | 0.08 | 0.05 | 0.84 | 0.03 | 0.51 |
| COTI220 | C18H20N6S | 0.07 | 0.02 | 0.12 | 0.05 | 0.22 | 0.02 | 0.93 |
| COTI219 | C17H18N6S | 0.34 | 0.03 | 0.15 | 0.06 | 0.52 | 0.03 | 0.6 |
| COTI2 | C19H22N6S | 0.05 | 0.03 | 0.13 | 0.06 | 0.8 | 0.03 | 0.93 |
| COTI5 | C20H24N6S | 0.21 | 0.03 | 0.2 | 0.07 | 0.58 | 0.04 | 0.87 |

Legend for Table 6:

Table 6 represents the estimated probabilities that the drug in question will undergo at least 20% of its phase 1 metabolism by one or more of the 7 major isoenzyme forms of Cytochrome P450 (CYP450). The isoenzyme forms of CYP450 in Table 6 are: 1A2, 2B6, 2C8 or 9, 2C19, 2D6, 2E1 and 3A4, 5 or 7; these 7 isoenzyme forms account for >80% of phase 1 metabolism of all drugs that are orally administered to humans. The majority of all orally administered drugs are metabolized by the CYP3A family of isoenzymes.

Table 7: Probability (CYP450 Iso Enzyme Inhibitor)

Table 7 shows that COTI-217, COTI-220, COTI-219, COTI-2 and COTI-5 are not expected to significantly inhibit any CYP450 isoenzyme.

| MolID | FORMULA | CYP1A2 | CYP2B6 | CYP2C8/9 | CYP2C19 | CYP2D6 | CYP2E1 | CYP3A457 |
|---|---|---|---|---|---|---|---|---|
| COTI217 | C17H22N6S | 0.1 | 0.06 | 0.08 | 0.07 | 0.22 | 0.07 | 0.22 |
| COTI220 | C18H20N6S | 0.09 | 0.06 | 0.33 | 0.12 | 0.16 | 0.06 | 0.12 |
| COTI219 | C17H18N6S | 0.11 | 0.06 | 0.22 | 0.08 | 0.12 | 0.06 | 0.1 |
| COTI2 | C19H22N6S | 0.09 | 0.06 | 0.33 | 0.18 | 0.37 | 0.07 | 0.4 |
| COTI5 | C20H24N6S | 0.11 | 0.06 | 0.23 | 0.16 | 0.31 | 0.07 | 0.37 |

Legend for Table 7:

Table 7 represents the estimated probabilities that the drug in question will inhibit a given CYP isoenzyme activity by at least 20%; the isoenzyme forms of CYP450 in table 7 are: 1A2, 2B6, 2C8 or 9, 2C19, 2D6, 2E1 and 3A4, 5 or 7; these 7 isoenzyme forms account for >80% of phase 1 metabolism of all drugs that are orally administered to humans.

Table 8: Probability (CYP450 Iso Enzyme Inducer)

Table 8 shows that COTI-217, COTI-220, COTI-219, COTI-2 and COTI-5 are not expected to induce any of the CYP450 isoenzymes.

| MolID | FORMULA | CYP1A2 | CYP2B6 | CYP2C8/9 | CYP2C19 | CYP2D6 | CYP2E1 | CYP3A457 |
|---|---|---|---|---|---|---|---|---|
| COTI217 | C17H22N6S | 0.06 | 0.05 | 0.05 | 0.05 | 0.05 | 0.05 | 0.05 |
| COTI220 | C18H20N6S | 0.23 | 0.05 | 0.05 | 0.05 | 0.05 | 0.05 | 0.05 |
| COTI219 | C17H18N6S | 0.06 | 0.05 | 0.05 | 0.05 | 0.05 | 0.05 | 0.07 |
| COTI2 | C19H22N6S | 0.07 | 0.05 | 0.05 | 0.05 | 0.05 | 0.05 | 0.09 |
| COTI5 | C20H24N6S | 0.07 | 0.05 | 0.05 | 0.05 | 0.05 | 0.05 | 0.07 |

Legend for Table 8:

Table 8 represents the estimated probabilities that the drug in question will induce a given CYP isoenzyme activity by at least 20%. The isoenzyme forms of CYP450 in table 8 are: 1A2, 2B6, 2C8 or 9, 2C19, 2D6, 2E1 and 3A4, 5 or 7; these 7 isoenzyme forms account for >80% of phase 1 metabolism of all drugs that are orally administered to humans.

Table 9: Probability of any Hepatic Toxicity

Table 9 shows that COTI-217, COTI-220, COTI-219, COTI-2 and COTI-5 are not expected to cause Hepatic Toxicity.

| MolID | FORMULA | ProbHepTox1 | ProbHepTox2 |
|---|---|---|---|
| COTI217 | C17H22N6S | 0.146 | 0.086 |
| COTI220 | C18H20N6S | 0.082 | 0.47 |
| COTI219 | C17H18N6S | 0.079 | 0.457 |
| COTI2 | C19H22N6S | 0.065 | 0.371 |
| COTI5 | C20H24N6S | 0.099 | 0.252 | either not be a substrate for P-gp or would inhibit P-gp activity, thereby reducing the likelihood of P-gp related drug resistance.

| MolID | FORMULA | Substrate | Inhibitor |
|---|---|---|---|
| COTI217 | C17H22N6S | 0.57 | 0.81 |
| COTI220 | C18H20N6S | 0.62 | 0.87 |
| COTI219 | C17H18N6S | 0.19 | 0.75 |

-continued

| MolID | FORMULA | Substrate | Inhibitor |
|---|---|---|---|
| COTI2 | C19H22N6S | 0.79 | 0.9 |
| COTI5 | C20H24N6S | 0.82 | 0.9 |

Legend for Table 10:

Table 10 represents the calculated probabilities from an ensemble of models that the drug in question will interact with P-glycoprotein (P-gp) as a substrate or inhibitor.

Table 11: Animal and Human Toxicity Predictions

Table 11 shows that COTI-217, COTI-220, COTI-219, COTI-2 and COTI-5 are expected to have low to moderate acute toxicity as measured by LD50 when given by the oral and intraperitoneal route.

| MolID | FORMULA | ORL-LD50 | Lower ORL-LD50 | IPR-LD50 | Lower IPR-LD50 | MRTD mg/kg/day | MRTD mg/day |
|---|---|---|---|---|---|---|---|
| COTI217 | C17H22N6S | 609.7 | 192.8 | 139.6 | 44.2 | 2 | 120.5 |
| COTI220 | C18H20N6S | 761.1 | 240.7 | 175.5 | 55.5 | 1.3 | 79.9 |
| COTI219 | C17H18N6S | 1022 | 323.2 | 227.8 | 72 | 1.2 | 70.4 |
| COTI2 | C19H22N6S | 842.8 | 266.5 | 195.3 | 61.8 | 1.6 | 99 |
| COTI5 | C20H24N6S | 773.9 | 244.7 | 151.5 | 47.9 | 1.1 | 67 |

Legend for Table 9:

ProbHepTox1 is the average calculated probability from an ensemble of models that the drug in question will cause liver toxicity;

ProbHepTox2 is the average calculated probability from a second, different ensemble of models that the drug in question will cause liver toxicity.

Table 10: Probability of P-Glycoprotein Interaction

Table 10 shows that COTI-217, COTI-220, COTI-219, COTI-2 and COTI-5 are expected to inhibit P-glycoprotein (P-gp) enzyme activity. COTI-2 and COTI-5 may also be substrates for P-gp, whereas COTI-219 is relatively unlikely to be a substrate for P-gp. P-gp is a protein expressed by many cancer cells and is felt to contribute to cellular resistance to many cancer drugs. Ideally, an effective cancer drug would Legend for Table 11:

ORL-LD50 is the calculated point estimate of the dose of the drug in mg/kg that would cause death in 50% of healthy test lab rats when the drug is given orally;

LowerORL-LD50 is the calculated lower 95% confidence interval point estimate of the dose of the drug in mg/kg that would cause death in 50% of healthy test lab rats when the drug is given orally;

IPR-LD50 is the calculated point estimate of the dose of the drug in mg/kg that would cause death in 50% of healthy test lab mice when the drug is given intraperitoneally;

LowerORL-LD50 is the calculated lower 95% confidence interval point estimate of the dose of the drug in mg/kg that would cause death in 50% of healthy test lab mice when the drug is given intraperitoneally;

MRTDmg/kg/day is the calculated maximum recommended therapeutic daily dose of the drug in milligrams per kg per day for the average 60 Kg human adult;

MRTDmg/day is the calculated maximum recommended therapeutic daily dose of the drug in milligrams per day for the average 60 Kg human adult.

Table 12: Predicted hERG Interaction

Table 12 shows that COTI-217, COTI-220, COTI-219, COTI-2 and COTI-5 are expected to have hERG IC50 values of >1 µmol/l in keeping with a decreased risk of cardiac toxicity. In general, a hERG IC50 of <1 µmol/L would be associated with an increased probability of potential drug induced cardiac toxicity.

| MolID | FORMULA | IC50 (µmol) | ProbIC50 > 1 µmol | ProbIC50 > 10 |
|---|---|---|---|---|
| COTI217 | C17H22N6S | 2.6 | 0.88 | 0.06 |
| COTI220 | C18H20N6S | 1.8 | 0.9 | 0.03 |
| COTI219 | C17H18N6S | 2.2 | 0.92 | 0.04 |
| COTI2 | C19H22N6S | 1.6 | 0.92 | 0.02 |
| COTI5 | C20H24N6S | 0.6 | 0.79 | 0.04 |

Legend for Table 12:

IC50(µmol) is the calculated concentration of the drug that inhibits 50% of the activity of the hERG potassium channel and is an estimate of potential cardiac toxicity;

ProbIC50>1 µmol is the calculated probability that the IC50 for the drug with regards to the hERG potassium channel is greater than 1 µmol/L;

ProbIC50>10 µmol is the calculated probability that the IC50 for the drug with regards to the hERG potassium channel is greater than 10 µmol/L;

Table 13: Predicted Genotoxicity

Table 13 shows that COTI-2 and 219 are expected to have a negative AMES test and that COTI-217, COTI-220, COTI-219, COTI-2 and COTI-5 are not expected to cause Polyploidicity in the Guinea Pig cell model.

| MolID | FORMULA | ProbAMES+ | PolyPldy |
|---|---|---|---|
| COTI217 | C17H22N6S | 0.94 | 0.15 |
| COTI220 | C18H20N6S | 0.06 | 0.16 |
| COTI219 | C17H18N6S | 0.06 | 0.15 |
| COTI2 | C19H22N6S | 0.06 | 0.16 |
| COTI5 | C20H24N6S | 0.06 | 0.23 |

Legend for Table 13:

ProbAMES+ is the probability that the drug will induce a recognized gene mutation in a standard strain of cultured bacteria;

PolyPldy is the probability that the drug will induce polyploidicity (i.e. an increased/abnormal number of chromosomes) in cultered guinea pig cells.

Example 2

In Vitro Efficacy Against Various Cancer Cell Lines

To assess the efficacy of compounds according to the present invention in the treatment of cancer, in vitro activity expressed as IC50 (represents the concentration of an inhibitor that is required for 50% inhibition of its target, in nmol) was measured for several cancer cell lines using standard methods for such tests known to persons skilled in the art. Briefly, cells were plated in plastic tissue culture plates and grown under standard conditions for each cell line, in carbon dioxide/oxygen atmosphere in plastic tissue culture plates, in the presence of COTI-2 or COTI-219 compounds at 35° C. for 3 days. Control cultures were treated with vehicle minus compound. Cells were counted after 3 days in culture and at a cell density of no more than 80%. The following cell lines, obtained from the National Cancer Institute, were tested: human SCLC cell lines DMS153, DMS114, SHP77; human NSCLC cell lines H226, A460, A560; human breast cancer cell lines T47D, MCF$_7$; human colon cancer cell line HT29; and, human Leukemia cell lines K562, HL60. The results of these assays are presented in Table 14.

TABLE 14 in vitro IC50 against cancer cell lines

| Cell Line | Tumor Type | COTI-2 IC50 (nM) | COTI-219 IC50 (nM) |
|---|---|---|---|
| SHP77 | SCLC | 156 +/− 8 | 787 +/− 61 |
| DMS153 | SCLC | 73 +/− 9 | 233 +/− 39 |
| DMS114 | SCLC | 51 +/− 9 | 267 +/− 40 |
| H226 | NSCLC | 15000 +/− 1129 | Not tested |
| A460 | NSCLC | 7900 +/− 620 | Not tested |
| A549 | NSCLC | 6300 +/− 671 | Not tested |
| T47D | Breast Cancer | 221 +/− 12 | 367 +/− 44 |
| MCF7 | Breast Cancer | 101 +/− 8 | 421 +/− 31 |
| HT29 | Colorectal Cancer | 121 +/− 11 | 403 +/− 32 |
| K562 | Leukemia | 176 +/− 22 | 222 +/− 28 |
| HL60 | Leukemia | 236 +/− 9 | 374 +/− 46 |

Table 14 shows that both COTI-2 and COTI-219 possess potent activity in the low nanomolar range against SCLC tumor cell types, as well as several other tumor cell types such as breast cancer, colorectal cancer and Leukemia. Both drugs had an IC50 of less than 850 nM for the SHP77 cell line, which is known to be resistant to several conventional therapeutic agents. COTI-2 did not possess nanomolar level activity against NSCLC cell types and COTI-219 was not tested against those cell types. At least COTI-2 therefore exhibits selectivity in lung cancer treatment towards SCLC cell types. The in vitro data also confirms the in-silico predictions of efficacy, which estimated that less than 1 µM (1000 nM) would be required for efficacy in the SHP 77 and DMS114 cell lines.

Example 3

In Vivo Efficacy in SCLC Treatment

The nude mouse model of human SCLC was used to evaluate the in vivo efficacy of compounds of the present invention in comparison with several known chemotherapeutic agents. Nude mice were obtained form the National Cancer Institute and the SHP-77 human SCLC cell line was chosen for metastatic tumor xenografts. The control group consisted of 10 animals, each of which were administered bilateral thigh injections of a prescribed volume of tumor cells. There were 6 treatment groups, each containing 5 animals: COTI-2, COTI-4, COTI-219, Taxotere® (docetaxel), Cisplatin® (cis-diamminedichloroplatinum) and Tarceva® (erlotinib) The therapeutic agent was administered by intraperitoneal (IP) injection on alternate days beginning on Day 3 post tumor cell injection. Each animal in a treatment group was administered bilateral thigh injections with the same prescribed volume of tumor cells as the control animals. Treatment continued for 31 days, following which the animals were euthanized and tissues were collected for subsequent analysis. The final tumor size in mm$^3$ is reported in FIG. 1 and the number of tumors is reported in FIG. 2.

Referring to FIG. 1, compounds according to the invention showed a marked decrease in tumor growth as compared with both the control and conventional agents. Control animals produced tumors having a mean volume of 260+/−33 mm³. Animals treated with COTI-2 produced tumors of mean volume 9.9 mm³, while those treated with COTI-219 produced tumors having mean volume 53+/−28 mm³. This compared well with those treated with Cisplatin®, which produced tumors having means volume 132+/−26 mm³ and those treated with Taxotere®, which produced tumors having mean volume 183 mm³. Animals treated with Tarceva® died before study conclusion at 31 days.

Figure 2:
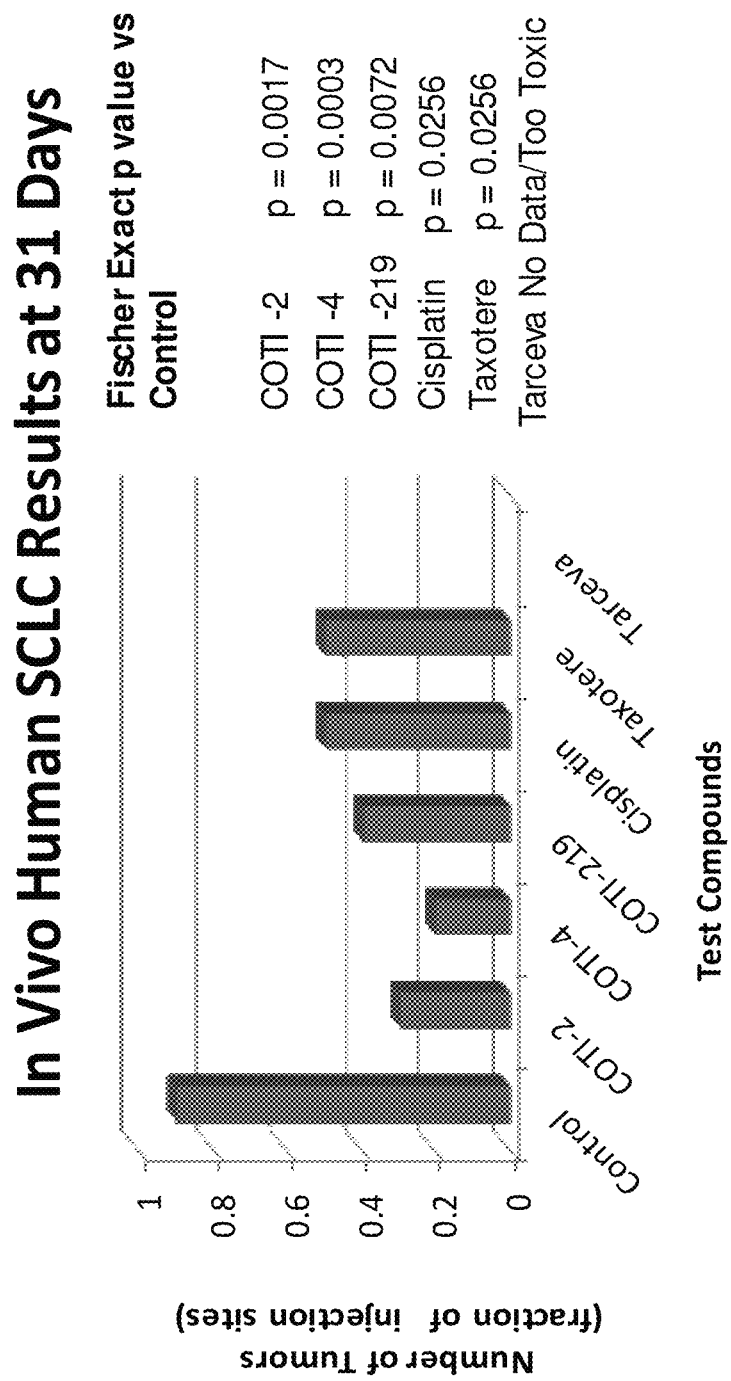
FIG. 2 shows number of SHP77 human SCLC tumours in nude mice treated with test compounds.

Referring to FIG. 2, compounds according to the invention showed a marked decrease in number of tumors as compared with both the control and conventional agents. Control animals produced an average of 0.9 tumors per injection site, whereas those treated with COTI-2 produced 0.28, those treated with COTI-219 produced 0.38, those treated with Cisplatin® produced 0.48 and those treated with Taxotere® produced 0.48 Animals treated with Tarceva® died before study conclusion at 31 days.

The above data show the efficacy of compounds according to the invention in vivo against SCLC cell lines. Furthermore, compounds according to the invention show better efficacy compared to conventionally administered therapeutic agents.

Example 4

In Vivo Effect of COTI-2 in SCLC Treatment on N417 Tumor Xenografts

Malignant N417 human SCLC cells in Matrigel™ were injected sub-cutaneously into hind legs of nude mice and xenograft tumors were allowed to grow to about 100 mm³. Mice were then administered daily intraperitoneal injections with indicated concentrations of COTI-2 (in isotonic saline, as a cloudy liquid, total volume of 1 ml per injection) for one week. Tumor volumes were estimated by caliper measurement. The results are shown in FIG. 3.

Figure 3:
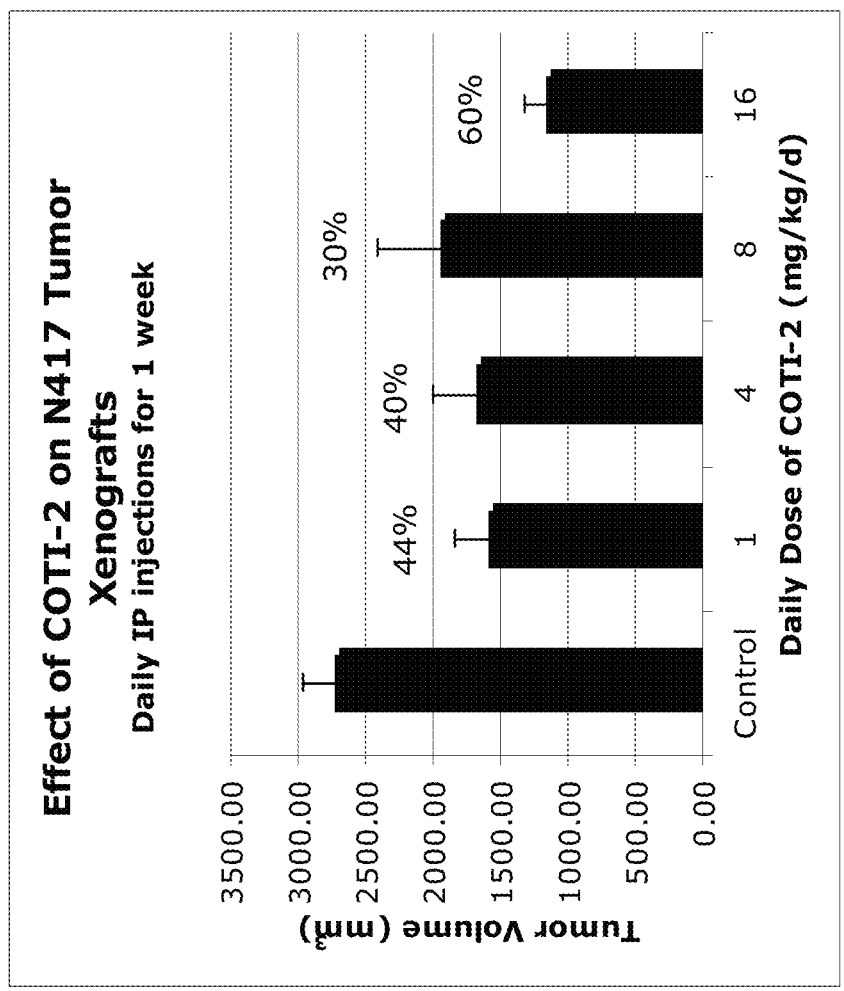
FIG. 3 shows the volume of N417 human SCLC tumour in nude mice treated with COTI-2 and control.

Referring to FIG. 3, tumor volumes were graphed as means±standard error (SE).

A significant difference in tumor growth was observed at all dosage levels. The decrease in efficacy seen at the 8 mg/kg level relative to other treatment levels is attributed to an error in solubilizing the compound, since a small amount of undissolved material was observed at the bottom of the treatment vial. Percentage values reported on FIG. 3 are for efficacy of the compound expressed in terms of inhibition of tumor growth according to the following formula:

$$(1-(Tf-Ti)/(Cf-Ci))*100$$

wherein Tf is the final tumor volume, Ti is the initial tumor volume at the onset of treatment, Cf is the final control tumor volume and Ci is the initial control tumor volume at the onset of treatment. Even when the 8 mg/kg dose is included, tumor growth inhibition of 30% or more was observed across all dosage levels. It is noted that the N417 cell line is generally regarded as the hardest SCLC cell line to treat. The compounds according to the invention therefore exhibit in vivo efficacy against a number of different SCLC cell lines.

Example 5

Resistance Testing

In order to evaluate the induction of resistance in vitro, compounds according to the invention were tested in head to head comparisons against conventional therapeutic agents Cisplatin® and Taxotere®. The compound designated COTI-4 (which is the subject of Applicant's co-pending U.S. provisional patent application entitled "Composition and Method for Treatment" filed Dec. 26, 2007) was also tested. The structure for COTI-4 is:

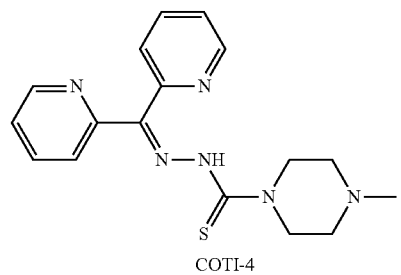

COTI-4

IC50 values were obtained using methods known to persons skilled in the art with two different human SCLC cell lines (DMS153 and SHP77) obtained from the National Cancer Institute. The surviving 50% of cells from the initial IC50 tested were harvested and cultured for 5 days, after which time this new generation of cells was re-treated with the same agent and a new IC50 value was established. The procedure was repeated for a total of 5 generations. Emerging resistance was identified by increasing IC50 values in successive generations. The results are shown in FIGS. 4 and 5 (DMS153 and SHP77 cell lines, respectively), where the ordinate axis is provided in terms of the ratio of the IC50 value to the IC50 value of the parental generation.

Figure 4:
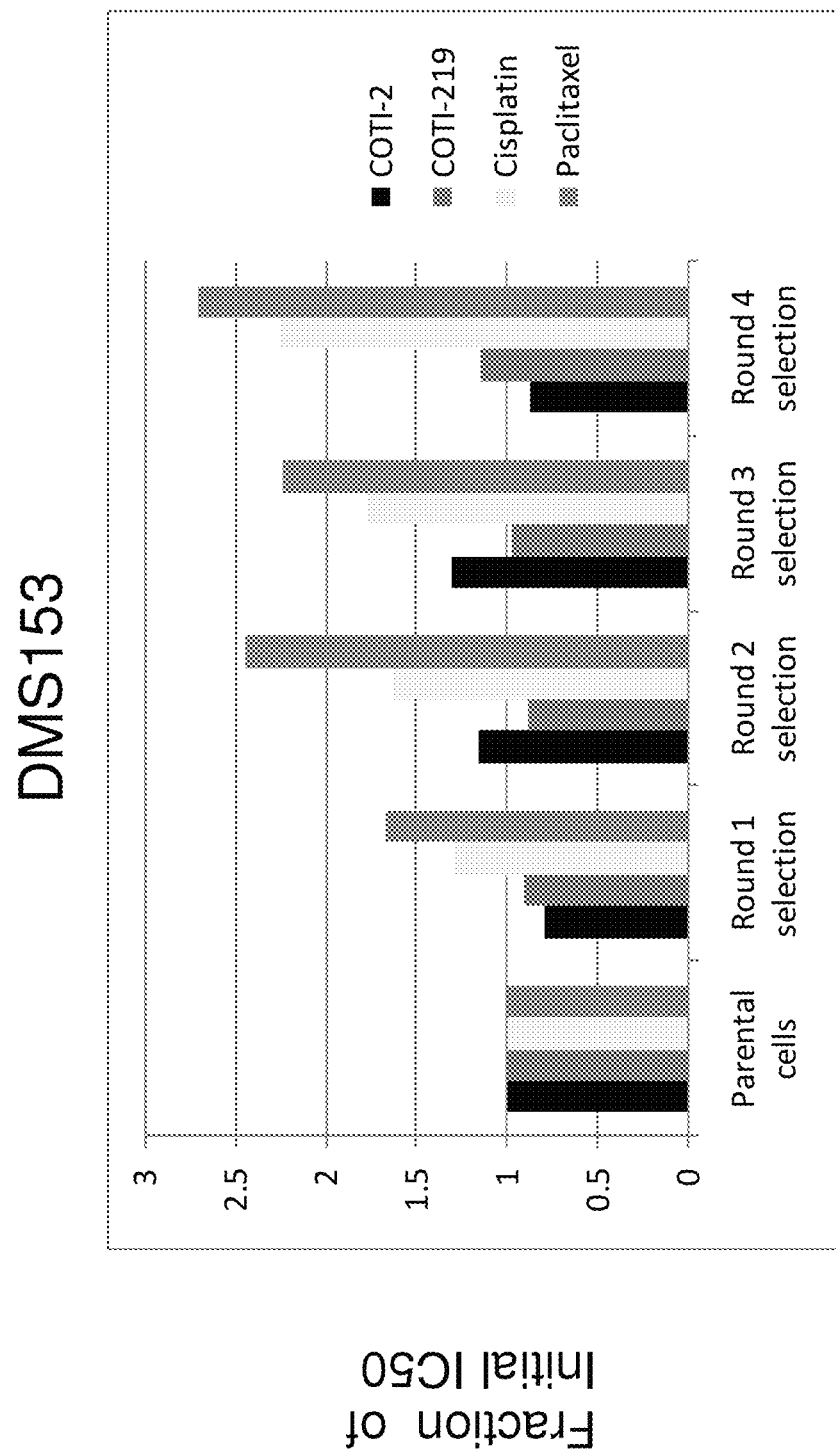
FIG. 4 shows lack of emerging resistance in DMS153 cells treated with COTI-2 and COTI-219.
Figure 5:
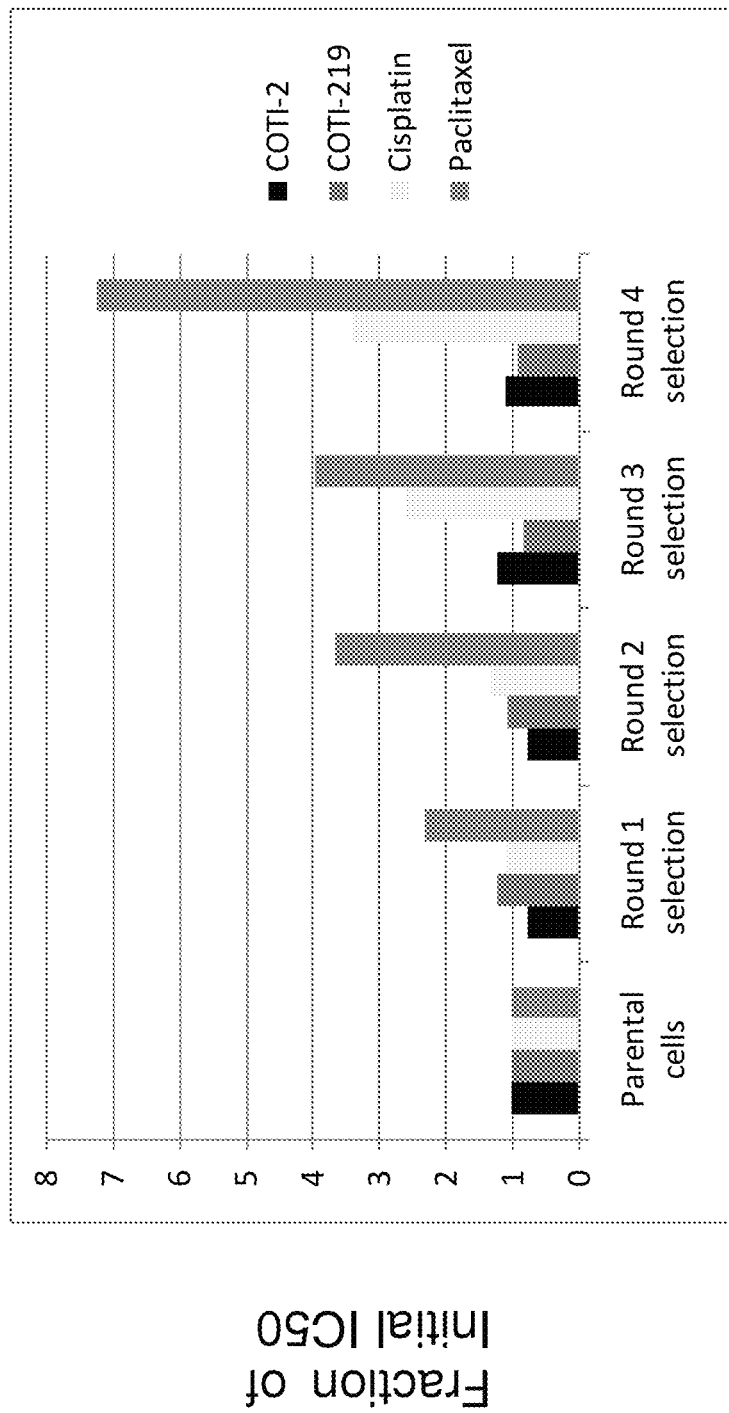
FIG. 5 shows lack of emerging resistance in SHP77 cells treated with COTI-2 and COTI-219.

Referring to FIGS. 4 and 5, both COTI-2 and 219 exhibited little to no emerging resistance over 5 generations. This was in marked contrast to the conventional therapies Cisplatin® and Taxotere® (labeled Paclitaxel in the figures), which showed significant increases in IC50 for both cell lines. The SHP77 cell line in particular is known to be resistant to conventional agents; however, neither COTI 2 nor 219 showed any tendency towards resistance in this cell line. In fact, COTI-2 demonstrated a statistically significant tendency to decrease resistance (IC50's less than 1 for successive generations) in both cell lines. COTI-2 therefore exhibits a collateral sensitivity whereby the resistance of cells is decreased over successive generations and the drug might actually become more effective over time against these cell lines. This corroborates the in-silico predictions for COTI-2 and 219; COTI-2 was predicted to be a strong P-glycoprotein inhibitor, which is consistent with decreasing the tendency towards drug resistance, whereas COTI-219 was predicted to be both a P-glycoprotein inhibitor and/or a weak substrate for P-glycoprotein, also consistent with minimal accumulation in resistance over successive generations. The in-silico predictions for resistance profile of compounds according to the invention are therefore confirmed by these assays.

Example 6

In Vitro Efficacy in Brain Cancer

In order to determine the efficacy of the present invention against human Glioma and Astrocytoma cell lines, IC50 values were determined by in vitro assay of four malignant human brain cancer cell lines (U87MG, grade III glioblastoma/astrocytoma; SNB-19, glioma/astrocytoma Grade IV, glioblastoma multiforme; SF-268, glioma; SF-295, glioma). Human brain cancers are notoriously difficult to treat.

Cell lines were obtained from the Human Tissue Culture Collection (ATCC), grown and maintained under ATCC-specified conditions, and tested to ensure viability and lack of contaminating mycoplasma and common viruses. Healthy cells were plated in 96-well culture plates in medium plus fetal bovine serum and allowed to adhere for 16 h, followed by addition of COTI-2, COTI-219, Cisplatin®, or BCNU (1,3-Bis(2-chloroethyl)-1-nitrosourea) at multiple concentrations ranging from those that had no effect on proliferation to those that inhibited proliferation by 90% or more. A viability stain (alamar Blue) was added to cells after 4-7 days of drug exposure (approximately 4 doublings of control cells; maximum cell density in wells approximately 80%), and assayed for total cellular metabolic activity (a function of population density of live cells) by absorbance. Concentrations of the agent required to inhibit proliferation by 50% (IC50 value) were derived by interpolation of plotted data (mean values derived from 3 independent experiments±standard error). Results are reported in Table 15.

TABLE 15

IC50 values for Human Glioma/Astrocytoma cell Lines

| Cell Line | COTI-2 (nM) | COTI-219 (nM) | Cisplatin (nM) | BCNU (nM) |
|---|---|---|---|---|
| U87 | 48 +/− 9 | 2370 +/− | 490 +/− 9 | 1520 +/− 130 |
| SNB-19 | 8 +/− 3 | 1990 +/− | 870 +/− 40 | 2250 +/− 700 |
| SF-268 | 66 +/− 8 | 1170 +/− 80 | Not tested | Not tested |
| SF-295 | 184 +/− 23 | 2390 +/− | Not tested | Not tested |

At least the COTI-2 compounds were shown to have better efficacy against glioma/astrocytoma cell lines as compared with the conventional agents Cisplatin® and BCNU. COTI-2 showed an order of magnitude greater efficacy than Cisplatin® against U87 and two orders of magnitude greater efficacy against SNB-19. These results show that at least COTI-2 compounds have efficacy against glioma/astrocytoma cell lines.

Example 7

In Vivo Effect of COTI-2 on Cancerous Brain Tumours

Malignant U87 human glioma (brain tumour) cells in Matrigel™ were injected subcutaneously into hind legs of nude mice, allowed to grow to 200-300 mm³, then treated 3 times per week (Mon, Wed, Fri) with indicated concentrations of COTI-2 (in isotonic saline, as a cloudy liquid, total volume of 1 ml per injection). Tumour volumes were estimated by caliper measurement. The results are shown in FIGS. 6A and 6B.

Figure 6A:
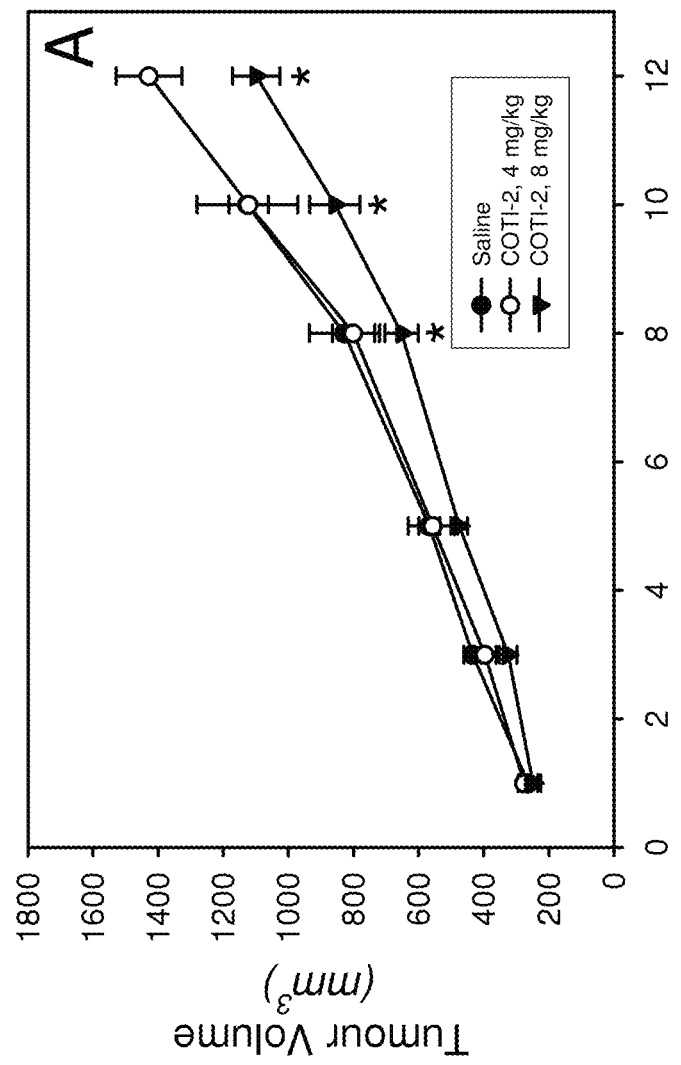
FIGS. 6A and 6B show volume of U87 human glioma tumours in nude mice treated with two different concentrations of COTI-2.

In FIG. 6A, tumour volumes were graphed as means±standard error (SE) (n=11-14 for each data point). The asterisk indicates a significant difference (p<0.05) between the 8 mg/kg treatment group and both the saline control and 4 mg/kg treatment groups. There was no significant difference between the 4 mg/kg group and the saline control group.

Figure 6B:
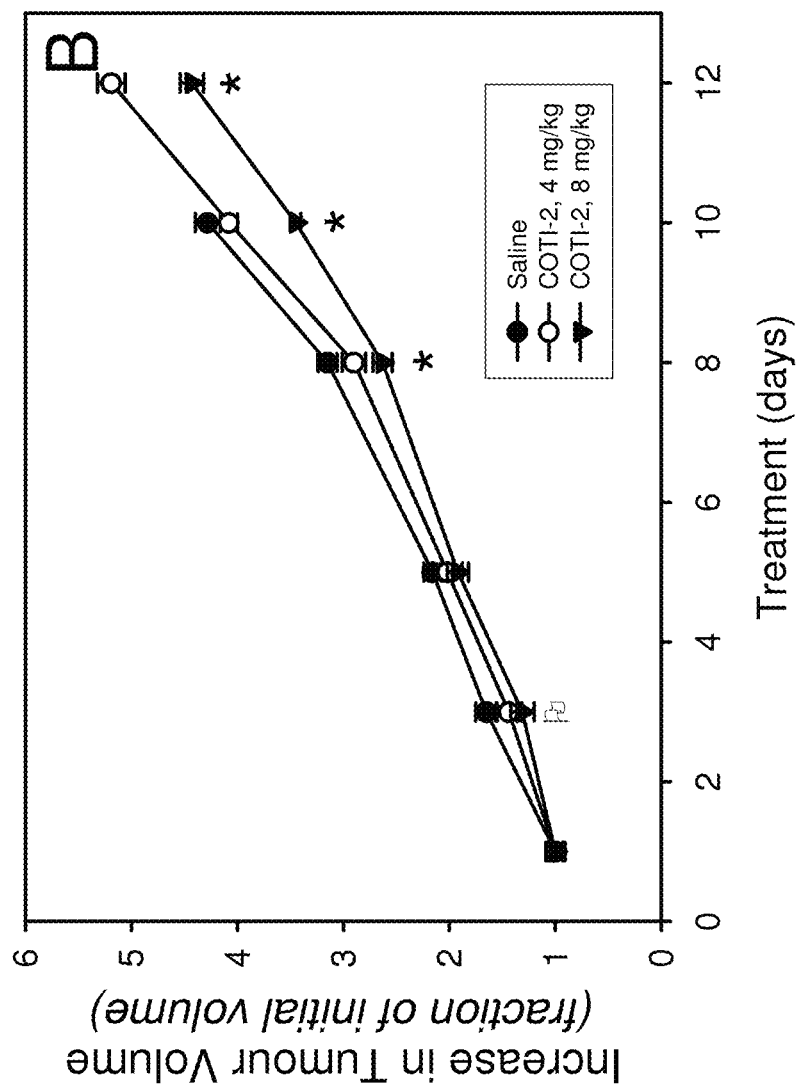

In FIG. 6B, tumour volumes were graphed as fractional increase in volume, to correct for differences in starting volume, ±SE. The asterisk indicates a significant difference (p<0.05) between the 8 mg/kg treatment group and both the saline control and 4 mg/kg treatment groups. There was no significant difference between the 4 mg/kg group and the saline control group. The flag (†) indicates a significant difference between the 8 mg/kg group and the saline group, but not between the 8 mg/kg group and the 4 mg/kg group.

FIGS. 6A and 6B show that compounds of the present invention are effective in the treatment of established human brain tumors. The compounds delayed tumor growth by about 25% at a dosage of 8 mg/kg given just three times per week. Although no significant effect was observed at a dosage of 4 mg/kg, more frequent administration may have produced a significant effect at this dosage.

Example 8

Toxicity Testing

An escalating dose acute toxicity study was conducted with COTI-2, COTI-4 and COTI-219. Standard lab mice were divided into four treatment groups (control, 4, 8, 16 mg/kg) with four animals per group. It should be noted that the highest dose was approximately 10 times the estimated effective dose. Mice were given alternate day IP injections for 28 days. Weight loss/gain of the mice was measured and the mice were observed for adverse effects such as vomiting, diarrhea, seizures, etc. Blood and tissue samples were harvested for histopathology. None of the drugs produced any weight loss at any of the administered doses over the entire 28 day period. No evidence of acute toxicity was obtained and no adverse effects were observed. The compounds according to the present invention are therefore believed to be safe and non-toxic.

Example 9

In Vitro Metabolic Stability in Human Liver Microsomes

To evaluate the stability of these compounds in terms of clearance by the liver, human liver microsomes (HLM) at a concentration of 0.5 mg/ml were incubated with 0.823 mM NADPH, 5 mM UDPGA, 1 mM $MgCl_2$ and COTI-2 or 219 at concentrations of 1, 10 and 100 µM. Sampling was conducted at 1, 20, 40, 60, 120, 180 and 240 minutes and the remaining concentration of each compound was evaluated. A half life ($T_{1/2}$) was calculated at each concentration, along with the rate of clearance by the liver ($C_L$). The results are provided in Table 16 for each compound. The $C_L$ values compare favorably with published values for other marketed therapeutic agents under identical conditions. The half life of compounds according to the invention is therefore likely to be long enough to permit convenient dosing, while not being so long as to lead to accumulation in patients with potential long term toxicity effects.

TABLE 16

Half-life and Liver Clearance Rate by HLM at 0.5 mg/mL

| Compound | Concentration (µM) | $T_{1/2}$ (min) | $C_L$ (µL/min/mg) |
|---|---|---|---|
| COTI-2 | 1 | 102.1 | 12 |
|  | 10 | 285.7 | 4 |
|  | 100 | 683.1 | 2 |
| COTI-219 | 1 | 301.2 | 4.2 |
|  | 10 | 420.7 | 3 |
|  | 100 | 508.5 | 2.5 |

The average half life for COTI-2 was 6 hours and for COTI-219 was 6.8 hours. The in-silico prediction for CL in the 95% confidence interval was from 3.1-14.3 for COTI-2 and from 1.4-6.6 for COTI-219; this compares well with the data presented in Table 3.

Example 10

Mechanism of Action

Without wishing to be limited by theory, it is believed that molecules according to the present invention, particularly COTI-2, act in the treatment of cancer in a manner consistent with the following mechanistic observations. The following observations were obtained using gene expression profiling techniques and targeted in vitro testing. Molecules of the present invention are believed to function as kinase inhibitors. Molecules of the present invention are also believed to function as promoters of apoptosis. Promotion of apoptosis is achieved by decreasing phosphorylation of Caspase 9; this has the effect of increasing active Caspase 9 and inducing apoptosis via Caspase 3.

Figure 7:
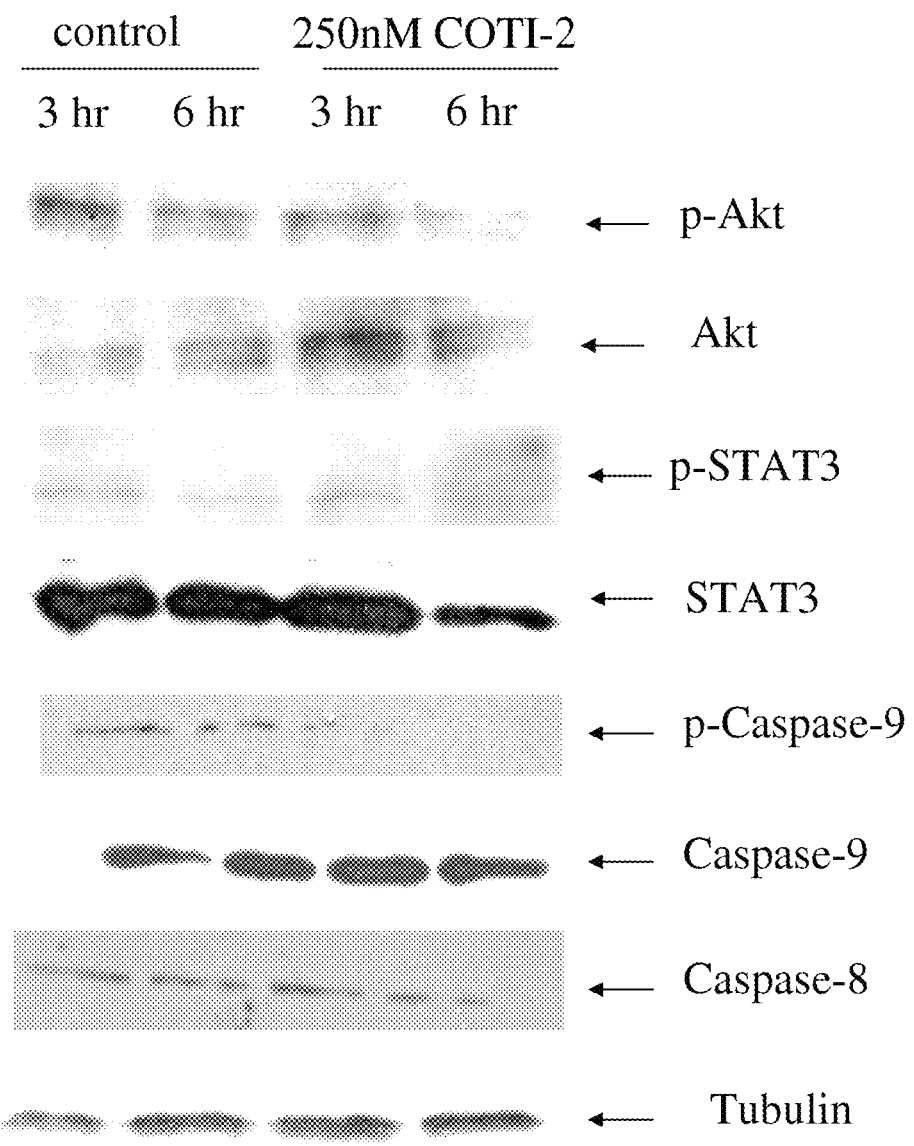
FIG. 7 shows Western blot analysis of cellular lysates of SHP77 cells that have been treated with COTI-2.

To confirm this mechanism SHP77 cells were treated with 250 nM of COTI-2 and incubated for 3 and 6 hours. Western blots of the cellular lysates are presented in FIG. 7. Phospho-Akt expression was decreased as compared to control at both 3 and 6 hours, with corresponding increases in Akt levels. There was no change in phospho-STAT3 expression, although a slight decrease in total STAT3 (~30%) was observed at 6 hrs. There was no observed reactivation of Caspase 8; its level of expression remained constant in treated and control cells. However, the most dramatic change was a profound suppression of phospho-Caspase 9 at both 3 and 6 hrs of incubation. These results confirm the proposed mechanism of action.

Example 11

In-Silico Comparative Data

The in-silico model was used to test properties of compounds described in PCT Publication No. WO2006/009765: NSC716768, NSC73306, NSC73303, NSC668496, and NSC693323. Compounds JBC271A, JBC271B (Journal of Biological Chemistry 271, 13515-13522 (1996)) and JICS75 (Journal of the Indian Chemical Society, 75, 392-394 (1998) and Journal of the Indian Chemical Society, 72, 403-405 (1995)) are as follows:

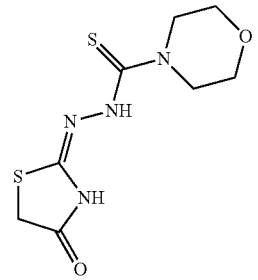

JBC271A

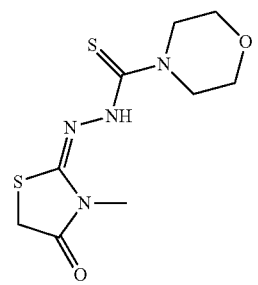

JBC271B

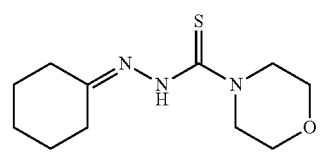

JICS75

Results of in-silico testing are shown in Tables 17 to 20. The legends for these tables correspond to those of Example 1, except where indicated, and the methodology used to create the Tables was identical.

Tables 17A and 17B: Physical Chemical Properties

Table 17 shows that all tested compounds are drug like with no alerts for poor absorption or bioavailability.

TABLE 17A

| MolID | FORMULA | MolWeight | MnLogP | HBnd Don | HBnd Acc |
|---|---|---|---|---|---|
| NSC716768 | C17H20N6O4S | 404.449 | 2.082079 | 2 | 10 |
| NSC73306 | C16H12Cl2N4O2S | 395.268 | 3.155598 | 3 | 6 |
| NSC73303 | C15H12N4OS | 296.352 | 2.564086 | 3 | 5 |
| NSC668496 | C15H18N4OS | 302.4 | 2.541123 | 2 | 5 |
| NSC693323 | C14H24N6S2 | 340.516 | 2.39891 | 2 | 6 |
| JBC271A | C8H12N4O2S2 | 260.338 | 0.257966 | 2 | 6 |
| JBC271B | C9H14N4O2S2 | 274.365 | 0.542592 | 1 | 6 |
| JICS75 | C11H19N3OS | 241.357 | 1.600519 | 1 | 4 |

TABLE 17B

| MolID | FORMULA | TPSA | RotBnds | Lipinski Alerts | Veber |
|---|---|---|---|---|---|
| NSC716768 | C17H20N6O4S | 112.7027 | 7 | 0 | 0 |
| NSC73306 | C16H12Cl2N4O2S | 75.9848 | 5 | 0 | 0 |
| NSC73303 | C15H12N4OS | 67.0547 | 4 | 0 | 0 |
| NSC668496 | C15H18N4OS | 57.597 | 3 | 0 | 0 |
| NSC693323 | C14H24N6S2 | 54.972 | 7 | 0 | 0 |

TABLE 17B-continued

| MolID | FORMULA | TPSA | RotBnds | Lipinski Alerts | Veber |
|---|---|---|---|---|---|
| JBC271A | C8H12N4O2S2 | 66.5271 | 3 | 0 | 0 |
| JBC271B | C9H14N4O2S2 | 57.0694 | 3 | 0 | 0 |
| JICS75 | C11H19N3OS | 36.4161 | 3 | 0 | 0 |

Table 18: Solubility Properties

Table 18 shows that all tested compounds have acceptable and comparable solubility with the COTI compounds except for NSC73306 which would be expected to have very poor water solubility.

| MolID | FORMULA | MnLogP | LogS |
|---|---|---|---|
| NSC716768 | C17H20N6O4S | 2.082079 | −3.46551 |
| NSC73306 | C16H12Cl2N4O2S | 3.155598 | −5.76993 |
| NSC73303 | C15H12N4OS | 2.564086 | −3.7869 |
| NSC668496 | C15H18N4OS | 2.541123 | −3.87371 |
| NSC693323 | C14H24N6S2 | 2.39891 | −3.27041 |
| JBC271A | C8H12N4O2S2 | 0.257966 | −1.76143 |
| JBC271B | C9H14N4O2S2 | 0.542592 | −1.83773 |
| JICS75 | C11H19N3OS | 1.600519 | −2.45438 |

Table 19: Efficacy (LogGI50)

Table 19 shows that all tested compounds except for NSC693323 are predicted to be inactive against human SCLC cell lines DMS114 and SHP-77 in vitro. Therefore, there is no rationale for use of any of the tested compounds except for NSC693323 as therapeutic agents in the treatment of SCLC. NSC693323 has an average GI50 of −6.3. By comparison, COTI-2 has LOG(GI50) for DMS114 determined in vitro of −7.2 to −7.4, representing ~10 times better in vitro efficacy than the predictions for NSC693323

| MolID | FORMULA | DMS 114 | SHP-77 | Predicted | Mean Over NCI/DTP 60 cell line panel |
|---|---|---|---|---|---|
| NSC716768 | C17H20N6O4S | <−6 | <−6 | Inactive | −4.7 |
| NSC73306 | C16H12Cl2N4O2S | <−6 | <−6 | Inactive | −4.9 |
| NSC73303 | C15H12N4OS | <−6 | <−6 | Inactive | ND |
| NSC668496 | C15H18N4OS | <−6 | <−6 | Inactive | −6.1 |
| NSC693323 | C14H24N6S2 | <−6 | <−6 | Active | −6.3 |
| JBC271A | C8H12N4O2S2 | <−6 | <−6 | Inactive | ND |
| JBC271B | C9H14N4O2S2 | <−6 | <−6 | Inactive | ND |
| JICS75 | C11H19N3OS | <−6 | <−6 | Inactive | ND |

Legend for Table 19:

Mean Over NCI/DTP 60 cell line panel is the mean of the GI50's for all 60 cell lines NOT including DMS114 and SHP-77;

ND means not done/not available.

Table 20: Oral Absorption and BBB Penetration

Table 20 shows that all tested compounds are predicted to have good oral absorption with variable to poor CNS penetration. The only potentially active drug, NSC693323, likely penetrates into the CNS poorly.

TABLE 20A

| MolID | FORMULA | Mn % OrlAbs | Min % Abs | HIA-T2(MD) |
|---|---|---|---|---|
| NSC716768 | C17H20N6O4S | 86.33807 | 71.33807 | 3.556507 |
| NSC73306 | C16H12Cl2N4O2S | 73.43512 | 58.43512 | 2.075257 |
| NSC73303 | C15H12N4OS | 88.14632 | 73.14632 | 0.078544 |
| NSC668496 | C15H18N4OS | 87.81207 | 72.81207 | 0.055115 |
| NSC693323 | C14H24N6S2 | 84.59752 | 69.59752 | 0.097439 |
| JBC271A | C8H12N4O2S2 | 80.28443 | 65.28443 | 2.273772 |
| JBC271B | C9H14N4O2S2 | 84.04259 | 69.04259 | 2.267253 |
| JICS75 | C11H19N3OS | 91.74003 | 76.74003 | 2.023605 |

TABLE 20B

| MolID | FORMULA | ProbBBBPene | LogBBB | BBB-T2(MD) |
|---|---|---|---|---|
| NSC716768 | C17H20N6O4S | 0.009519 | <<−1.00 | 9.681481 |
| NSC73306 | C16H12Cl2N4O2S | 0.051291 | −0.1554 | 4.758413 |
| NSC73303 | C15H12N4OS | 0.359669 | −0.41974 | 1.216003 |
| NSC668496 | C15H18N4OS | 0.306419 | −0.26927 | 0.426904 |
| NSC693323 | C14H24N6S2 | 0.265543 | −0.24742 | 0.294411 |
| JBC271A | C8H12N4O2S2 | 0.818135 | −1.12483 | 3.888207 |
| JBC271B | C9H14N4O2S2 | 0.806343 | −0.91155 | 3.439832 |
| JICS75 | C11H19N3OS | 0.840636 | −0.25614 | 1.981566 |

Example 12

AKT Kinase Activity Inhibition

Methods

Cell Lines

DMS-114 and SHP-77 SCLC cell lines were routinely grown in RPMI media supplemented with 10% fetal calf serum and antibiotics to prevent bacterial growth, and maintained by twice-weekly passaging at a ratio of 1:3. Typically, 0.5–1.0×$10^6$ cells were incubated with COTI-2 or an equivalent volume (2-5 μL) of DMSO to observe changes in Akt activity or gene expression.

Measurement of Akt Kinase Activity

Cells were incubated in 10 cm dishes with DMSO or 250 nM of COTI-2 for 2, 4, 8, 16, or 24 hrs after which kinase activity was measured with a non-radioactive Akt kinase kit (cat #9840) from Cell Signaling. Briefly, after lysing the cells in a protein non-denaturing buffer, Akt is immunoprecipitated with immobilized antibody. The kinase reaction catalyzed by immunoprecipitated Akt consists of in vitro phosphorylation of supplemented recombinant GSK-3, a natural in vivo Akt substrate, in the presence of added ATP. The amount of phosphorylated GSK-3 is determined by western blot analysis with phospho-GSK-3αβ (Ser21/9) antibody.

Measurement of Total Akt by Western Blot Analysis

Duplicate 10 cm tissue culture dishes seeded with 0.5-1.0× $10^6$ cells were incubated with 250 nM of COTI-2 for 0, 2, 4, 8, 16, 24, 48, and 96 hrs. Cell viability was determined at 24, 48, and 96 hrs by the trypan exclusion method. Whole cell lysates were prepared using standard procedures and fifty micrograms of lysate protein was separated on SDS-PAGE gels and analyzed by western blotting.

Results and Discussion

COTI-2 is an Inhibitor of Akt Kinase Activity in SCLC Cell Lines

Figure 8:
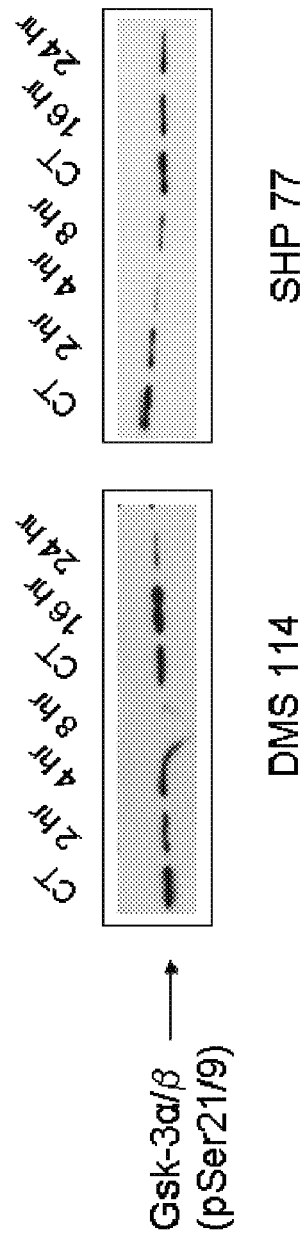
FIG. 8 shows inhibition of AKT kinase activity by COTI-2.
Figure 9:
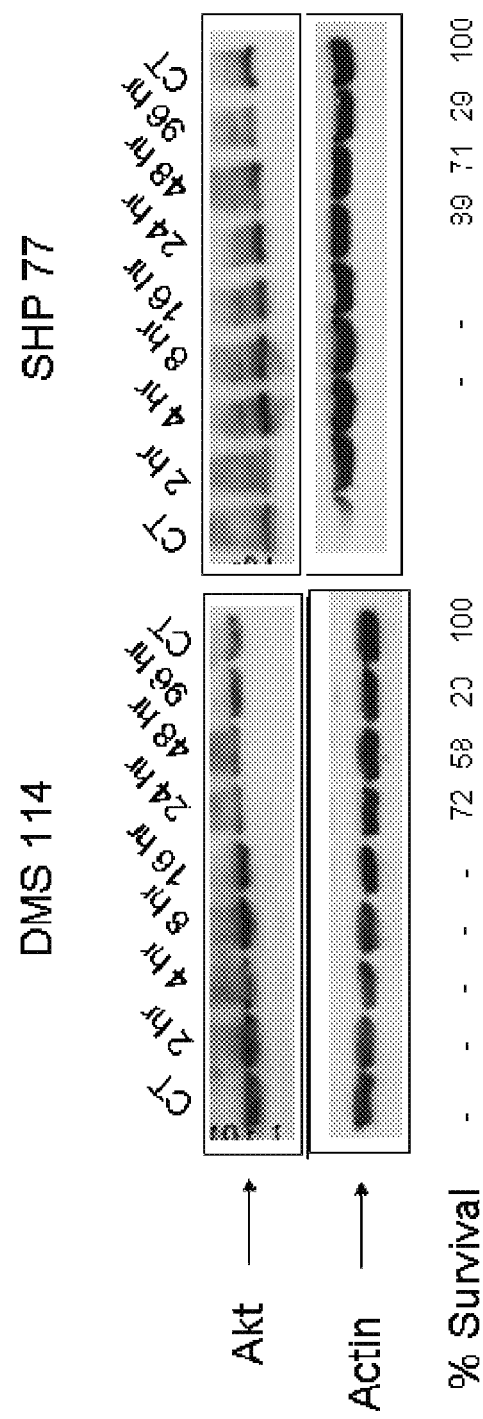
FIG. 9 shows a time course of AKT expression following incubation with COTI-2.

Incubation of DMS-114 and SHP-77 cells with 250 nM of COTI-2 resulted in a time-related decrease in Akt kinase activity starting at 2 hrs and extending over the 24 hrs duration of the experiment. In DMS-114 cells the kinase activity was below the threshold for measurement at 8 hrs and remained significantly lower relative to the control group at 24 hrs (FIG. 8). In SHP-77 cells there was a more gradual decrease in kinase activity over the course of the experiment, with a tendency for the activity to return towards control levels after 24 hrs of incubation (FIG. 8). In both cell lines, total Akt protein decreased after 24 hrs of incubation with COTI-2, analogous to the changes in kinase activity observed at this time (FIG. 9). Cell viability assays using trypan blue exclusion confirmed that this dose of COTI-2 effectively kills up to 80% of the original tumor cells within four days of incubation. These results indicate that COTI-2 inhibits Akt kinase activity either by preventing activation of Akt (directly or indirectly) or by preventing Akt from activating its downstream target(s).

Example 13 mTOR-Rictor Complex Formation

Mechanism of COTI-2 Apoptosis in SCLC Cells: Evidence from Kinase Experiments and Transcriptome Analysis In order to confirm the involvement of AKT in COTI-2 induced apoptosis, proteomic analyses of time-dependent changes in AKT kinase activity and AKT phosphorylation was performed using 2 SCLC cell lines (DMS114 and SHP77). Furthermore, to identify additional mechanistic targets for this compound, microarray experiments were followed by differential gene expression analysis. In summary, the results showed that, in response to COTI-2, AKT is down-regulated at the gene expression, whole protein, and kinase levels, thus showing that this critical cellular regulator is a direct/indirect target for COTI-2. Furthermore, the down-regulation of mTOR-Rictor, proposed to phosphorylate AKT at Ser473 site, by COTI-2 provides additional evidence for the proposed mechanism of action of this compound.

Methods:

Cell Lines:

DMS114 and SHP77 cell lines were routinely grown in RPMI media supplemented with 10% fetal calf serum and antibiotics to prevent bacterial growth, and maintained by twice-weekly passaging at a ratio of 1:3. Typically, 0.5-1.0× $10^6$ cells were incubated with COTI-2 or an equivalent volume (2-5 µl) of DMSO to observe changes in AKT activity or gene expression.

Measurement of AKT Kinase Activity:

Cells were incubated in 10 cm dishes with DMSO or 250 nM of COTI-2 for 2, 4, 8, 16, or 24 h after which kinase activity was measured with a non-radioactive AKT kinase kit (cat #9840) from Cell Signaling. Briefly, after lysing the cells in a protein non-denaturing buffer, AKT was immunoprecipitated with immobilized antibody. The kinase reaction catalyzed by immunoprecipitated AKT consists of in vitro phosphorylation of supplemented recombinant GSK-3, a natural in vivo AKT substrate, in the presence of added ATP. The amount of phosphorylated GSK-3 was determined by western blot analysis with phospho-GSK-3αβ(Ser21/9) antibody.

Measurement of Total Akt by Western Blot Analysis:

Duplicate 10 cm tissue culture dishes seeded with 0.5-1.0× $10^6$ cells were incubated with 250 nM of COTI-2 for 0, 2, 4, 8, 16, 48, and 96 h. Cell viability was determined at 24, 48, and 96 h by the trypan exclusion method. Whole cell lysates were prepared using standard procedures and 50 µg of lysate protein was separated on SDS-PAGE gels and analyzed by western blotting.

Microarray Experiments:

For each cell line, four sets of microarray experiments were performed, with each set consisting of control and treated cells exposed for 6 h either to DMSO or COTI-2 at 150 or 300 nM total concentration. Total RNA was prepared with RNeasy (Qiagen) and converted to Cy3 or Cy5-labelled cRNA according to procedures provided with the linear amplification kit from Agilent Technologies. Two hundred micrograms of labeled cRNA were hybridized to 4×44K Agilent whole genome microarrays, the arrays were washed, scanned and relevant features were extracted according to the manufacturer's protocol and further analyzed as described by Wolber et al. (Methods in Enzymology 410:28-57), which is incorporated herein by reference in its entirety.

Gene Expression Analysis:

Cy5 and Cy3 features were extracted and normalized by median centering the expression values relative to the median value of the 8 hybridization experiments performed on each microarray slide. Thus, for each gene, 4 control and 4 treatment values (two each for 150 and 300 nM) were obtained. Quality control (QC) reports showed that data was of good quality and spot saturation or abnormal features were seldom observed. Statistically significant changes in gene expression between treatment and control groups were determined by SAM analysis using TIGR software from The Institute of Genomic Research or by t tests with false discovery correction. Only genes that were differentially expressed in all 4 biologically-independent groups were further analyzed. (An independent analysis of gene expression at the lower 150 nM level of COTI-2 yield additional results reflecting changes in gene expression at this lower concentration). Gene ontology analysis of the differentially expressed genes was performed as previously described (Bioinformatics 8: 426). Statistical analysis of ontology-based gene overrepresentation between DMS114 and SHP77 cell lines was performed as described by Al Sharour et al. (Nucleic Acids Res. 35: W91-W96). The intersection of common genes was determined using GeneVenn (http://mcbc.usm.edu/genevenn/genevenn.htm). Network analysis was performed as described by Rhodes et al. (Natl Biotechnol. 23: 951-959) and Franke et al. (Am J Hum Genet. 78: 1011-1025) Overrepresentation of transcription factor binding sites in the promoters of up- or down-regulated genes was calculated as described by Ho Sui et al. (Nucleic Acids Res. 33: 3154-3164).

Results and Discussion:

The AKT kinase activity was determined by measuring the phosphorylation of GSK-3, which is a downstream target of activated AKT. Incubation of DMS114 and SHP77 cells with 250 nM of COTI-2 resulted in a time-related decrease in AKT activity starting at 2 h and extending over the 24-h duration of the experiment (FIG. 8). In DMS114 cells, the kinase activity was below the threshold for measurement at 8 h and remained significantly lower relative to the control group at 24 h. In SHP77 cells, there was a more gradual decrease in kinase activity over the course of the experiment, with a tendency for the activity to return towards control levels after 24 h of incubation. In both cell lines, total AKT protein decreased after 24 h of incubation with COTI-2, analogous to the changes in kinase activity observed at this time (FIG. 9).

Figure 10:
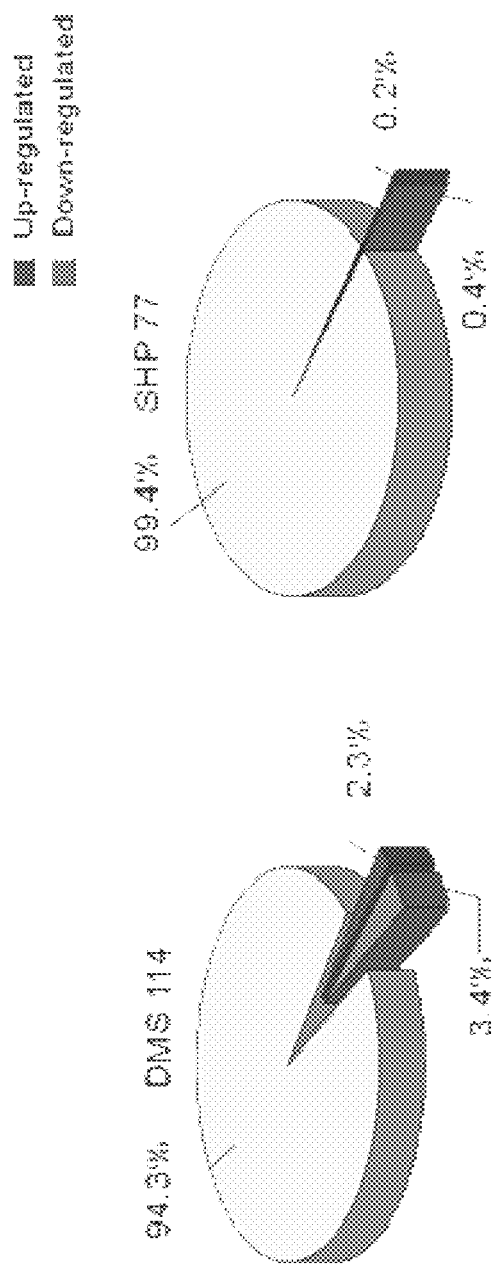
FIG. 10 shows a percent change and direction of differentially expressed genes.
Figure 11A:
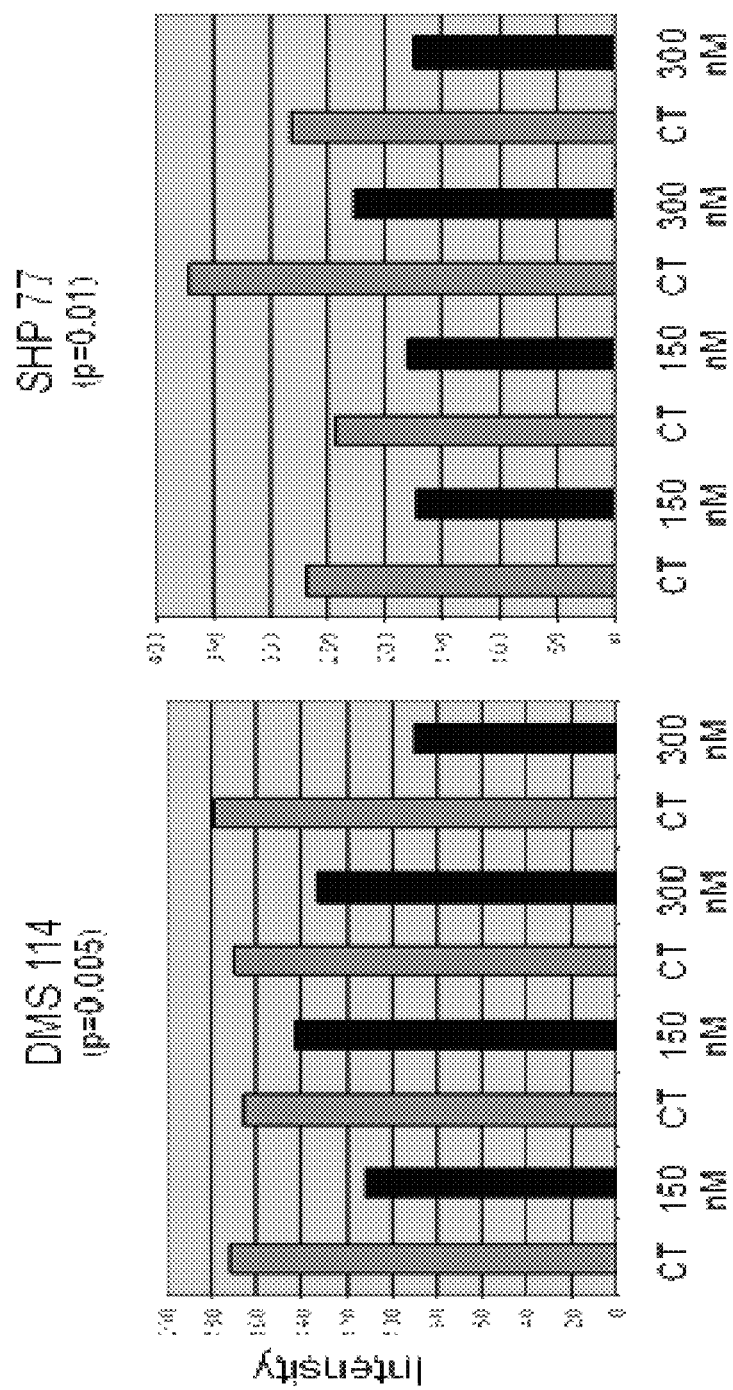
FIG. 11A-11C show expression levels of AKT1 (FIG. 11A), AKT2 (FIG. 11B), and mTOR-Rictor (FIG. 11C) in DMS114 and SHP77 cell lines following incubation for 6 h in the presence (150 or 300 nM) or absence of COTI-2.
Figure 11B:
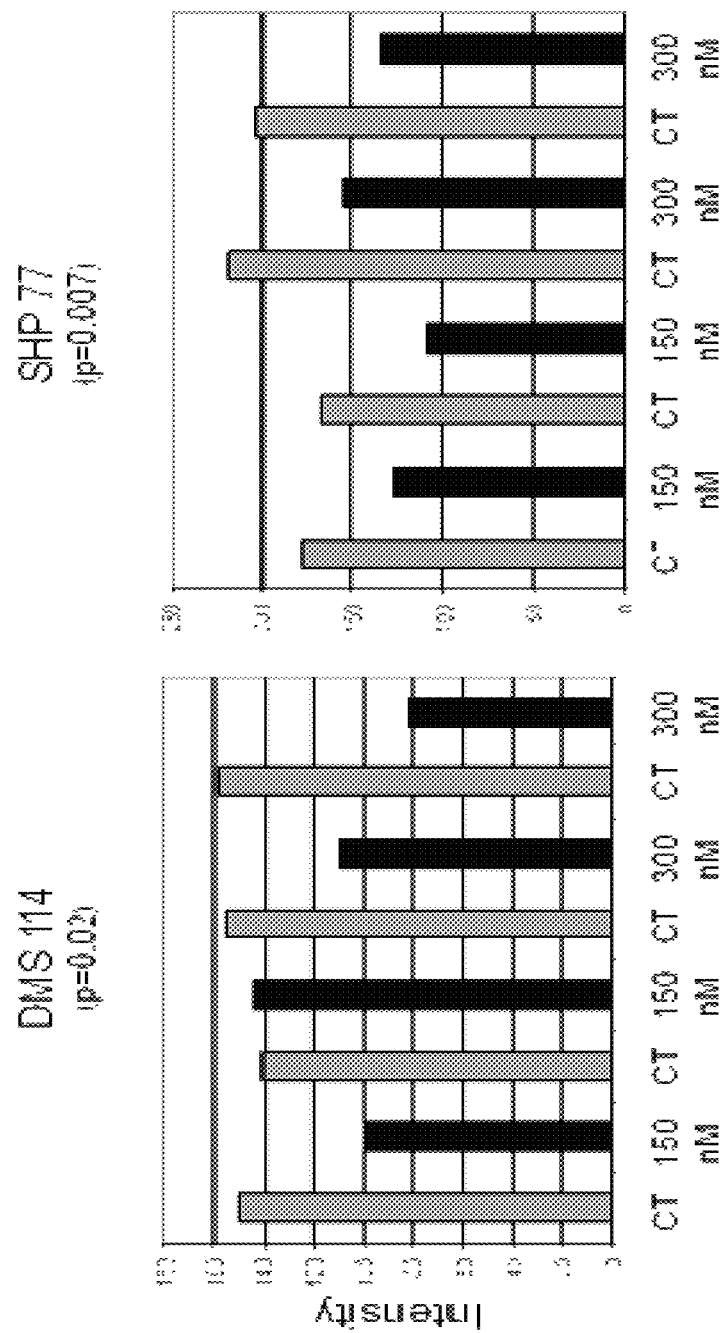
Figure 11C:
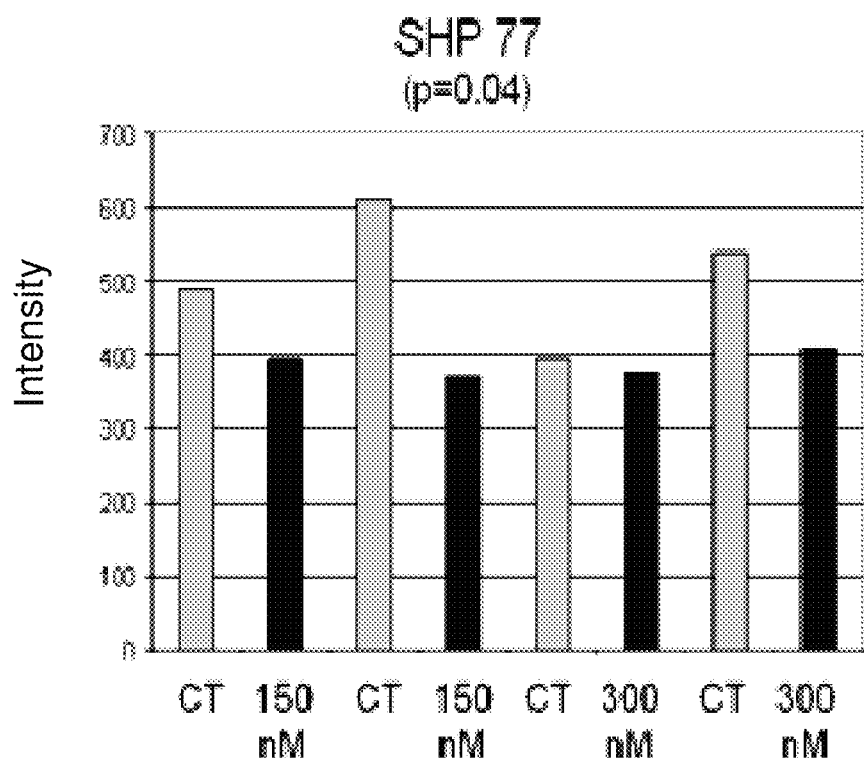

The transcriptional activity of DMS114 and SHP77 cell lines were documented following a 6-h incubation with COTI-2 (150 or 300 nM) or vehicle only control. A number of genes were differentially regulated in both cell lines (FIG. 10). Of particular interest, the AKT gene expression data (FIGS. 11A-11B) is consistent with the observed down-regulation of AKT protein observed by western blot analysis (FIG. 9), and the down-regulation of Rictor (FIG. 11C) is also consistent with the observed decreased AKT kinase activity (FIG. 8). Interestingly, the analysis of the promoters of the differentially regulated genes indicates an over-representation of promoters regulated by the forkhead family of transcriptional factors. These data provide additional evidence for AKT as the target of COTI-2, since AKT inactivates these transcriptional factors via phosphorylation; therefore, the inactivation of AKT by COTI-2 would expectedly lead to the dysregulation of genes regulated by the forkhead transcription factors.

Example 14

COTI-2 Induced Apoptosis does not Involve Downregulated PI3K Activity but is Associated with Decreased mTOR Activation This determined whether COTI-2 interfered with the upstream regulators of AKT, namely PI3 kinase I, PDK1, and mTOR-Rictor complexes ("PDK2" activity). Four cancer cell lines, A549 & H460 (NSCLC) and DMS114 & SHP77 (SCLC) were utilized.
Methods:
Cells were grown to 60-80% confluency in RPMI media supplemented with 10% fetal calf serum and antibiotics to prevent bacterial growth. $1 \times 10^6$ cells were incubated with 100, 250, 500, or 1000 nM COTI-2 either for 4 h, to observe the effect on kinase-mediated events, or for 24 h, to observe the effect on the levels of pro/anti-apoptotic molecules. As a negative control, an equivalent volume of DMSO was utilized. Whole cell lysates were prepared using standard procedures and 50 μg of lysate protein was separated on SDS-PAGE gels and analyzed by western blotting. To measure PI3-K activity, a commercial kit was purchased from Echelon. Following the procedures recommended by the manufacturer, membrane lipids were extracted in several steps and the resulting PIP3 was immobilized to nitrocellulose and measured by its interaction with a PH-domain containing protein and HRP-conjugated antibody supplied with the kit. As an additional control in these experiments, the specific PI3-K inhibitor, LY294002 was used to inhibit PI3-K and thus stop PIP3 production.

Figure 12:
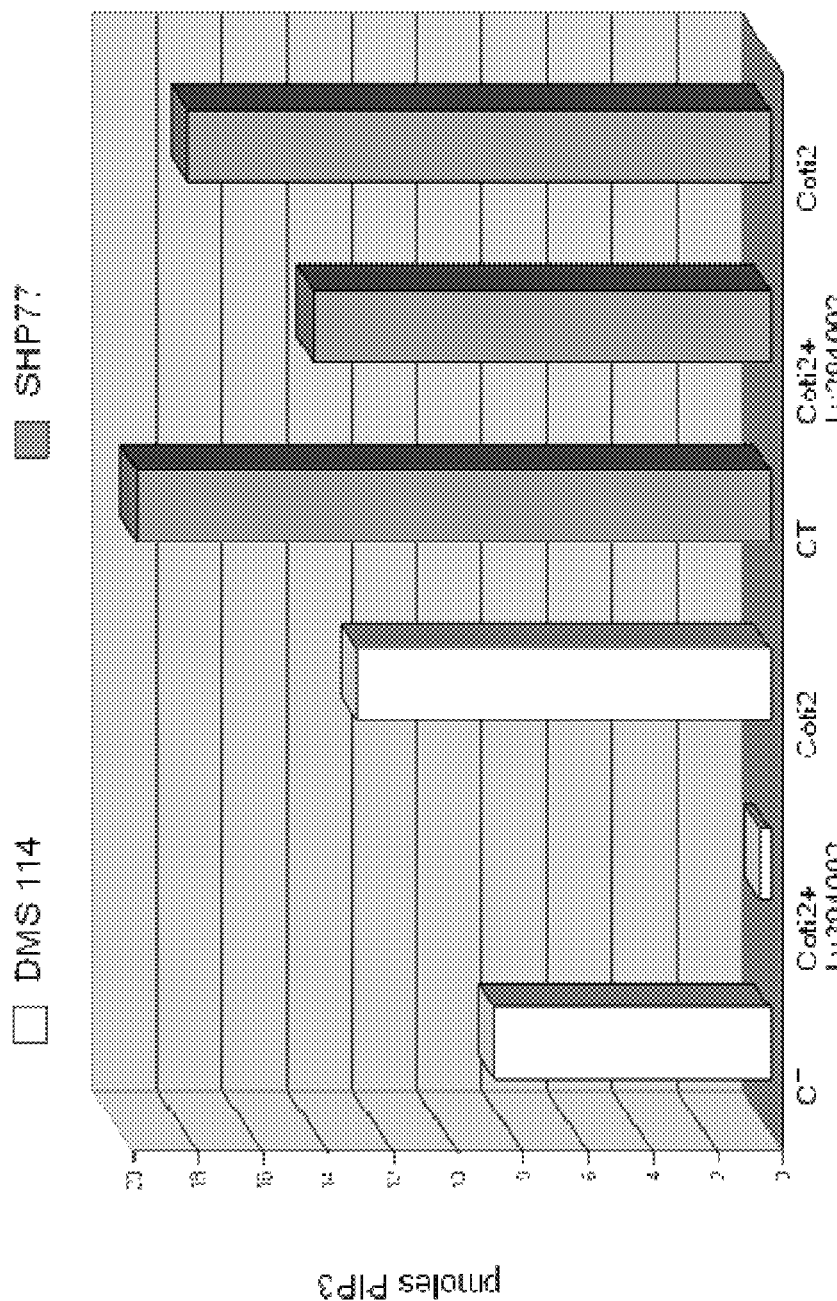
FIG. 12 shows PIP5 levels in DMS114 and SHP77 cells following incubation with 250 nM COTI-2 alone, 250 nM COTI-2+LY294002, or DMSO (solvent) alone.

To determine the effect of 250 nM concentration of COTI-2 on PI3-K activity, cells grown to 60-80% confluence in 10 cm cell culture dishes were treated with COTI-2 or an equivalent volume of DMSO. In addition, controls were pre-incubated with 50 μM of the PI3-K inhibitor LY294002 for 15 minutes prior to the addition of COTI-2. Treatment with COTI-2 lasted for 20 minutes after which the cells were processed for PIP3 detection according to Echelon's protocol.
Results and Discussion:
COTI-2 has Minimal Effect on PI3-K Activity in SCLC Cells:
To determine the effect of COTI-2 on PI3K activity, both DMS114 and SHP77 cells were grown and exposed to 250 nM COTI-2 alone, 250 nM COTI-2+LY294002, or DMSO (solvent) alone. Subsequently, the PIP3 levels were detected. The PIP3 levels are an indication of the activity of PI3K since PI3K converts inactive PIP2 to active PIP3, which is then able to bring Akt and its activators (PDK1 and PD1(2)) into close proximity in the cell membrane. As expected, the results indicated that in the presence of the PI3K-inhibitor, LY204002, there was little detectable PIP3 in DMS114 cells (FIG. 12). However, LY204002 did not inhibit PI3K activity in SHP77 cells since approximately 14 pmol of PIP3 was detected. This data can be explained by the non-specificity of LY204002 for PI3K, since this inhibitor was shown to inhibit PI3K-related kinases, for example mTOR (EMBO J 15: 5256-5267 and Cancer Research 59: 2581-2586). Alternatively, it is also possible that PI3-K is mutated in this cell line and thus unable to respond to the inhibitor as well as to COTI-2. Several mutations that abolish PI3-K activity have been described and are catalogued in the human protein mutation database MutDB (http://mutdb.org/). Nevertheless, COTI-2 alone did not inhibit PI3K activity as indicated by the PIP3 levels in both DMS114 and SHP77 cell lines (FIG. 12). In fact, there was a small increase in PI3K activity in DMS114 cells as evidenced by approximately 25% increase in activity. This data is also consistent with the hypothesis that AKT is the direct or indirect target of COTI-2 because inhibiting AKT results in the inhibition of its downstream targets mTORC1 and S6K (S6 kinase 1), which are involved in a negative-feedback loop that blocks signaling to PI3K (Biochem. Soc. Trans. 37: 217-222). Therefore, the inhibition of AKT prevents the activation of the negative-feedback loop and allows the increased activity of PI3K.

Figure 13:
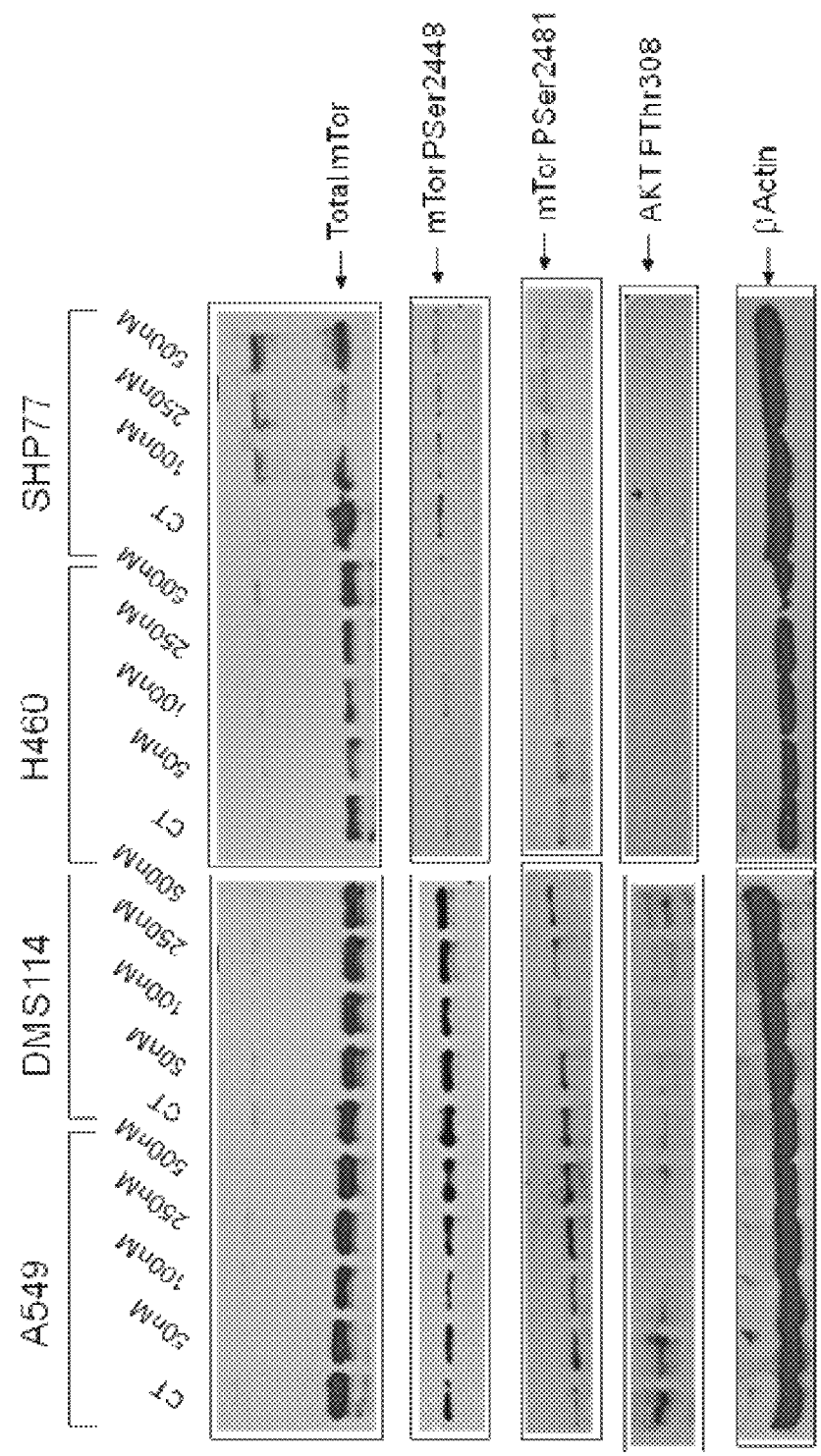
FIG. 13 shows an effect of various concentrations of COTI-2 relative to control (DMSO) on total mTOR, mTOR phospho-Ser2448, mTOR phospho-Ser2481, and Akt phospho-Thr308 levels, β actin levels act as positive controls for the experiment.

In conclusion, since COTI-2 does not act on PI3K, it does not inhibit AKT via upstream regulation. COTI-2 therefore seems to prevent the activation of AKT through direct interaction.
COTI-2 Impairs mTOR Activation and Decreases Phospho-Thr308 Levels of PKB/Akt:

Four cancer cell lines, namely A549 & H460 (NSCLC) and DMS114 & SHP77 (SCLC), were treated for 4 h with various concentrations of COTI-2 or DMSO (solvent). Similar levels of total mTOR, before and after incubation with COTI-2, were observed in A549, H460, and DMS114 cell lines (FIG. 13). In SHP77 cells, more than in the other cell lines, a higher order complex that reacted positive with mTOR antibody, but not with other antibodies, accumulated at the bottom of the loading wells and was not resolved by SDS-PAGE. Presumably because of this, less mTOR was detected at the appropriate molecular weight on the western blot. One possible interpretation of this finding is that in this cell line, COTI-2 could preferentially bind to mTOR or to one of its complexes with Rictor, Raptor, or other proteins, resulting in large protein aggregates that may be functionally impaired. Consistent with this, the level of mTOR phospho-Ser2448 that is necessary for mTOR activity was also reduced in this cell line. Taken together with previous results showing that COTI-2 decreases phospho-Ser473 levels of PKB/Akt, these findings suggested that in SCLC cells, COTI-2 inhibits mTOR activity, and consequently the activity of PKB/Akt. PKB/Akt phospho-Thr308 levels decreased in A549 cells (and to a lesser extent in SHP 77 cells, shown by the asterisk) after incubation with COTI-2.

These experiments provide further evidence that COTI-2 acts to inhibit Akt phosphorylation through mTOR-Rictor complex formation.

Example 15

Synergistic Effect with mTOR Inhibitors

Effects of Temsirolimus and Rapamycin on the Cytotoxicity of COTI-219 and COTI-2 Against the Human Glioblastoma Cell Line U87

Figure 14:
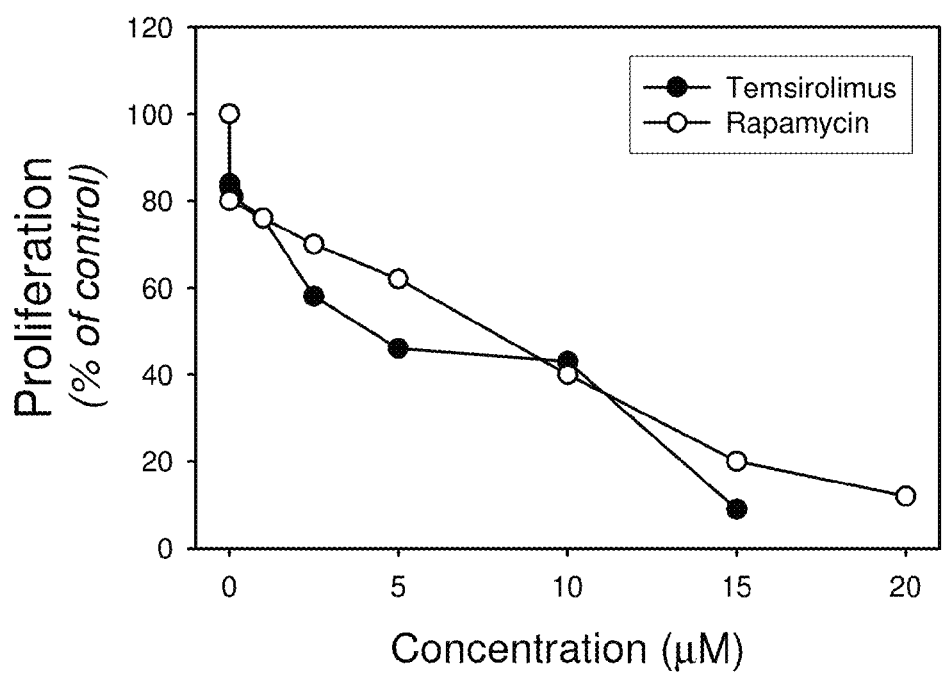
FIG. 14 shows that temsirolimus and rapamycin both inhibit proliferation of human U87 glioblastoma cells, as single agents.

In vitro IC50 values were obtained for combinations of compounds of the present invention with temsirolimus or rapamycin in the treatment of U87 glioblastoma cells. Temsirolimus and rapamycin both inhibit proliferation of human U87 glioblastoma cells, as single agents (FIG. 14). FIG. 14 shows the typical dose-response of U87 cells to temsirolimus or rapamycin. Both inhibit proliferation of these cells with increasing concentration. Over triplicate experiments: $IC_{50}$ (Temsirolimus)=3.6 μM±1.4 μM and $IC_{50}$ (Rapamycin)=9.9 μM±1.8 μM.

It was found that both temsirolimus and rapamycin, in combination with COTI-219, exert greater-than-additive growth inhibitory effects on U87 cells. Both temsirolimus and rapamycin, in combination with COTI-2 (at COTI-2 concentrations less than the IC50), exert some greater-than-additive growth inhibitory effects on U87 cells.

In Combination with COTI-219, Temsirolimus Had a Greater-than-Additive Inhibitory Effect on Proliferation of U87 Glioblastoma Cells Temsirolimus was provided in liquid form from the London Regional Cancer Program (LRCP) Pharmacy. COTI-219 was prepared as a 50 mM stock in DMSO, then diluted to 10 mM in DMSO followed by serial dilution water for addition to medium overlaying cells. Cells were incubated with temsirolimus in combination with COTI-219 for 4 days (in wells of 96 well plates) followed by analysis of live cell density using the fluorescent vital stain alamarBlue.

Figure 15:
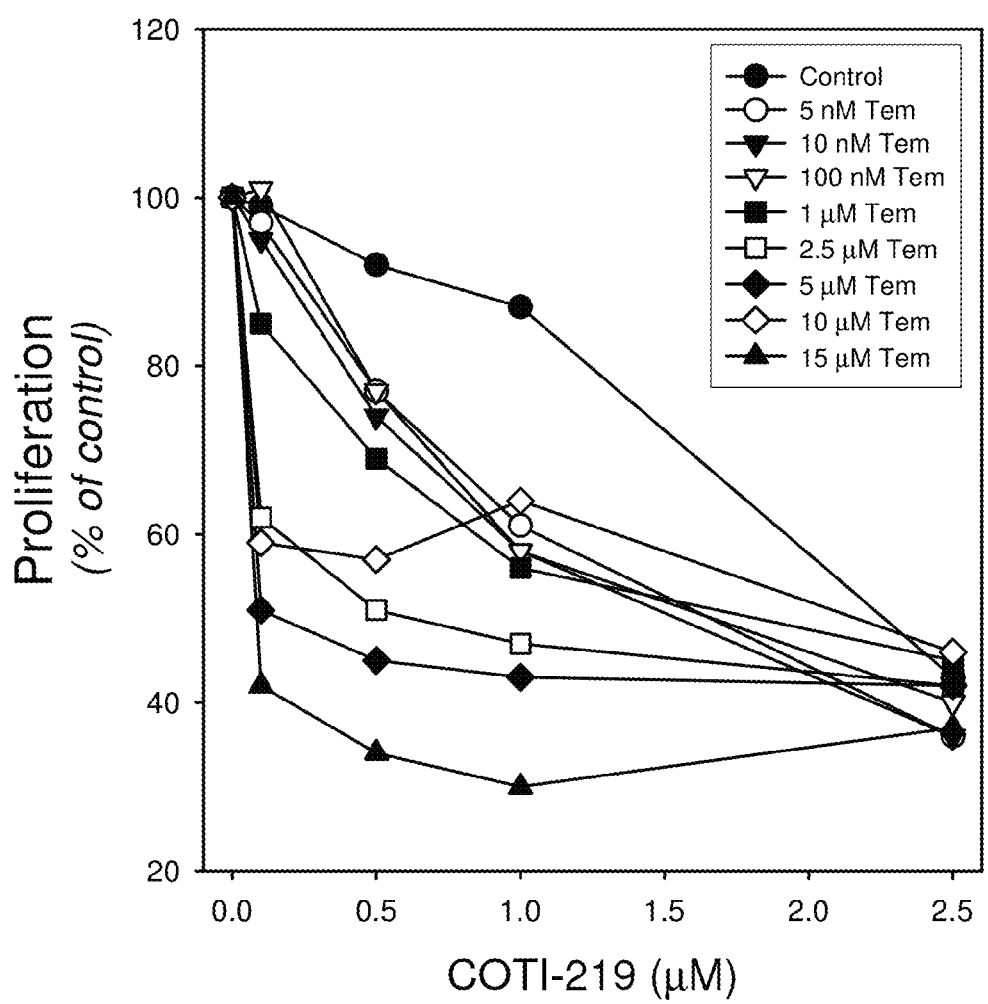
FIG. 15 shows that COTI-219, in combination with temsirolimus, had a greater-than-additive inhibitory effect on proliferation of U87 glioblastoma cells.

Referring to FIG. 15, relative cell density was plotted against concentration of COTI-219, normalized to the inhibitory effect of temsirolimus alone (this ranged from 20-30% inhibition at very low concentrations to 80-90% inhibition at the higher end of concentrations used in this study). Thus, data points indicating proliferation less than control values indicate greater-than-additive inhibition of proliferation by COTI-219 plus temsirolimus. All data points are means±SEM (n=6). Error bars are, in every case, smaller than the size of the symbol.

Temsirolimus (10 nM or greater) plus 0.1 µM COTI-219 had greater-than-additive inhibition of proliferation. All temsirolimus concentrations plus 0.5 or 1.0 µM COTI-219 had greater-than-additive effects.

In Combination with COTI-219, Rapamycin Had a Strongly Greater-than-Additive Inhibitory Effect on Proliferation of U87 Glioblastoma Cells Rapamycin was prepared by crushing and extracting a tablet (supplied from the LRCP Pharmacy) with DMSO, followed by centrifugation to remove particulate matter. COTI-219 was prepared as a 50 mM stock in DMSO, then diluted to 10 mM in DMSO followed by serial dilution water for addition to medium overlaying cells. Cells were incubated with rapamycin in combination with COTI-219 for 4 days (in wells of 96 well plates) followed by analysis of live cell density using the fluorescent vital stain alamarBlue.

Figure 16:
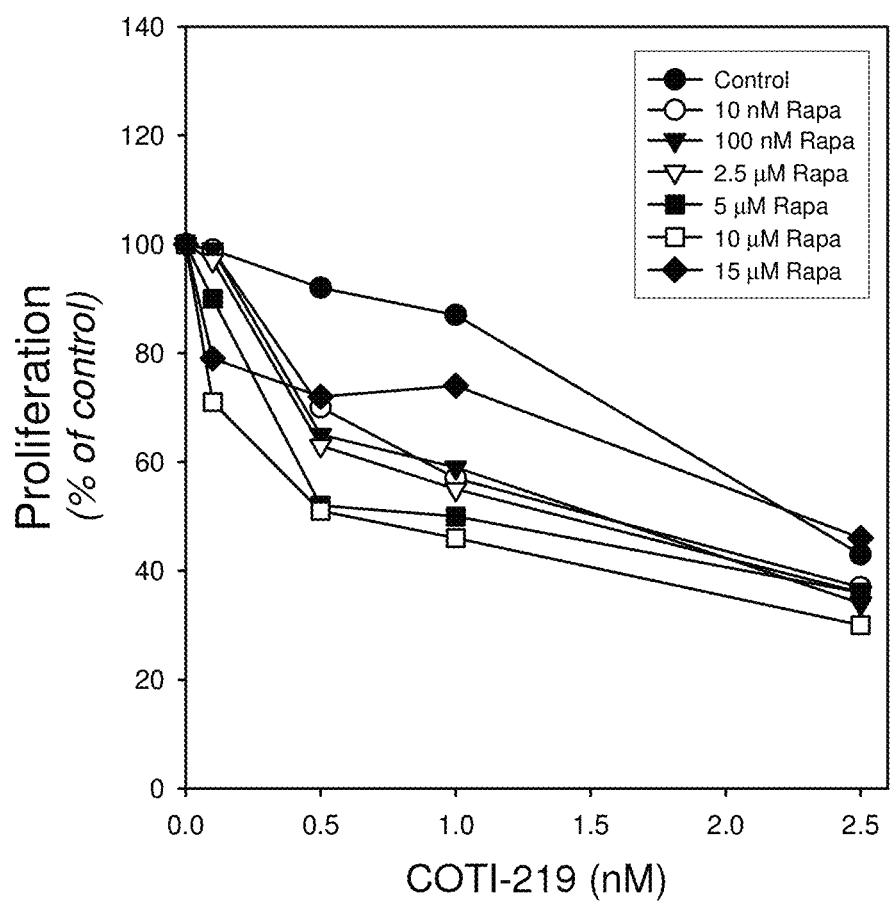
FIG. 16 shows that COTI-219, in combination with rapamycin, had a greater-than-additive inhibitory effect on proliferation of U87 glioblastoma cells.

Referring to FIG. 16, relative cell density was plotted against concentration of COTI-219, normalized to the inhibitory effect of rapamycin alone (this ranged from 20-30% inhibition at very low concentrations to 80-90% inhibition at the higher end of concentrations used in this study). Thus, data points indicating proliferation less than control values indicate greater-than-additive inhibition of proliferation by COTI-219 plus rapamycin.

All data points are means±SEM (n=6). Error bars are, in every case, smaller than the size of the symbol.

Rapamycin (5 µM or greater) plus 0.1 µM COTI-219 had greater-than-additive inhibition of proliferation. All rapamycin concentrations plus 0.5 or 1.0 µM COTI-219 had greater-than-additive effects.

In Combination with COTI-2, Temsirolimus Had a Greater-than-Additive Inhibitory Effect on Proliferation of U87 Glioblastoma Cells Temsirolimus was provided in liquid form from the LRCP Pharmacy. COTI-2 was prepared as a 50 mM stock in DMSO, then diluted to 10 mM in DMSO followed by serial dilution water for addition to medium overlaying cells. Cells were incubated with temsirolimus in combination with COTI-2 for 4 days (in wells of 96 well plates) followed by analysis of live cell density using the fluorescent vital stain alamarBlue.

Figure 17:
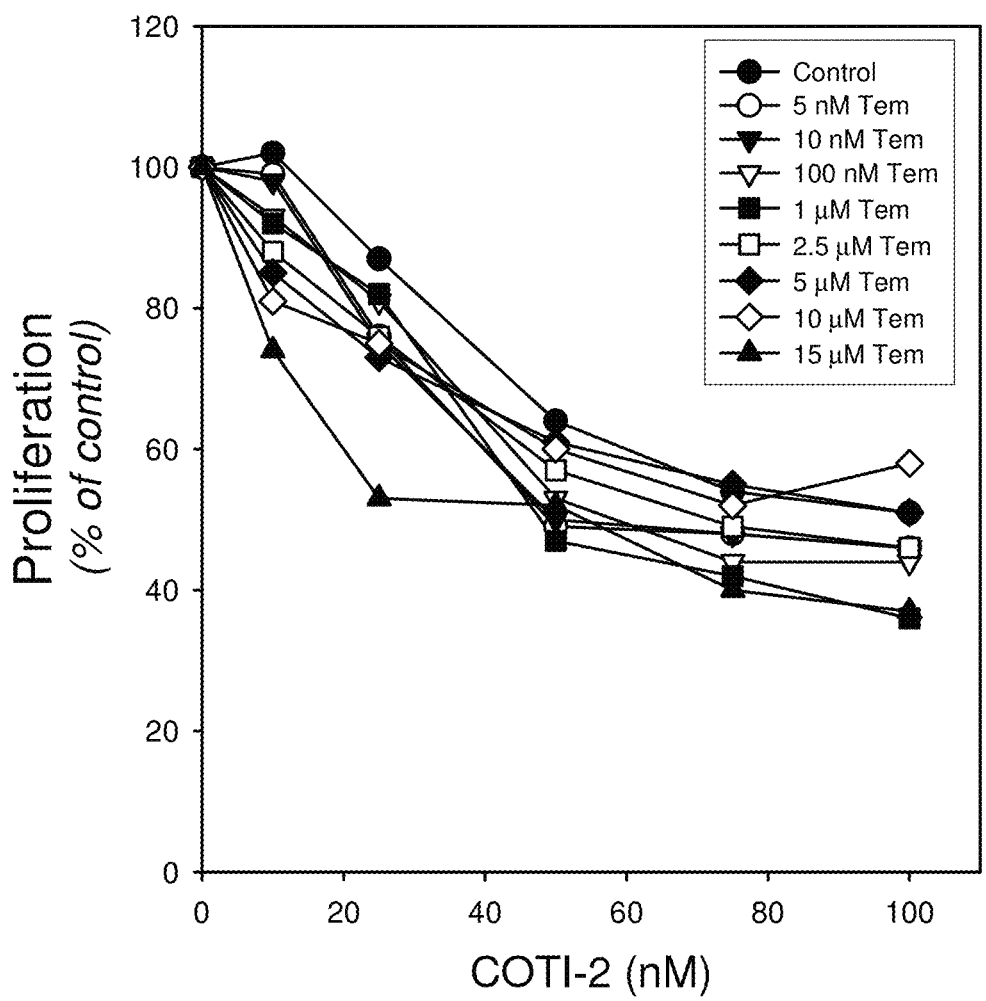
FIG. 17 shows that COTI-2, in combination with temsirolimus, had a greater-than-additive inhibitory effect on proliferation of U87 glioblastoma cells.

Referring to FIG. 17, relative cell density was plotted against concentration of COTI-2, normalized to the inhibitory effect of temsirolimus alone (this ranged from 20-30% inhibition at very low concentrations to 80-90% inhibition at the higher end of concentrations used in this study). Thus, data points indicating proliferation less than control values indicate greater-than-additive inhibition of proliferation by COTI-2 plus temsirolimus.

All data points are means±SEM (n=6). Error bars are, in every case, smaller than the size of the symbol.

Temsirolimus (100 nM or greater) plus 10 nM COTI-2 had greater-than-additive inhibition of proliferation. All temsirolimus concentrations plus 25, 50, or 75 nM COTI-2 had greater-than-additive effects.

In Combination with COTI-2, Rapamycin Had Either a Greater-than-Additive Inhibitory Effect or a Potentially Antagonistic Effect, at High Concentration, on Proliferation of U87 Glioblastoma Cells Rapamycin was prepared by crushing and extracting a tablet (supplied from the LRCP Pharmacy) with DMSO, followed by centrifugation to remove particulate matter. COTI-2 was prepared as a 50 mM stock in DMSO, then diluted to 10 mM in DMSO followed by serial dilution water for addition to medium overlaying cells. Cells were incubated with rapamycin in combination with COTI-2 for 4 days (in wells of 96 well plates) followed by analysis of live cell density using the fluorescent vital stain alamarBlue.

Figure 18:
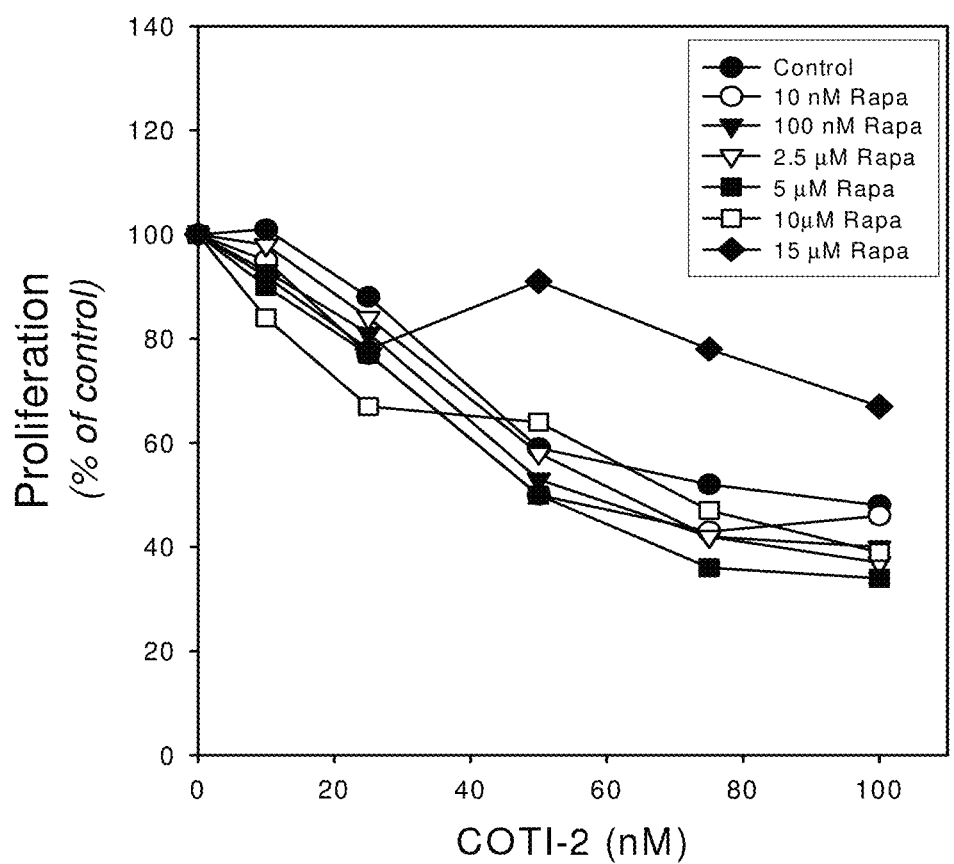
FIG. 18 shows that COTI-2, in combination with rapamycin, had a greater-than-additive inhibitory effect on proliferation of U87 glioblastoma cells.

Referring to FIG. 18, relative cell density was plotted against concentration of COTI-2, normalized to the inhibitory effect of rapamycin alone (this ranged from 20-30% inhibition at very low concentrations to approximately 50% inhibition at the higher end of concentrations). Thus, data points indicating proliferation less than control values indicate greater-than-additive inhibition of proliferation by COTI-2 plus rapamycin.

All data points are means±SEM (n=6). Error bars are, in every case, smaller than the size of the symbol.

All concentrations of rapamycin plus 10 or 25 nM COTI-2 resulted in greater-than-additive inhibition of proliferation. High rapamycin concentration (15 µM) may have antagonized COTI-2 when COTI-2 was used at concentrations of 50 nM or higher. COTI-2 (50 nM or higher) had additive or greater-than-additive effects with rapamycin (10 µM or lower).

In conclusion, these experiments show that synergistic improvements in efficacy are obtained for combinations of mTOR-Raptor inhibitors, such as temsirolimus and rapamycin, with mTOR-Rictor inhibitors, such as COTI-2 and COTI-219, in the treatment of cancer, particularly cancers that are treatable by mTOR inhibitors.

Example 16

Synergistic Effect with Cytotoxic Agents

Figure 19:
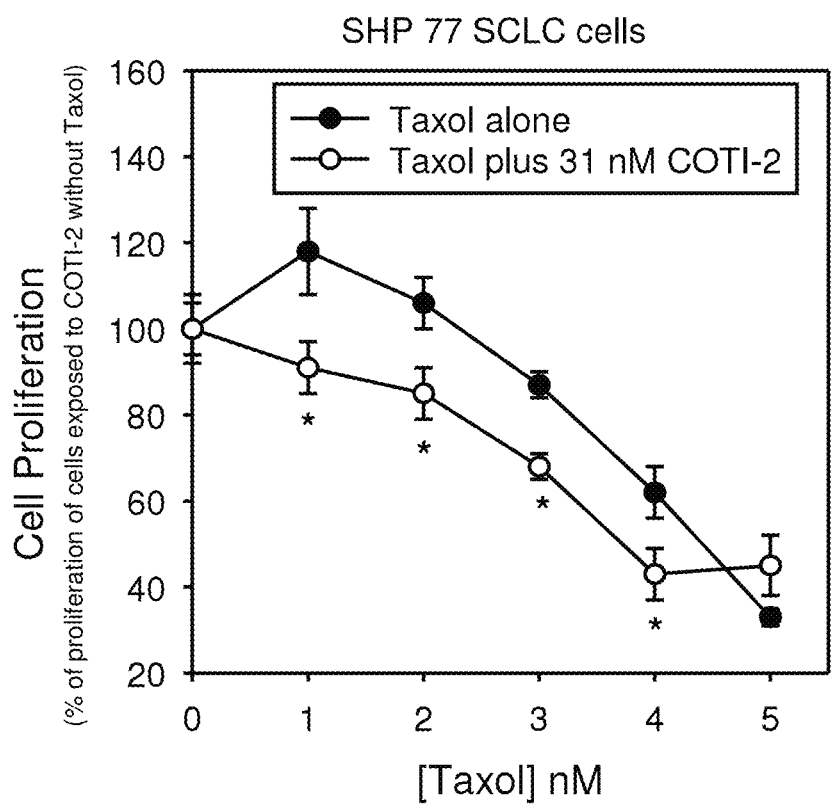
FIG. 19 shows SHP 77 cells treated with Taxol™ or with Taxol™ plus COTI-2.
Figure 20:
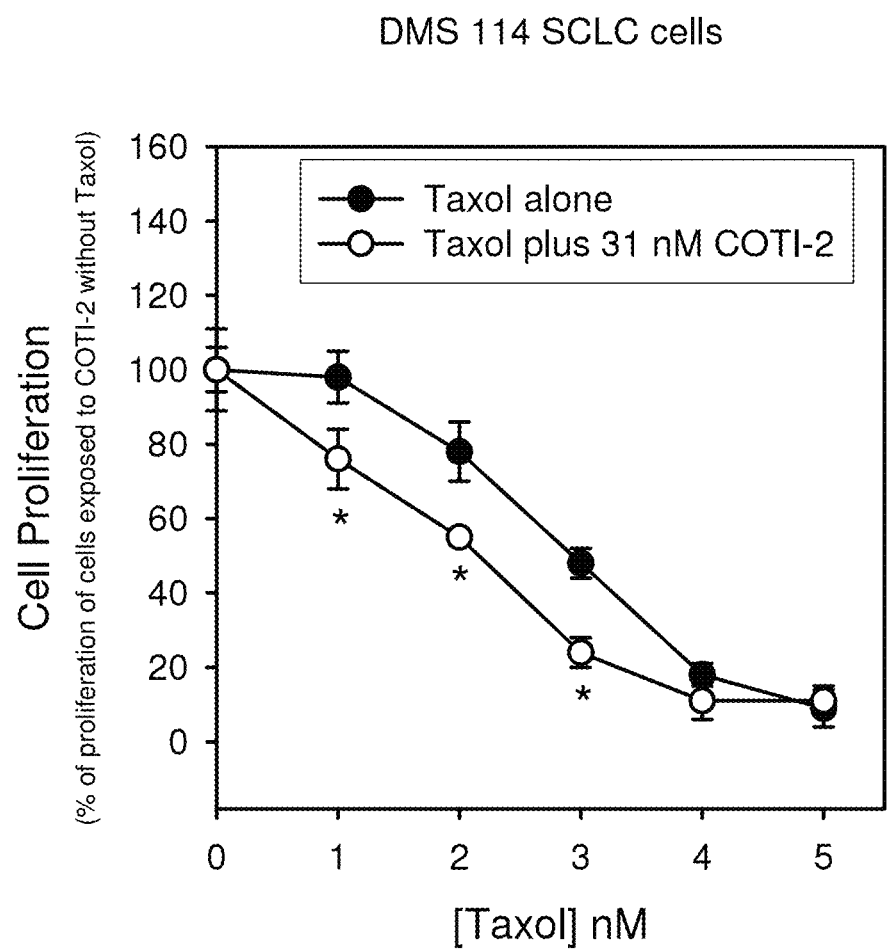
FIG. 20 shows DMS114 cells treated with Taxol™ or with Taxol™ plus COTI-2.
Figure 21:
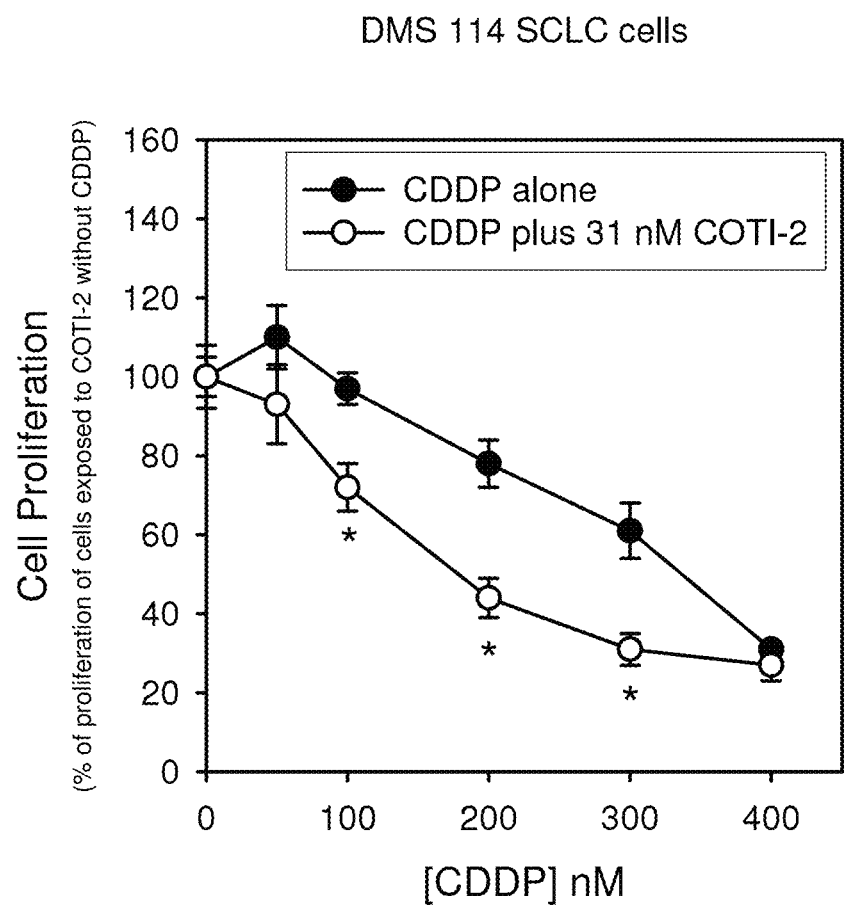
FIG. 21 shows DMS114 cells treated with cisplatin (CDDP) or with CDDP plus COTI-2.

A synergistic effect or greater than additive benefit may be observed when compounds described herein are administered in combination with other anti-cancer agents, in particular cytotoxic agents such as cisplatin, carboplatin and paclitaxel (see FIGS. 19-22). In FIG. 19, SHP 77 cells were treated with Taxol™ at the concentrations shown or with Taxol™ plus COTI-2 (31 nM, which, as a single agent, reduces proliferation by 25%). The combination of COTI-2 and Taxol™ has a greater-than-additive effect (indicated by differences between data points at each concentration) where indicated by asterisks. In FIG. 20, DMS114 cells were treated with Taxol™ at the concentrations shown or with Taxol™ plus COTI-2 (31 nM, which, as a single agent, reduces proliferation by 25%). The combination of COTI-2 and Taxol™ has a greater-than-additive effect (indicated by differences between data points at each concentration) where indicated by asterisks. In FIG. 21, DMS114 cells were treated with cisplatin (CDDP) at the concentrations shown or with CDDP plus COTI-2 (31 nM, which, as a single agent, reduces proliferation by 25%). The combination of COTI-2 and CDDP has a greater-than-additive effect (indicated by differences between data points at each concentration) where indicated by asterisks.

Figure 22:
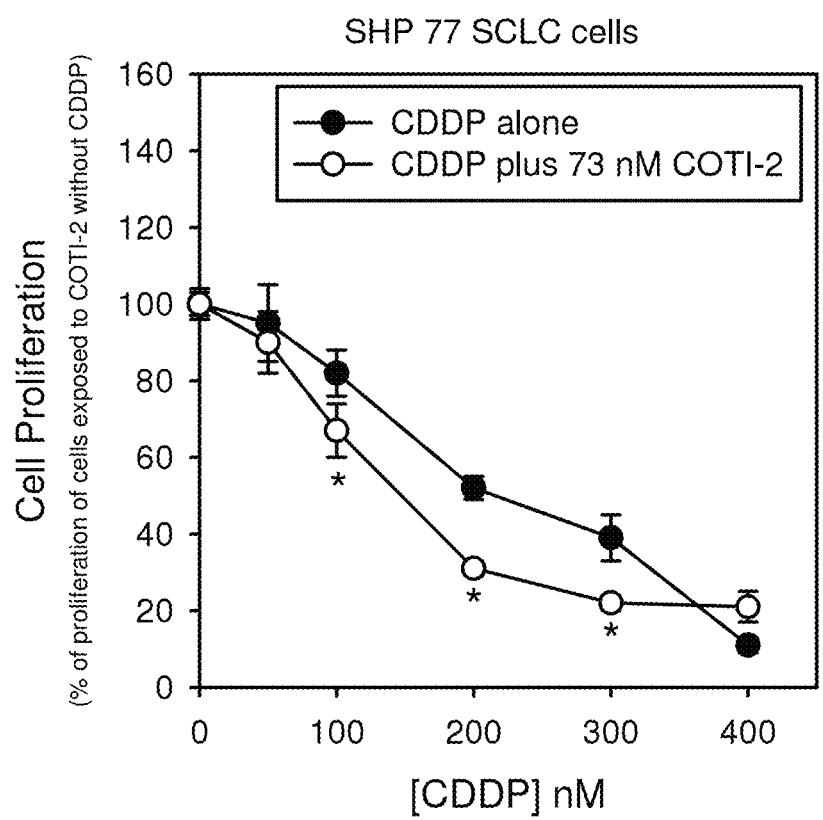
FIG. 22 shows SHP 77 cells treated with cisplatin (CDDP) or with CDDP plus COTI-2.
Figure 23:
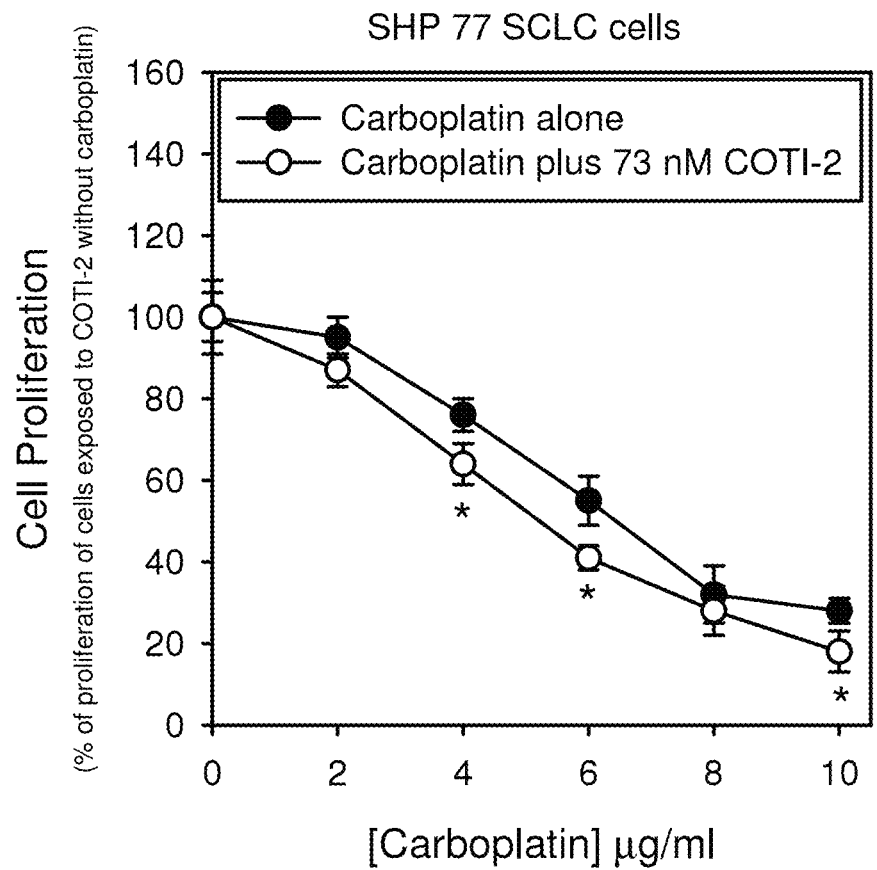
FIG. 23 shows SHP 77 cells treated with carboplatin or with carboplatin plus COTI-2.
Figure 24:
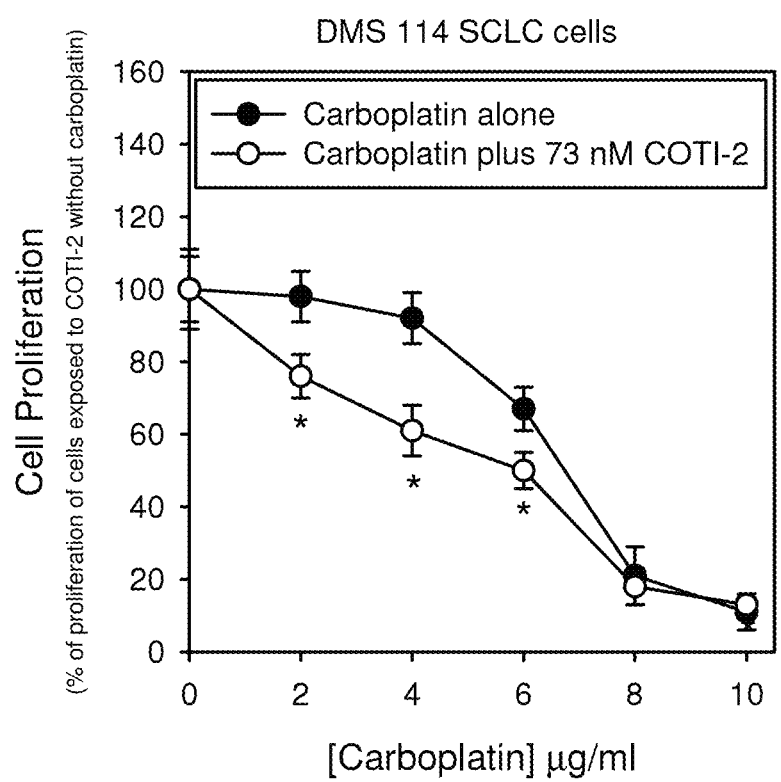
FIG. 24 shows DMS114 cells treated with carboplatin or with carboplatin plus COTI-2.
Figure 25:
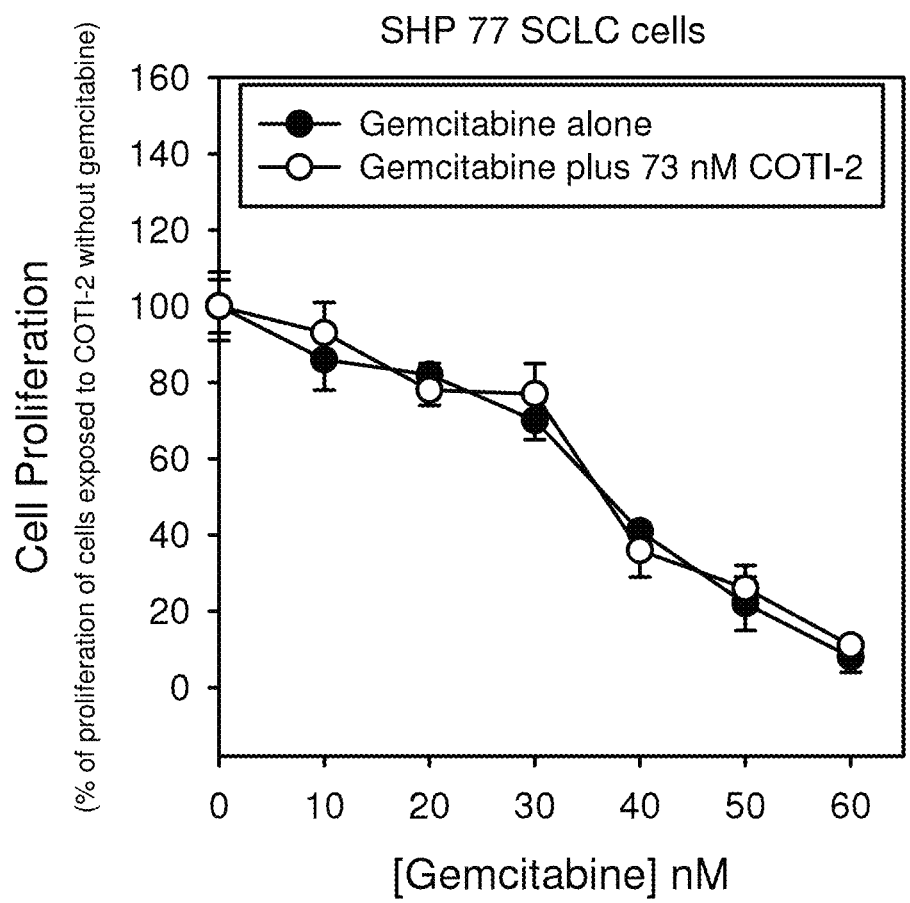
FIG. 25 shows SHP 77 cells treated with gemcitabine alone or with gemcitabine plus COTI-2.
Figure 26:
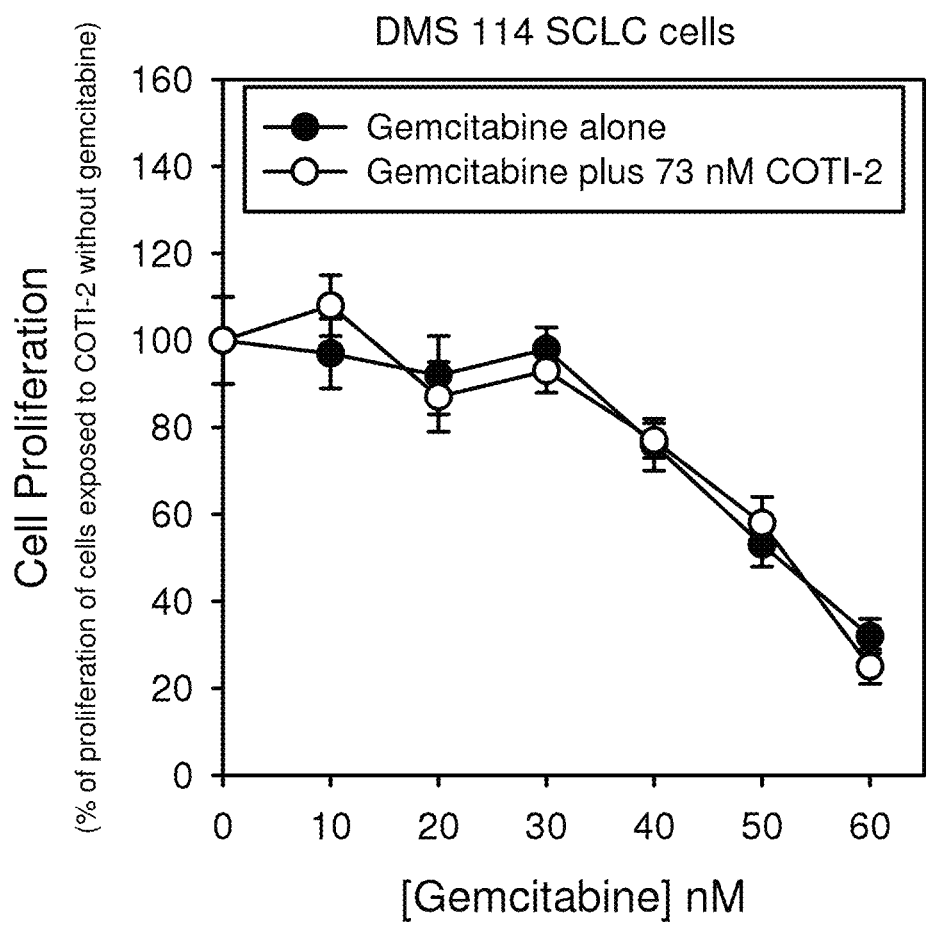
FIG. 26 shows DMS114 cells treated with gemcitabine alone or with gemcitabine plus COTI-2.
Figure 27:
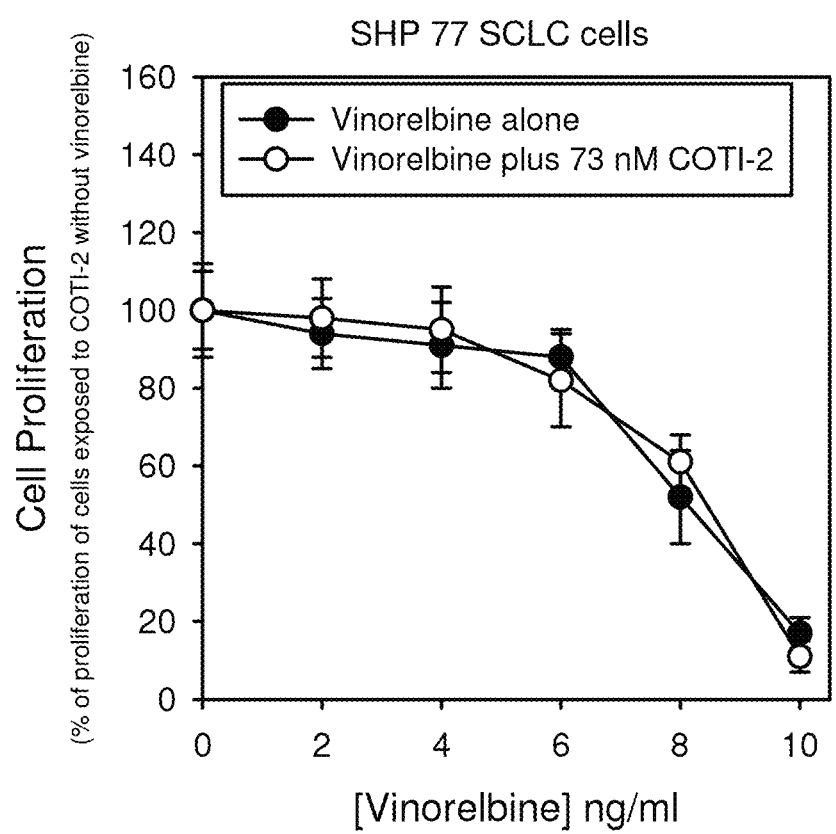
FIG. 27 shows SHP 77 cells treated with vinorelbine alone or with vinorelbine plus COTI-2.
Figure 28:
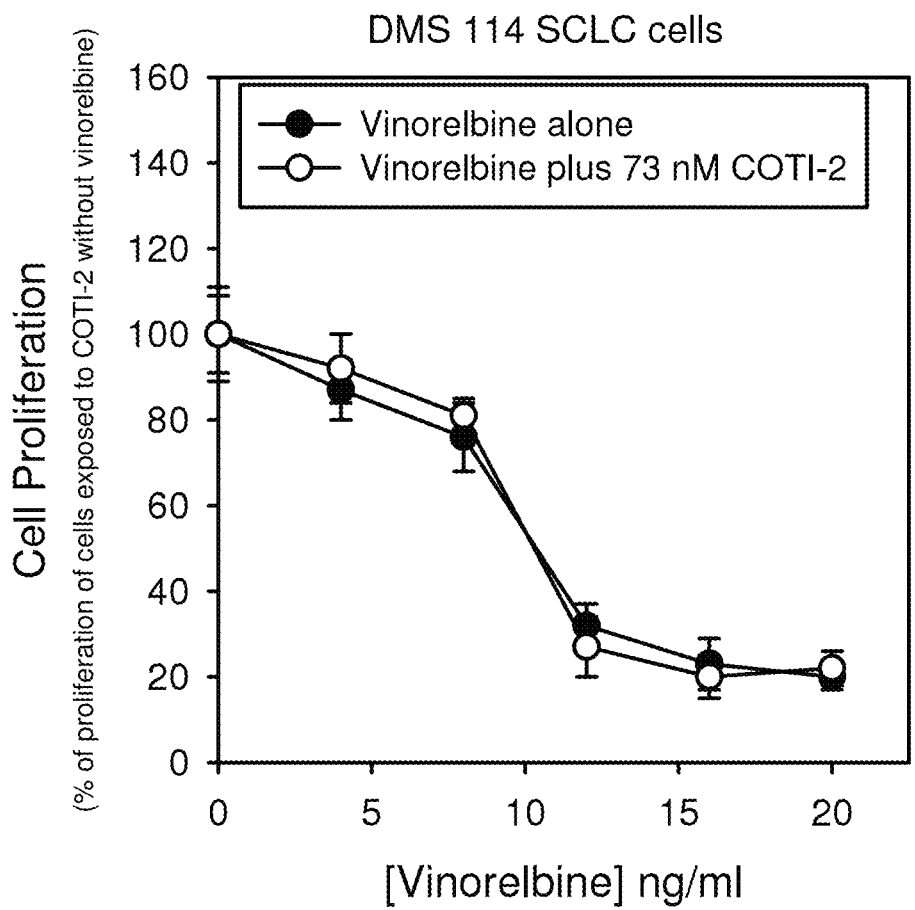
FIG. 28 shows DMS114 cells treated with vinorelbine alone or with vinorelbine plus COTI-2.
Figure 29A:
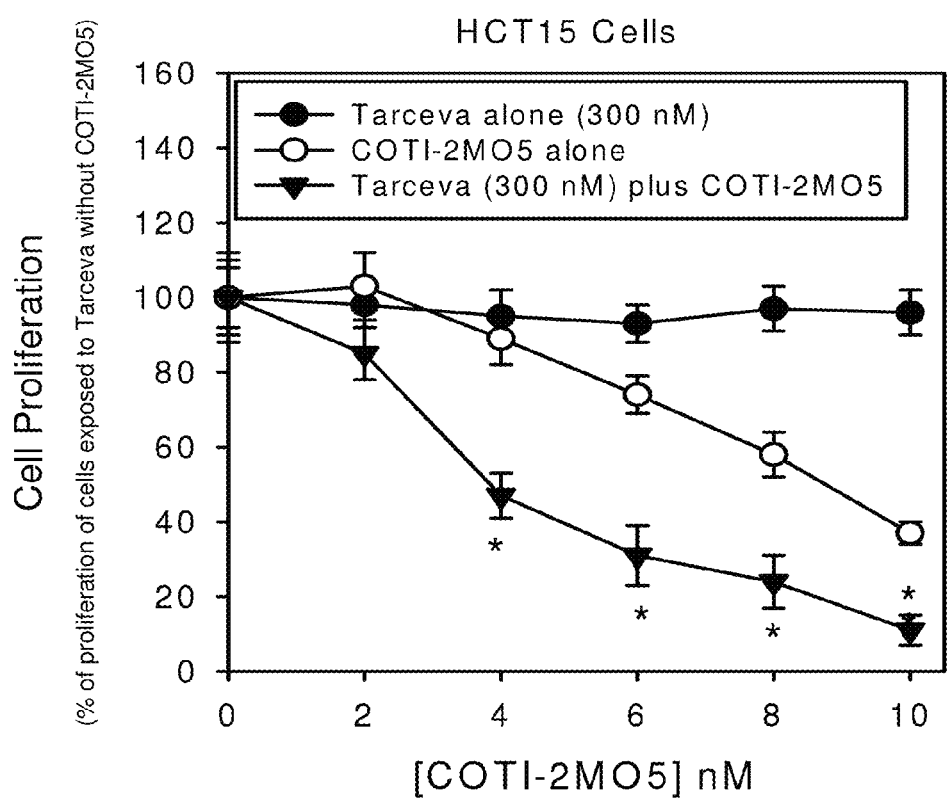
FIGS. 29A-C show greater-than-additive effects of COTI-2 in combination with Tarceva in HCT-15 (FIG. 29A), COLO-205 (FIG. 29B), and SW620 (FIG. 29C) cells.
Figure 29B:
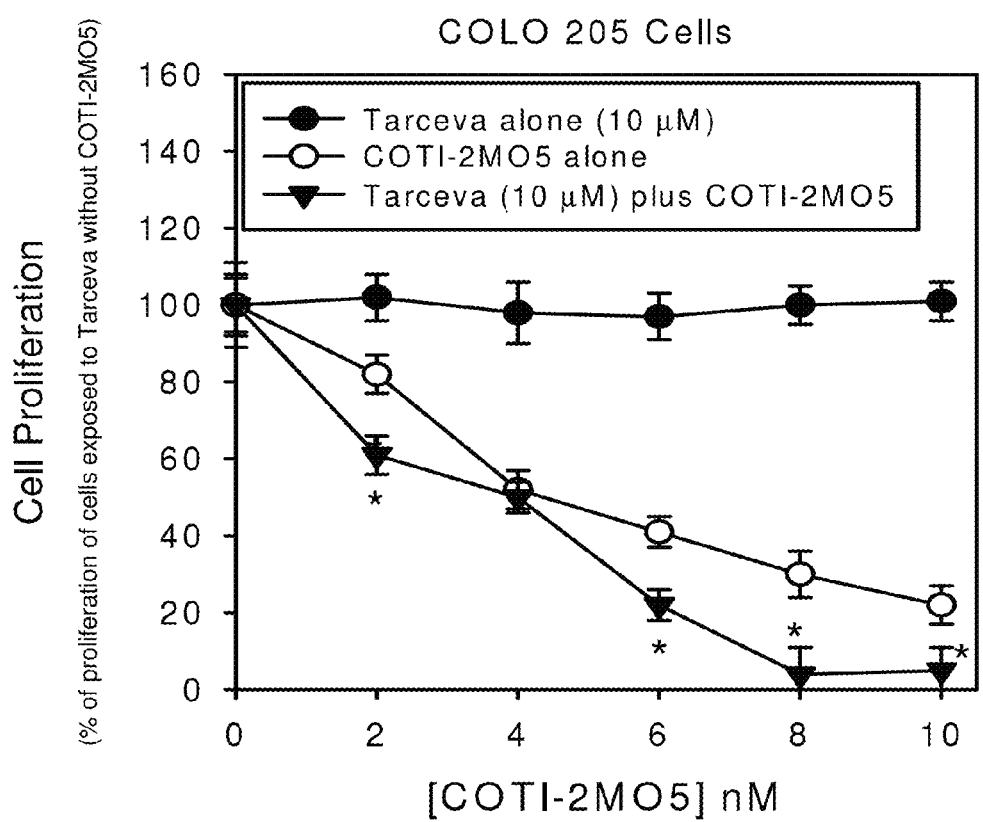
Figure 29C:
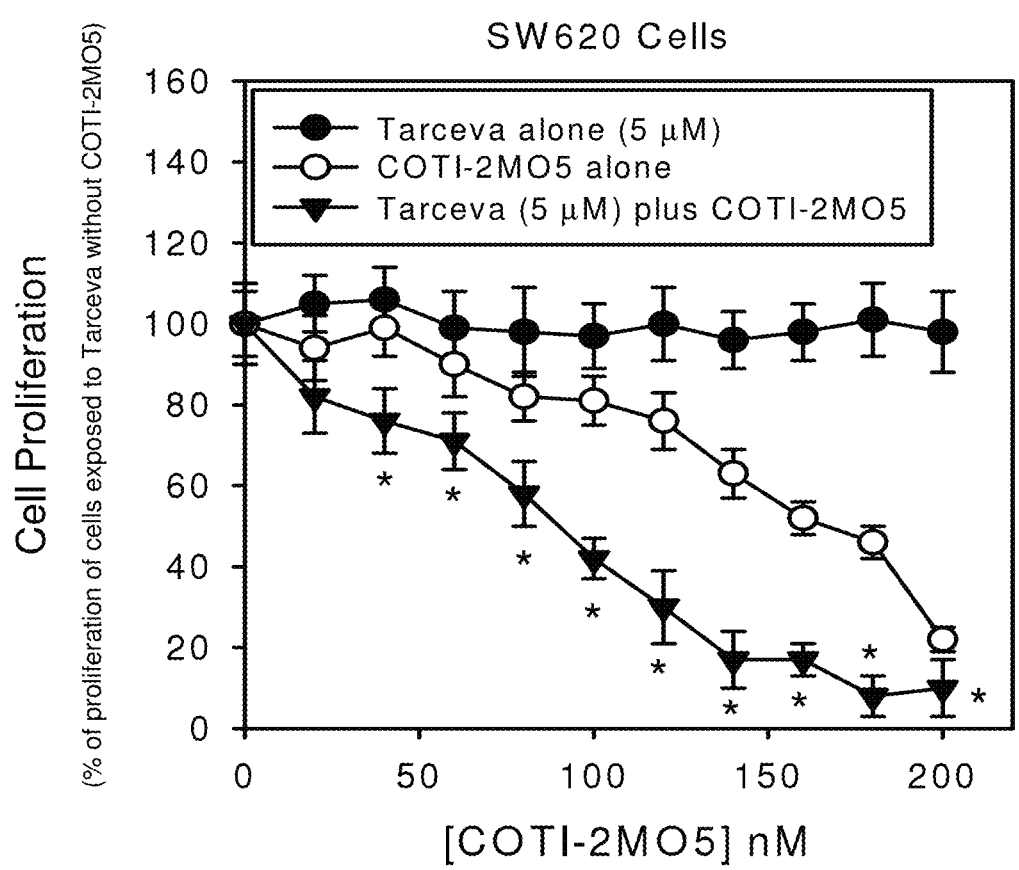
Figure 30A:
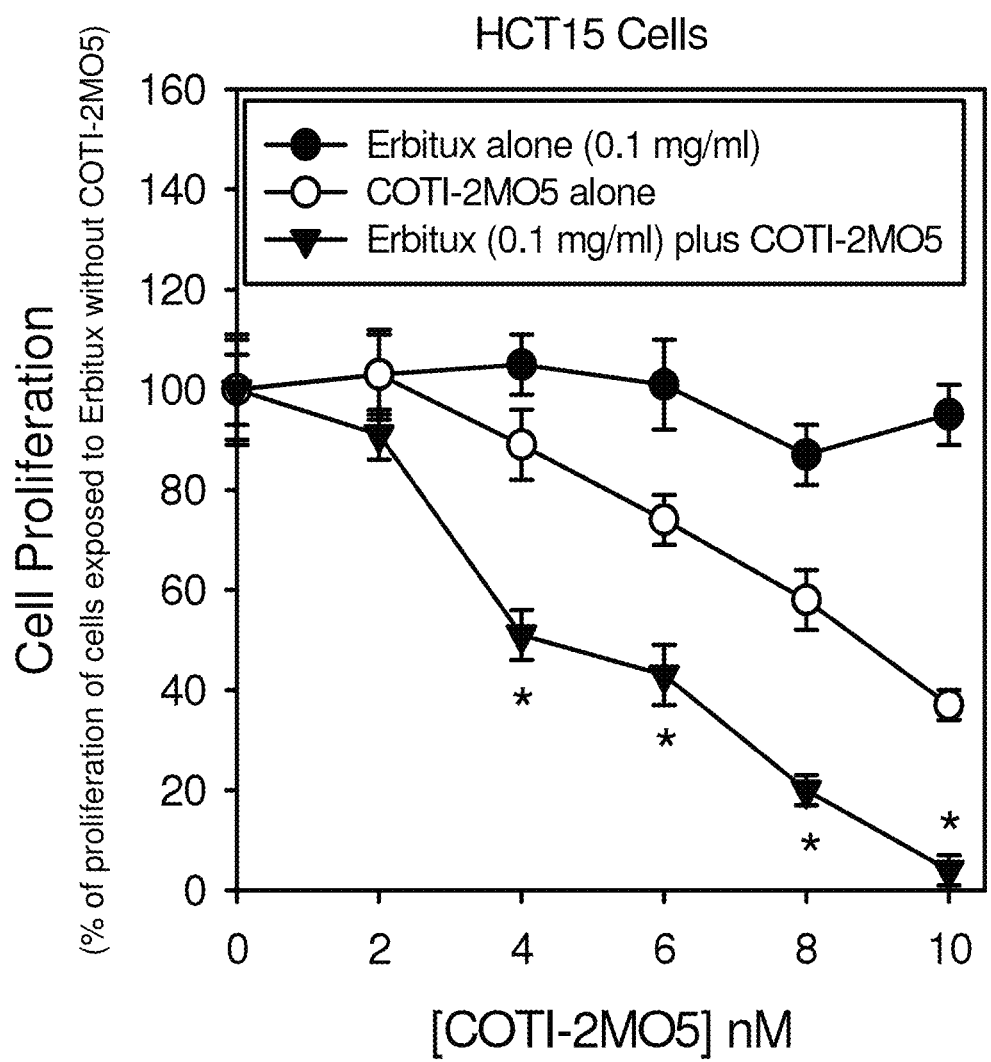
FIGS. 30A-C show greater-than-additive effects of COTI-2 in combination with Erbitux® in HCT-15 (FIG. 30A), COLO-205 (FIG. 30B), and SW620 cells (FIG. 30C)
Figure 30B:
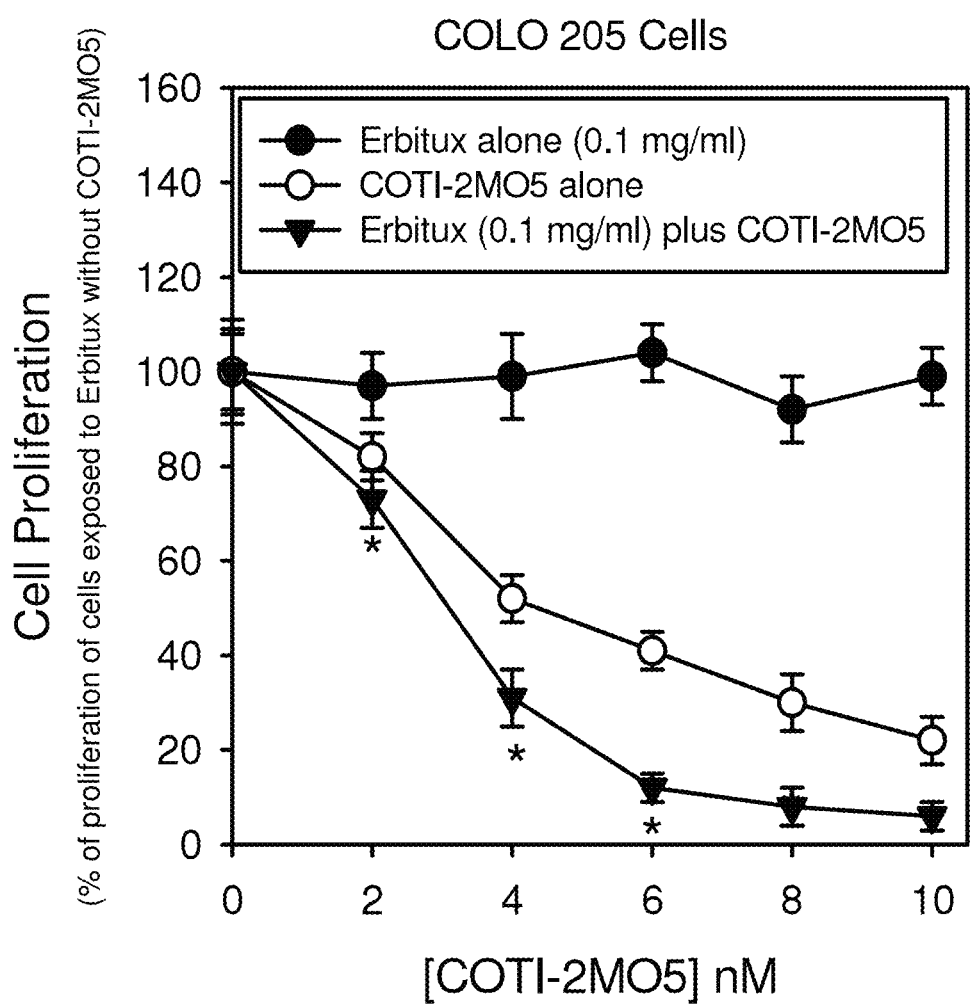
Figure 30C:
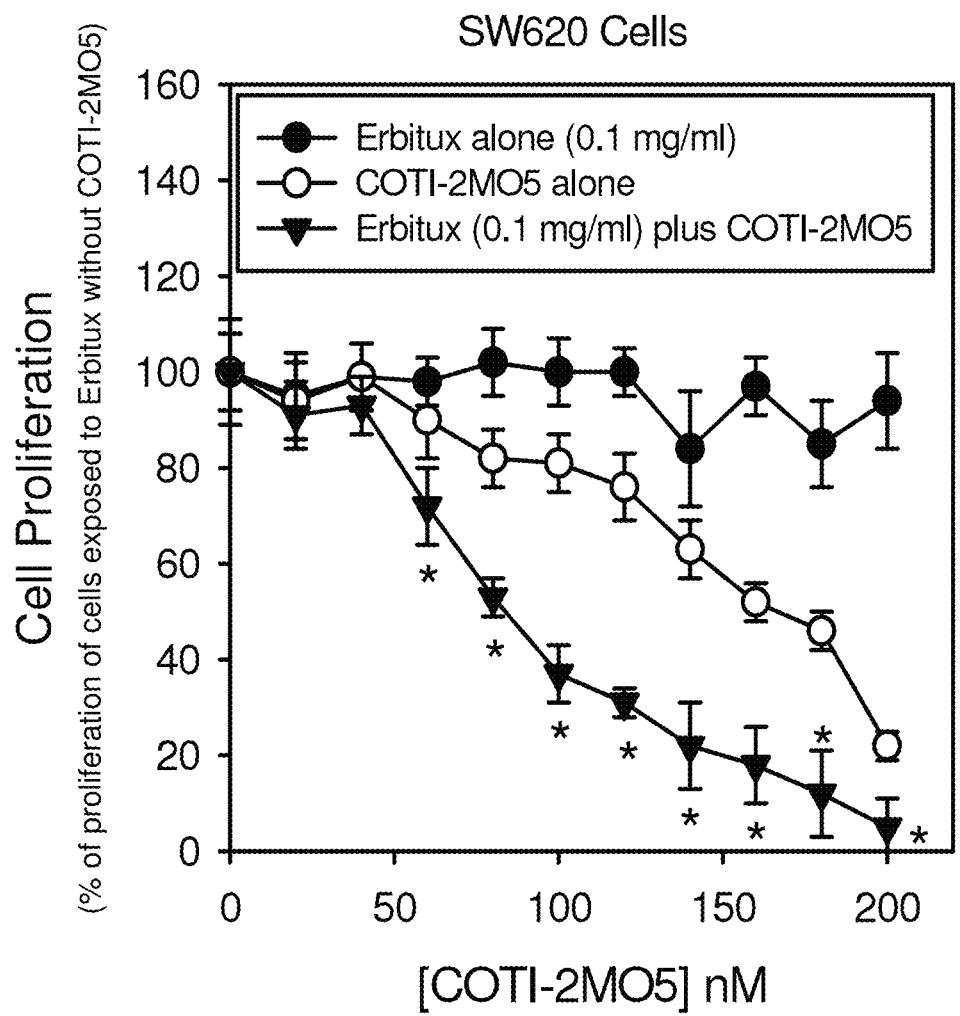
Figure 31A:
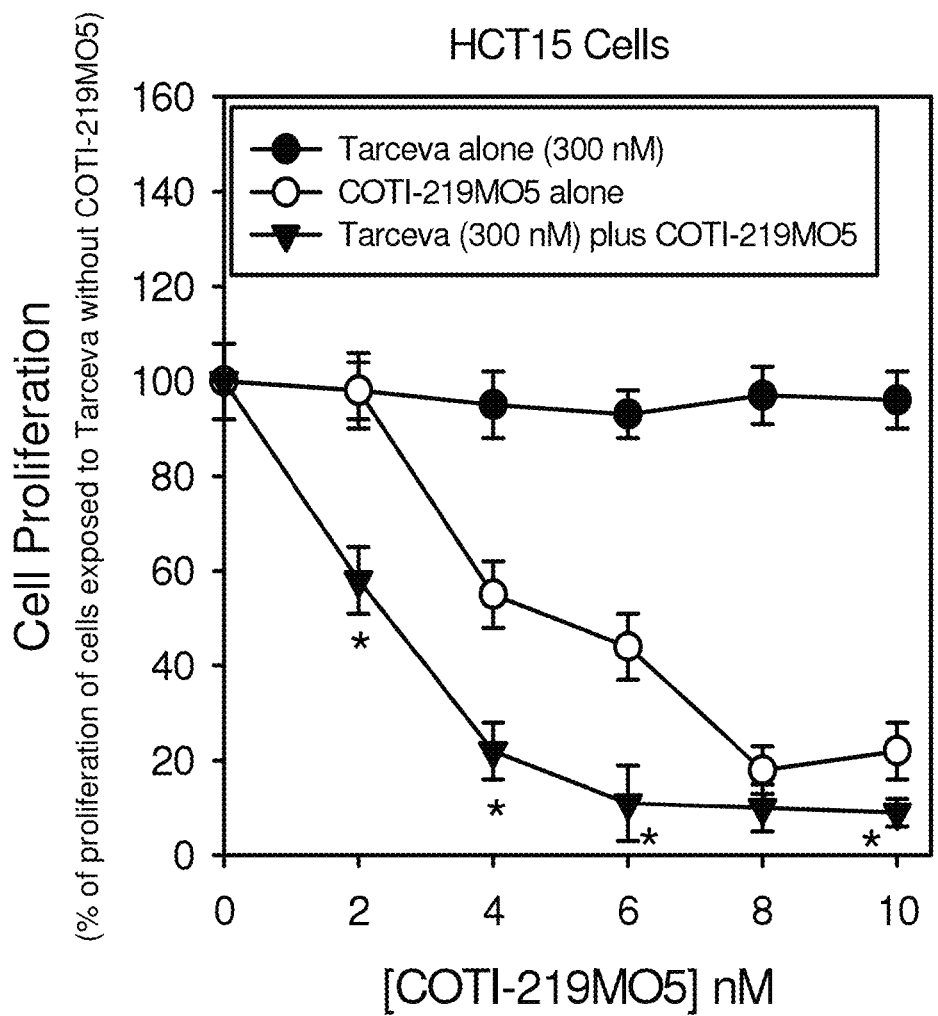
FIGS. 31A-C show greater-than-additive effects of COTI-219 in combination with Tarceva® in HCT-15 (FIG. 31A), COLO-205 (FIG. 31B), and SW620 cells (FIG. 31C)
Figure 31B:
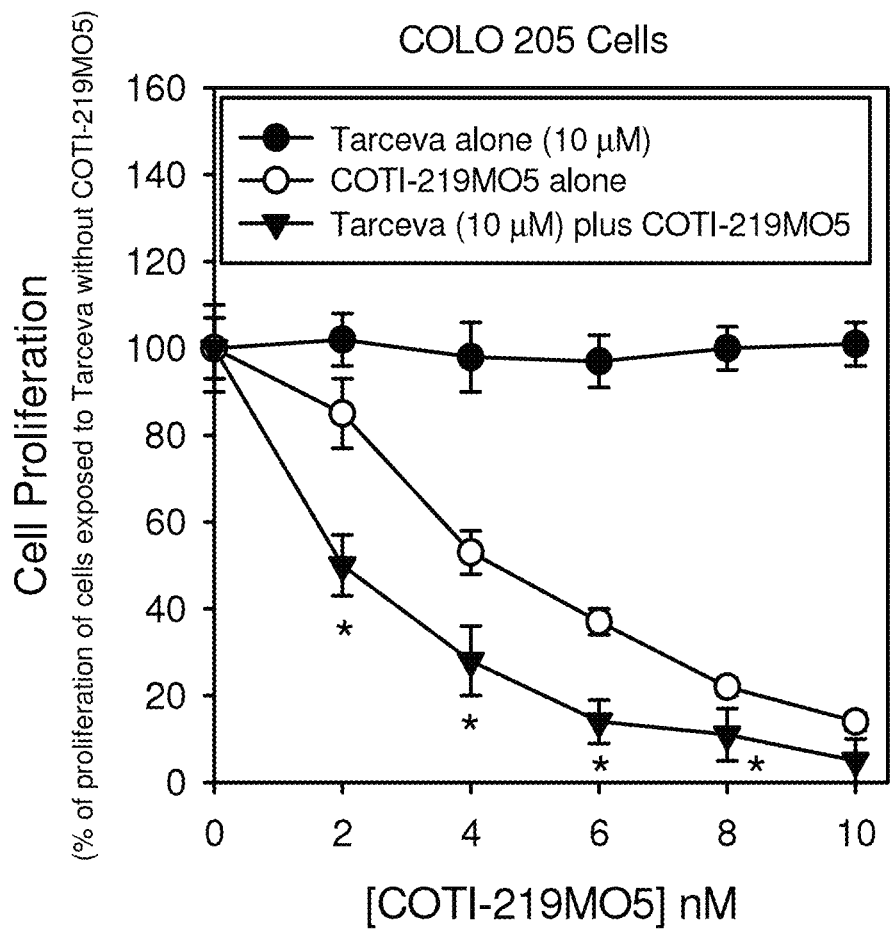
Figure 31C:
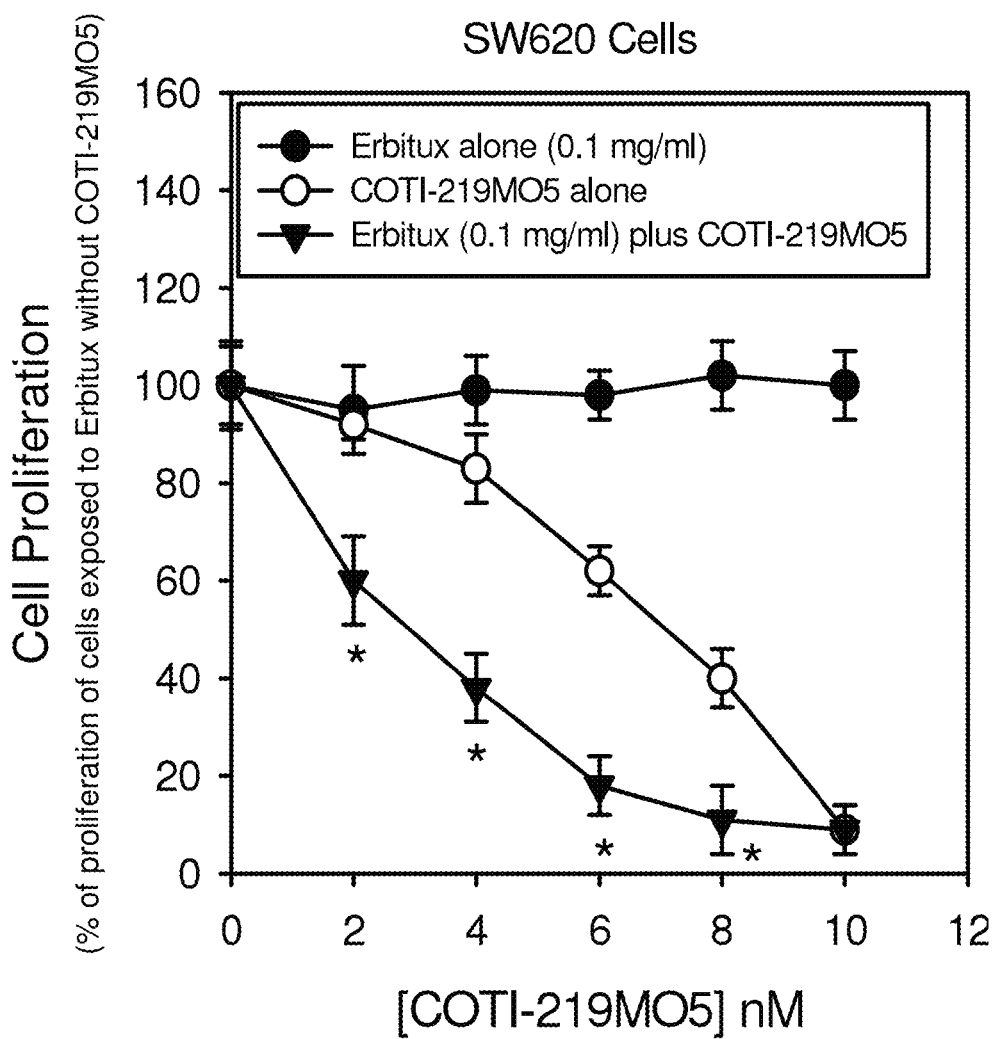
Figure 32A:
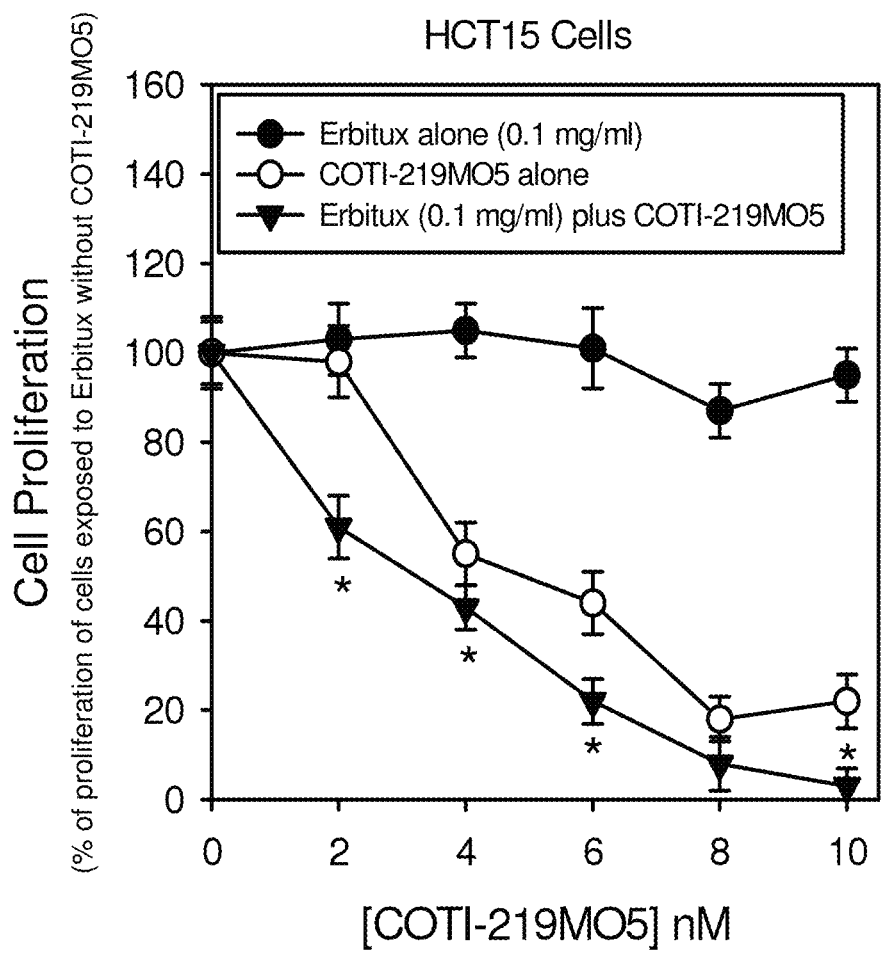
FIGS. 32A-C show greater-than-additive effects of COTI-219 in combination with Erbitux® in HCT-15 (FIG. 32A), COLO-205 (FIG. 32B), and SW620 cells (FIG. 32C)
Figure 32B:
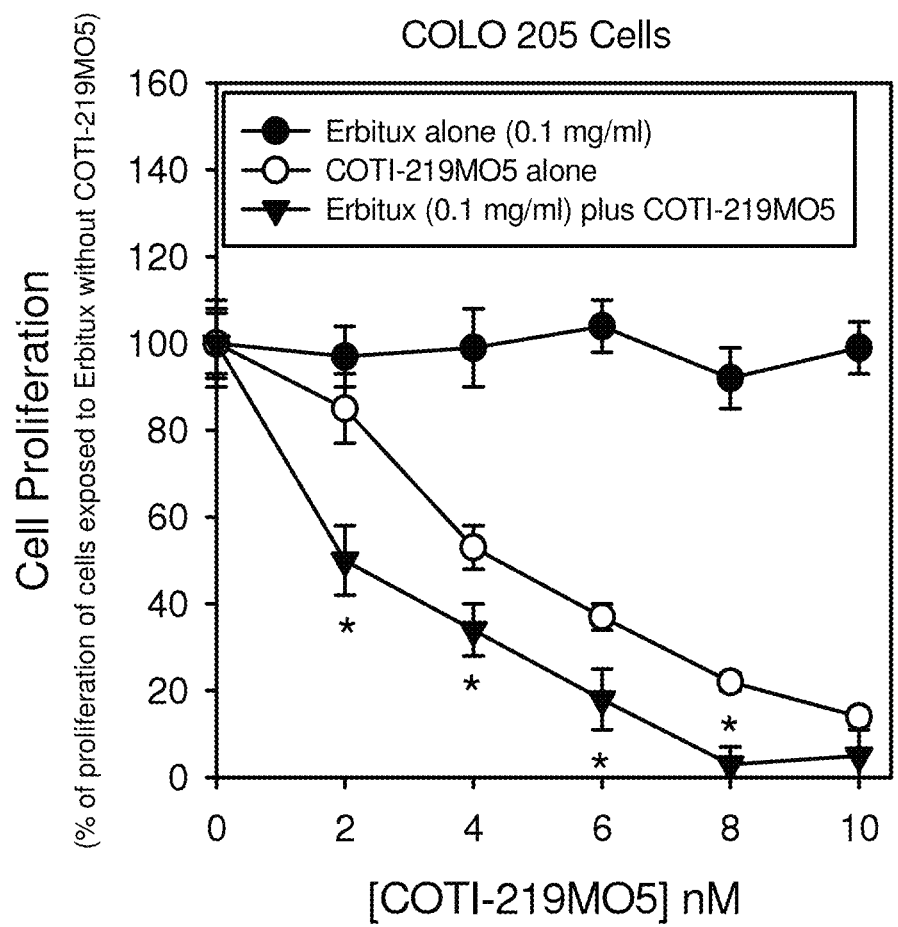
Figure 32C:
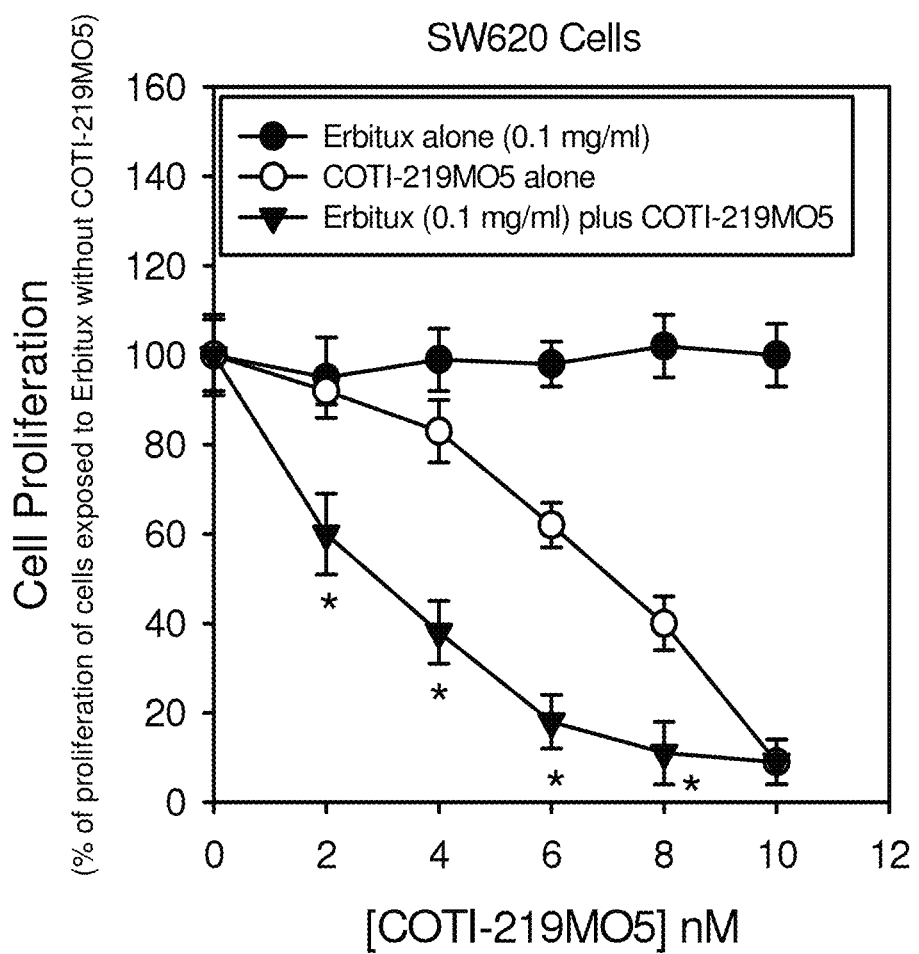

In FIG. 22, SHP 77 cells were treated with cisplatin (CDDP) at the concentrations shown or with CDDP plus COTI-2 (73 nM, which, as a single agent, reduces proliferation by 25%). The combination of COTI-2 and CDDP has a greater-than-additive effect (indicated by differences between data points at each concentration) where indicated by asterisks. In FIG. 23, SHP 77 cells were treated with carboplatin at the concentrations shown or with carboplatin plus COTI-2 (73 nM, which, as a single agent, reduces proliferation by 25%). The combination of COTI-2 and carboplatin has a greater-than-additive effect (indicated by differences between data points at each concentration) where indicated by asterisks. In FIG. 24, DMS114 cells were treated with carboplatin at the concentrations shown or with carboplatin plus COTI-2 (73 nM, which, as a single agent, reduces proliferation by 25%). The combination of COTI-2 and carboplatin has a greater-than-additive effect (indicated by differences between data points at each concentration) where indicated by asterisks.

In conclusion, these experiments show that synergistic improvements in efficacy are obtained for combinations of cytotoxic agents, such as cisplatin, carboplatin and paclitaxel, with mTOR-Rictor inhibitors, such as COTI-2 and COTI-219, in the treatment of various cancer cell lines, particularly those cell lines treatable by cytotoxic agents.

Example 17

Additive Effect with Certain Anti-Cancer Agents

For the combination of COTI-2 and certain anti-cancer agents, an additive effect is observed. As shown in FIGS. 25-28, Gemcitabine and Vinorelbine had an additive effect. Gemcitabine is a pyrimidine analog antimetabolite and is not known to be an mTOR-Raptor complex inhibitor. Vinorelbine does not have a major effect on either the Akt pathway or mTOR signaling pathways. No antagonistic drug interactions were observed. The lack of synergy with these agents supports the earlier mechanistic observations, which indicate that compounds of the present invention have synergy when combined with drugs that affect the Akt pathway, such as the mTOR-Raptor inhibitors, but not necessarily those that function by other pathways.

Example 18

In Vitro Activity of COTI-2 and COTI-219 as Combination Agents with Erlotinib and Cetuximab The therapeutic effects of COTI-2 and COTI-219 were evaluated as single agents and in combinations with the commercially available anti-cancer agents erlotinib (Tarceva®) and cetuximab (Erbitux®) in colorectal cancer and NSCLC cell lines (Table 21).
Methods:
Cell Lines—HT29, HCT116, H292, and H1975:

A 50-mM stock of COTI-2 or COTI-219 was formulated by dissolving an appropriate amount in DMSO. The stock concentration was further diluted to 1 mM and added to a drug plate. In the drug plate, the 1 mM COTI-2 and COTI-219 were serially diluted 10-fold in DMSO. Following dilution, 2 µl of test agent was transferred to the corresponding wells of a cell-containing 96-well plate with 198 µl of growth media. Tarceva® (erlotinib) was supplied by LC Labs (Woburn, Mass.). Erbitux® (cetuximab) was supplied by ImClone (New York, N.Y.). Cells were treated 24 h after plating with vehicle, COTI-2 (concentrations between 0.01 µM-10 µM), Tarceva® (concentrations between 0.1 µM-100 µM), or Erbitux® (concentrations between $1\times10^{-11}$ mg/ml [0.1 fM]-0.1 mg/ml [0.7 nM]). For combination studies, a fixed concentration of Tarceva® or Erbitux® and varying concentrations of COTI-2 or COTI-219 were used.

Cells were grown to 70% confluency, trypsinized, counted, and seeded in 96-well flat-bottom plates at a final concentration of $2.5\times10^3$-$5\times10^3$ cells/well (Day 0). Cells were allowed to incubate in growth media for 24 h to allow for maximum adhesion. Treatment with COTI-2 or COTI-219 or standard agents (Tarceva® & Erbitux®) began on Day 1 and continued for 72 h without re-treatment. At the 72-h time-point, treatment-containing media was removed. Viable cell numbers were quantified by the CellTiter-Blue® cell viability assay, which measures the conversion of the indicator dye (resazurin) to resorufin, an indicator of cell viability. Experiments were repeated at least twice with the same concentrations to determine growth inhibitory activity. Results from these studies were used to calculate an $IC_{50}$ value (concentration of drug that inhibits cell growth by 50% of control) for each compound.
Cell Lines—COLO-205, HCT15, and SW620:

The capacity of COTI-2 or COTI-219 to reduce tumor cell proliferation, alone or in combination with Tarceva® or Erbitux® was assessed in all 3 human colon tumor cell lines. The 3 cell lines were treated as follows:
Day 1: Cells were Plated in 96-Well Flat Bottom Plates (VWR, Mississauga, ON, Canada) and Allowed to Adhere Overnight.

Day 2: Addition of COTI-2, COTI-219, Tarceva®, Erbitux®, or combinations thereof. Stock solutions of COTI-2 and COTI-219 were prepared as described above (i.e., solid material was dissolved in DMSO to yield a 50 mM stock; 50 mM stock was serially diluted in DMSO to yield solutions such that, when 2 µl was added to wells in a 96 well plate, the desired concentrations of COTI compounds in a total volume of 200 µl media surrounding treated cells was achieved). All treated and control cells were, therefore, exposed to a 1% DMSO concentration plus the desired concentration of COTI-2.

Tarceva® (erlotinib) was manufactured by LC Labs (Woburn, Mass.) and Erbitux® (cetuximab) was manufactured by ImClone (New York, N.Y.). Both Erbitux® and Tarceva® were provided by the London Regional Cancer Program Pharmacy. All cell lines were treated with a range of Erbitux® or Tarceva® concentrations to determine, where possible, $IC_{50}$ values. Erbitux® concentrations up to 0.1 mg/ml had no significant effect, as a single agent, on any of the cell lines tested. For combination studies, therefore, 0.1 mg/ml Erbitux® was the single concentration chosen to combine with various concentrations of COTI-2 to assess combinatorial effects on growth. Tarceva® concentrations up to 10 µM were not sufficient to reduce growth of COLO-205 or SW620 by 50% over the 4 day assessment of the study (i.e., not sufficient to reach an $IC_{50}$). The highest concentration of Tarceva® that did not significantly affect growth of each of these cell lines were: COLO 205, 10 µM Tarceva®; and, SW620, 5 µM Tarceva®. Therefore, these concentrations were chosen to combine with various concentrations of COTI-2 or COTI-219 to assess combinatorial effects on growth.

Combination Studies:

For combination studies, a fixed concentration of Tarceva® or Erbitux® and varying concentrations of COTI-2 and COTI-219 were used. The fixed concentration of Tarceva® and Erbitux® used varied depending on the cell lines as mentioned above. In some cell lines the $IC_{30}$ concentration was used, whereas in others the highest concentration that did not significantly affect growth was used. After the Tarceva® or Erbitux® were added to the cells, varying concentrations of COTI-2 or COTI-219 were added to generate a dose-response curve. The concentration of COTI-2 or COTI-219 at which 50% of the cells were inhibited was recorded as the combination $IC_{50}$ and is reported in Tables 22 to 25.

Results and Discussion:

Test Compounds as Single Agents:

As single agents, both COTI-2 and COTI-219 showed potent activity in all seven tumor cell lines tested. Tarceva® single agent treatment in the H292 EGFR wild-type cell line resulted in sub-micromolar activity. However, fractional activity was seen in the EGFR mutant NSCLC cell line, H1975 (Tables 22 and 24), indicating that the T790M mutation in this cell line is conferring resistance against Tarceva®, as documented above. Furthermore, Tarceva® exhibited very low activity against the colon cancer cell lines regardless of their KRAS status. No dose response was detected for Erbitux in this assay even at concentrations >0.1 mg/ml (Tables 23 and 25).

Combination treatment with COTI-2 and Tarceva® resulted in a combination index of 1 (additive) against the H292 cell line, and a combination index of <1.0 (synergism) in the EGFR mutant NSCLC cell line, H1975 (Table 22). These data provide strong evidence for the effectiveness of COTI-2 against cell lines with EGFR mutations that confer resistance to tyrosine kinase inhibitors. In fact, COTI-2 increases the inhibitory activity of Tarceva® in combination therapy regardless of EGFR status of the cell lines. Furthermore, the combination of COTI-2 and Tarceva® was synergistic (CI<1.0) for the remaining three colorectal cancer cell lines (COLO-205, HCT-15, and SW620), regardless of KRAS status (Table 22). Similarly, the combination treatment of COTI-219 and Tarceva resulted in a combination index of <1.0 (synergism) regardless of the KRAS mutation status (Table 24).

Combination treatment of COTI-2 with Erbitux® resulted in positive interactions against all the colorectal cancer cell lines (HT29, COLO-205, HCT-15, HCT116 and SW620), indicating a combination index of <1.0 (synergism) (Table 23). Evidence indicates that the KRAS mutation status is a strong predictor for the outcome of Erbitux® therapy in colon cancer (103). Consequently, the data from this study provide evidence that COTI-2 in combination with Erbitux® rescues the acquired resistance conferred by KRAS mutations. Furthermore, as a single agent COTI-2 is highly effective against these cell lines regardless of KRAS mutation status. The combination of COTI-219 and Erbitux® yielded similar results, such that a synergistic activity was observed (combination index <1.0) regardless of the KRAS mutation status of the cell lines tested (Table 25).

In conclusion, both COTI-2 and COTI-219 displayed a potent single agent activity against 7 human tumor cell lines. Combination interaction assessment showed positive combination interaction for COTI-2 and COTI-219 in combination with Tarceva® or Erbitux®.

TABLE 21

Cell Lines.

| Cell line | Tissue Type | Histology | EGFR status | KRAS status |
|---|---|---|---|---|
| COLO-205 | Colon | C | WT | WT |
| HT-29 | Colon | AC | WT | WT |
| HCT-15 | Colon | AC | WT | Mut (G13D) |
| HCT-116 | Colon | AC | WT | Mut (G13D) |
| SW620 | Colon | AC | WT | Mut (G12V) |
| H292 | NSCLC | C | WT | WT |
| H1975 | NSCLC | AC | Mut (L858R, T790M) | WT |

TABLE 22

Mean $IC_{50}$ for COTI-2, Tarceva ®, and Combinations.

| Cell Line | Tissue type & EGFR/ KRAS status | Test Agent COTI-2 (nM) | Combination COTI-2 + Tarceva ® (nM) | Standard Agent Tarceva ® (nM) | CI at $IC_{50}$ COTI-2 + Tarceva ® (nM) |
|---|---|---|---|---|---|
| H292 | NSCLC EGFR-WT | 3.9 | 70.0 | 20.0 | 1.0 (Additive) |
| H1975 | NSCLC EGFR-MUT | 10.0 | 40.0 | >100,000 | <1.0 (Synergism) |
| COLO-205 | Colon KRAS-WT | 4.7 | 4.0 | >10,000 | <1.0 (Synergism) |
| HCT-15 | Colon KRAS-MUT | 8.3 | 3.8 | 5,100 | <1.0 (Synergism) |
| SW620 | Colon KRAS-MUT | 165.0 | 90.0 | >10,000 | <1.0 (Synergism) |

TABLE 23

Mean $IC_{50}$ for COTI-2, Erbitux ®, and Combinations.

| Cell Line | Tissue type & EGFR/ KRAS status | Test Agent COTI-2 (nM) | Combination COTI-2 + Erbitux ® (nM) | Standard Agent Erbitux ® (mg/ml) | CI at $IC_{50}$ COTI-2 + Erbitux ® (nM) |
|---|---|---|---|---|---|
| HT-29 | Colon KRAS-WT | 200.0 | 6.4 | >0.1 | <1.0 (Synergism) |
| COLO-205 | Colon KRAS-WT | 4.7 | 3.0 | >0.1 | <1.0 (Synergism) |
| HCT-15 | Colon KRAS-MUT | 8.3 | 4.0 | >0.1 | <1.0 (Synergism) |
| HCT-116 | Colon KRAS-MUT | 3.6 | 4.1 | >0.1 | <1.0 (Synergism) |
| SW620 | Colon KRAS-MUT | 165.0 | 82.0 | >0.1 | <1.0 (Synergism) |

TABLE 24

Mean $IC_{50}$ for COTI-219, Tarceva ®, and Combinations.

| Cell Line | Tissue type & EGFR/ KRAS status | Test Agent COTI-219 (nM) | Combination COTI-219 + Tarceva ® (nM) | Standard Agent Tarceva ® (nM) | CI at $IC_{50}$ COTI-219 + Tarceva ® (nM) |
|---|---|---|---|---|---|
| H292 | NSCLC EGFR-WT | 20.0 | 100.0 | 20.0 | <1.0 (Synergism) |
| H1975 | NSCLC EGFR-MUT | 100.0 | 700.0 | >100,000 | <1.0 (Synergism) |

TABLE 24-continued

Mean IC$_{50}$ for COTI-219, Tarceva ®, and Combinations.

| Cell Line | Tissue type & EGFR/ KRAS status | Test Agent COTI- 219 (nM) | Combination COTI-219 + Tarceva ® (nM) | Standard Agent Tarceva ® (nM) | CI at IC$_{50}$ COTI-219 + Tarceva ® (nM) |
|---|---|---|---|---|---|
| COLO-205 | Colon KRAS-WT | 4.3 | 2.0 | >10,000 | <1.0 (Synergism) |
| HCT-15 | Colon KRAS-MUT | 5.1 | 2.4 | 5,100 | <1.0 (Synergism) |
| SW620 | Colon KRAS-MUT | 7.4 | 3.1 | >10,000 | <1.0 (Synergism) |

TABLE 25

Mean IC$_{50}$ for COTI-219, Erbitux ®, and Combinations.

| Cell Line | Tissue type & EGFR/KRAS status | Test Agent COTI- 219 (nM) | Combination COTI-219 + Erbitux ® (nM) | Standard Agent Erbitux ® (mg/ml) | CI at IC$_{50}$ COTI-219 + Erbitux ® (nM) |
|---|---|---|---|---|---|
| HT-29 | Colon KRAS-WT | 7.4 | 30.0 | >0.1 | <1.0 (Synergism) |
| COLO-205 | Colon KRAS-WT | 4.3 | 2.0 | >0.1 | <1.0 (Synergism) |
| HCT-15 | Colon KRAS-MUT | 5.1 | 3.1 | >0.1 | <1.0 (Synergism) |
| HCT-116 | Colon KRAS-MUT | 8.7 | 300.0 | >0.1 | <1.0 (Synergism) |
| SW620 | Colon KRAS-MUT | 7.4 | 2.8 | >0.1 | <1.0 (Synergism) |

Combination indexes (CIs) are described by Chou and Talalay (Trends Pharmacol. Sci. 4, 450-454), which is incorporated herein by reference. The CI, a numerical value calculated as described in equation A, also provides a quantitative measure of the extent of drug interaction. A CI of less than, equal to, and more than 1 indicates synergy, additivity, and antagonism, respectively.

$$CI=(C_{A,x}/IC_{x,A})+(C_{B,x}/IC_{x,B})$$  Equation A

Where $C_{A,x}$ and $C_{B,x}$ are the concentrations of drug A and drug B used in combination to achieve x % drug effect. $IC_{x,A}$ and $IC_{x,B}$ are the concentrations for single agents to achieve the same effect.

Example 19

Akt as a Biomarker for COTI-2 Efficacy

It was previously demonstrated that COTI-2 interferes with the function of AKT in SCLC cell lines, by down-regulating AKT transcription as well as producing a functional impairment of AKT kinase activity. Therefore, the aim of the current set of experiments was to determine the extent of the correlation between the expression of total AKT, its isoforms (AKT1, 2, & 3), and susceptibility to COTI-2 apoptosis.

Methods:

Tissue Culture:

Cell cultures were maintained under regular tissue culture conditions and passaged 1-2 times a week as recommended by ATCC. For siRNA experiments the manufacturer's conditions for growth and transfection were followed. All siRNA reagents for AKT and AKT2 transfections were obtained from Cell Signaling.

Cells were treated for 48 h with 0-100 ng of AKT or AKT2 siRNA before incubation with COTI-2 at various concentrations (0-500 nM). Following incubation for 48 h, cell viability was determined by MTT assay.

Western Blotting:

Routine laboratory methods were employed for the production of cellular lysates, protein quantification, SDS-PAGE and western blotting. All antibodies were obtained from Cell Signaling and Abcam. To determine total AKT & AKT2 in DMS114 cells, $5\times10^4$ cells were incubated for 48 h with 10-100 ng of AKT2 siRNA or a scrambled control oligonucleotide. Cells were lysed and 50 µg of protein was separated by SDS-PAGE and blotted with antibody to total AKT or AKT2.

Figure 33:
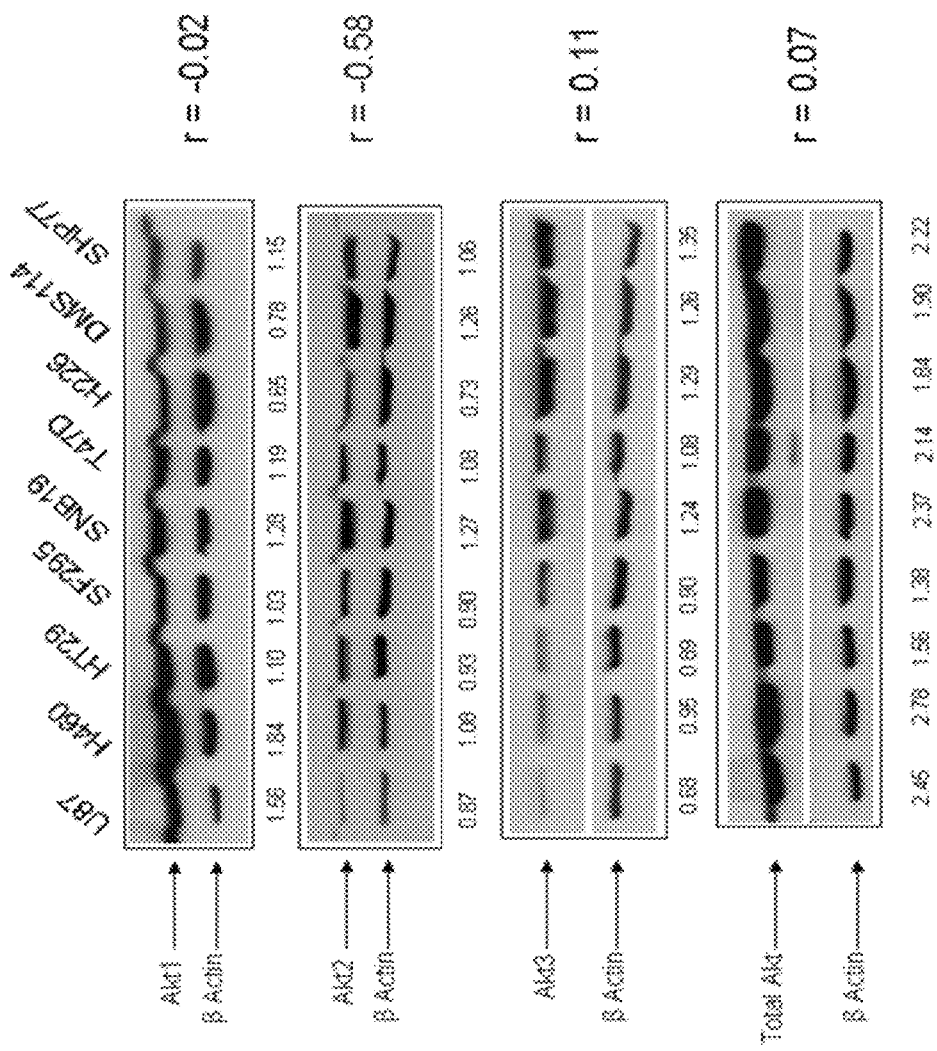
FIG. 33 shows the correlation between AKT isoforms (1, 2, & 3) expression and COTI-2 IC50, lane numbers represent the ratios of AKT isoform expression relative to β-actin expression, and R values represent the correlation between normalized AKT levels and IC50 values.
Figure 34:
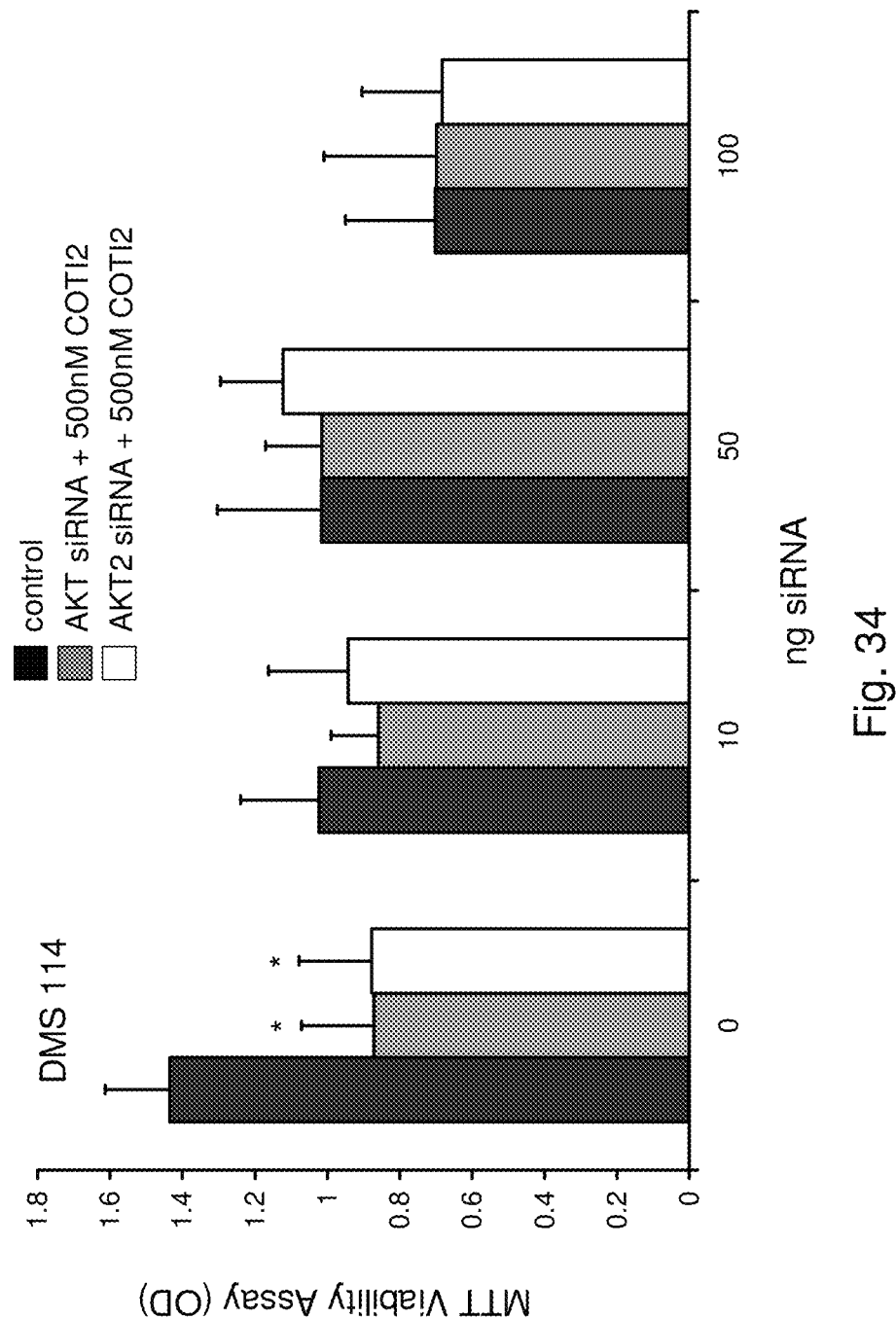
FIG. 34 shows an effect of AKT/AKT2 siRNA on COTI-2 induced apoptosis in DMS114 SCLC cells, the asterisk (*) indicates statistical significance (p<0.05)
Figure 35:
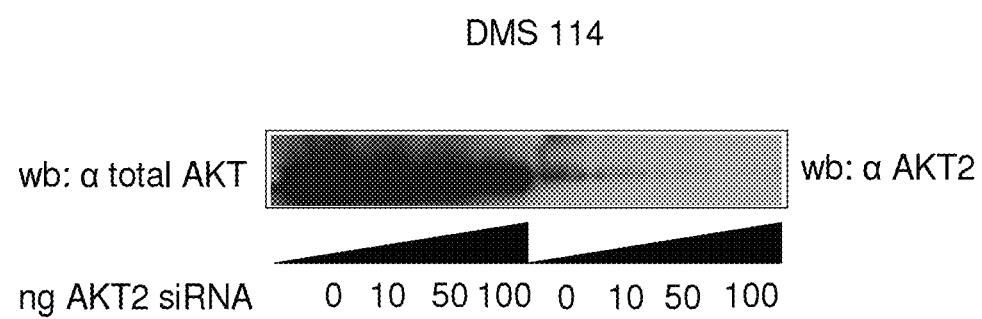
FIG. 35 shows the total AKT and AKT2 expression levels in DMS114 cells incubated with 0-100 ng AKT2 siRNA.

Results and Discussion:

The expression of AKT1, AKT2, AKT3, total AKT and β-actin were examined in a panel of cell lines representing various types of cancers, with the aim of determining if a correlation exists with the pre-determined IC50's for these cell lines. As shown in FIG. 33, when corrected for total AKT expression, only AKT2 expression was statistically significantly and inversely correlated to the COTI-2 IC50 for this panel of cell lines. In order to confirm that AKT2 expression is needed for COTI-2 induced apoptosis, DMS114 and SHP77 cell lines were treated for 48 h with 0-100 ng of AKT or AKT2 siRNA before incubation with 500 nM of COTI-2 (FIG. 34). Both total AKT and AKT2 siRNA in the absence of COTI-2 caused significant apoptosis of DMS114 cells indicating that the siRNA functions as expected. The viability of DMS114 cells incubated with AKT siRNA in the presence or absence of COTI-2 is unchanged, thus indicating that AKT and more specifically AKT2 is the cellular target of COTI2. If COTI-2 had an alternate target, one would expect differential cell death in the presence and absence of COTI-2. The down-regulation of AKT2 prior to the addition of COTI-2 was confirmed with western blotting in DMS114 cell lines using an antibody to AKT2 (FIG. 35). Overall, these data indicate that in the absence of its cellular target (AKT2) which was knocked-down by siRNA specific for AKT2, COTI-2 was unable to exert additional significant cytotoxicity on the cell lines.

Figure 36:
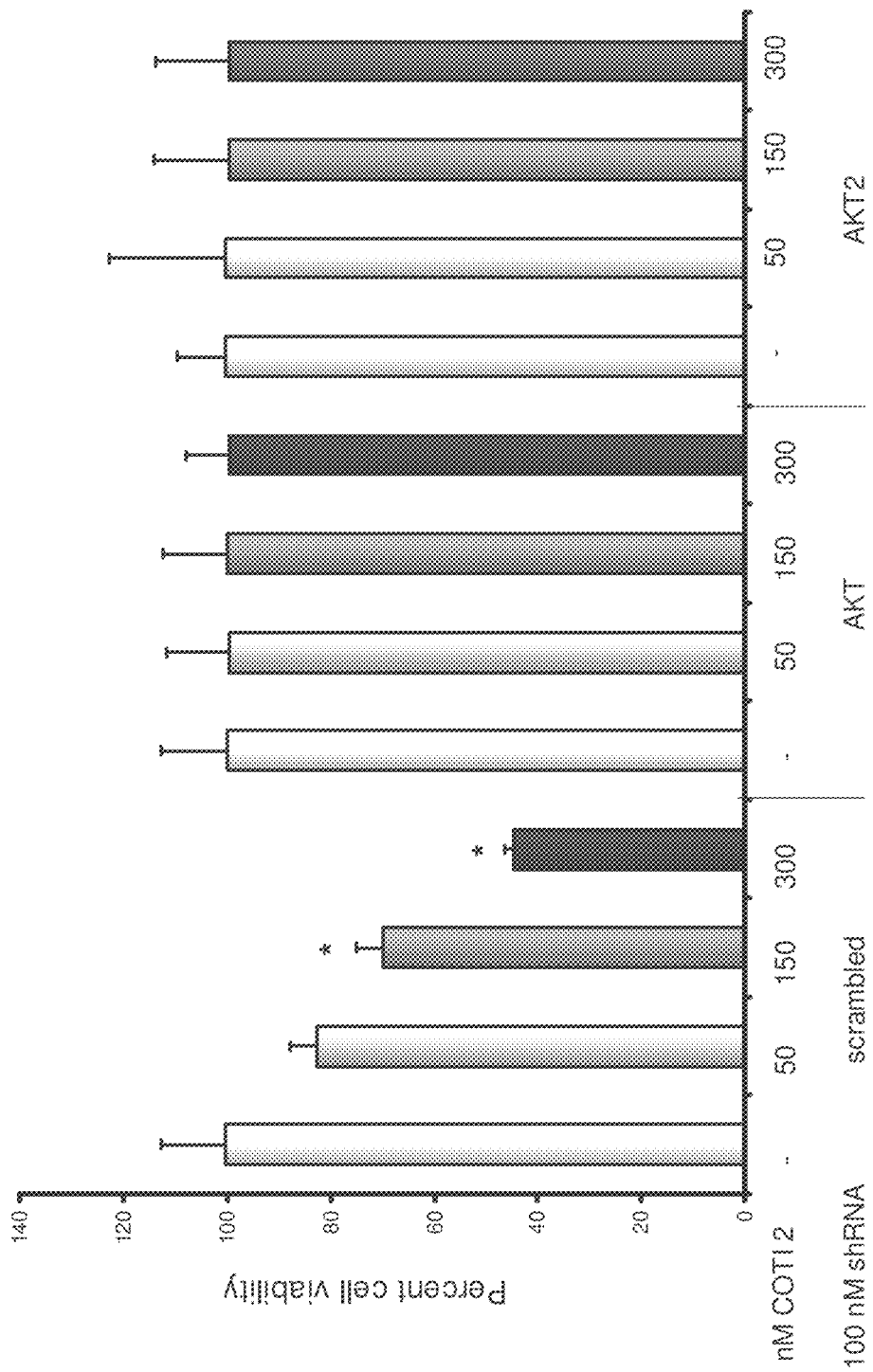
FIG. 36 shows the percent viability of SHP77 cells transfected with scrambled, total AKT, or AKT2 siRNA and in the presence/absence of various concentrations COTI-2, the asterisk (*) indicates statistical significance (p<0.05)
Figure 37:
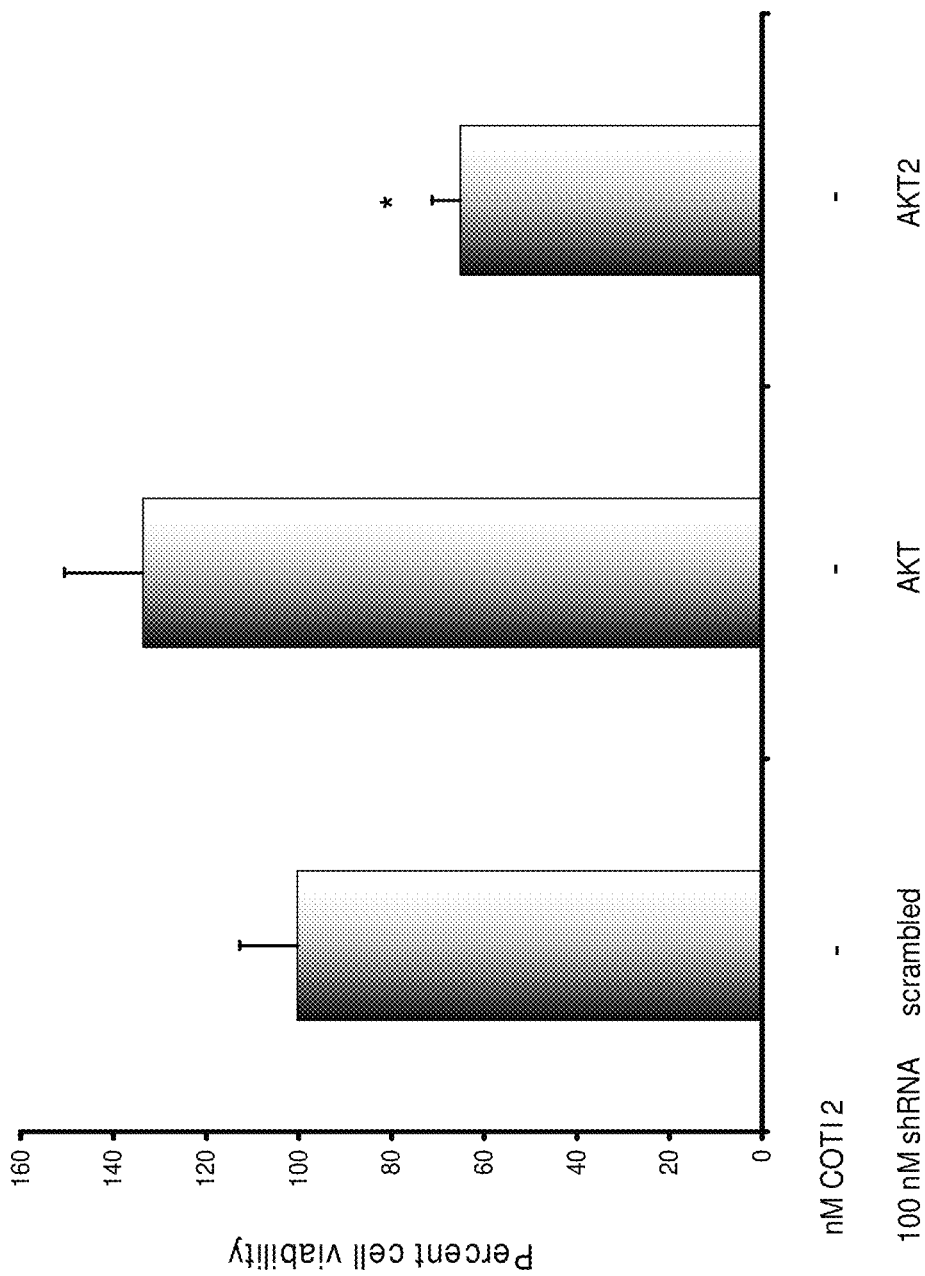
FIG. 37 shows the percent viability of SHP77 cells in the presence of scrambled, total AKT, or AKT2 siRNA, the asterisk (*) indicates statistical significance (p<0.05)

Similar results were obtained with SHP77 cell lines, such that no significant difference in cell death was observed when the cells were treated with total AKT or AKT2 siRNA in the presence or absence of COTI-2 (FIG. 36). Therefore, total AKT and AKT2 siRNA abrogates COTI-2 induced apoptosis in SHP77 cells. Furthermore, transfection with 100 nM of AKT2 siRNA, but not with total AKT siRNA, caused significant apoptosis in SHP77 cell lines (FIG. 37).

Figure 38:
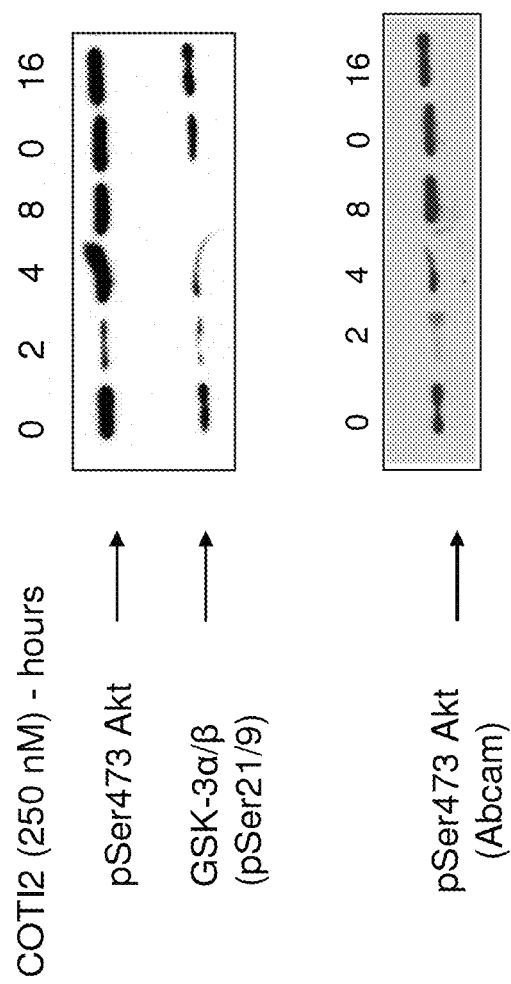
FIG. 38 shows the levels of phosphorylation of AKT at Ser473 site and GSK-3α/β at Ser21/9 site in the presence of 250 nM COTI-2 at 0, 2, 4, 8, and 16 h post-incubation, the levels of phospho-Ser473 of AKT were confirmed with antibodies from 2 providers, Cell Signaling and Abcam.
Figure 39:
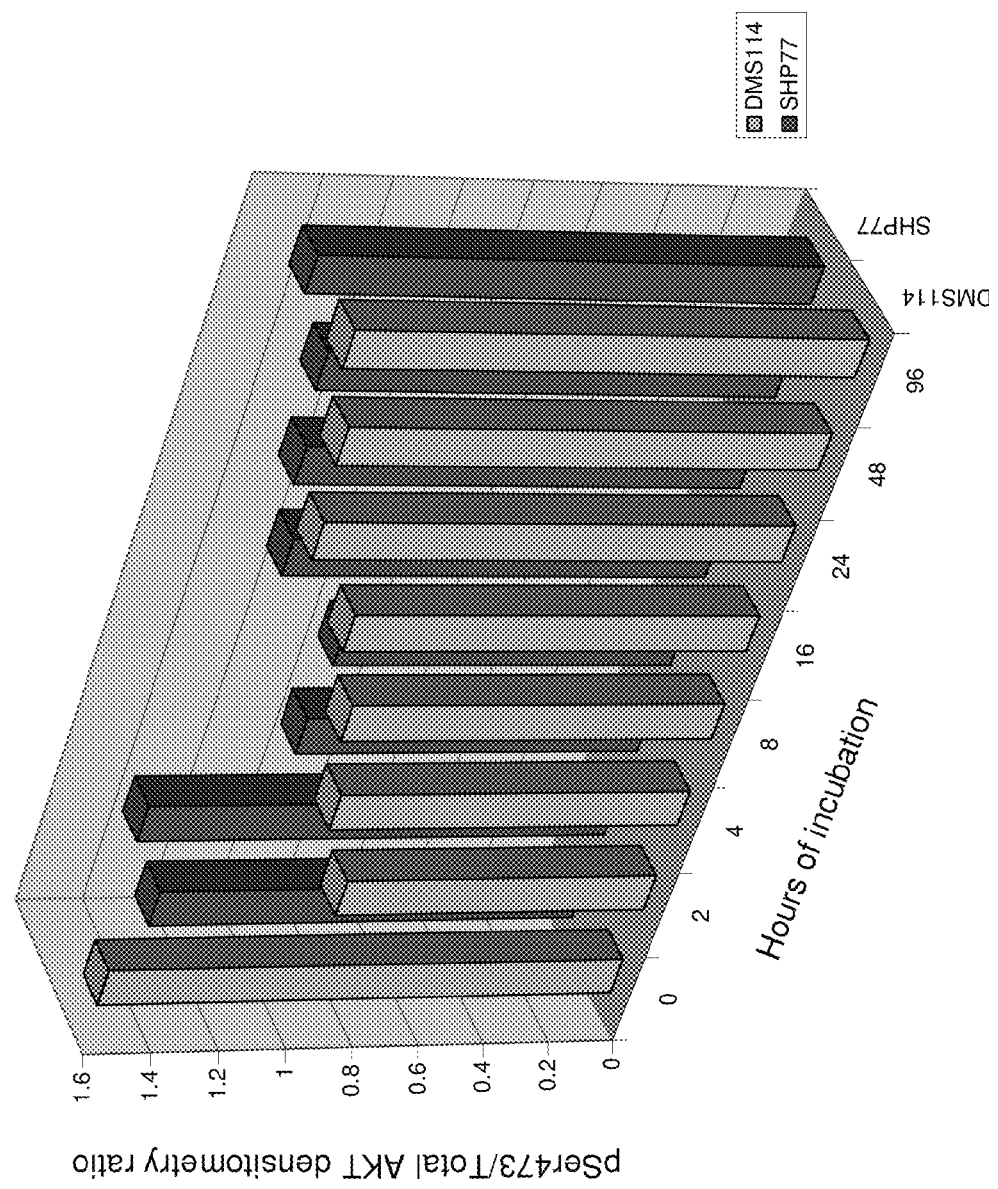
FIG. 39 shows the time-course of COTI-2 effect on AKT pSer473 in two SCLC cell lines, DMS114 and SHP77.
Figure 40:
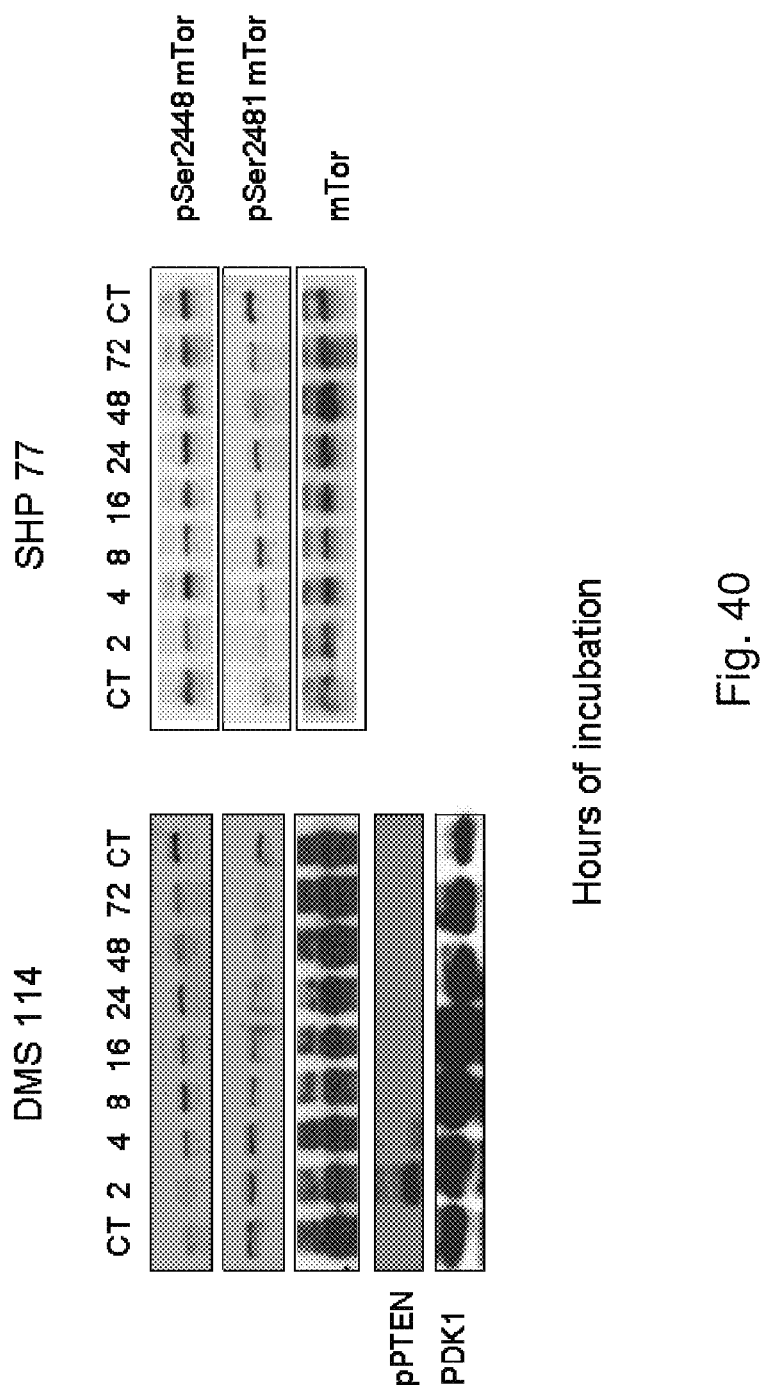
FIG. 40 shows changes in AKT phospho-protein targets, total protein lysates were obtained at different time points following incubation with 300 nM of COTI-2, following SDS-PAGE separation of 50 µg of protein the blots were probed with the indicated antibodies.
Figure 41A:
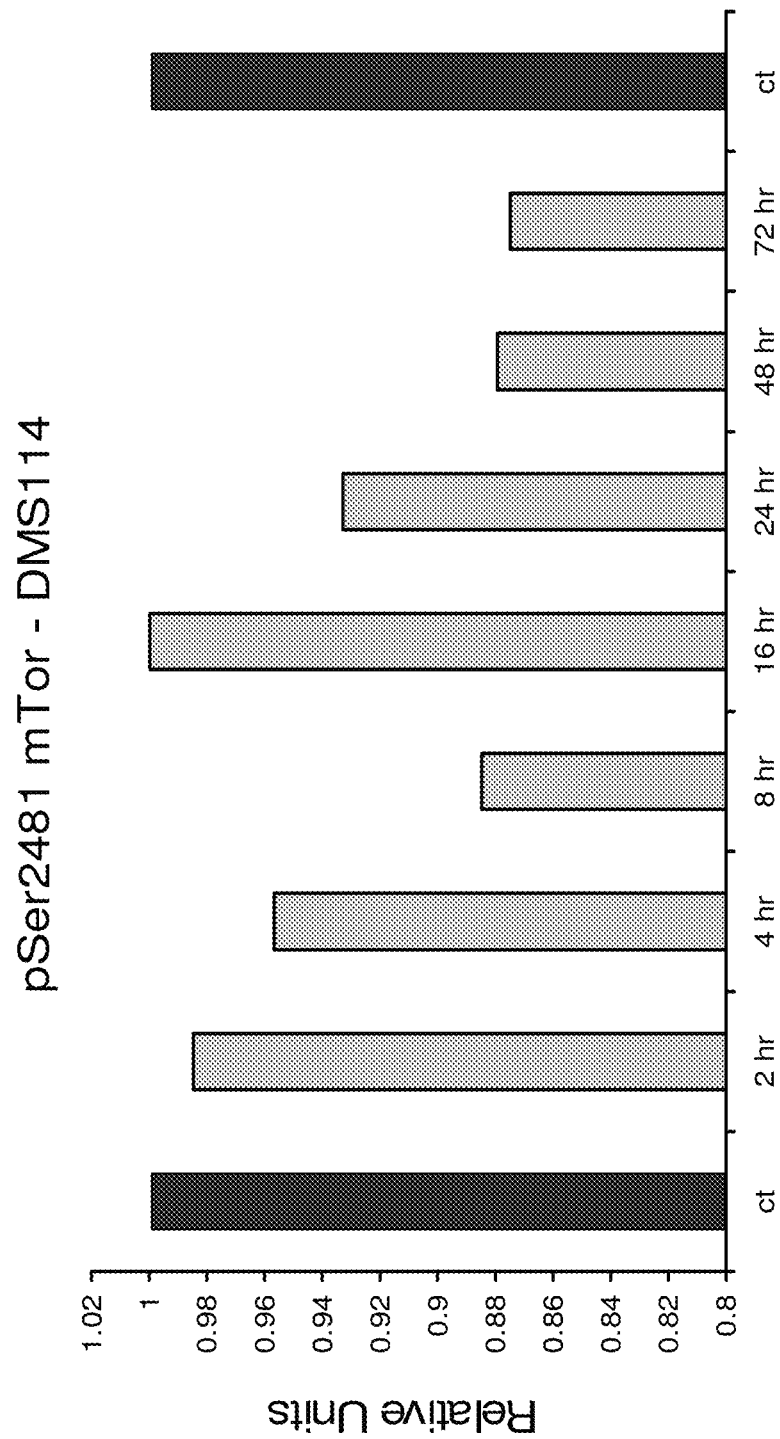
FIGS. 41A and 41B show mTor pSer2481 and AKT pSer473 in DMS114, the blots shown in FIG. 37 were scanned and quantitated with ImageJ software, and phospho-protein expression was corrected to total mTOR levels.
Figure 41B:
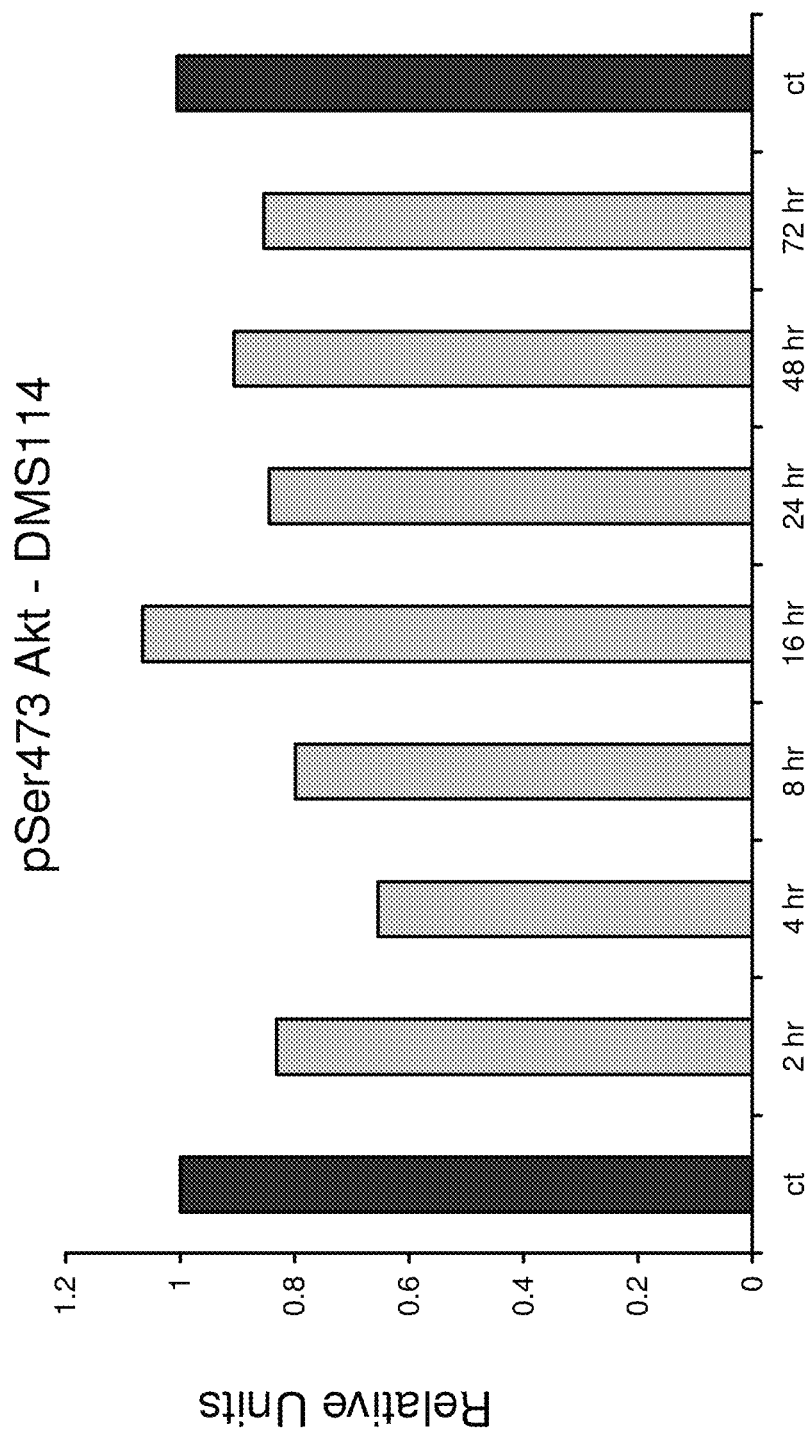
Figure 42:
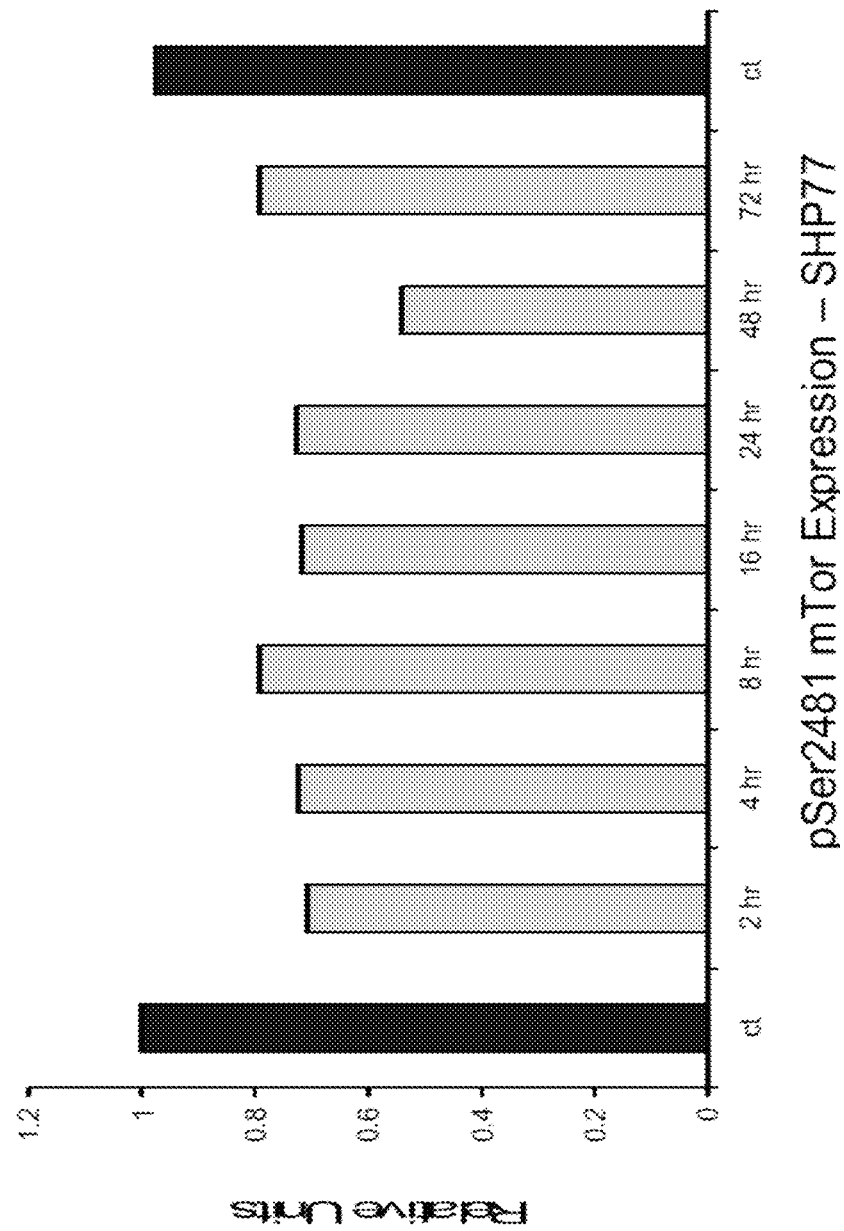
FIGS. 42A and 42B show mTOR pSer2448/pSer2481 in SHP77 cells, the blots shown in FIG. 40 were scanned and quantitated with ImageJ software, and phospho-protein expression was corrected to total mTOR levels.
Figure 42B:
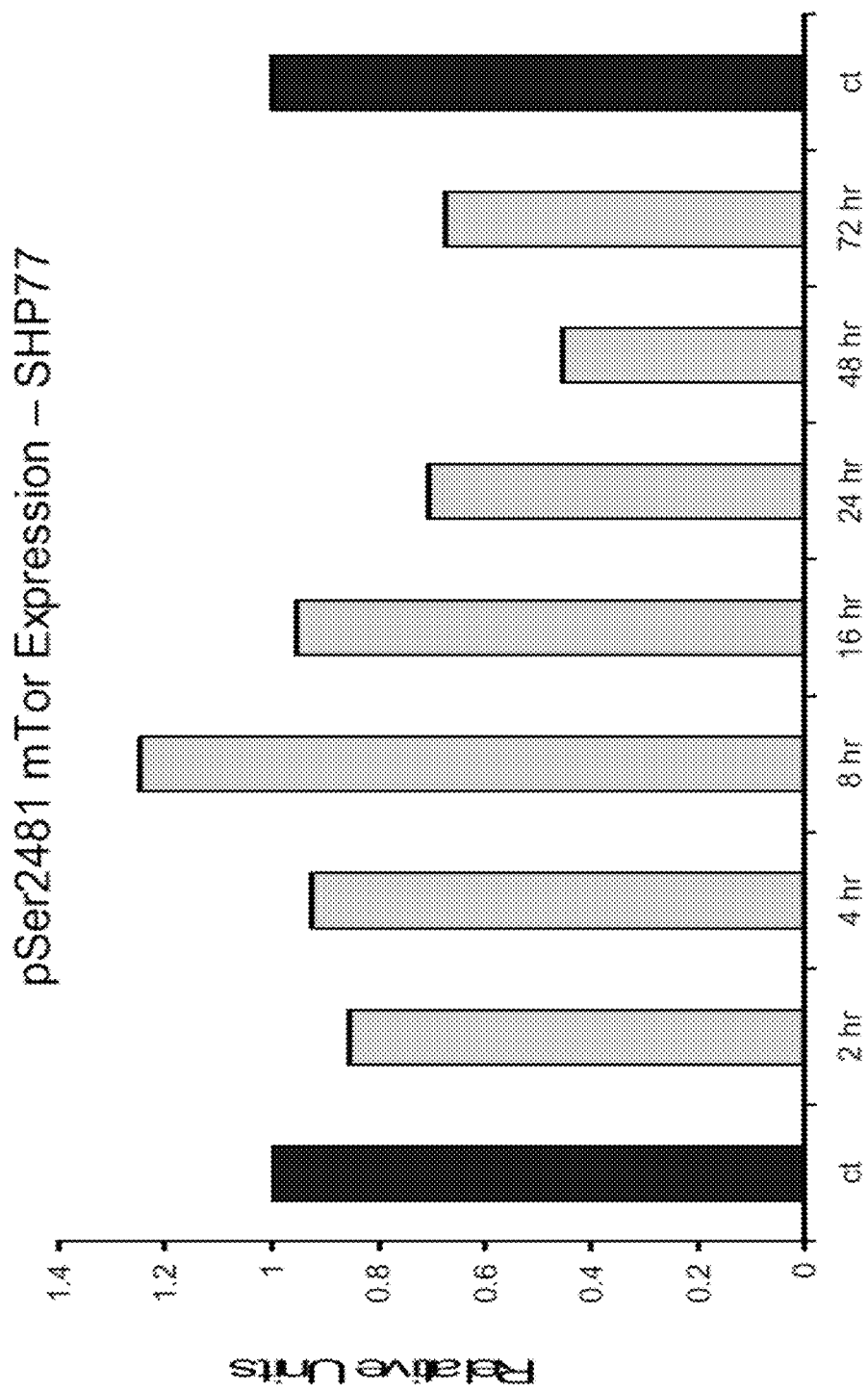
Figure 43A:
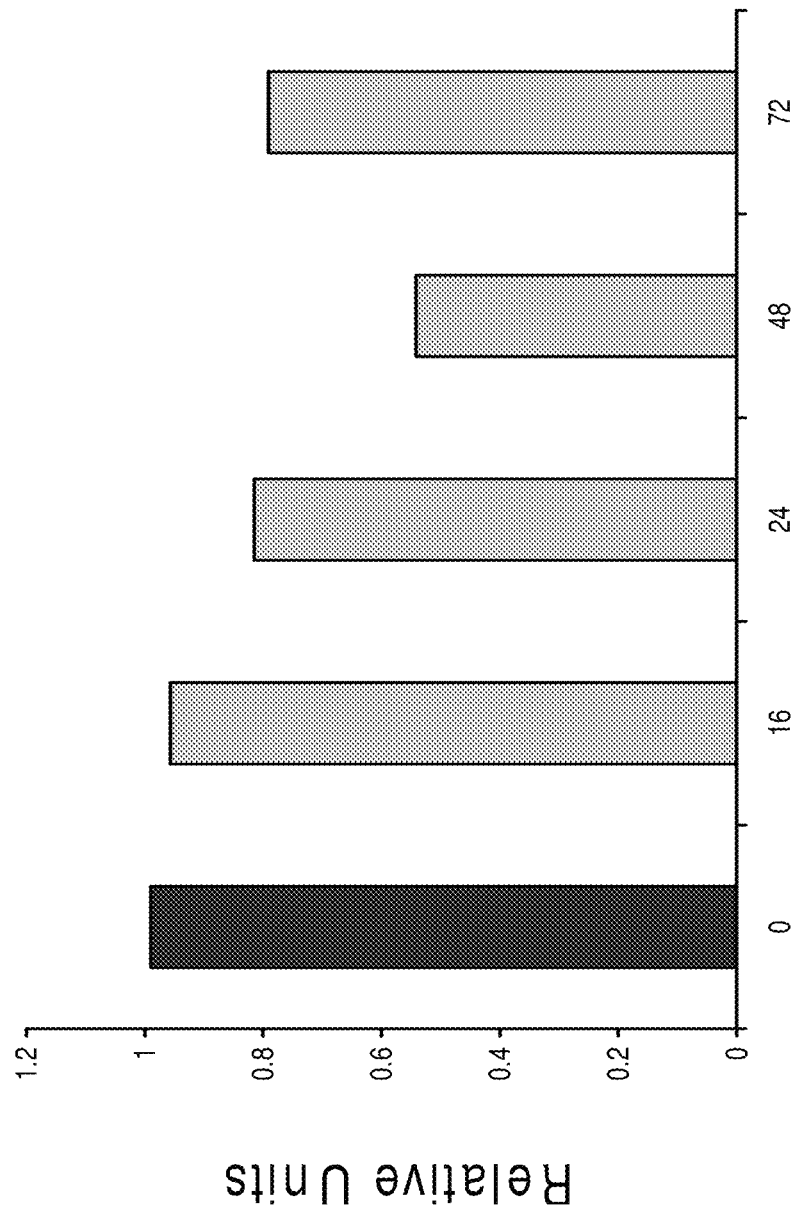

The phospho-AKT status at Ser473 was determined in the presence of COTI-2 utilizing western blotting. A profound inhibition of AKT Ser473 phosphorylation is noticeable at 2 h, the earliest time-point following incubation with 250 nM COTI2 (FIG. 38). These data were confirmed using 2 different antibody preparations from Cell signaling and Abcam. The inhibition of AKT phosphorylation at Ser473 correlates with the reduction in the phosphorylation of GSK-3α/β (pSer21/9), which is a downstream target of activated phospho-AKT. Therefore, these data indicate that AKT is the cellular target of COTI-2, since COTI-2 prevents phospho-activation of AKT and consequently AKT is unable to phospho-inhibit its downstream target, GSK-3α/β at Ser21/9. The complete time course of the AKT phospho-Ser473 status in DMS114 and SHP77 cells during incubation with COTI-2 is documented in FIG. 39.

A complex relationship exists between Raptor- and Rictor-containing mTor complexes mTORC1 and mTORC2, respectively, and AKT. mTORC2 activates AKT by Ser473 phosphorylation; in turn, activated AKT phosphorylates TSC2, which prevents its interaction with Rheb and thus the hydrolysis of GTP associated with Rheb. As a result, Rheb-GTP activates mTOR by phosphorylation on Ser2448. These events suggest that COTI-2, by inhibiting the formation of active phospho-Ser473 AKT, would also lead to a decrease in mTOR phospho-Ser2448 phosphorylation, as less Rheb-GTP becomes available, due to its increased sequestration in complexes with TSC2. The results shown in FIGS. 40-45 agree with this hypothesis. In DMS114 cells incubated with COTI-2 there is an initial decrease in phospho-Ser 2448 at 2 hrs followed by a more sustained decrease at 24 and 48 hrs. In SHP77 cells, only the decrease at 2 hrs of incubation was observed. Interestingly, in both cell lines there is a delayed effect that impairs the autophosphorylation of mTOR on Ser2481. This event was shown to be wortmannin sensitive but a direct connection between inhibition of PI3K and impaired mTOR phospho-Ser2481 has not been demonstrated (J Biol Chem, 275: 7416-7423). Surprisingly, a strong but transient increase in PTEN phospho-Ser380 was observed in DMS114 cells. Phosphorylation of the PTEN C terminal was reported to stabilize PTEN and protect against ubiquitin-mediated degradation (Nat Rev Cancer, 6: 184-192). One implication of this observation is that COTI-2 may activate PTEN and thus, by reducing the amount of PIPS, contribute to the inhibition of AKT activity.

These experimental results provide yet further evidence that the cellular target of COTI-2 is AKT, specifically AKT2, and that COTI-2 is likely implicated in mTOR-Rictor complex formation.

Example 20

PTEN siRNA Knockdown in Human Tumor Cell Lines (HeLa and MCF-7) Results in Increased Resistance to COTI-2

The activation of Akt is negatively regulated by the tumor suppressor PTEN (phosphatase with tensin homology), which is a lipid phosphatase, therefore, inactivation of PTEN by siRNA results in increased levels of active Akt. In order to further investigate whether Akt is the likely target of COTI-2, the susceptibility to killing by COTI-2 was evaluated in 2 human tumor cell lines (HeLa and MCF-7) transfected with PTEN siRNA. Previous work has demonstrated that increased PTEN activity reduces Akt activity, and knockdown of PTEN has been shown to increase Akt activity in human tumour cells (Cancer Cell, 12:395-402). Therefore, if Akt is the target for COTI-2, then it is expected that increased levels of Akt resulting from PTEN siRNA inactivation will cause increased resistance to COTI-2. Transfected cells were confirmed by western blot analysis and reverse transcription PCR were grown and proliferation assessed in the presence or absence of COTI-2.

Methods:

Briefly, HeLa and MCF-7 cells were transfected with 100 nM PTEN siRNA or control non-targeted siRNA at 48 or 144 h prior to exposure to various concentrations of COTI-2.

Western Blot Analysis:

Tranfected HeLa cells were confirmed by western analysis as described. Western blot analysis of extracts from HeLa cells transfected with non-targeted (−) or targeted (+) siRNA (Cell Signaling Technologies, Inc., SignalSilence PTEN siRNA, human-specific; and control, non-targeted SignalSilence siRNA from the same manufacturer). PTEN was detected using the PTEN Antibody #9552, and p42 was detected using the p42 MAPK Antibody #9108. The PTEN Antibody confirms silencing of PTEN expression, and the p42 MAPK Antibody is used to control for loading and specificity of PTEN siRNA (data obtained from Cell Signaling Technology website, http://www.cellsignal.com/products/6251.html). Since PTEN siRNA was capable of downregulating PTEN protein in HeLa cells (supported by data generated by Cell Signaling Technologies, Inc.), PTEN siRNA and non-targeting control siRNA used for the experiments described below were obtained from New England Biolabs Ltd. (Ontario, Canada).

Effect of COTI-2 on Cell Proliferation:

To assess the capacity of transient siRNA transfection to alter the ability of cells to proliferate in the presence or absence of COTI-2, HeLa or MCF-7 cells (both PTEN-positive) were plated in T25 flasks and transfected 24 h later with PTEN siRNA or non-targeting control siRNA (100 nM in both cases), using Oligofectamine Reagent (Invitrogen) according to the manufacturer's instructions and as previously described (J Pharmacol Exp Ther, 322:123-132). In brief, siRNA:Oligofectamine Reagent complexes were formed in DMEM without FBS, then serially diluted to generate desired transfection concentrations. siRNA complexes in DMEM were added to HeLa or MCF-7 cells grown to 50 to 60% confluence. PTEN and 18S rRNA mRNA levels were determined by semi-quantitative reverse transcription PCR. PTEN primers were: PTEN forward (5'CCACCACAGCTA-GAACTTATC3'; PTEN reverse (5'ATCTGCACGCTC-TATACTGC3'). GAPDH primers were as described previously (J Pharmacol Exp Ther, 322:123-132). The reverse transcription/PCR method was as described in the same publication. The ratio of PTEN mRNA/18S rRNA for untransfected cells was normalized to 100% and all other PTEN mRNA/18S rRNA ratios were reported as a percent of that 100% value.

For determination of drug sensitivity, HeLa and MCF-7 cells (transfected with PTEN siRNA or control, non-targeted siRNA 48 or 144 hours prior) were re-plated in 96-well plates (VWR, Mississauga, ON, Canada) at 1700 (MCF-7) and 1200 (HeLa) cells per well in a volume of 100 µl of DMEM+10% FBS. Cells were allowed to adhere to tissue culture plastic for 18 h before addition of COTI-2M05 at various concentrations. COTI-2 was added in a volume of 100 µl (from a stock DMSO/DMEM solution) so that the final DMSO concentration on cells was less than 0.1%. Cells were then grown for 4 days, and viable cell numbers were assessed by the alamar Blue fluorescence assay using a Wallac Victor$^2$ multilabel counter (PerkinElmer Wallac, Gaithersburg, Md.). For each concentration of COTI-2M05, proliferation was defined as the "number of viable cells transfected with PTEN siRNA, expressed as a % of the number of viable cells transfected with control, non-targeting siRNA". This calculation method corrected for minor effects of PTEN knockdown alone on growth rate and/or cell viability.

Statistical Analysis:

Data are presented as means±S.E. To determine the significance of differences between means, a Student's t test was performed. The level of significance for all statistical analyses was chosen a priori to be $p<0.05$.

Figure 44:
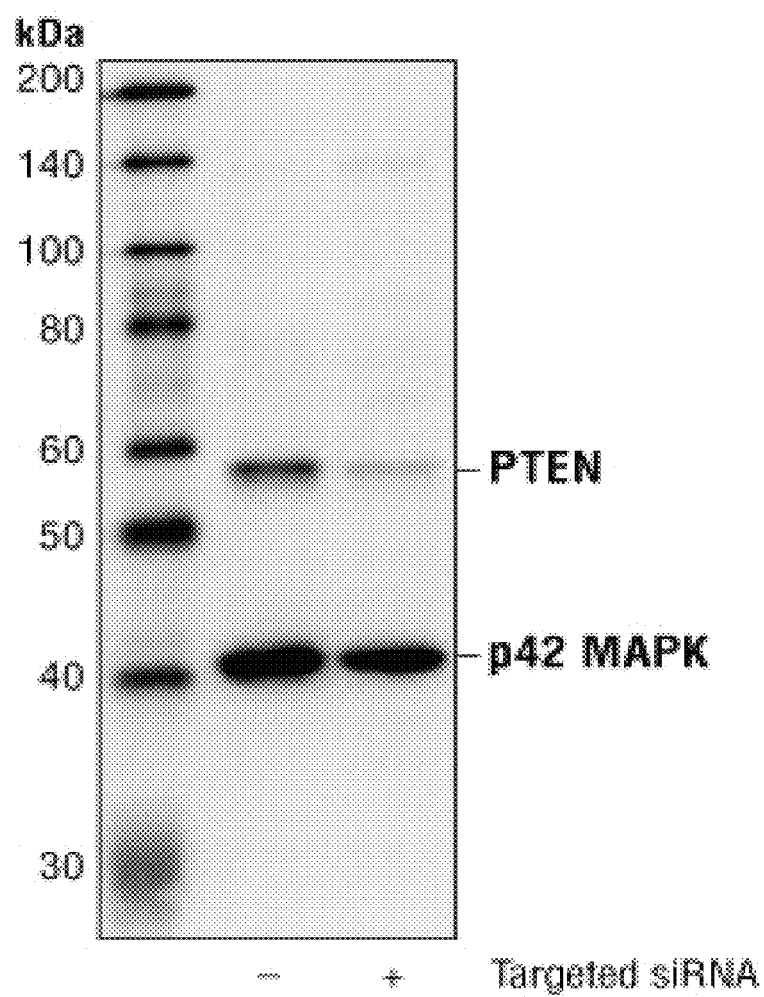
FIG. 44 shows a western blot analysis of PTEN in HeLa cells tranfected with PTEN targeted siRNA (+) and non-targeted siRNA (−)
Figure 45A:
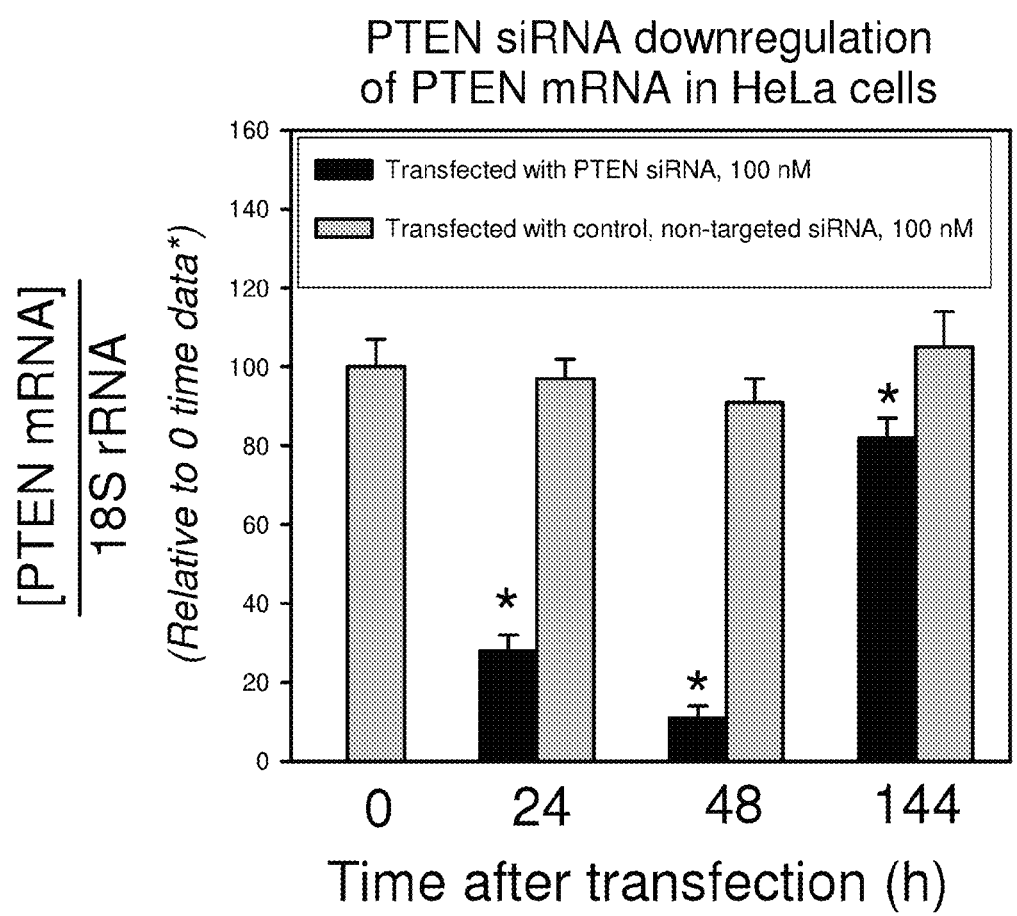
FIGS. 45A and 45B shows reverse transcription PCR of HeLa (FIG. 45A) and MCF-7 cells (FIG. 45B) transfected with 100 nM targeted PTEN siRNA or non-targeted siRNA, cells were evaluated at 0, 24, 48, and 144 h post-transfection.
Figure 45B:
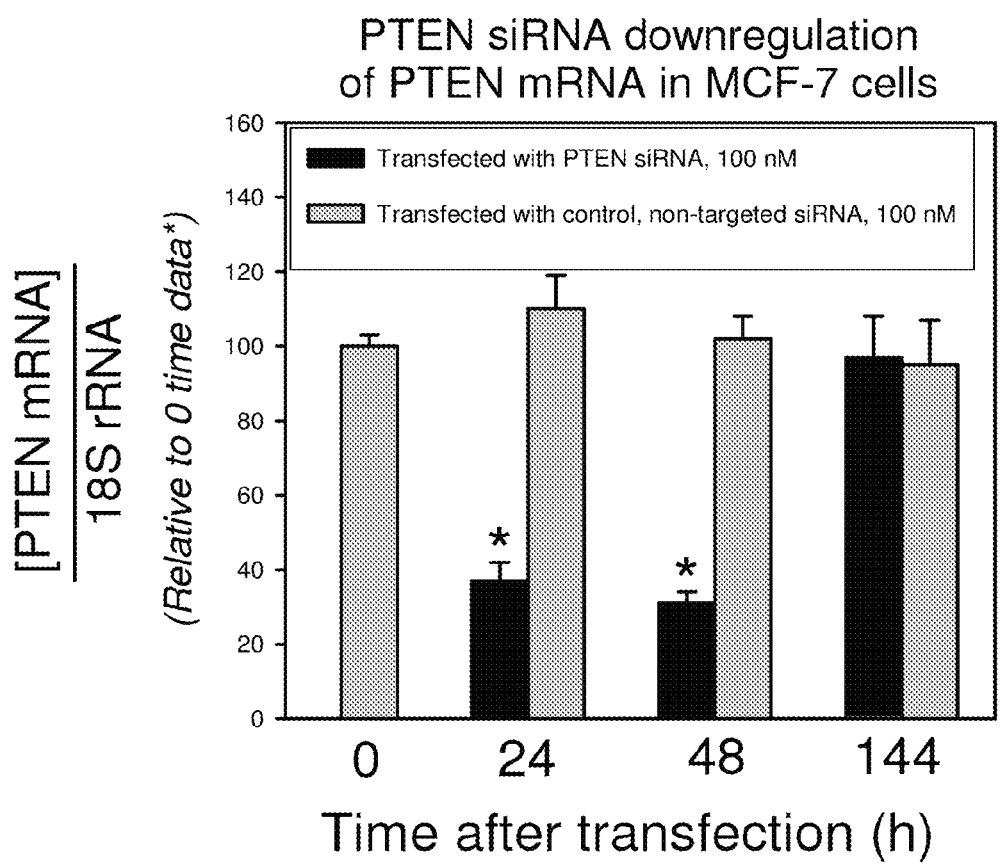

Results and Discussion:

Western blot analysis of HeLa transfected with targeted (+) and non-targeted (−) siRNA confirm that the PTEN siRNA specifically knocks-down the expression of PTEN (FIG. 44). Furthermore, reverse transcription PCR analysis indicated that PTEN siRNA transfection knocked down PTEN mRNA levels by a maximum of approximately 90% in HeLa cells (FIG. 45A) and 70% in MCF-7 cells (FIG. 45B), by 48 h post-transfection. By 114 h (6 days post-transfection), PTEN levels had recovered to control values in both HeLa (FIG. 45A) and MCF-7 (FIG. 45B) cells (in accord with the capacity the mRNA levels of the cells to recover from targeting siRNAs). These data show that the transfection of both cells lines with PTEN siRNA was specific and by 114 h the inhibitory effect of the PTEN siRNA no longer exists.

Figure 46A:
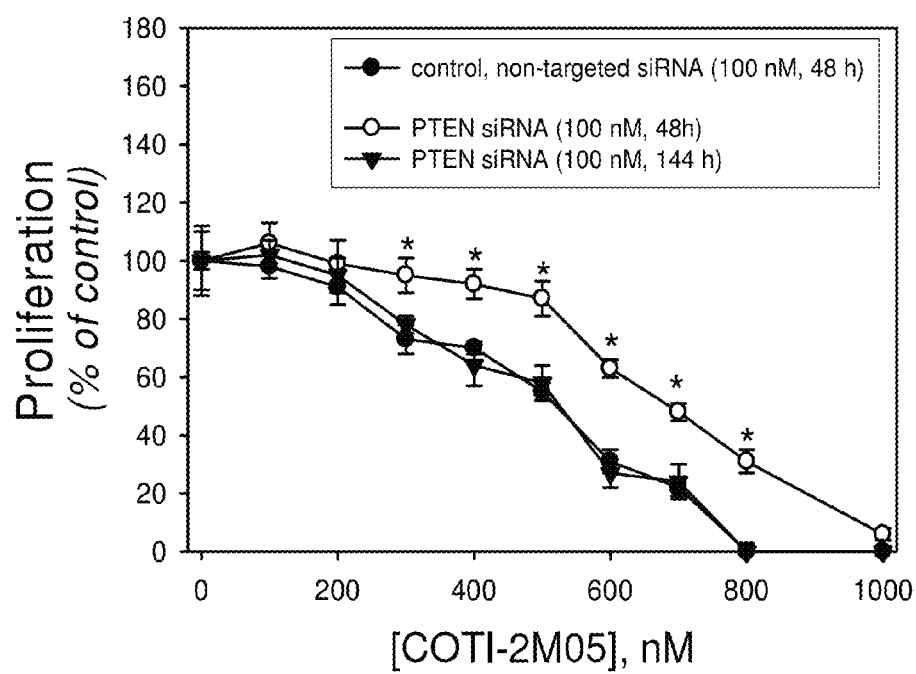
FIGS. 46A & 46B show the effect of knockdown of PTEN mRNA with PTEN siRNA on HeLa (FIG. 46A) and MCF-7 (FIG. 46B) cell sensitivity to COTI-2.
Figure 46B:
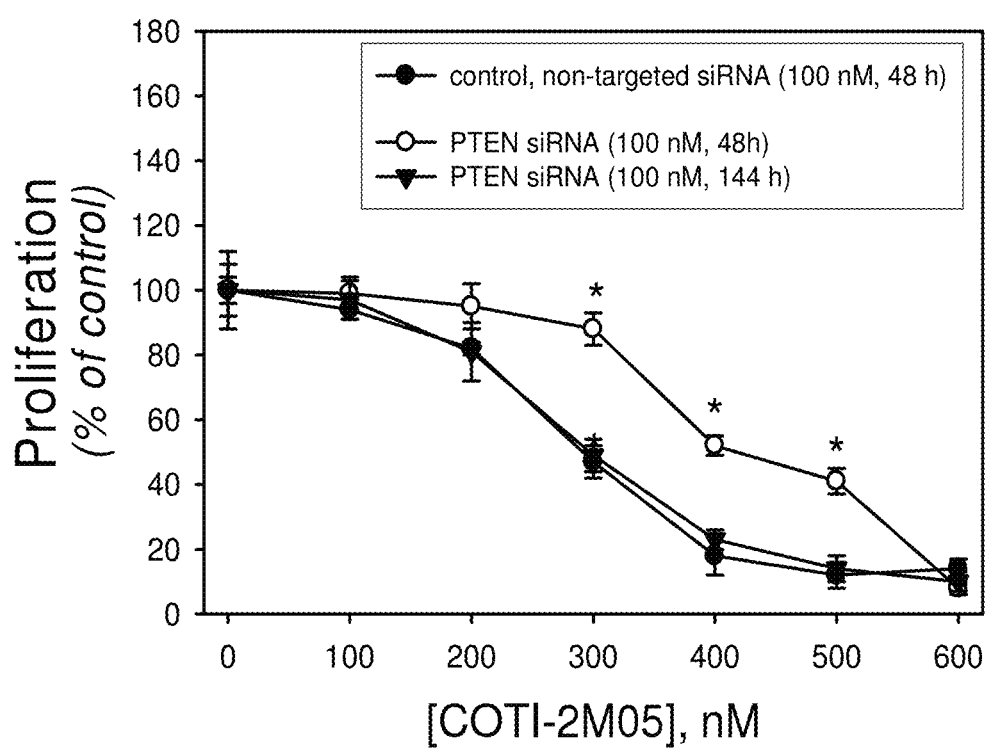

The tranfected cells were then analyzed for their susceptibility to killing by COTI-2 using the alamar Blue fluorescence assay described previously. The transfection of cells with PTEN siRNA resulted in a significant increase in the resistance of both cell lines (HeLa and MCF-7) to COTI-2 at 48 h post-transfection (FIGS. 46A & 46B, respectively). By 144 h post-transfection there is no significant difference in the killing of cells tranfected with PTEN siRNA or non-targeted siRNA. These data are consistent with the recovery of normal PTEN mRNA levels by 144 h (refer to FIGS. 45A and 45B). The increased resistance to COTI-2 in the 2 PTEN-positive human tumor cell lines (HeLa and MCF-7) after siRNA knockdown of PTEN and presumed increased Akt activity is consistent with the hypothesis that Akt is a direct or indirect target of COTI-2 in human tumor cells. The multiple confirmations of Akt, and particularly Akt2, as the molecular target of the compounds of the present invention, particularly COTI-2, indicate that these compounds should be effective in the treatment of cancers characterized by over-expression of Akt. Compounds of the present invention are presumed to be efficacious in the treatment of all cancers characterized by overexpression of Akt, in particular those cancers in addition to lung cancer, cervical cancer, ovarian cancer, cancer of CNS, skin cancer, prostate cancer, sarcoma, breast cancer, leukemia, colorectal cancer, head cancer, neck cancer or kidney cancer, which are already listed above.

Example 21

Sensitivity of Human Tumour Cell Lines (H226 NSCLC and HL-60 Promyelocytic Leukemia) and Normal Primary Peripheral Blood Mononuclear Cells (PBMCs) to COTI-2

The $IC_{50}$ of COTI2-M05 was determined against normal human peripheral blood mononuclear cells (PBMCs) as an indication of the toxicity of the compound against healthy non-cancerous cells. Both human promyeloctic leukemia human (HL-60) and human NSCLC (H226) cell lines were used as a comparator against the PBMCs.

Methods:

All cell lines were grown and exposed to various concentrations of COTI-2 or vehicle only control and the percentage of dead or dying cells were determined 24 and 48 h post-exposure by Annexin V and propidium iodide.

Tumour Cell Lines and Primary Non-Tumour Human Peripheral Blood Mononuclear Cells:

HL-60 (human promyelocytic leukemia) cells were grown as non-adherent cells in flasks in RPMI 1640 medium supplemented with 10% FBS. H226 (human non-small cell lung cancer) cells were grown in Eagle's MEM supplemented with 10% FBS. Both cell lines were obtained from the American Type Culture Collection (ATCC)(Rockville, Md.) and maintained at 37° C. in a humidified 5% $CO_2$ atmosphere.

Blood samples from 2 healthy human volunteers (male, 22 years of age; female, 23 years of age) were obtained in 5 ml Vacutainersi® containing 100 USP sodium heparin (Becton Dickinson, Franklin Lake, N.J.) and rocked gently to mix, then kept at room temperature. Blood was diluted 1:1 with phosphate buffered saline (PBS) and layered over an equal volume of room temperature Histopaque-1083® (Sigma Diagnostics, St. Louis, Mo.) in a 15 ml conical bottom polyethylene (PET) centrifuge tube (Corning Corporation, Corning, N.Y.). This was centrifuged at 400×g for 30 minutes at 20° C. (no brake), to allow separation of mononuclear cells from whole blood. The serum layer was removed by Pasteur pipette and discarded. The mononuclear cell layer at the top of the Histopaque was removed by Pasteur pipette and placed in 15 ml PET centrifuge tube. Cells were washed twice with 10 ml PBS, with centrifugation at 250×g for 15 minutes (maximum brake) to precipitate cells away from the PBS wash fluid. The pellet was suspended in 37° C. RPMI 1640 media (Gibco BRL, Grand Island, N.Y.) with or without 10% fetal bovine serum (Gibco BRL, Grand Island, N.Y.), depending on experimental requirements.

Flow Cytometric Analysis of Cell Death:

Cells were plated in 25-$cm^2$ flasks and treated with COTI-2 (0-100 µM) added from a stock DMSO/DMEM solution such that DMSO concentrations never exceeded 0.5%. Control cells were treated with stock DMSO/DMEM. At 24 and 48 h after addition of drug or control (vehicle alone), supernatant medium (containing all HL-60 cells or any non-adherent H226 cells or non-tumour primary peripheral blood mononuclear cells) was collected into 13 ml conical centrifuge tubes. Remaining adherent cells were rinsed with ice-cold PBS, trypsinized, and added to the non-adherent fraction. Cells were centrifuged (100×g for 10 min at 4° C.), washed once more in ice-cold PBS, re-precipitated by centrifugation, and re-suspended (1000 cells per µl) in binding buffer (140 mM $NaCl_2$, 2.5 mM $CaCl_2$, 10 mM HEPES). Resuspended cells (100 µl) were incubated in the dark with 10 µl propidium iodide (PI, 50 ng per ml; Sigma, St. Lous, Mo.) plus Annexin V-FITC (25 ng per ml, green fluorescence; BD Biosciences, Mississauga, Ontario). The Annexin V-positive cells indicate dying or apoptotic cells and dead cells, whereas the propidium iodide stains for dead cells. Samples were analyzed for combined Annexin V/PI staining (to assess dead plus apoptotic cells) using a Beckman Coulter EPCS XL-MCL flow cytometer (Beckman Coulter, Hileah, Fla.) and the data were analyzed with CellQuest software.

Figure 47:
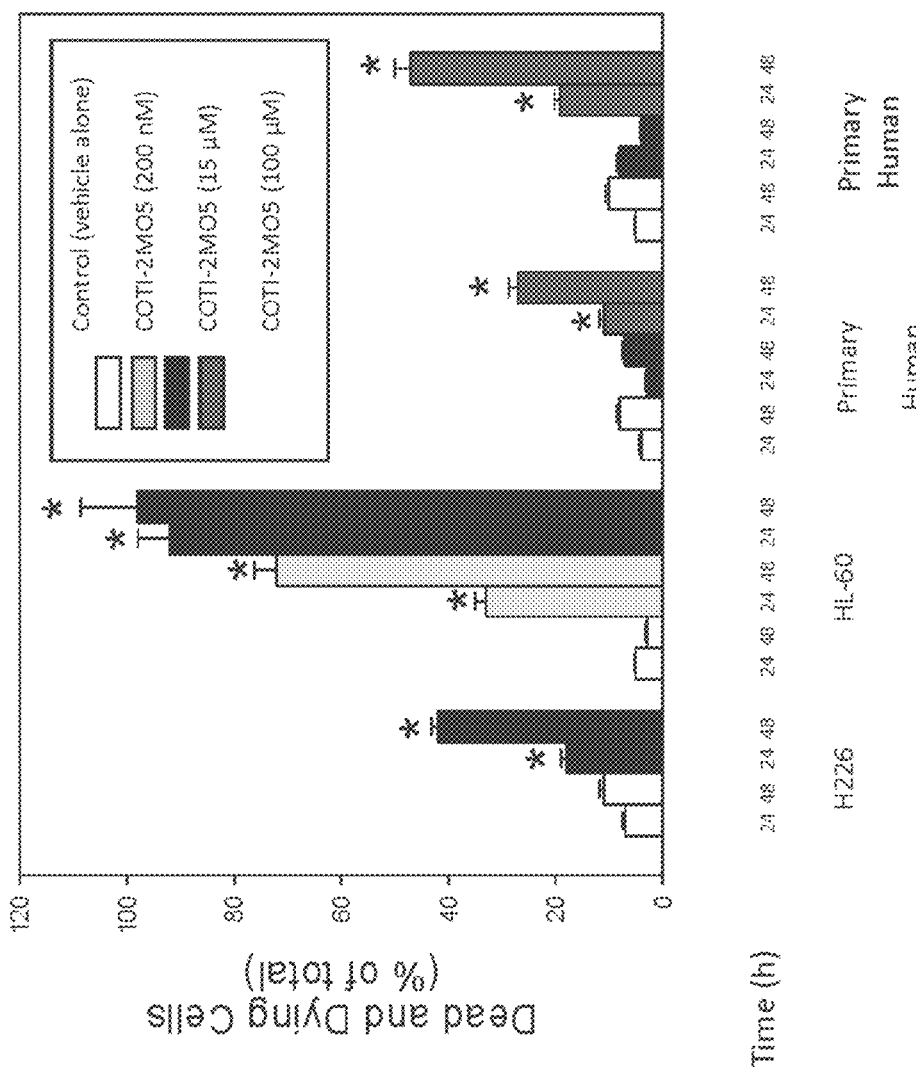
FIG. 47 shows sensitivity of human tumor cell lines (H226 & HL-60) and primary human peripheral blood mononuclear cells (PBMCs) to COTI2-M05, data are represented as the mean of 5 measurements±standard error and the asterisk (*) indicates a significant difference from controls (p<0.05)

Results and Discussion:

The H226 promyeloctic leukemia cell lines were chosen for this study since they exhibited the least sensitivity of the panel of human tumor cell lines previously tested for sensitivity to growth inhibition by COTI-2. The induction of apoptosis and death in approximately 40% of these cells at 48 h after treatment with 15 µM of COTI2-M05 is consistent with the previously determined $IC_{50}$ (FIG. 47). Similarly, induction of greater than 30% death at 24 h and greater than 70% death at 48 h in HL-60 cells after treatment with 200 nM of COTI-2 is consistent with our previous report of an $IC_{50}$ for HL-60 cells of 236 nM (±9) (FIG. 47).

PBMCs from healthy adult human male and female subjects were more than 500-fold less sensitive than HL-60 cells (derived from human monocytes) to death induction by COTI2-M05 (FIG. 47). The healthy PBMCs were exposed to COTI2-M05 at a concentration of 100 µM, which is the maximum practical concentration to which these normal mononuclear cells could be exposed. At this concentration, COTI-2 induced some cell death in male and female PBMCs compared to vehicle only controls, however, this concentration was less than the $IC_{50}$ of these cells (i.e., $IC_{50}$>100 µM). Furthermore, compared to H226 cells, normal PBMCs were 6- to 7-fold less sensitive to death induction by COTI-2 (FIG. 47).

In conclusion, these experiments indicate that normal differentiated human cells were much less sensitive than human tumor cells to apoptotic death by COTI2-M05. One limitation of these experiments is that immortalized human tumor cell lines (HL-60 & H226) capable of ex vivo proliferation were compared against non-immortalized human PBMCs that are not capable of ex vivo growth under the conditions used. Interestingly, despite this limitation, we see a significant difference in cell death in tumor cell lines relative to non-tumor healthy cells.

Example 22

Molecular Target Validation for COTI-219 in SCLC Cell Lines

Figure 48:
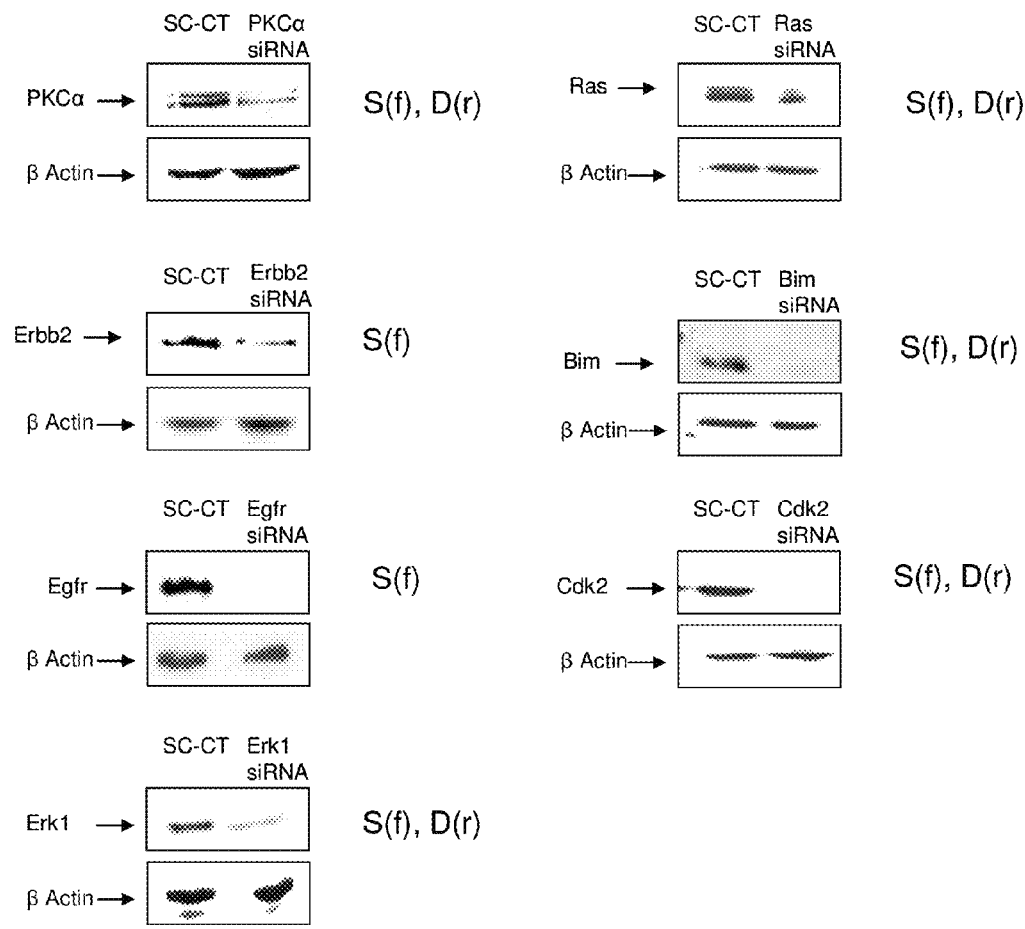
FIG. 48 shows representative western blot analysis of DMS114 and SHP77 cells transfected with gene-specific siRNA or scrambled control oligonucleotide for 48 h.

Gene expression profile/MPM analysis of the molecular pathways responsible for COTI-2,9-induced apoptosis in small cell lung cancer (SCLC) cell lines identified several potential targets for this compound. The principal aim of the experiments described here was to provide validation for these targets and further help define the mechanism of action of COTI-219. siRNA technology was used to knock-down Ras, Bim, CDK2, Egfr, Erbb2, Erk1/2, and PKC-α, in 2 SCLC cell lines, namely DMS114 and SHP77.
Methods:

In brief, cells DMS114 and SHP77 cells were transfected with gene specific siRNA in the presence or absence of COTI-219 and cell viability determined after 24 to 48 h post-incubation using the trypan blue exclusion method.
Tissue Culture and siRNA Experiments:

Cell cultures were maintained under regular tissue culture conditions and passaged 1-2 times a week as recommended by ATCC. With the exception of the siRNA for Bim (Signal Silence Bim siRNA kit #6460 from Cell Signaling), all other siRNA reagents for gene knock-down experiments was obtained from Ambion (Silencer Negative Control #1 siRNA #AM4611, CDK2 Silencer Select #s204, HRAS Silencer Select #s807, Protein kinase C alpha Silencer Validated #301, MAPK3/Erk Silencer Pre-designed #214749, EGFR Silencer Select #s563, and ERBB2 Silencer Select #s611). Initially, the manufacturer's suggested conditions for transfection were followed but the extent of knock-down obtained was in some cases poor and unsuitable for drug target validation experiments. The tranfection method required optimization such that a knock-down of the target gene greater than ~75% was achieved and confirmed by western blot analyses. In some cases, siRNA concentrations up to 100 nM were required to produce a useful degree of target knock-down. Furthermore, for some siRNA's useful target knock-downs were achieved by forward transfection protocols while for others reverse transfection was necessary. For forward transfection protocols, up to $2.0 \times 10^5$ cells were plated overnight, followed by incubation with the siRNA reagent for an additional 48 hrs. In reverse transfection protocols ~$0.1 \times 10^5$ cells were incubated with the siRNA reagent at the time of plating, omitting the 24 h pre-plating step. For each siRNA used in the gene knock-down experiments the transfection protocol was optimized with respect to the number of cells, amount of siRNA and transfection method so that a knock-down of the target gene >75% was achieved. Following an optimal knock-down level at >75%, $2 \times 10^5$ cells were incubated with 500 nM COTI-219 and number of viable cells was measured at 48 h.
Cell Viability and Western Blotting:

Cell viability assays were performed 24 to 48 h following incubation with COTI-219 by the trypan blue exclusion method using a Beckman-Coulter Vi-CELL XR 2.03 automated cell counter. Routine laboratory methods were employed for the production of cellular lysates, protein quantitation, SDS-PAGE and western blotting. All antibodies were obtained from Cell Signaling (Erk1/2 #4695, Ras #3965, CDK2 #2546, PKCalpha #2056, EGFR #2232, and ERBB2 #2165). A Student's T-test was used to compare control and COTI-219 treated cells in order to determine a significant difference (p<0.01).
Cell Cycle Analysis:

Approximately $2 \times 10^5$ DMS114 cells were incubated for 24 h with the indicated concentrations of COTI-219. Following incubation with COTI-219 the cells were washed and re-suspended in 0.5 ml of BP Pharmingen Propidium Iodide staining solution (Cat. No. 556463) for FACS analysis in order to determine the changes in the cell cycle.
Results and Discussion:

The tranfection method required optimization such that a knock-down of the target gene greater than ~75% was achieved and confirmed by western blot analyses. Representative western blot analysis of DMS114 and SHP77 cells transfected with gene-specific siRNA or scrambled control siRNA after 48 h incubation are illustrated in FIG. 48 in order to demonstrate the extent of down-regulation of target genes obtained. Notably, Egfr and Erbb2 expression was very low in DMS114 cells, but SHP 77 cells express robust levels of these proteins.

FIG. 48 shows representative western blot analysis of DMS114 and SHP77 cells transfected with gene-specific siRNA or scrambled control oligonucleotide for 48 h. Actin control blots (not shown) demonstrated that similar amounts of protein were loaded. SC-CT, scrambled control oligonucleotide; D, DMS114; S, SHP77; f, forward and r, reverse transfection protocols.

Figure 49A:
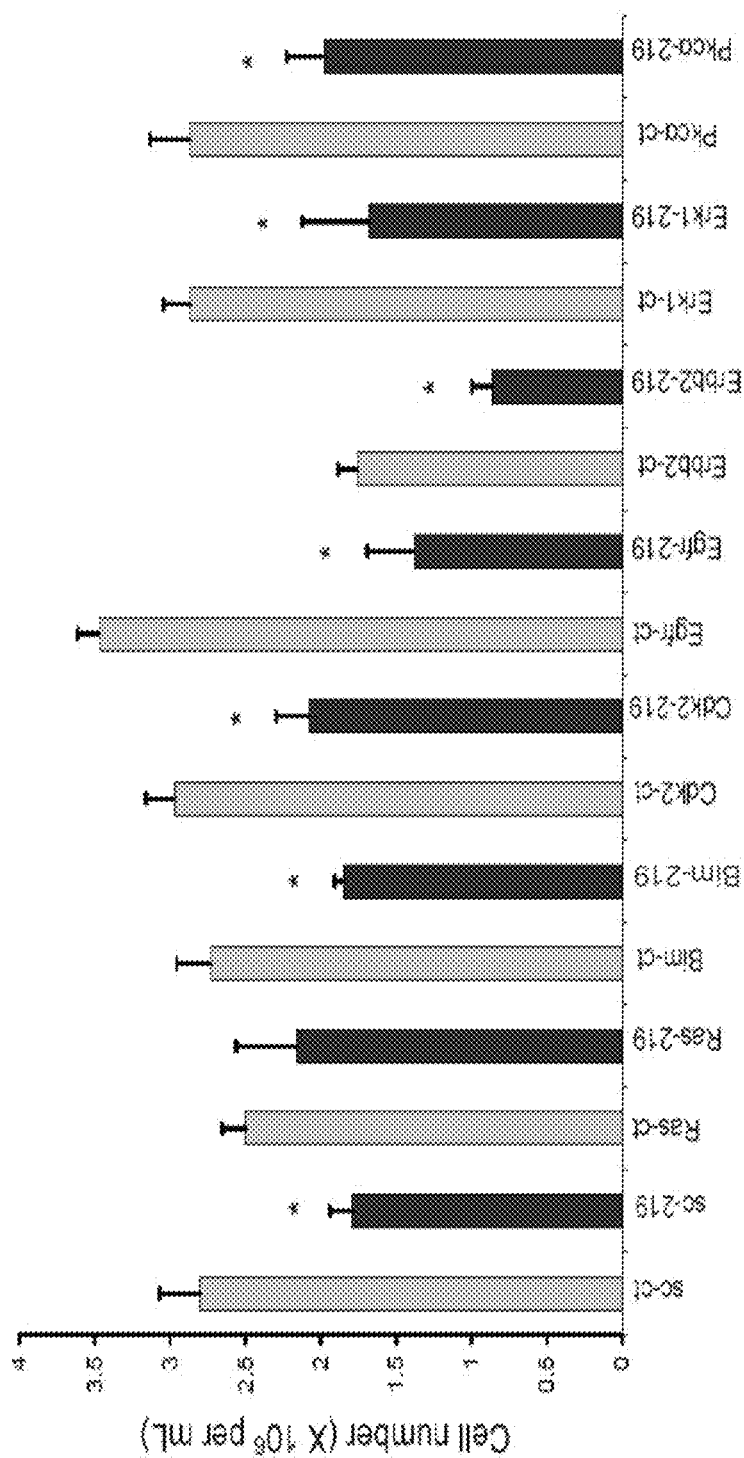
FIGS. 49A-B show determination of apoptosis following target knock-down with gene-specific or scrambled (sc) siRNA in the absence or presence of 500 nM COTI-219 in DMS114 (FIG. 50A) and SHP77 (FIG. 49B) cells; Asterisks (*) denote significant differences (p<0.01) between control and COTI-219 treated cells.
Figure 49B:
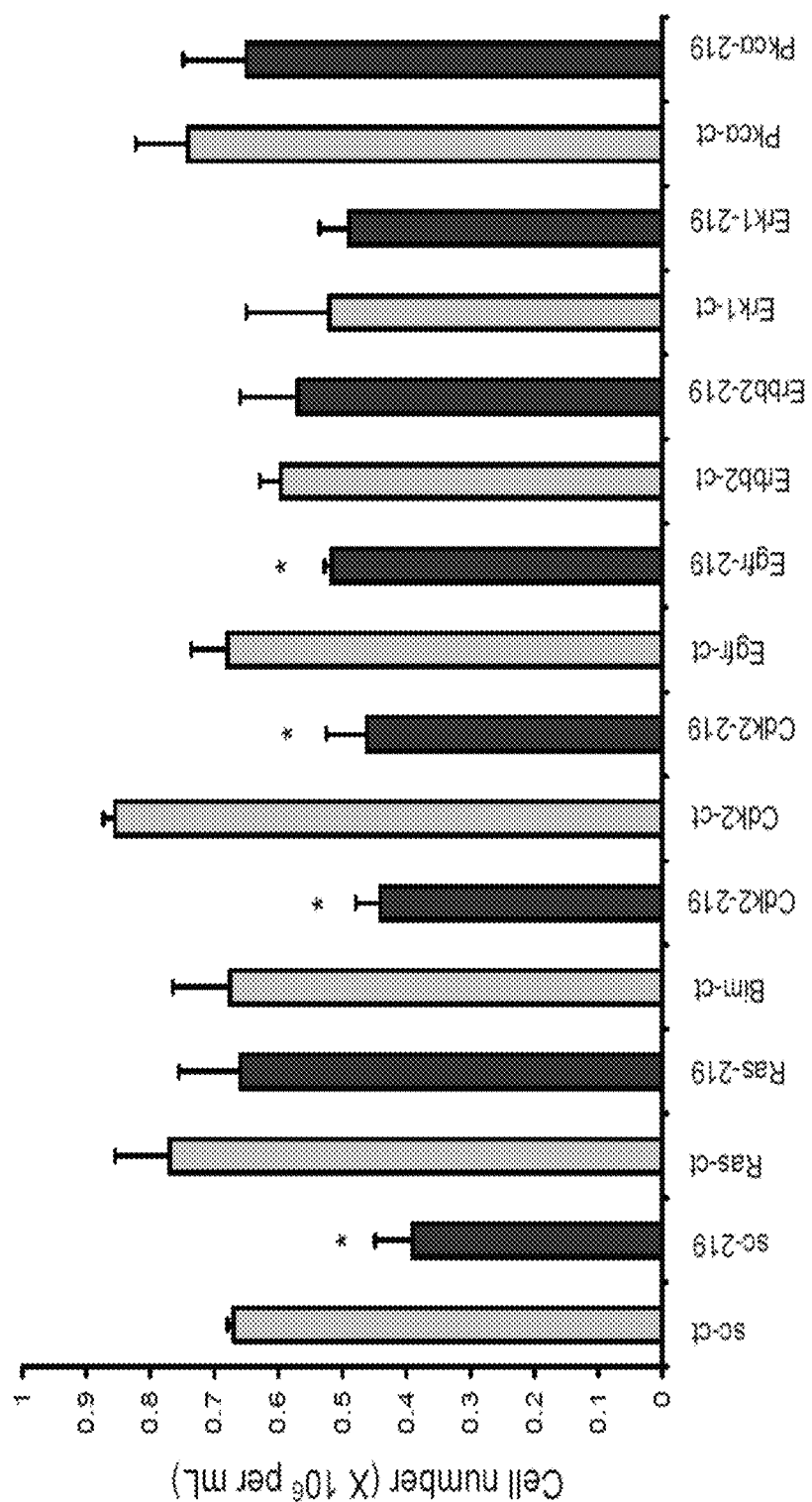

Following optimization of siRNA transfection, cells were incubated for 48 h with 500 nM COTI-219 and cell viability determined. In DMS114 cells only the Ras knock-down was able to suppress the action of COTI-219 on apoptosis/cell growth (FIG. 49A). The fact that knock-down of Erbb2 significantly decreases cell viability even in the absence of COTI-219 is surprising given than Erbb2 protein levels were barely detectable in this cell line. It is unclear if this represents a non-specific event. Unlike DMS114, SHP77 cells express robust levels of Egfr and Erbb2. In this cell line, not only Ras but Erbb2, Erk1, and PKC-α all suppressed the apoptotic/cell growth inhibitory effect of COTI-219 (FIG. 49B). A possible explanation is that Erbb2, PKC-α, and Erk1/2 knock-downs are likely to slow-down cellular proliferation by inhibiting cyclin D1 activity. Cyclin D1 mRNA is only moderately expressed in SHP77 cells as opposed to non-small cell lung cancer cells, where gene amplification has been reported. As a result, Erbb2 and its downstream effectors, including PKC-α and Erk1/2 may play a significant role in cyclin D1 up-regulation. In the absence of sustained levels of Erbb2, PKC-α, or Erk1/2 to regulate cyclin D1 expression the ability of COTI-219 to induce G1 arrest and apoptosis may be impaired. Since the cell viability assay reflects the compounded effects of apoptosis and growth inhibition it cannot differentiate between the relative effects of the knock-down on the two processes. Furthermore, COTI-219 induces both apoptosis and cycle arrest at the concentration used in these experiments (FIG. 49A-B). Therefore, while knockdown of Ras likely suppresses COTI-219 apoptosis, the knock-down of Erbb2, may suppress the growth inhibitory effects of COTI-219.

In lung cancer, oncogenic Ras exerts anti-apoptotic effects, in part by up-regulating the multi-functional PKB/AKT kinase. Activated PKB/AKT phosphorylates and inhibits caspase 9 activation. In order to determine whether caspase 9 activation mediates COTI-219 apoptosis, cells were incubated for 12 h with vehicle or increasing concentrations of COTI-219 and the expression levels of cleaved caspases 3 and 9 were determined. There was a dose-dependent increase in the levels of both cleaved caspases, peaking at 0.5 µM of COTI-219. Beyond this concentration, activated caspase 9 was not detectable and there was a decline in cleaved caspase 3. These results demonstrated that COTI-219 can induce apoptosis by a different mechanism(s), which is dose-dependent.

Figure 50:
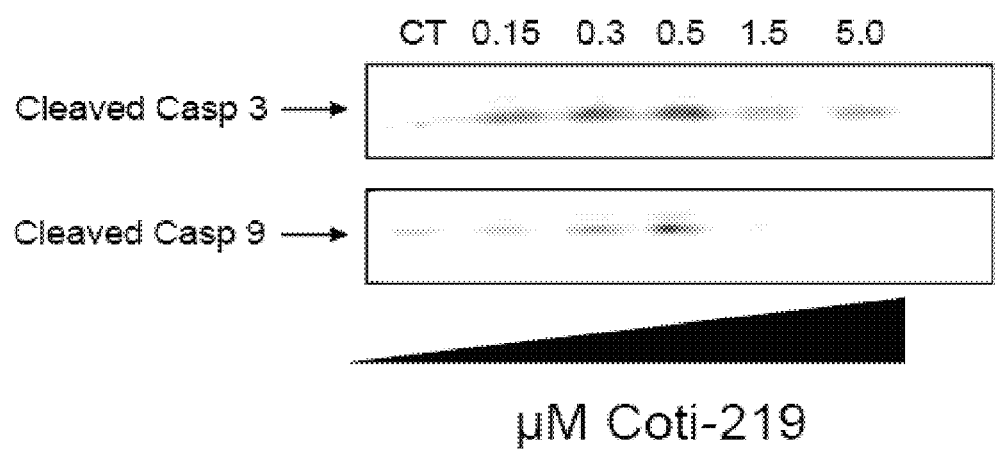
FIG. 50 shows apoptotic cascade activation by COTI-219 as determined by relative expression of cleaved caspase 3 and 9 using western blot analysis following 12 h incubation with various concentrations of COTI-219.
Figure 51A:
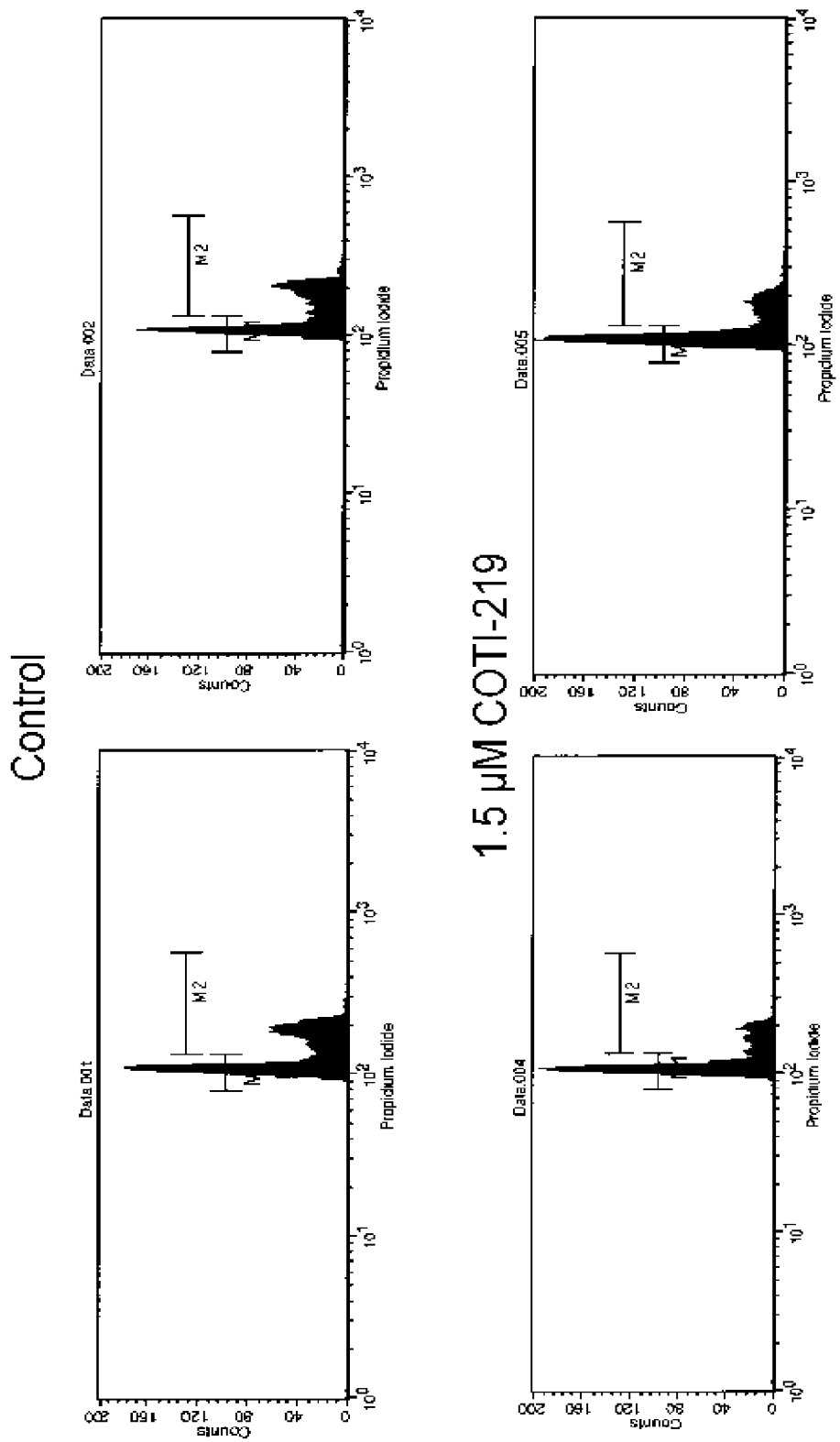
FIGS. 51A and 51B show cell cycle analysis of DMS114 cells by FACS following incubation for 24 h with indicated concentrations of COTI-219; duplicate experiments are shown; M1, Go/G1; M2, S/G.
Figure 51B:
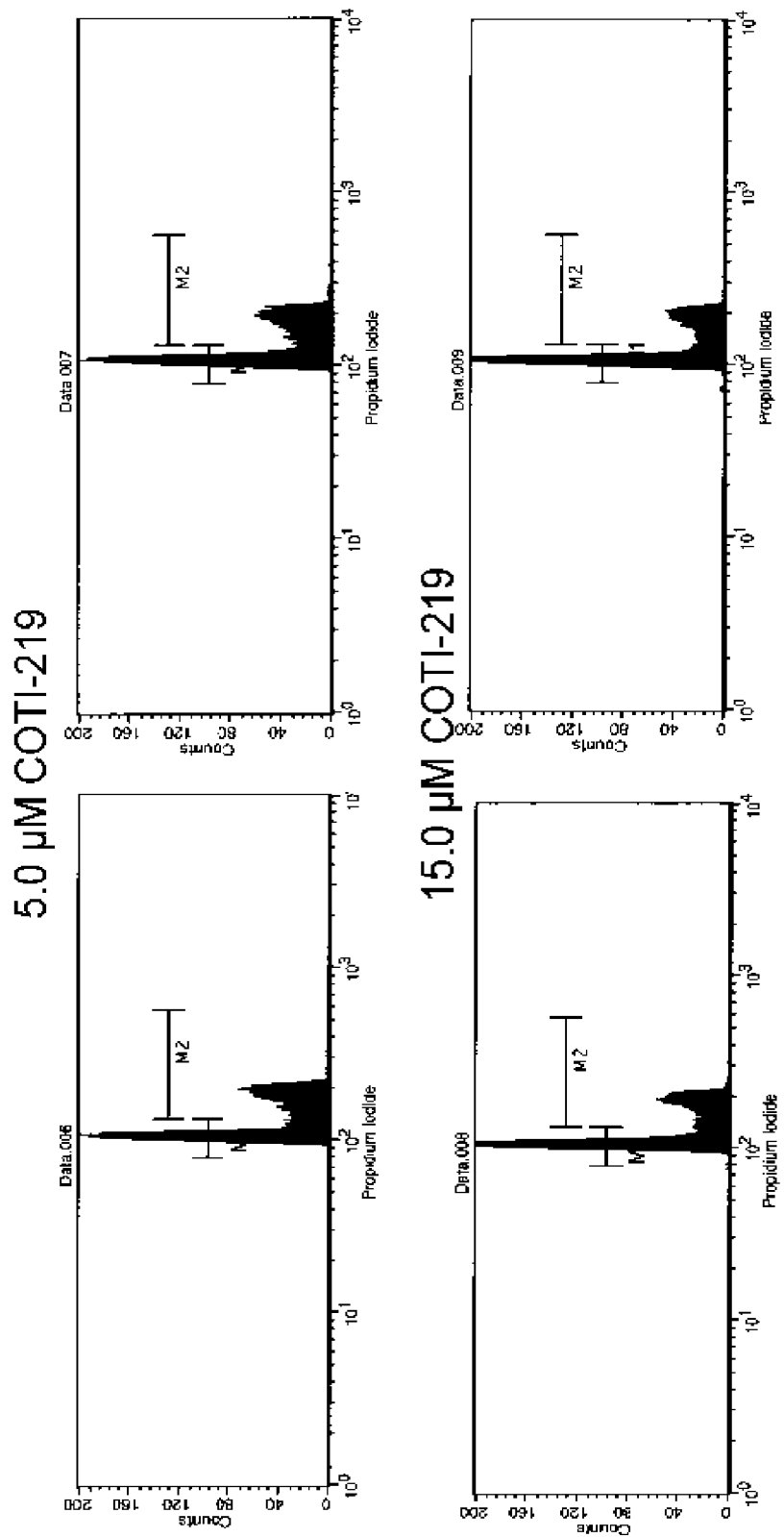

Cells were incubated with increasing concentrations of COTI-219 and cell cycle analyzed in order to further investigate the mechanism of action of COTI-219 since at concentrations ≥0.5 µM there was no detectable caspase 9 cleavage (FIG. 50). Control cells displayed the characteristic pattern of stained nuclei in the Go/G1/S/G2 stages of the cell cycle (FIG. 51). However, incubation with 1.5 µM of COTI-219 produced cell cycle arrest in G1. At higher doses of COTI-219 cells escape G1 arrest and the cell cycle appears to be normal. These observations further strengthen the observation that different mechanisms are responsible for COTI-219 apoptosis, depending upon the concentration of the compound.

The role of the pro-apoptotic regulator Biml remains uncertain. Although it has been reported that small molecule inhibitors of the Egfr/Erbb2 pathway can induce apoptosis by up-regulating Biml expression, and consequently sequestering anti-apoptotic Bc12, knock-down of Bim did not interfere with COTI-219 apoptosis. However, cells that survived COTI-219 apoptosis had significantly lower levels of Bim than did control cells (not shown), suggesting that Biml may play a role in the observed effects of COTI-219.

In conclusion the cumulative data presented in this study suggest that, at nanomolar ranges of concentrations (≤500 nM), COTI219 induces apoptosis through its inhibitory effect on Ras; whereas, at higher micromolar concentrations (≥1.5 µM), COTI219 induces cell cycle arrest through an unidentified target. This concentration of COTI-219 is important in understanding the mechanism of action of COTI-219, as higher concentrations may affect a different set of molecular targets and induce apoptosis by different mechanisms (see further).

Example 23

In Vitro Pharmacokinetics (ADME Toxicology)

The pharmacokinetics of many antineoplastic agents are associated with treatment outcome, which makes it desirable to evaluate these parameters in various in vitro and in vivo screens (Nat Rev Cancer 5: 447-458). ADMET, which is an acronym for absorption, distribution, metabolism, excretion and toxicity, describes the disposition of a pharmaceutical compound within an organism (Nat Rev Cancer 6: 546-558). These criteria all influence the drug levels and kinetics of exposure to the tissues and hence influence the performance and pharmacological activity of the compound. An ensemble of tests is used to characterize a compound's properties with respect to the criteria listed above. Consequently, COTI-2 was evaluated for its plasma protein binding, absorption (Pgp substrate/inhibitor), metabolic stability, and CYP450 inhibition potential using in vitro experiments to characterize its pharmacokinetics.

Methods:
Plasma Protein Binding:
The experimental method employed which was described previously (J Pharm Sci 92: 967-974) is outlined below.

| Assay | Test Compound | Equilibration/Incubation | Analytical Method |
|---|---|---|---|
| Plasma Protein Binding (human) | 10 µM (n = 2) 1% DMSO | At least 8 hours at 37° C. in human plasma 12-14K MWCO dialysis membrane 0.05M phosphate buffer, pH 7.5 | HPLC-MS/MS |
| Plasma Protein Binding (rat, mixed breeds) | 10 µM (n = 2) 1% DMSO | At least 8 hours at 37° C. in rat plasma 12-14K MWCO dialysis membrane 0.05M phosphate buffer, pH 7.5 | HPLC-MS/MS |
| Plasma Protein Binding (dog, mixed breeds) | 10 µM (n = 2) 1% DMSO | At least 8 hours at 37° C. in dog plasma 12-14K MWCO dialysis membrane 0.05M phosphate buffer, pH 7.5 | HPLC-MS/MS |

Notes:
96-well dialysis apparatus: from HTDialysis LLC (Gates Ferry, CT), part #1006

Abbreviations:
DMSO: Dimethylsulfoxide
HPLC-MS/MS: HPLC coupled with tandem mass spectrometry (Instrumentation: Thermo Finnigan)
HPLC: High performance liquid chromatography
MWCO: Molecular weight cut-off Commercially obtained (Rockland Immunochemicals Inc.), non-sterile, species-specific plasma (human, monkey, and dog) with sodium anticoagulant added was utilized for this study. An equilibrium dialysis experiment was performed in a 96-well format in a dialysis block constructed from Teflon (J Pharm Sci 92: 967-974). Dialysis membrane strips (12-14K MWCO) were presoaked in water and ethanol, rinsed and then kept in buffer until use. Following assembly of the 96-well dialysis apparatus, 0.15 ml of the dialysis block was assembled and membrane strips placed between the dialysis and sample compartments. The dialysate compartment was loaded with 0.15 ml phosphate buffer was added to the dialysis side of each well. Plasma (unfiltered) was spiked with 10 µM COTI-2 (1% DMSO) and 0.15 ml added to the sample side of each well. After loading, samples are covered and incubated at 37° C. until equilibrium was reached (at least 8 hours). Equal volumes of sample were removed from the buffer and plasma sides of each well, diluted with acetonitrile/buffer and centrifuged. Also at this time an additional sample was prepared (in duplicate) by spiking COTI-2 in plasma at 10 µM, followed by sampling and diluting in acetonitrile/buffer in the same manner as the incubated plasma sample. This calibration sample served as the basis of a recovery determination. The supernatants were analyzed by HPLC-MS/MS and the peak response of COTI-2 in both dialysis and sample compartments, and in the calibration sample, were subsequently determined in two independent replicates. Acebutolol, quinidine and warfarin were included in each assay as reference compounds. The reference compounds yield protein binding values that represent low, medium and high binding to plasma proteins, respectively. Samples were analyzed via (RP)HPLC-MS/MS using selected reaction monitoring (SRM). The HPLC conditions consist of a binary LC pump with autosampler, a C18 column (2×20 mm), and gradient elution. The percent bound to plasma/serum proteins and percent recovery of the compounds were calculated. The recovery determination serves as an indicator as to the reliability of the calculated protein binding value.

In Vitro Absorption (Pgp Substrate or Inhibitor):
The general procedures are outlined below.

| Assay | Test Concentration | Biological Conditions | Analytical Methods |
|---|---|---|---|
| A-B Permeability (TC7, pH 7.4/7.4) | 10 μM in HBSS 1% DMSO (n = 2) | A-to-B flux at 37° C. with shaking 96-well Multiscreen plate pH 7.4 in A and pH 7.4 in B Donor samples: time 0 and 60 min Receiver samples: time 60 min | HPLC-MS/MS |
| A-B Permeability (TC7, pH 7.4/7.4) + verapamil | 10 μM in HBSS 100 μM verapamil in A and B sides, 1% DMSO (n = 2) | A-to-B flux at 37° C. with shaking 96-well Multiscreen plate pH 7.4 in A and pH 7.4 in B Donor samples: time 0 and 60 min Receiver samples: time 60 min | HPLC-MS/MS |
| B-A Permeability (TC7, pH 7.4/7.4) | 10 μM in HBSS 1% DMSO (n = 2) | B-to-A flux at 37° C. with shaking 96-well Multiscreen plate pH 7.4 in A and pH 7.4 in B Donor samples: time 0 and 40 min Receiver samples: time 40 min | HPLC-MS/MS |
| B-A Permeability (TC7, pH 7.4/7.4) + verapamil | 10 μM in HBSS 100 μM verapamil in A and B sides, 1% DMSO (n = 2) | B-to-A flux at 37° C. with shaking 96-well Multiscreen plate pH 6.5 in A and pH 7.4 in B Donor samples: time 0 and 40 min Receiver samples: time 40 min | HPLC-MS/MS |
| P-glycoprotein inhibition (TC7, $^3$H-digoxin substrate) | Test compound (0.03, 0.3, 1, 3, 5, 10, 30 and 100 μM in both A and B sides) $^3$H-digoxin in B side, digoxin (10 μM) in A side and B side in HBSS, 0.1% BSA, 1% DMSO (n = 2) | B-to-A flux at 37° C. with shaking 96-well Multiscreen plate pH 7.4 in A and B sides Donor samples: time 180 min Receiver samples: time 180 min | Scintillation counting |

Notes:
Multiscreen plate: 96-well plate, from Millipore, catalog number MACACO2S5
Abbreviations:
A: Apical side
B: Basolateral side
DMSO: Dimethylsulfoxide
HBSS: Hank's balanced salt solution, from Invitrogen, catalog number 14065-056, plus 5 mM HEPES, from Sigma, catalog number H 3375, pH 7.4
HEPES: N-(2-hydroxyethyl)-piperazine-N'-(2-ethanesulfonic acid)
HPLC-MS/MS: HPLC coupled with tandem mass spectrometry (Instrumentation: Thermo Finnigan)
HPLC: High performance liquid chromatography

| Assay | Cell | Passage Number | Days in Culture | Reference Compound | Bibliography |
|---|---|---|---|---|---|
| A-B Permeability (TC7, pH 7.4/7.4) | TC7 (human intestinal epithelial cells) | 15 passages in culture between passages 20 and 40 | 13 to 25 | 4 reference compounds (set 2) | Gres et al. (1998) |
| A-B Permeability (TC7, pH 7.4/7.4) + verapamil | TC7 (human intestinal epithelial cells) | 15 passages in culture between passages 20 and 40 | 13 to 25 | | Gres et al. (1998) |
| B-A Permeability (TC7, pH 7.4/7.4) | TC7 (human intestinal epithelial cells) | 15 passages in culture between passages 20 and 40 | 13 to 25 | 4 reference compounds (set 2) | Horio M. et al. (1989) |
| B-A Permeability (TC7, pH 7.4/7.4) + verapamil | TC7 (human intestinal epithelial cells) | 15 passages in culture between passages 20 and 40 | 13 to 25 | | Hunter et al. (1993) |
| P-glycoprotein inhibition (TC7, $^3$H-digoxin substrate) | TC7 (human intestinal epithelial cells) | 15 passages in culture between passages 20 and 40 | 13 to 25 | Verapamil | Cavet et al. (1996) |

Notes:
TC7 is a sub-clone of the Caco-2 cell line.
4 Reference compounds (set 2): Propranolol, Ranitidine, Colchicine and Labetalol.

TC7 cells were seeded at 1×10$^5$ cells/cm$^2$ on porous polycarbonate membrane in 96-well Multiscreen™ plates (Millipore). Cells were fed every 2 to 3 days and the day before the permeability assay. Permeability assays are performed with the cells at days 13-25 post-seeding. The assay directions included apical to basolateral (A-B) and basolateral to apical (B-A). The working solution for COTI-2 was prepared at 10 μM in HBSS-MES (5 mM), pH 6.5, or HBSS-HEPES (5 mM), pH 7.4, from a 1 mM DMSO stock solution. The working solution was then centrifuged and the supernatant was added to the apical or basolateral side with a final DMSO concentration of 1%. The assay was incubated for 60 or 40 mM with gentle shaking at 37° C. The sampling scheme consisted of donor time zero, donor time 60 or 40 min, and receiver time 60 or 40 min. Samples were analyzed via (RP) HPLC-MS/MS using selected reaction monitoring (SRM). Reference compounds included, propranolol (highly permeable), labetalol (moderately permeable), ranitidine (poorly permeable), and colchicine (P-glycoprotein substrate) were included in each assay. The cell monolayer integrity was confirmed by fluorescein permeability assessment (in the A-B direction at pH 7.4 on both sides with 1 h incubation) after the permeability assay with COTI-2. The cell monolayer that has a fluorescein permeability of less than 0.5×10$^{-6}$ cm/s was considered intact. The apparent permeability coefficient ($P_{app}$) of COTI-2 in the apical to the basolateral and apical direction and the percent recovery of the compounds were calculated.

For the P-glycoprotein inhibition assay using $^3$H-digoxin as substrate, the TC7 cells were grown as above.

Two working solutions, working solution I and II, were prepared and each added to the apical and basolateral sides, respectively. Working solution I consisted of COTI-2 at various concentrations ranging from 0.01 to 100 μM in HBSS-HEPES (5 mM)/0.1% BSA, at pH 7.4 from a 10 mM DMSO stock solution. Digoxin (10 μM) and Fluorescein (10 μM) were included in this working solution. The working solution I was then mixed and added to the apical side with a final DMSO concentration of no more than 1%. Working solution II consisted of various concentrations (0.01 to 100 μM) of COTI-2 prepared in HBSS-HEPES (5 mM)/0.1% BSA, at pH 7.4 from a 10 mM DMSO stock solution. Digoxin (10 μM) and $^3$H-digoxin were included in the working solution. The working solution II was then mixed and added to the basolateral side with a final DMSO concentration of no more than 1%. The assay was incubated for 3 h with gentle shaking at 37° C. The assay was sampled at 3 h and analyzed by liquid scintillation counting for $^3$H-digoxin and fluorescence detection for Fluorescein. As a reference, verapamil (0.001-0.002 µM) was added to both the A and B sides. Cell monolayer integrated was assessed by the addition of 10 µM to the apical side and background fluorescence determined from the basolateral side at time 0 and compared to time 3 h. An apparent permeability of <0.5×10$^{-6}$ cm/s for fluorescein corresponds to an intact monolayer. The percent inhibition of the permeation of $^3$H-digoxin was calculated following scintillation count.

Metabolic Stability:
The experimental conditions are outlined below.

by adding COTI-2 (1 µM final concentration) and incubated in a final volume of 400 µl for 0 min and 60 mM in the 37° C. shaking water bath. The reaction was stopped by transferring 100 µL of the incubation mixture to 100 µl of acetonitrile/methanol (50/50, v/v) in a 0.8 ml V-bottom 96-well plate. Samples were then mixed on a plate shaker for 5 mM and centrifuged at 2550×g for 15 mM at room temperature. Each supernatant (150 µl) was transferred to a clean cluster tube, followed by HPLC-MS/MS analysis on a Thermo Electron triple-quadrupole system. Four reference substrates (1 µM) were tested simultaneously with COTI-2. Propranolol and imipramine are relatively stable, whereas verapamil and ter-

| Assay | Substrate/Cofactor | Incubation | Detected Component | Analytical Method |
|---|---|---|---|---|
| Metabolic Stability (liver microsomes, human) | Test compound (1 µM), NADP (1 mM), G6P (5 mM), G6PDHase (1 U/mL) with 0.6% methanol, 0.6% acetonitrile (n = 2) | 0 and 60 min. 37° C. Phosphate buffer, pH 7.4 | Product ion corresponding to the test coumpound via SRM | HPLC-MS/MS |
| Metabolic Stability (liver microsomes, monkey, Cynomolgus) | Test compound (1 µM), NADP (1 mM), G6P (5 mM), G6PDHase (1 U/mL) with 0.6% methanol, 0.6% acetonitrile (n = 2) | 0 and 60 min. 37° C. Phosphate buffer, pH 7.4 | Product ion corresponding to the test coumpound via SRM | HPLC-MS/MS |
| Metabolic Stability (liver microsomes, dog, Beagle) | Test compound (1 µM), NADP (1 mM), G6P (5 mM), G6PDHase (1 U/mL) with 0.6% methanol, 0.6% acetonitrile (n = 2) | 0 and 60 min. 37° C. Phosphate buffer, pH 7.4 | Product ion corresponding to the test coumpound via SRM | HPLC-MS/MS |
| Metabolic Stability (liver microsomes, rat, Sprague-Dawley) | Test compound (1 µM), NADP (1 mM), G6P (5 mM), G6PDHase (1 U/mL) with 0.6% methanol, 0.6% acetonitrile (n = 2) | 0 and 60 min. 37° C. Phosphate buffer, pH 7.4 | Product ion corresponding to the test coumpound via SRM | HPLC-MS/MS |

Abbreviations:
CYP: Cytochrome P450
G6P: D-Glucose-6-phosphate, from Sigma, catalog number G-7772
G6PDHase: Glucose-6-phosphate dehydrogenase, from Sigma, catalog number G-4134
HPLC-MS/MS: HPLC coupled with tandem mass spectrometry (Instrumentation: Thermo Finnigan)
HPLC: High performance liquid chromatrography
NADP: β-Nicotinamide adenine dinucleotide phosphate, from Sigma, catalog number N-0505
SRM: Selected reaction monitoring Metabolic stability was determined in human (mixed gender and pool of 50), monkey (male Cynomolgus, pool of 6 or more), dog (male, beagle, pool of 4 or more), and rat (male, Sprague-Dawley, pool of 100 or more) liver microsomes. Pooled liver microsomes were pre-incubated with NADPH-generating system (1 mM NADP, 5 mM G6P, and 1 U/ml G6PDHase) in phosphate buffer (pH 7.4) containing 3 mM MgCl$_2$ and 1 mM EDTA in a 2 ml-block 96-well plate for 10 min in a 37° C. shaking water bath. The reaction was initiated fenadine are relatively unstable with human liver microsomes. Peak areas corresponding to COTI-2 were recorded by HPLC-MS/MS. Metabolic stability, expressed as percent of COTI-2 remaining, was calculated by comparing the peak area of COTI-2 at 60 mM to time zero.

CYP450 Inhibition:
The general procedures described previously (Drug Metal Dispos 29: 23-29) are outlined below:

| Assay | Substrate/Cofactor | Incubation | Detected Component | Analytical Method |
|---|---|---|---|---|
| CYP1A Inhibition (HLM, phenacetin substrate) | Test Compound (10 µM), Phenacetin (10 µM), NADP (1.3 mM), G6P (3.3 mM), G6PDHase (0.4 U/mL) (n = 2) | 15 min, 37° C. | Acetaminophen | HPLC-MS/MS |
| CYP2B6 Inhibition (HLM, bupropion substrate) | Test Compound (10 µM), Bupropion (100 µM), NADP (1.3 mM), G6P (3.3 mM), G6PDHase (0.4 U/mL) (n = 2) | 15 min, 37° C. | Hydroxy-bupropion | HPLC-MS/MS |

-continued

| Assay | Substrate/Cofactor | Incubation | Detected Component | Analytical Method |
|---|---|---|---|---|
| CYP2C8 Inhibition (HLM, paclitaxel substrate) | Test Compound (10 µM), Paclitaxel (10 µM), NADP (1.3 mM), G6P (3.3 mM), G6PDHase (0.4 U/mL) (n = 2) | 15 min, 37° C. | 6α Hydroxypaclitaxel | HPLC-MS/MS |
| CYP2C9 Inhibition (HLM, diclofenac substrate) | Test Compound (10 µM), Diclofenac (10 µM), NADP (1.3 mM), G6P (3.3 mM), G6PDHase (0.4 U/mL) (n = 2) | 15 min, 37° C. | 4'-hydroxydiclofenac | HPLC-MS/MS |
| CYP2C19 Inhibition (HLM, omeprazole substrate) | Test Compound (10 µM), Omeprazole (0.5 µM), NADP (1.3 mM), G6P (3.3 mM), G6PDHase (0.4 U/mL) (n = 2) | 15 min, 37° C. | 5-hydroxyomeprazole | HPLC-MS/MS |
| CYP2D6 Inhibition (HLM, dextromethorphan substrate) | Test Compound (10 µM), Dextromethorphan (5 µM), NADP (1.3 mM), G6P (3.3 mM), G6PDHase (0.4 U/mL) (n = 2) | 15 min, 37° C. | Dextrorphan | HPLC-MS/MS |
| CYP2E1 Inhibition (HLM, chlorzoxanzone substrate) | Test Compound (10 µM), Chlorzoxazone (100 µM), NADP (1.3 mM), G6P (3.3 mM), G6PDHase (0.4 U/mL) (n = 2) | 15 min, 37° C. | 6-hydroxychlorzoxazone | HPLC-MS/MS |
| CYP3A Inhibition (HLM, midazolam substrate) | Test Compound (10 µM), Midazolam (5 µM), NADP (1.3 mM), G6P (3.3 mM), G6PDHase (0.4 U/mL) (n = 2) | 15 min, 37° C. | 1-hydroxy-midazolam | HPLC-MS/MS |
| CYP3A Inhibition (HLM, testosterone substrate) | Test Compound (10 µM), Testosterone (50 µM), NADP (1.3 mM), G6P (3.3 mM), G6PDHase (0.4 U/mL) (n = 2) | 15 min, 37° C. | 6β-hydroxytestosterone | HPLC-MS/MS |

COTI-2 (10 µM), reference inhibitor, or the vehicle control was pre-incubated with the CYP specific substrate (10 µM) and NADPH-generating system (1.3 mM NADP, 3.3 mM G6P, and 0.4 U/ml G6PDHase) in phosphate buffer (pH 7.4) in a 2 ml-block 96-well plate for 10 min in a 37° C. shaking water bath. The reaction was initiated by adding pooled human liver microsomes (mixed gender, pool of 50 donors, 0.2 mg/ml). The final incubation volume was 200 µl. The reaction was allowed for 15 min in the 37° C. shaking water bath and stopped by transferring 100 µl of the reaction mixture to 100 µl of acetonitrile/methanol (1/1, v/v) in a 0.8 ml V-bottom 96-well plate. Samples are mixed on a plate shaker for 5 min and centrifuged at 2550×g for 15 min at room temperature. The supernatant (150 µl) is then transferred to a clean cluster tube, followed by HPLC-MS/MS analysis on a Thermo Electron triple-quadrupole system to detect the metabolite. Each CYP specific inhibitor was tested simultaneously with reference compounds at several concentrations to obtain the $IC_{50}$ value. Peak areas corresponding to metabolite were recorded. The percent of control activity was calculated by comparing the peak area in incubations containing COTI-2 at 15 min to the control samples containing the same solvent vehicle at 15 min Subsequently, the percent inhibition was calculated by subtracting the percent control activity from 100.

Results and Discussion:
Plasma Protein Binding:

The binding of pharmaceutical agents to plasma proteins, mostly to serum albumin, lipoprotein and α-acid glycoprotein, is one of many factors that influences the pharmacokinetic and pharmacodynamic properties of an agent. It is widely accepted that a compound's efficacy may be affected by the degree to which it binds to plasma proteins, such that the unbound concentration of an agent in plasma is available to diffuse extra-vascular spaces (organs and tissues), cell membranes, and interact with the pharmacological target (Clin Pharmacokinet 39: 345-367). The plasma-bound form of the therapeutic agent can also serve as a reservoir from which the agent is released to an unbound form. Consequently, tests have been designed to determine the bound & unbound fractions of the total compound concentration. The two most commonly employed methods used to determine plasma protein-binding of compounds are ultrafiltration and equilibrium dialysis (Clin Pharmacokinet 23: 449-468 & Fundam Clin Pharmacol 4(suppl2): 151s-161s).

COTI-2 was evaluated for binding plasma proteins in 3 species, namely human, monkey, and dog, using an equilibrium dialysis technique that separates the fraction of compound that is unbound from that which is bound. As a control, a calibration sample was utilized to determine percent recovery. Both percent protein binding and recovery were calculated (Table 26) and compared against plasma protein binding of the reference compounds, acetbutolol, quinidine and warfarin, which represent compounds with low, medium, and high binding to plasma proteins, respectively (Table 27). The data indicate that COTI-2 exhibits high binding to plasma proteins from all 3 species tested (>99%). These data, however, should be interpreted with caution since the percent recovery values are low (<50%). The percent recovery is an indicator of the reliability of the percent protein bound values. Low recovery values indicate that the test compound is lost during the assay due to non-specific interactions (e.g., binding to the apparatus, membrane, etc) or due to degradation by enzymatic activity. Having said that, these data indicate that since the plasma protein binding of COTI-2 among the 3 species examined is highly similar, plasma protein levels are not anticipated to complicate the understanding of interspecies pharmacodynamic and toxicological effects. This is particularly important when evaluating the nonclinical toxicological data generated in rats and dogs necessary for First-in-Human (FIH) trials.

TABLE 26

Percent protein bound and recovery of COTI-2 in human, rat, and dog plasma.

| Assay Cerep Compound I.D. | Client Compound I.D. | Test Concentration (M) | % Protein Bound | | | % Recovery | | |
|---|---|---|---|---|---|---|---|---|
| | | | $1^{st}$ | $2^{nd}$ | Mean | $1^{st}$ | $2^{nd}$ | Mean |
| Plasma Protein Binding (human) | | | | | | | | |
| 15731-1 | COTI2-M05 | 1.0E−05 | 99.8 | >99.9 | 99.8 | 6.7 | 2.9 | 4.8 |
| Plasma Protein Binding (rat, mixed breeds) | | | | | | | | |
| 15731-1 | COTI2-M05 | 1.0E−05 | >99.9 | >99.9 | >99.9 | 16.4 | 25.1 | 20.7 |
| Plasma Protein Binding (dog, mixed breeds) | | | | | | | | |
| 15731-1 | COTI2-M05 | 1.0E−05 | 99.1 | 99.7 | 99.4 | 42.6 | 32.8 | 37.7 |

TABLE 27

Percent protein bound of reference compounds, acebutolol, quinidine, and warfarin, in human, rat, and dog plasma.

| Assay Reference Compound | Test Concentration (M) | % Protein Bound | | |
|---|---|---|---|---|
| | | $1^{st}$ | $2^{nd}$ | Mean |
| Plasma Protein Binding (human) | | | | |
| Acebutolol | 1.0E−05 | 14.9 | 12.8 | 13.8 |
| Quinidine | 1.0E−05 | 52.5 | 48.1 | 50.3 |
| Warfarin | 1.0E−05 | 94.2 | 96.4 | 95.3 |
| Plasma Protein Binding (rat, mixed breeds) | | | | |
| Acebutolol | 1.0E−05 | 8.0 | 3.4 | 5.7 |
| Quinidine | 1.0E−05 | 67.7 | 62.8 | 65.2 |
| Warfarin | 1.0E−05 | 97.8 | 97.6 | 97.7 |
| Plasma Protein Binding (dog, mixed breeds) | | | | |
| Acebutolol | 1.0E−05 | 18.9 | 5.3 | 12.1 |
| Quinidine | 1.0E−05 | 70.8 | 83.4 | 77.1 |
| Warfarin | 1.0E−05 | 95.8 | 96.1 | 95.9 |

In Vitro Absorption (Pgp Substrate or Inhibitor):

An understanding of intestinal transport is crucial for evaluating the potential for oral dosing of pharmacological agents (Drug Discov Today 13: 379-393). As a rule, a given pharmacological agent will interact with membrane transporter(s) at some point of its route in the body. Of particular importance are the multiple drug resistance (MDR) transporters, especially P-glycoprotein (Pgp), which plays an important role in limiting oral drug delivery by active efflux of pharmacological agents from the intestinal mucosa and into the lumen (Xenobiotica 38: 802-832). Pgp is also located at the blood-brain barrier among other tissues, thus may exclude pharmacological agents targeted to the central nervous system from the brain affects and result in poor brain penetration. In addition, Pgp confers multidrug-resistance to cancer cells (Nat Rev Drug Discov 5: 219-234). The bi-directional transport assay, which also measures intestinal permeability, is regarded as the definitive assay for identifying Pgp substrates and inhibitors because it measures drug efflux in a more direct manner than other methods (Xenobiotica 38: 802-832).

In vitro cell culture systems, such as Caco-2 and TC-7, have been used to predict human in vivo intestinal permeability (Cell Biol Toxicol 21: 1-26 & Pharm Res 15: 726-733). The Caco-2 cell line, derived from gastrointestinal tumors, has been used for decades to study intestinal permeability. The TC-7 cell line, which is a sub-clone of Caco-2, has been shown to be a valuable alternative to the Caco-2 cells based on morphological, biochemical, and drug transport characteristics. Furthermore, the apically-located Pgp, the monocarboxylic acid transporter, the dipeptided transporter, and the transporter for large neutral amino acids are expressed in both Caco-2 and the subclone TC-7 cells at similar levels. Therefore, the latter cell line was used for evaluating the intestinal permeability of COTI-2 and for determining whether COTI-2 is a Pgp substrate or inhibitor.

The TC-7 cells were grown to a monolayer and 10 μM COTI-2 added either to the apical (A) or basolateral (B) side of the monolayer to measure permeability. Verapamil, which is an inhibitor of Pgp, was added on both the apical and basolateral sides of the monolayer in the presence of COTI-2, as a control to determine whether the efflux of COTI-2 is Pgp-mediated. The data are represented as apparent permeability coefficient ($P_{app}$ [$10^{-6}$ cm/s]) and percent recovery. The reference compounds included in the assay are propranolol (highly permeable), labetalol (moderately permeable, ranitidine (poorly permeable), and colchicines (Pgp substrate) (Table 28). The TC-7 permeability classification is as follows:

| | |
|---|---|
| $P_{app} < 2 \times 10^{-6}$ cm/s | Low permeability |
| $2 \times 10^{-6}$ cm/s $< P_{app} < 20 \times 10^{-6}$ cm/s | Medium permeability |
| $P_{app} > 20 \times 10^{-6}$ cm/s | High permeability |

Although the A-B permeability of COTI-2 was less than $0.3 \times 10^{-6}$ cm/s (Table 29), which indicates low permeability according to the TC-7 permeability classification, the mean recovery (22%) suggests the loss of COTI-2 during the assay due to non-specific interactions or degradation. In fact, pharmacokinetics data in rats following a single oral dose of 20 mg/kg of the parent COTI-2 form demonstrated 17.7% bioavailability by comparison against IV administration. Therefore, based on this previous in vivo pharmacokinetic study, the unformulated and un-ground parent base COTI-2 does appear to penetrate the intestinal barrier.

To evaluate whether a compound is a Pgp substrate, it is important to calculate the efflux ratio (E ratio). The E ratio is the permeability value in the B-A direction divided by the permeability value in the A-B direction. Compounds with an E ratio greater than 2 are possible Pgp substrates. Furthermore, in the presence of verapamil, the net efflux ratio should approach unity or be significantly decreased from the E ratio in the absence of verapamil to indicate a Pgp substrate. The E ratio of COTI-2 in the absence of verapamil is approximately 4.5, suggesting that COTI-2 is a possible substrate of Pgp (Table 29). However, in the presence of verapamil, the E ratio is about 4.0, which is not significantly different than without verapamil (4.5). Thus, COTI-2 is unlikely to be a Pgp substrate. There may be some efflux occurring, but it is not related to Pgp. Verapamil may be affecting other efflux systems in the cells. If COTI-2 were a Pgp substrate, one would expect not only the ratio to be reduced, but also the B-A permeability to be decreased in the presence of verapamil since verapamil decreases B-A permeability of a Pgp substrate by inhibiting Pgp. In fact, the B-A permeability of COTI-2 increased in the presence of verapamil and the B-A permeability of COTI-2 in the absence of verapamil (Table 29) is lower than all the reference compounds (Table 28). These data allow for a confident assessment that COTI-2 is not a substrate of Pgp.

TABLE 28

The permeability and percent recovery of the reference compounds colchicines, labetalol, propranolol, and ranitidine determined using TC-7 cell lines.

| Assay Reference Compound | Test Concentration (M) | Permeability | | | Percent Recovery | | |
|---|---|---|---|---|---|---|---|
| | | $1^{st}$ ($10^{-6}$ cm/sec) | $2^{nd}$ ($10^{-6}$ cm/sec) | Mean ($10^{-6}$ cm/sec) | $1^{st}$ (%) | $2^{nd}$ (%) | Mean (%) |
| A-B Permeability (TC7, pH 7.4/7.4) | | | | | | | |
| Colchicine | 1.0E−05 | 0.04 | 0.02 | 0.0 | 98 | 98 | 98 |
| Labetalol | 1.0E−05 | 7.93 | 5.69 | 6.8 | 80 | 79 | 80 |
| Propranolol | 1.0E−05 | 54.87 | 48.59 | 51.7 | 58 | 59 | 58 |
| Ranitidine | 1.0E−05 | 0.48 | 0.48 | 0.5 | 98 | 101 | 99 |
| B-A Permeability (TC7, pH 7.4/7.4) | | | | | | | |
| Colchicine | 1.0E−05 | 6.43 | 6.45 | 6.4 | 103 | 100 | 101 |
| Labetalol | 1.0E−05 | 39.56 | 37.42 | 38.5 | 103 | 97 | 100 |
| Propranolol | 1.0E−05 | 18.70 | 18.81 | 18.8 | 96 | 96 | 96 |
| Ranitidine | 1.0E−05 | 4.20 | 4.20 | 4.2 | 110 | 110 | 110 |

TABLE 29

The permeability and percent recovery of COTI-2 determined using TC-7 cell lines.

| Assay Cerep Compound I.D. | Client Compound I.D. | Test Concentration (M) | Permeability | | | | Percent Recovery | | |
|---|---|---|---|---|---|---|---|---|---|
| | | | $1^{st}$ ($10^{-6}$ cm/sec) | $2^{nd}$ ($10^{-6}$ cm/sec) | Mean ($10^{-6}$ cm/sec) | Flags | $1^{st}$ (%) | $2^{nd}$ (%) | Mean (%) |
| A-B Permeability (TC7, pH 7.4/7.4) | | | | | | | | | |
| 15731-1 | COTI2-M05 | 1.0E−05 | 0.33 | 0.32 | <0.3 | BLQ | 23 | 21 | 22 |
| A-B Permeability (TC7, pH 7.4/7.4) + verapamil | | | | | | | | | |
| 15731-1 | COTI2-M05 | 1.0E−05 | 2.37 | 3.96 | 3.2 | | 17 | 13 | 15 |
| B-A Permeability (TC7, pH 7.4/7.4) | | | | | | | | | |
| 15731-1 | COTI2-M05 | 1.0E−05 | 1.37 | 1.47 | 1.4 | | 114 | 90 | 102 |
| B-A Permeability (TC7, pH 7.4/7.4) + verapamil | | | | | | | | | |
| 15731-1 | COTI2-M05 | 1.0E−05 | 15.85 | 9.13 | 12.5 | | 49 | 46 | 47 |

BLQ Below the Limit of Quantitation. Test compound was well detected in donor samples but not detected in receiver samples. The concentration of test compound in receiver sample was below the limit of quantitation.

A compound can either be a substrate or inhibitor of Pgp. In order to determine whether COTI-2 is an inhibitor of Pgp an inhibition assay was performed using Digoxin, which is a well-known substrate of Pgp. The $IC_{50}$ of COTI-2 was determined by determining amount of radiolabelled digoxin in the presence or absence of various concentrations of COTI-2. Verapamil was used as a positive control. The $IC_{50}$ of COTI-2 (39 µM) was less than 10-fold the $IC_{50}$ of verapamil (5.5 µM), which is a strong inhibitor of Pgp (Table 30). These data indicate that COTI-2 is likely to be a moderate inhibitor of Pgp. The role of Pgp in cancer therapy is becoming increasingly recognized, since Pgp efflux has been linked to multidrug resistance (IDrugs 5: 349-355 & Nat Rev Drug Discov 5: 219-234). In fact, co-administration of Pgp inhibiting agents as part of chemotherapy is an area that is being extensively studied in the hope of finding an ideal drug that inhibits Pgp but does not cause wide-ranging adverse effects (Xenobiotica 38: 802-832). Therefore, an anticancer therapeutic like COTI-2, which inhibits Pgp efflux can potentially increase oral bioavailability or reduce multidrug resistance.

TABLE 30

The Pgp inhibition of COTI-2 and verapamil in the TC-7 cell line.

| Assay Cerep Compound I.D. | Client Compound I.D. | $IC_{50}$ (M) | $n_H$ |
|---|---|---|---|
| P-glycoprotein Inhibition (TC7, $^3$H-digoxin substrate) | | | |
| 15731-1 | COTI2-M05 | 3.9E−05 | 0.5 |
| Assay Reference Compound | | $IC_{50}$ (M) | $n_H$ |
| P-glycoprotein Inhibition (TC7, $^3$H-digoxin substrate) | | | |
| Verapamil | | 5.5E−06 | 0.9 |

Metabolic Stability:

The clearance and bioavailability of most pharmacological agents are strongly influence by their first-pass metabolism in the liver (Nat Rev Cancer 6: 546-558). It is possible to estimate the relative hepatic "metabolic stability" in vitro by incubating compounds with liver microsomes and determining the initial versus the final amount of the test compound in the incubation mixtures.

The relative stability of 1.0 µM COTI-2 in liver microsomes of human, monkey, dog, and rat was evaluated at 60 min post-incubation and data presented as mean percent remaining of COTI-2. Four reference substrates (1.0 µM) were tested, including propranolol and imipramine, which are relatively stable, whereas verapamil and terfenadine, which are relatively unstable with human liver microsomes (Table 32). COTI-2 appears to be most stable in human liver microsomes compared to monkey, dog, and rat liver microsomes (Table 31). These data, which will be used to guide preclinical toxicological studies, predict that COTI-2 will be cleared at a higher rate in the preclinical in vivo models relative to clearance in humans. Furthermore, the stability of COTI-2 in human liver microsomes (31% remaining at 60 min) appears to be moderate compared to the reference substrates.

TABLE 31

Metabolic stability of COTI-2 in human, monkey, dog, and rat liver microsomes as indicated by percent remaining.

| Assay Cerep Compound I.D. | Client Compound I.D. | Test Concentration (M) | Mean Parent Remaining (%) |
|---|---|---|---|
| Metabolic Stability (liver microsomes, human) | | | |
| 15731-1 | COTI2-M05 | 1.0E−06 | 31 |
| Metabolic Stability (liver microsomes, monkey, Cynomolgus) | | | |
| 15731-1 | COTI2-M05 | 1.0E−06 | 2 |
| Metabolic Stability (liver microsomes, dog, Beagle) | | | |
| 15731-1 | COTI2-M05 | 1.0E−06 | 5 |
| Metabolic Stability (liver microsomes, rat, Sprague-Dawley) | | | |
| 15731-1 | COTI2-M05 | 1.0E−06 | 1 |

TABLE 32

Metabolic stability of reference compounds in human, monkey, dog and rat liver microsomes as indicated by percent remaining.

| Assay Reference Compound | Test Concentration (M) | Parent Remaining $1^{st}$ (%) | $2^{nd}$ (%) | Mean (%) |
|---|---|---|---|---|
| Metabolic Stability (liver microsomes, human) | | | | |
| Imipramine | 1.0E−06 | 68.8 | 71.1 | 70 |
| Propranolol | 1.0E−06 | 77.6 | 76.7 | 77 |
| Terfenadine | 1.0E−06 | 9.2 | 8.7 | 9 |
| Verapamil | 1.0E−06 | 17.3 | 17.0 | 17 |
| Metabolic Stability (liver microsomes, monkey, Cynomolgus) | | | | |
| Imipramine | 1.0E−06 | 0.3 | 0.3 | 0 |
| Propranolol | 1.0E−06 | 23.3 | 21.5 | 22 |
| Terfenadine | 1.0E−06 | 0.6 | 0.5 | 1 |
| Verapamil | 1.0E−06 | 0.4 | 0.1 | 0 |
| Metabolic Stability (liver microsomes, dog, Beagle) | | | | |
| Imipramine | 1.0E−06 | 1.2 | 0.9 | 1 |
| Propranolol | 1.0E−06 | 24.4 | 25.4 | 25 |
| Terfenadine | 1.0E−06 | 88.2 | 88.9 | 89 |
| Verapamil | 1.0E−06 | 18.1 | 18.0 | 18 |
| Metabolic Stability (liver microsomes, rat, Sprague-Dawley) | | | | |
| Imipramine | 1.0E−06 | 0.3 | 0.2 | 0 |
| Propranolol | 1.0E−06 | 0.0 | 0.0 | 0 |
| Terfenadine | 1.0E−06 | 4.1 | 3.5 | 4 |
| Verapamil | 1.0E−06 | 13.3 | 13.5 | 13 |

CYP450 Inhibition:

The metabolism-based drug-drug interactions occur when a pharmacological agent inhibits or induces the activity of a drug metabolizing enzyme, which catalyzes the metabolism of any concomitant drugs. The metabolism-based drug-drug interaction is one of the major factors that cause drug failures during drug development. The major metabolic pathways involved can be classified into 2 groups, phase I and phase II reactions (J Clin Pharmacol 41: 1149-1179). The cytochrome P450 (CYP450), which is an enzyme superfamily of hemoproteins that catalyze the phase I reactions, are estimated to account for the biotransformation of approximately 60% of the commonly prescribed drugs in the US. A number of in vitro assays for CYP450 inhibition have been developed, which differ in CYP enzyme source and composition (i.e., recombinant cDNA expressed human CYP isozymes, human liver microsomes, probe substrates, and detection [e.g., LC-MS, fluorescence, radioactivity]). Microsomes and recombinant P450 enzymes are the preferred test system as they are more readily available than human hepatocytes, and P450 kinetic measurements are not confounded with other metabolic processes or cellular uptake (Drug Metab Dispos 31: 815-832).

The metabolism of COTI-2 by the CYP enzymes of major importance in drug metabolism was analyzed by determining the percent inhibition relative to solvent only control (which is considered 100% uninhibited enzyme activity) Inhibition of greater than 50% suggests an inhibitory activity of a test compound towards a specific CYP450 enzyme and requires further investigation by $IC_{50}$ determination. The inhibition by COTI-2 for all the CYP450 enzymes tested was well below 50%, thus indicating that it is not likely to be a significant inhibitor of the CYP enzymes (Table 33). The negative inhibition values, resulting from interaction of the components in the reaction mixture, also indicate that COTI-2 is not an inhibitor of CYP enzymes. Represented in Table 34 are the $IC_{50}$ values of known inhibitors of each of the assayed CYP450 enzymes.

TABLE 33

Percent inhibition of CYP450 enzymes by COTI-2 relative to control (vehicle alone) values as determined by a human liver microsomal assay.

| Assay Cerep Compound I.D. | Client Compound I.D. | Test Concentration (M) | % Inhibition of Control Values |
|---|---|---|---|
| CYP1A Inhibition (HLM, phenacetin substrate) | | | |
| 15731-1 | COTI2-M05 | 1.0E−05 | −2 |
| CYP2B6 Inhibition (HLM, bupropion substrate) | | | |
| 15731-1 | COTI2-M05 | 1.0E−05 | 5 |
| CYP2C8 Inhibition (HLM, paclitaxel substrate) | | | |
| 15731-1 | COTI2-M05 | 1.0E−05 | 10 |
| CYP2C9 Inhibition (HLM, diclofenac substrate) | | | |
| 15731-1 | COTI2-M05 | 1.0E−05 | 2 |
| CYP2C19 Inhibition (HLM, omeprazole substrate) | | | |
| 15731-1 | COTI2-M05 | 1.0E−05 | 4 |
| CYP2D6 Inhibition (HLM, dextromethorphan substrate) | | | |
| 15731-1 | COTI2-M05 | 1.0E−05 | 2 |
| CYP2E1 Inhibition (HLM, chlorzoxazone substrate) | | | |
| 15731-1 | COTI2-M05 | 1.0E−05 | −2 |
| CYP3A Inhibition (HLM, midazolam substrate) | | | |
| 15731-1 | COTI2-M05 | 1.0E−05 | 7 |
| CYP3A Inhibition (HLM, testosterone substrate) | | | |
| 15731-1 | COTI2-M05 | 1.0E−05 | −4 |

TABLE 34

$IC_{50}$ values of known inhibitors of the CYP450 enzymes as determined by a human liver microsomal assay.

| Assay Reference Compound | IC50 (M) | $n_H$ |
|---|---|---|
| CYP1A Inhibition (HLM, phenacetin substrate) | | |
| Furafylline | 4.9E−06 | 0.8 |
| CYP2B6 Inhibition (HLM, bupopion substrate) | | |
| Clopidogrel | 6.4E−07 | 2.7 |
| CYP2C8 Inhibition (HLM, paclitaxel substrate) | | |
| Nicardipine | 2.3E−06 | 1.2 |
| CYP2C9 Inhibition (HLM, diclofenac substrate) | | |
| Sulfaphenazole | 9.5E−07 | 1.1 |
| CYP2C19 Inhibition (HLM, omeprazole substrate) | | |
| Oxybutynin | 6.6E−06 | 1.1 |
| CYP2D6 Inhibition (HLM, dextromethorphan substrate) | | |
| Quinidine | 1.4E−07 | 0.9 |
| CYP2E1 Inhibition (HLM, chlorzoxazone substrate) | | |
| 4-Mehylpyrazole | 3.3E−07 | 1.0 |
| CYP3A Inhibition (HLM, midazolam substrate) | | |
| Ketoconazole | 2.4E−07 | 1.8 |
| CYP3A Inhibition (HLM, testosterone substrate) | | |
| Ketoconazole | 5.0E−07 | 0.9 |

Example 24

In Vivo Pharmacokinetics

Pharmacokinetic studies in animal models provide valuable information that enables prediction of metabolism in humans. There are a large variety of animal models that allow for the pharmacokinetic evaluation of compounds by providing information on serum, plasma, and tissue levels. One of the major differences between animal and human pharmacokinetics is that a compound is cleared at a faster rate in animals, particularly rodents, compared to clearance in humans (Int J Antimicrob Agents 19: 261-268). As a result, it is important to keep this phenomenon in mind during extrapolations from animal to human metabolism. An initial pharmacokinetic assessment of COTI-2, administered both intravenously and orally, in its parent formulation and as both an oxalate and tartrate salt were evaluated in rats.

Methods:

Intrinsic Clearance and Half-Life Determination:

The incubation mixture (500 μl) consisted of 100 μl of COTI-2, 150 μl of liver microsomal fractions (1.67 mg/ml rat/human) 35.5 μl of 100 mM phosphate buffer and 214.5 μl co-factor (NADPH, UDPGA, and $MgCl_2$). The COTI-2 compound mixture and co-factor were pre-warmed at 37° C. for 5 min, with shaking at 150 rpm. The reaction was started by adding co-factor to the test compound mixture. The final concentration of the incubation mixture was as follows:

| | |
|---|---|
| Microsomal protein: 0.5 mg/ml | NADPH: 0.823 mM |
| UDPGA: 5 mM | $MgCl_2$: 1 mM |

Blank incubation was performed with the co-factors. The sampling time points included 0 and 240 min for the blank sample, and 0, 20, 40, 60, 120, 180, and 240 min for COTI-2. At each time point 50 μl of sample was added to 150 μl of methanol to stop the reaction. The sample plates were centrifuged at 4200 rpm for 15 min and the supernatant was injected into LC-MS/MS for analysis. The percent compound remaining, rate of elimination ($K_{el}$), half-life (T1/2), and intrinsic clearance (CL) using standard calculations.

Results and Discussion:

A single oral or IV dose of the COTI-2 free-base or the aforementioned salt forms was administered to groups of male and female rats and blood samples collected and processed at several time-points post-treatment. The pharmacokinetic parameters following IV administration are summarized in Table 35. The extrapolated $C_{initial}$ values for COTI-2 oxalate and tartrate formulations were approximately 4-fold and 2-fold higher than the parent formulation, respectively. The calculated extent of exposure over the 24-hour post-dose sampling period ($AUC_{0-24hrs}$) for the oxalate and tartrate formulations were approximately 2-fold higher than the parent COTI-2. The rate of elimination ($K_e$) of COTI-2 oxalate was approximately 2-fold higher than parent and tartrate formulations, corresponding to a decreased half-life of elimination ($T_{1/2(e)}$, total half-life ($T_{1/2(TOTAL)}$) and mean residence time (MRT) in plasma. The parent COTI-2 exhibited the highest rate of clearance (CL) from plasma, approximately 1.4- and 2.3-fold higher than the oxalate and tartrate formulations, respectively, due to an increased calculated volume of distribution ($V_d$).

TABLE 35

A summary of the pharmacokinetic parameters following IV dosing.

| Parameter | Unit | Parent COTI2 (5 mg/kg) | Oxalate COTI2 (5 mg/kg) | Tartrate COTI2** (5 mg/kg) |
|---|---|---|---|---|
| $C_{initial}$ | ng/mL | 1310.0 | 5205.7 | 2016.2 |
| $K_e$ | hr | 0.023 | 0.052 | 0.021 |
| $T_{1/2(e)}$ | hr | 30.28 | 13.39 | 32.58 |
| $AUC_{0-24\,hrs}$ | ng * hr/mL | 9184.3 | 20901.1 | 20184.0 |
| $AUC_{0-\infty}$ | ng * hr/mL | 19958.3 | 28614.2 | 46650.4 |
| $AUMC_{0-\infty}$ | ng * hr²/mL | 813242.7 | 501668.9 | 2069699.4 |
| MRT | hr | 40.7 | 17.5 | 44.4 |
| $V_d$ | l | 23.79 | 4.62 | 11.65 |
| CL | mL/hr/kg | 250.52 | 174.74 | 107.18 |
| $T_{1/2\,(TOTAL)}$* | hr | 30.3 | 13.4 | 32.6 |

*calculated from $V_d$ and CL
**n = 5 for 24-hour time point: data from female rat #075 omitted The pharmacokinetic parameters following oral dosing are summarized in Table 36. The $C_{max}$ values for COTI-2 oxalate and tartrate formulations were approximately 1.75-fold and 3.3-fold higher than the parent formulation, respectively, and the $T_{max}$ values were significantly shorter (15 min vs. 4 h). The calculated rate of absorption ($K_a$) of parent COTI-2 was approximately 3-fold higher than the other formulations; this was due to increasing plasma concentrations of parent COTI-2 at the 15- and 30-min post-dose time points, compared to decreasing concentration of COTI-2 oxalate and tartrate at the 30-min post-dose time point. The calculated extent of exposure over the 24-hour post-dose sampling period ($AUC_{0-24hrs}$) for the oxalate and tartrate formulations were comparable to parent COTI-2, with extent of exposure to the tartrate formulation slightly increased by approximately 1.4-fold. The rates ($K_e$) and times ($T_{1/2(e)}$) of elimination and mean residence times (MRT) of all formulations were comparable. The parent COTI-2 exhibited the highest rate of clearance (CL) from plasma, approximately 2-fold higher than the oxalate and tartrate formulations. The bioavailability (F) of parent COTI-2, COTI-2 oxalate and COTI-2 tartrate formulations after oral administration, as determined by comparison with IV administration, was 17.7%, 7.6% and 11.0%, respectively.

TABLE 36

A summary of the pharmacokinetic parameters following oral dosing.

| Parameter | Unit | Parent COTI2 (20 mg/kg) | Oxalate COTI2 (20 mg/kg) | Tartrate COTI2 (20 mg/kg) |
|---|---|---|---|---|
| $C_{max}$ | ng/ml | 882.0 | 1541.7 | 2903.8 |
| $T_{max}$ | hr | 4.0 | 0.25 | 0.25 |
| $K_a$ | hr⁻¹ | 0.681 | 0.210 | 0.230 |
| $T_{1/2(a)}$ | hr | 1.02 | 3.30 | 3.02 |
| $K_e$ | hr⁻¹ | 0.055 | 0.070 | 0.078 |
| $T_{1/2(e)}$ | hr | 12.49 | 9.97 | 8.86 |
| $AUC_{0-24\,hrs}$ | ng * hr/mL | 6500.6 | 6314.8 | 8893.5 |
| $AUC_{0-\infty}$ | ng * hr/mL | 7578.6 | 7237.8 | 10053.8 |
| $AUMC_{0-\infty}$ | ng * hr²/mL | 81677.0 | 72613.6 | 96208.9 |
| MRT | hr | 10.8 | 10.0 | 9.6 |
| CL* | mL/hr/kg | 467.10 | 210.01 | 200.92 |
| F | % | 17.7 | 7.6 | 11.0 |

*calculated from F as determined by comparison with IV dose kinetics

Figure 52A:
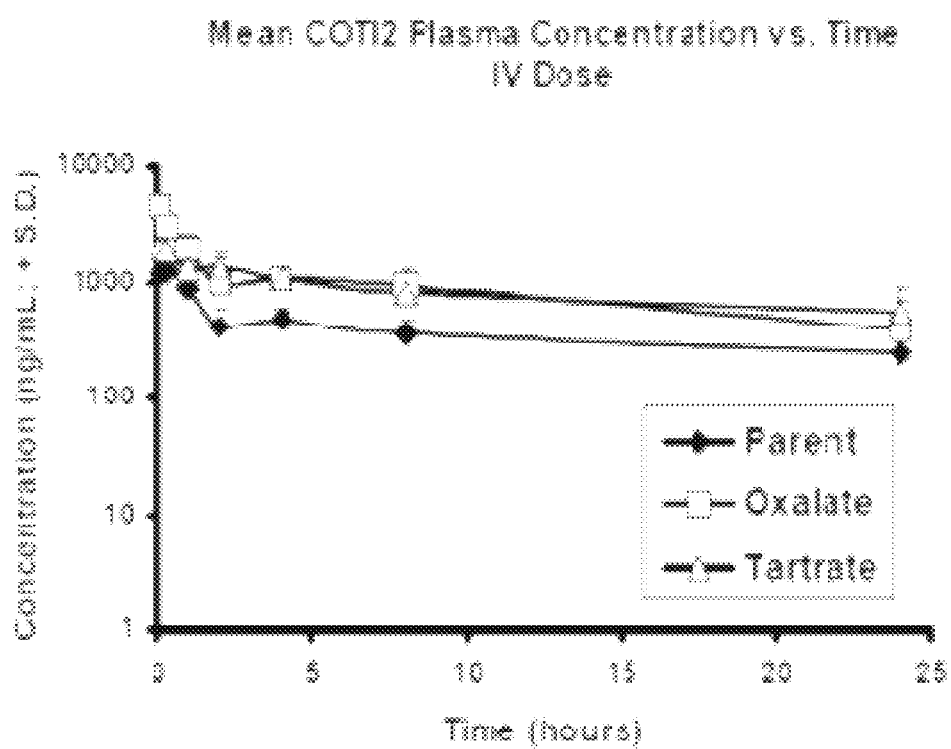
FIGS. 52A-B show a semi-log plot of the mean plasma concentration versus time following oral (FIG. 52A) and IV dosing (FIG. 52B).
Figure 52B:
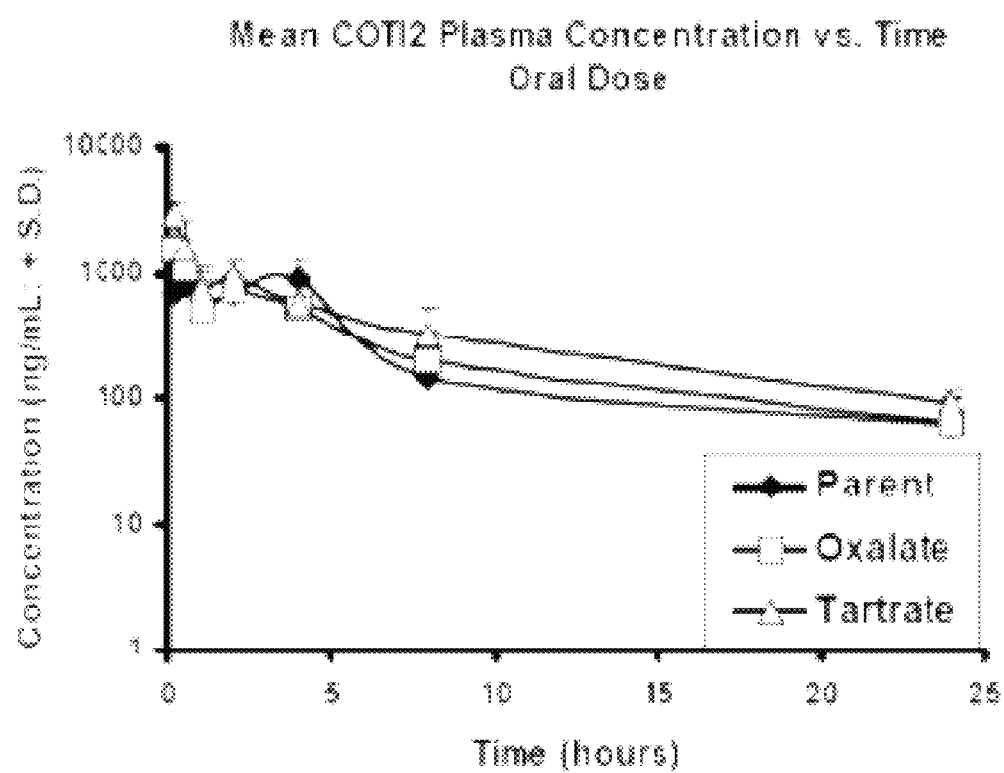

The graphical representation of the plasma concentration of each agent following IV and oral dosing are represented in FIGS. 52A-B.

Example 25

Determination of Plasma Exposure and Efficacy of COTI-2 In Vivo as a Single Agent and in Combination with Taxol® (Paclitaxel) in the AN3-CA Human Endometrial Tumor Xenograft Model The purpose of this study was to evaluate the antitumor activity of COTI-2 as a single agent and in combination with paclitaxel in the AN3-CA human endometrial tumor xenograft model.

Materials and Methods:

Reagents and Compounds

COTI-2 mono-HCl salt (Lot# CKL-2-148) was stored at −20° C. until ready for use. A stock solution of COTI-2 was made at a concentration of 12 mg/ml; 235 mg of COTI-2 was mixed with 4.84 g of Captisol® (Lot# CY-04A-05006 Cydex Pharmaceuticals; Lenexa, Kans.) in 10.0 ml of Sterile Water for Injection (Hospira, Inc., Lake Forest, Ill.). The solution was prepared in a 60 ml amber vial and left to stir at 400 rpm for 1 h. The solution was then filtered with a 0.2 µm PVDF filter to achieve the 12 mg/ml stock concentration. The stock was further diluted to 6 mg/ml with 50 mM Captisol® solution in sterile water (at pH 3.0). The 6 mg/ml solution was also filtered with a 0.2 µm PVDF filter. Taxol® (paclitaxel) (Lot# U026849AA) was received from Hospira, Inc. (Lake Forest, Ill.), and diluted in a 0.9% NaCl solution (Baxter, Deerfield, Ill.) to a concentration of 0.5 mg/ml to deliver 5 mg/kg in a 10 ml/kg dose volume. All preparations were made fresh prior to their administration.

Cell Culture

The AN3-CA endometrial tumor cell line was received from American Type Culture Collection (ATCC, Manassas, Va.). Cultures were maintained in RPMI 1640 (Hyclone, Logan, Utah) supplemented with 5% fetal bovine serum, and housed in a 10% $CO_2$ atmosphere. The cultures were expanded in tissue culture flasks at a 1:7 split ratio until a sufficient amount of cells were harvested.

Animals

Female athymic nude mice (CrTac:NCR-Foxnl$^{nu}$) were supplied by Taconic (Germantown, N.Y.). Mice were received at four weeks of age and were acclimated for seven days prior to handling. The mice were housed in microisolator cages (Lab Products, Seaford, Del.) and maintained under specific pathogen-free conditions. The mice were fed Pico-Lab® irradiated mouse chow (Lab Diet, Richmond, Ind.) and autoclaved water was freely available. All procedures were carried out under the institutional guidelines of TGen Drug Development Services Institutional Animal Care and Use Committee (Protocol #09002, Approved February 2009).

AN3-CA Human Endometrial Tumor Xenograft Model

Eighty-eight mice were inoculated subcutaneously in the right flank with 0.1 ml of a 50% RPMI/50% Matrigel™ (BD Biosciences, Bedford, Mass.) mixture containing a suspension of AN3-CA tumor cells (approximately $1 \times 10^7$ cells/mouse). Nine days following inoculation, tumors were measured using calipers and tumor weight was calculated using the animal study management software, Study Director V.1.6.80 (Study Log) (Cancer Res 59: 1049-1053). Seventy mice with tumor sizes of 52-243 mg were pair-matched into the seven groups of ten mice by random equilibration, using Study Director (Day 1). Body weights were recorded when the mice were pair-matched. Body weights were taken twice weekly thereafter in conjunction with tumor measurements. On Day 1, COTI-2, vehicle control, and paclitaxel, were administered intravenously. The dosing schedule for COTI-2 and the vehicle control was three times weekly until study end. The schedule for paclitaxel was daily for five days (QD× 5). This dosing regimen was repeated only to the paclitaxel single agent group starting on Day 27. The paclitaxel single agent group was treated with COTI-2 (25 mg/kg) for five days (QD×5) starting on Day 32. When the mean tumor weight of each mouse reached an approximate end-point of 2000 mg, mice were sacrificed with regulated $CO_2$.

Data and Statistical Analysis:

Mean Tumor Growth Inhibition (TGI) was Calculated Utilizing the Following Formula:

$$TGI = \left[1 - \frac{(\bar{X}_{Treated(Final)} - \bar{X}_{Treated(Day1)})}{(\bar{X}_{Control(Final)} - \bar{X}_{Control(Day1)})}\right] \times 100\%$$

Tumors that regressed from the Day 1 starting size were removed from the calculations. Individual tumor shrinkage (TS) was calculated using the formula below for tumors that showed regression relative to Day 1 tumor weight. The mean tumor shrinkage of each group was calculated and reported.

$$TS = \left[1 - \frac{(Tumor\ Weight_{(Final)})}{(Tumor\ Weight_{(Day1)})}\right] \times 100\%$$

All statistical analyses in the xenograft study were performed with GraphPad Prism® v4 software. Differences in tumor weights were confirmed using the Analysis of Variance (ANOVA) with the Tukey's Post Test and the One-tailed Student's T test. Increase in survival fraction was confirmed by the log rank test.

Results and Discussion:

This study determined the antitumor effects of COTI-2 when administered as a single agent and when administered in combination with paclitaxel. The treatment regimens were tested against the AN3-CA human endometrial tumor xenograft model. Efficacy was assessed by comparison of tumor weights (Table 37 and FIG. 53) and survival at an endpoint of 2000 mg (Table 38).

Figure 53:
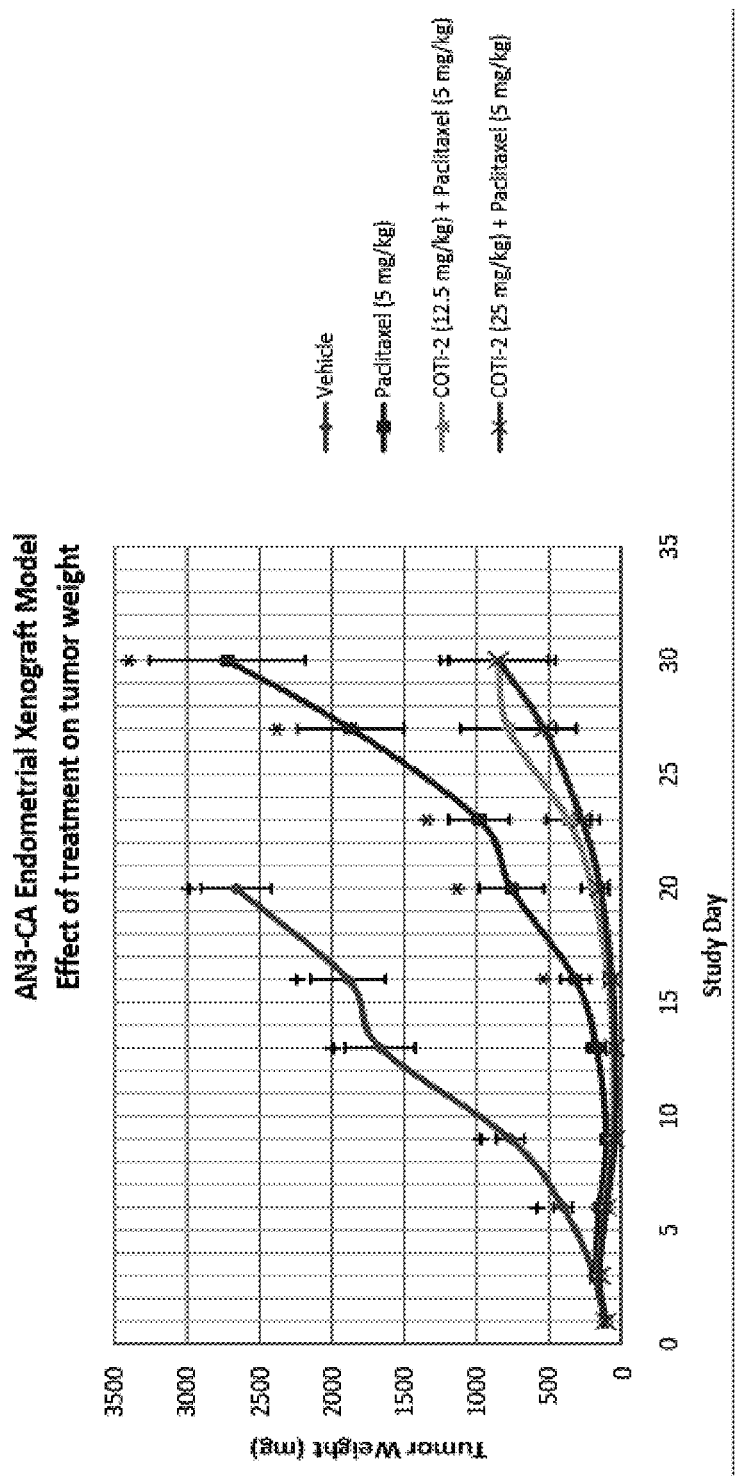
FIG. 53 shows the effect of treatment on tumor weight. Tumor weights were graphed as means (±SEM). The plus sign (+) indicates a statistically significant difference in tumor weight of the vehicle only group compared to each of the combination & single agents on the same day (P<0.05). The asterix (*) indicates a statistically significant difference in tumor weight of the paclitaxel (Taxol®) only group compared to the COTI-2 and paclitaxel (Taxol®) combination agent groups on the same day (P<0.05). Statistical significance was determined using a Student's T test.

Overall, single agent treatment of the test agent resulted in slight toxicity in the higher doses and in combination with paclitaxel. Mice exhibited lethargy and hypoactivity with continued dosing at 50 mg/kg. Deaths in the 25 mg/kg and 50 mg/kg groups were possibly due to drug toxicity and tumor burden, since both groups had tumors over 1500 mg at the time of death. COTI-2 as a single agent did not show any statistical differences in tumor weights or survival, when compared to control (Tables 37 and 38). However, in combination with paclitaxel, COTI-2 showed positive interaction with 90-100% tumor regression in the combination groups compared to 50% regression observed in the single agent paclitaxel treated group. The combination treatments significantly increased survival relative to paclitaxel alone survival (Table 38). A COTI-2 dose level dependency was also observed in the combination treatments (FIG. 53). In conclusion, COTI-2 dosed at 25 mg/kg in combination with paclitaxel resulted in the highest anti-tumor activity against the AN3-CA human endometrial xenograft model.

TABLE 37

Summary of tumor weights between groups on Day 13 of the study.

| Group | N | Dose (mg/kg) | Route | Schedule (Day) | Maximum weight loss (%) (Day #) | Day 13 Mean tumor weight (mg) | Day 13 TGI (%) | Day 13 TS[1] | CS[2] |
|---|---|---|---|---|---|---|---|---|---|
| Vehicle Control | 10 | — | IV | 3X Weekly to end | 5.6% (Day 9) | 1,667.8 ± 240.7 | — | — | 0 |
| COTI-2 | 10 | 12.5 | IV | 3X Weekly to end | 8.2% (Day 21) | 1,828.9 ± 265.8 | — | — | 0 |
| COTI-2 | 10 | 25.0 | IV | 3X Weekly to end | 4.7% (Day 6) | 2,108.7 ± 263.0 | — | — | 0 |
| COTI-2 | 10 | 50.0 | IV | 3X Weekly to end | 5.4% (Day 21) | 1,542.7 ± 217.2 | 7.8 | — | 0 |
| Paclitaxel | 10 | 2.0 | IV | QD X 5 | 8.0% (Day 6) | 175.1 ± 62.44 | 89.7 | 33.9 (5/10) | 0 |
| COTI-2 Paclitaxel | 10 | 12.5 2.0 | IV IV | 3X Weekly to end QD X 5 | 11.0% (Day 6) | 58.4 ± 12.7 | 98.9 | 54.5 (9/10) | 3 |
| COTI-2 Paclitaxel | 10 | 25.0 2.0 | IV IV | 3X Weekly to end QD X 5 | 10.8% (Day 6) | 48.0 ± 8.7 | — | 55.6 (10/10) | 4 |

TS[1] = Tumor Shrinkage
CS[2] = Complete Shrinkage

TABLE 38

Summary of survival between groups at an end point of 2000 mg.

| Group | N | Dose (mg/kg) | Route | Schedule (Day) | Mean days of Survival (Day ± SEM) | Deaths |
|---|---|---|---|---|---|---|
| Vehicle Control | 10 | — | IV | 3X Weekly to end | 17.0 ± 1.0 | 0 |
| COTI-2 | 10 | 12.5 | IV | 3X Weekly to end | 16.7 ± 0.8 | 0 |
| COTI-2 | 10 | 25.0 | IV | 3X Weekly to end | 15.8 ± 0.9 | 1 |
| COTI-2 | 10 | 50.0 | IV | 3X Weekly to end | 17.2 ± 0.7 | 1 |
| Paclitaxel | 10 | 2.0 | IV | QD X 5 | 32.1 ± 1.5 | 0 |
| COTI-2 Paclitaxel | 10 | 12.5 2.0 | IV IV | 3X Weekly to end QD X 5 | 33.9 ± 1.3 | 0 |
| COTI-2 Paclitaxel | 10 | 25.0 2.0 | IV IV | 3X Weekly to end QD X 5 | 35.3 ± 0.9 | 0 |

Example 26

Evaluation of COTI-2 as a Single Agent and in Combination with Doxil® in the A2780 Human Ovarian Tumor Xenograft Model The purpose of this study was to determine the single agent efficacy of COTI-2 in the A2780 human ovarian tumor xenograft model. COTI-2 was also studied in comparison, as well as in combination, with the standard agent Doxil®.
Materials and Methods:
Reagents and Compounds COTI-2 mono-HCl salt (Lot# CKL-2-148) was stored at −20° C. until ready for use. A stock solution of COTI-2 mono-HCl salt was made at a concentration of 12 mg/ml; 235 mg of COTI-2 was mixed with 4.84 g of Captisol® (Lot# CY-04A-05006 Cydex Pharmaceuticals; Lenexa, Kans.) in 10.0 ml of Sterile Water for Injection (Hospira, Inc., Lake Forest, Ill.). The solution was prepared in a 60 ml amber vial and left to stir at 400 rpm for 1 h. The solution was then filtered with a 0.2 μm PVDF filter to achieve the 12 mg/ml stock concentration. The stock was further diluted to 6 mg/ml with 50 mM Captisol® solution in sterile water (at pH 3.0). The 6 mg/ml solution was also filtered with a 0.2 μm PVDF filter. Doxil® (Lot#0821642), was manufactured by Ortho Biotech (Raritan, N.J.), and was stored at 4° C. until used. It was diluted in a 0.9% NaCl solution to a concentration of 0.2 mg/ml to deliver a 2 mg/kg dose intravenously in a 10 ml/kg dose volume. All preparations were made fresh prior to their administration.
Cell Culture The A2780 human ovarian tumor cell line was received from American Type Culture Collection (ATCC, Manassas, Va.). Cultures were maintained in RPMI 1640 (Hylcone Labs, Logan, Utah) supplemented with 5% fetal bovine serum, and housed in a 5% CO2 atmosphere. The cultures were expanded in tissue culture flasks at a 1:4 split ratio until a sufficient amount of cells were harvested.
Animals Female athymic nude mice (CrTac: NCR-Foxnl$^{nu}$) were supplied by Taconic (Germantown, N.Y.). Mice were received at four weeks of age. All mice were acclimated for seven days prior to handling. The mice were housed in microisolator cages (Lab Products, Seaford, Del.) and maintained under specific pathogen-free conditions. The mice were fed PicoLab® irradiated mouse chow (Lab Diet, Richmond, Ind.) and autoclaved water was freely available. All procedures were carried out under the institutional guidelines of TGen Drug Development Services Institutional Animal Care and Use Committee (Protocol #06001, Approved January 2006).
A2780 Human Ovarian Tumor Xenograft Ninety mice were inoculated subcutaneously in the right flank with 0.1 ml of a 50% RPMI/50% Matrigel™ (BD Biosciences, Bedford, Mass.) mixture containing a suspension of A2780 tumor cells (approximately 1×10$^7$ cells/mouse). Four days following inoculation, tumors were measured using vernier calipers and tumor weight was calculated using the animal study management software, Study Director V1.6.80 (Study Log) (Cancer Res 59: 1049-1053). Seventy mice with an average group tumor size of 108 mg, with mice ranging from 61 to 184 mg, were pair-matched into seven groups of ten by random equilibration using Study Director (Day 1). Body weights were recorded when the mice were pair-matched and then taken twice weekly thereafter in conjunction with tumor measurements throughout the study. Gross observations were made at least once a day. The dosing schedule, indicated on Table 39, shows that with minor variation COTI-2 was dosed every other day 3 times weekly and Doxil® (2 mg/kg) was administered intravenously on Day 1 at a 10-ml/kg dose volume. The mice were sacrificed by regulated $CO_2$ when the mean tumor volume of the control group reached approximately 2000 mg.
Data and Statistical Analysis Mean tumor growth inhibition (TGI) was calculated utilizing the following formula:

$$TGI = \left[1 - \frac{(\bar{X}_{Treated(Final)} - \bar{X}_{Treated(Day1)})}{(\bar{X}_{Control(Final)} - \bar{X}_{Control(Day1)})}\right] \times 100\%$$

Tumors that regressed from the Day 1 starting size were removed from the calculations. All statistical analyses in the xenograft study were performed with GraphPad Prism® v4 software. Differences in Day 17 tumor weights were confirmed using Analysis of Variance (ANOVA) with the Tukey's Post Test. In addition to an ANOVA, a One-tailed Student's T test was used to compare the vehicle only group to each of the combination agent groups and single agent Doxil®. Increase in survival fraction was confirmed by the log rank test.
Results and Discussion:

This study determined the single agent efficacy of COTI-2 in the A2780 human ovarian tumor xenograft model. COTI-2 was also studied in comparison, as well as in combination, with the standard agent Doxil®. Efficacy was assessed by comparison of mean tumor weights.

Overall, each test agent was moderately tolerated with a weight loss of up to ≈10% (Table 39). Single agent COTI-2 and Doxil® treatments did result in tumor growth inhibition (up to 25.76%). Furthermore, the combination agent treatment groups exhibited better tumor growth inhibition (up to 53.80%) relative to the single agent treatment groups.

TABLE 39

Summary of the study parameters and results.

| Group | N | Dose (mg/kg) | Route | Schedule (Day) | Maximum weight loss (%) (Day #) | Day 17 Mean tumor weight (mg) | Day 17 TGI (%) | Day 17 CS* |
|---|---|---|---|---|---|---|---|---|
| Vehicle Control | 10 | — | IV | 1, 3, 5, 7, 8, 10, 12, 15, 16, 17 | 10.84% (Day 15) | 2,150.7 ± 352.5 | — | 0 |
| COTI-2 | 10 | 12.5 | IV | 1, 3, 5, 7, 8, 10, 12, 15, 16, 17 | 10.35% (Day 11) | 1,699.2 ± 241.4 | 22.04 | 0 |
| COTI-2 | 10 | 25.0 | IV | 1, 3, 5, 7, 8, 10, 12, 15, 16, 17 | 9.37% (Day 8) | 1,738.4 ± 216.0 | 20.12 | 0 |
| COTI-2 | 10 | 50.0 | IV | 1, 3, 5, 7, 8, 10, 12, 15, 17 | 8.65% (Day 8) | 1,622.8 ± 403.0 | 25.76 | 0 |
| Doxil® | 10 | 2.0 | IV | 1 | 3.76% (Day 4) | 1,607.1 ± 343.4 | 25.35 | 0 |
| COTI-2 Doxil® | 10 | 12.5 2.0 | IV IV | 1, 2, 5, 8, 10, 12, 15, 17 1 | 7.67% (Day 11) | 1,045.3 ± 305.7 | 47.44 | 1/10 |
| COTI-2 Doxil® | 10 | 25.0 2.0 | IV IV | 1, 2, 5, 8, 10, 12, 15, 17 1 | 7.68% (Day 8) | 1,046.0 ± 261.3 | 53.80 | 0 |

*CS = Complete Tumor Shrinkage

Figure 54:
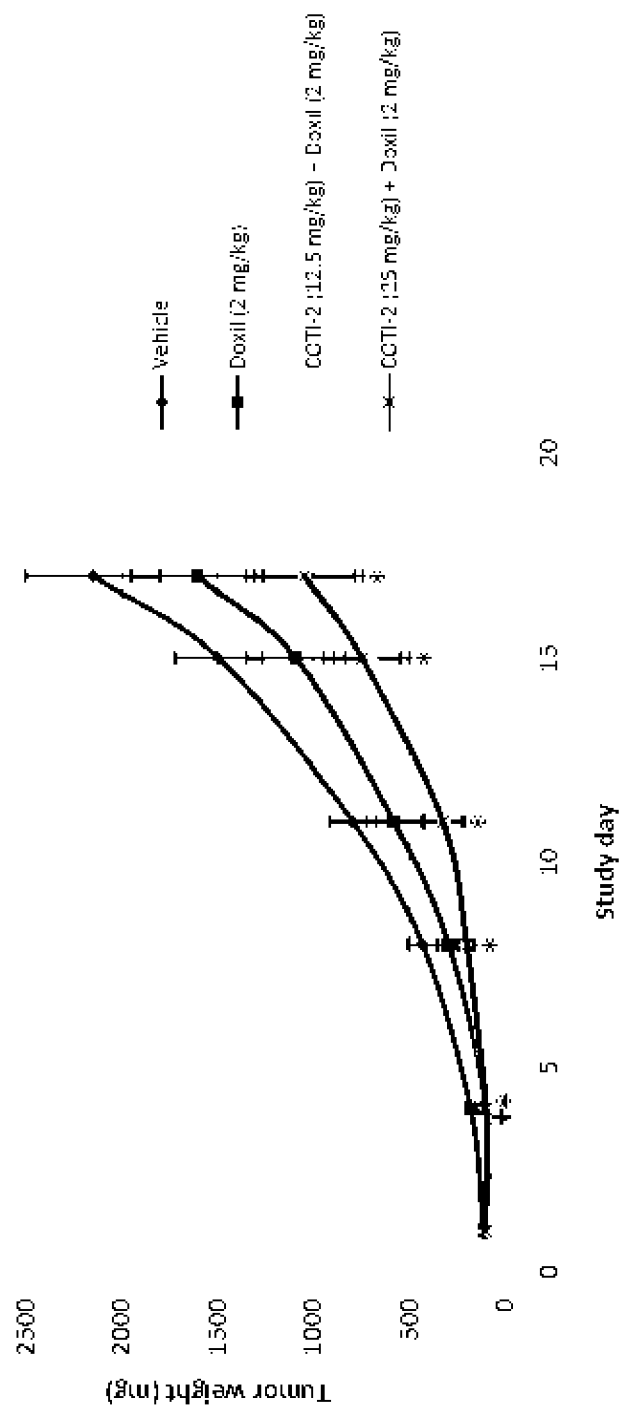
FIG. 54 shows the effect of treatment on tumor weight. Tumor weights are graphed as means (±SE). The asterix (*) indicates a statistically significant difference in tumor weight of COTI-2 and Doxil® combination agent groups relative to the vehicle only control group on the same day (P<0.05). The plus sign (+) indicates statistically significant difference in tumor weight of the Doxil® single agent group versus the vehicle only control group on the same day (P<0.05). Statistical significance was determined using a Student's T test.

The combination of COTI-2 and Doxil® resulted in positive interaction trends (FIG. 54). In fact, the combination agents exhibited significantly smaller tumors compared to the vehicle control group (P<0.05), whereas there was no statistically significant difference in tumor size of the Doxil® single agent group relative to the vehicle control group (P>0.05), except at day 4. These data indicate that the COTI-2 and Doxil® combination agents perform better than the Doxil® single agent in this xenograft model.

Example 27

Evaluation of COTI-2 as a Single Agent and in Combination with Erbitux® in the HT-29 Human Colon Tumor Xenograft Model The purpose of this study was to evaluate the activity of COTI-2 as a single agent and in combination with Erbitux® in the HT-29 human colon tumor xenograft model.

Materials and Methods:

Reagents and Compounds:

COTI-2 mono-HCl salt (Lot# CKL-2-148) stored at −20° C. until ready for use. A stock solution of COTI-2 was made at a concentration of 12 mg/ml; 235 mg of COTI-2 was mixed with 4.84 g of Captisol® (Lot# CY-04A-05006 Cydex Pharmaceuticals; Lenexa, Kans.) in 10.0 ml of Sterile Water for Injection (Hospira, Inc., Lake Forest, Ill.). The solution was prepared in a 60 ml amber vial and left to stir at 400 rpm for 1 h. The solution was then filtered with a 0.2 µm PVDF filter to achieve the 12 mg/ml stock concentration. The stock was further diluted to 6 mg/ml with 50 mM Captisol® solution in sterile water (at pH 3.0). The 6 mg/ml solution was also filtered with a 0.2 µm PVDF filter and was administered intravenously with respect to the individual groups. Erbitux® (Lot#07C00373B), was manufactured by Bristol-Myers Squibb Company (Princeton, N.J.), and was stored at 4° C. until used. Erbitux® was given intraperitoneally at a volume of 0.5 ml per mouse to deliver 1 mg/dose every three days for five treatments (q3d×5). All preparations were made fresh prior to their administration.

Cell Culture

The HT-29 human colon tumor cell line was received from American Type Culture Collection (ATCC, Manassas, Va.). Cultures were maintained in RPMI 1640 (Hylcone Labs, Logan, Utah) supplemented with 5% fetal bovine serum, and housed in a 5% $CO_2$ atmosphere. The cultures were expanded in tissue culture flasks at a 1:4 split ratio until a sufficient amount of cells were harvested.

Animals

Female athymic nude mice (CrTac: NCR-Foxnl$^{nu}$) were supplied by Taconic (Germantown, N.Y.). Mice were received at four weeks of age. All mice were acclimated for seven days prior to handling. The mice were housed in microisolator cages (Lab Products, Seaford, Del.) and maintained under specific pathogen-free conditions. The mice were fed PicoLab® irradiated mouse chow (Lab Diet, Richmond, Ind.) and autoclaved water was freely available. All procedures were carried out under the institutional guidelines of TGen Drug Development Services Institutional Animal Care and Use Committee (Protocol #09002, Approved February 2009).

HT-29 Human Colon Tumor Xenograft

Eighty five mice were inoculated subcutaneously in the right flank with 0.1 ml of a 50% RPMI/50% Matrigel™ (BD Biosciences, Bedford, Mass.) mixture containing a suspension of HT-29 tumor cells (approximately $5 \times 10^6$ cells/mouse). Seven days following inoculation, tumors were measured using vernier calipers and tumor weight was calculated using the animal study management software, Study Director V.1.6.80 (Study Log) (Cancer Res 59: 1049-1053). Seventy mice with average group tumor sizes of 189 mg, with mice ranging from 123 to 252 mg, were pair-matched into seven groups of ten by random equilibration using Study Director (Day 1). Body weights were recorded when the mice were pair-matched and then taken twice weekly thereafter in conjunction with tumor measurements throughout the study. Gross observations were made at least once a day. On Day 1 all groups were dosed intravenously and/or intraperitoneally with respect to their group (See Table 40). The vehicle, COTI-2 (12.5 mg/kg) and COTI-2 (25 mg/kg) groups were dosed daily 5 times per week via IV injection, except for the first week. COTI-2 in the remaining groups was dosed 3 times per week on every other day via IV injection. Erbitux® (1 mg/dose) was administered intraperitoneally every three days for five treatments (q3dx5) at 0.5 ml/mouse dose volume. The mice were sacrificed by regulated $CO_2$ when the individual mouse tumor volume reached approximately 2000 mg.

Data and Statistical Analysis

Mean tumor growth inhibition (TGI) was calculated utilizing the following formula:

$$TGI = \left[1 - \frac{(\bar{X}_{Treated(Final)} - \bar{X}_{Treated(Day1)})}{(\bar{X}_{Control(Final)} - \bar{X}_{Control(Day1)})}\right] \times 100\%$$

Tumors that regressed from the Day 1 starting size were removed from the calculations. All statistical analyses in the xenograft study were performed with GraphPad Prism® v4 software. Differences in Day 15 tumor weights were confined using the Analysis of Variance (ANOVA) with the Tukey's Post Test. In addition to an ANOVA, a One-tailed Student's T test was used to compare the vehicle only group to each of the combination agent groups and single agent Erbitux® group. Increase in survival fraction was confirmed by the log rank test.

Results and Discussion:

This study determined the single agent efficacy of COTI-2 in the HT-29 human colon tumor xenograft model. COTI-2 was also studied in combination with the standard agent, Erbitux®.

Erbitux® was well-tolerated and produced no weight loss alone. Interestingly, weight loss was also not observed in the COTI-2 (12.5 mg/kg) and Erbitux® combination group in which COTI-2 was administered 3 times per week on every other day.

Figure 55:
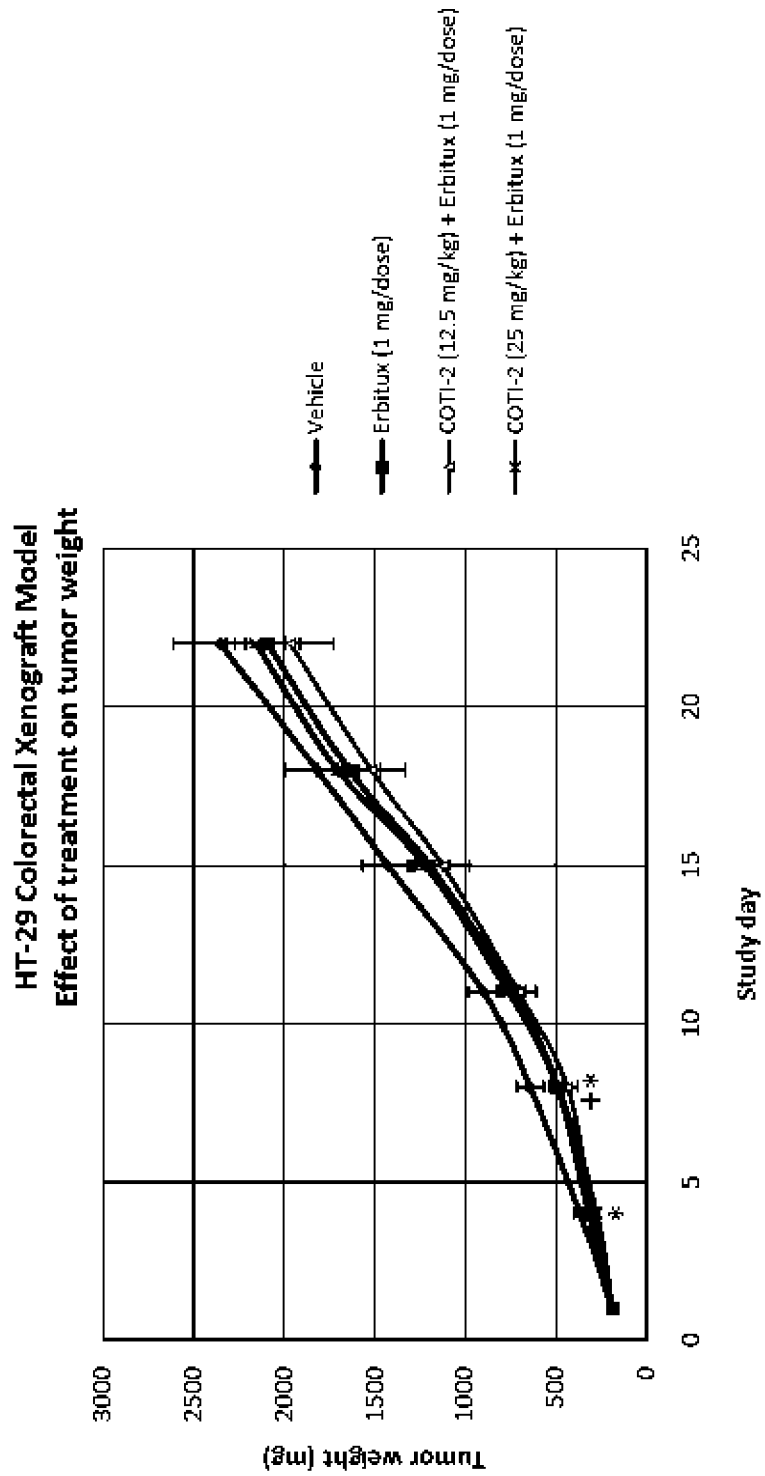
FIG. 55 shows the effect of treatment on tumor weight. Tumor weights are graphed as means (±SE). The asterix (*) indicates a statistically significant difference in tumor weight of the COTI-2 (25 mg/kg) and Erbitux® (1 mg/dose) combination agent group relative to the vehicle only control group on the same day (P<0.05). The plus sign (+) indicates a statistically significant difference in tumor weight of the COTI-2 (12.5 mg/kg) and Erbitux® (1 mg/dose) combination agent group versus the vehicle only control group on the same day (P<0.05). Statistical significance was determined using a Student's T test.

The combination agent groups exhibited a significant tumor reduction early during the study (days 4 & 8) relative to the vehicle control group (FIG. 55). However, there was no significant difference in tumor weight between the single agent Erbitux® group and the vehicle control group. These data suggest that the COTI-2 and Erbitux® combination performs better than the single agent COTI-2 or Erbitux®.

Example 28

Evaluation of COTI-2 as a Single Agent and in Combination with Erbitux® in the HCT-116 Human Colon Tumor Xenograft Model The purpose of this study was to evaluate the activity of COTI-2 as a single agent and in combination with Erbitux® in the HCT-116 human colon tumor xenograft model.

Materials and Methods:

Reagents and Compounds

COTI-2 mono HCl salt (Lot# CKL-2-148) was stored at −20° C. until ready for use. A stock solution of COTI-2 was made at a concentration of 12 mg/ml; 235 mg of COTI-2 was mixed with 4.84 g of Captisol® (Lot# CY-04A-05006 Cydex Pharmaceuticals; Lenexa, Kans.) in 10.0 ml of Sterile Water for Injection (Hospira, Inc., Lake Forest, Ill.). The solution was prepared in a 60 ml amber vial and left to stir at 400 rpm for 1 h. The solution was then filtered with a 0.2 µm PVDF filter to achieve the 12 mg/ml stock concentration. The stock was further diluted to 6 mg/ml with 50 mM Captisol® solution in sterile water (at pH 3.0). The 6 mg/ml solution was also filtered with a 0.2 µm PVDF filter and was given intravenously with respect to the individual groups. Erbitux® (Lot#07C00373B), was manufactured by Bristol Meyers Squibb Company (Princeton, N.J.), and was stored at 4° C. until used. Erbitux® was given intraperitoneally at a volume of 0.5 ml per mouse to deliver a 1 mg/dose every three days for four treatments (q3dx4). All preparations were made fresh prior to their administration.

Cell Culture

The HCT-116 human colon tumor cell line was received from American Type Culture Collection (ATCC, Manassas, Va.). Cultures were maintained in RPMI 1640 (Hylcone Labs, Logan, Utah) supplemented with 5% fetal bovine serum, and housed in a 5% $CO_2$ atmosphere. The cultures were expanded in tissue culture flasks at a 1:6 split ratio until a sufficient amount of cells were harvested.

Animals

Female athymic nude mice (CrTac: NCR-Foxnl$^{nu}$) were supplied by Taconic (Germantown, N.Y.). Mice were received at four weeks of age. All mice were acclimated for seven days prior to handling. The mice were housed in microisolator cages (Lab Products, Seaford, Del.) and maintained under specific pathogen-free conditions. The mice were fed PicoLab® irradiated mouse chow (Lab Diet, Richmond, Ind.) and autoclaved water was freely available. All procedures were carried out under the institutional guidelines of TGen Drug Development Services Institutional Animal Care and Use Committee (Protocol #06001, Approved January 2006).

HCT-116 Human Colon Tumor Xenograft

Ninety mice were inoculated subcutaneously in the right flank with 0.1 ml of a 50% RPMI/50% Matrigel™ (BD Biosciences, Bedford, Mass.) mixture containing a suspension of HCT-116 tumor cells (approximately $5 \times 10^6$ cells/mouse). Three days following inoculation, tumors were measured using vernier calipers and tumor weight was calculated using the animal study management software, Study Director V.1.6.80 (Study Log) (Cancer Res 59: 1049-1053). Seventy mice with average group tumor sizes of 136 mg, with mice ranging from 73 to 194 mg, were pair-matched into seven groups of ten by random equilibration using Study Director (Day 1). Body weights were recorded when the mice were pair-matched and then taken twice weekly thereafter in conjunction with tumor measurements throughout the study. Gross observations were made at least once a day. On Day 1 all groups were dosed intravenously and/or intraperitoneally with respect to their assigned group (See Table 40). The COTI-2 single agent groups were treated 3 times per week on every other day for the first week of the study then dosed 5 times per week for the remainder of the study. In the COTI-2 and Erbitux® combination treatment groups, COTI-2 was administered 3 times per week on every other day. Erbitux® (1 mg/dose) was administered intraperitoneally every three days for five treatments (q3dx5) at 0.5 ml/mouse dose volume. The mice were sacrificed by regulated $CO_2$ when the individual mouse tumor volume reached approximately 2000 mg.

Data and Statistical Analysis

All statistical analyses in the xenograft study were performed with GraphPad Prism® v4 software. Increase in survival fraction was confirmed by the log rank test. A Student's T test was used to evaluate difference in tumor weight among the treatment groups.

Results and discussion:

This study determined the single agent efficacy of COTI-2 in the HCT-116 human colon tumor xenograft model. COTI-2 was also studied in combination with the standard agent, Erbitux®.

The HCT-116 model is an aggressive model in terms of growth kinetics. Therefore, it is likely that treatment was less tolerated due to the early onset of cachexia observed in colon tumor xenograft models. There was an increase in body weight loss by the test agent groups compared to vehicle control (Table 40); in addition, it may be possible that the COTI-2 treated mice experienced a drug accumulation effect. Erbitux® was well-tolerated and produced a moderate weight loss, which may have been a result of tumor burden.

TABLE 40

Summary of the study parameters and results.

| Group | N | Dose (mg/kg) | Route | Schedule (Day) | Maximum weight loss (%) (Day #) | Day 15 Mean tumor weight (mg) | Mean survival (Day ± SEM) | Deaths |
|---|---|---|---|---|---|---|---|---|
| Vehicle Control | 10 | — | IV | 1, 3, 4, 5, 8, 10, 11, 12, 15 | 17.1% (Day 15) | 1,426.8 ± 141.5 | 11.5 ± 1.03 | 3 |
| COTI-2 | 10 | 12.5 | IV | 1, 3, 4, 5, 8, 10, 11, 12, 15, 16, 17 | 20.96% (Day 17) | 1,471.3 ± 155.9 | 12.8 ± 0.76 | 1 |
| COTI-2 | 10 | 25.0 | IV | 1, 3, 4, 5, 8, 10, 11, 12, 15 | 11.12% (Day 8) | 1,376.9 ± 139.4 | 11.5 ± 0.65 | 2 |
| COTI-2 | 10 | 50.0 | IV | 1, 3, 5, 8, 10, 11, 12, 15, 16, 17, 18, 19, 22 | 18.43% (Day 22) | 1,353.4 ± 127.3 | 12.6 ± 0.83 | 2 |
| Erbitux® | 10 | 2.0 | IP | 1, 4, 7, 10, 13 | 17.15% (Day 15) | 1,196.2 ± 104.1 | 13.6 ± 0.73 | 0 |
| COTI-2 Erbitux® | 10 | 12.5 2.0 | IV IP | 1, 3, 5, 8, 10, 12, 15, 17, 19, 22 1, 4, 7, 10, 13 | 15.87% (Day 15) | 1,126.2 ± 147.7 | 13.5 ± 1.19 | 1 |
| COTI-2 Erbitux® | 10 | 25.0 2.0 | IV IP | 1, 3, 5, 8, 10, 12, 15, 17 1, 4, 7, 10, 13 | 19.85% (Day 17) | 1,221.2 ± 93.7 | 14.2 ± 0.74 | 0 |

Figure 56:
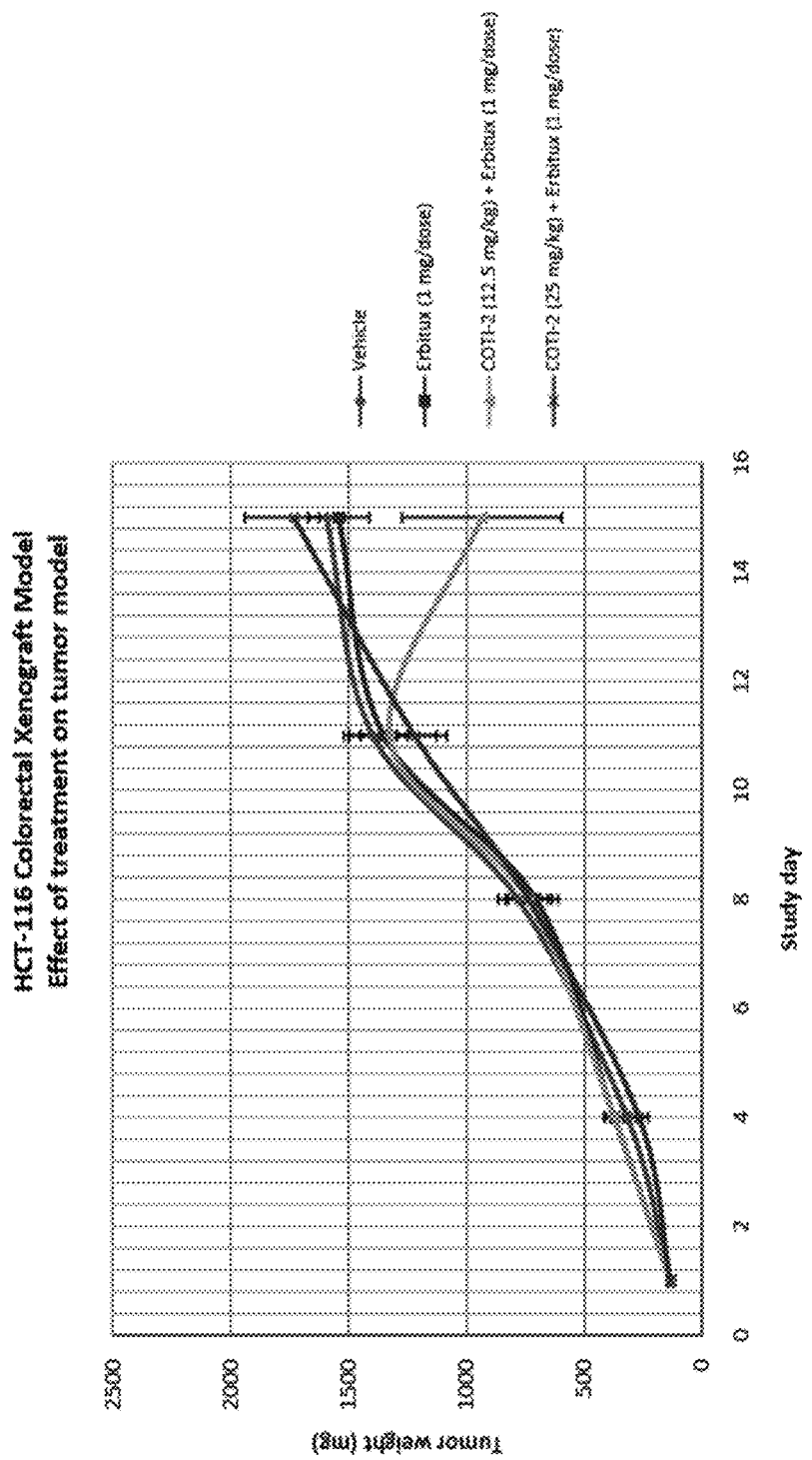
FIG. 56 shows the effect of treatment on tumor weight. Tumor weights are graphed as means (±SE). Statistical significance was determined using a Student's T test.

FIG. 56 shows a trend with respect to a decrease in tumor size with the COTI-2 (12.5 mg/kg) and Erbitux® (1 mg/dose) combination regimen. The COTI-2 (25 mg/kg) and Erbitux® (1 mg/dose) combination regimen produced a survival fraction that was significantly increased from the vehicle control group ($p<0.05$). There was no significant difference in the mean survival of the Erbitux® only treated group when compared to the vehicle control group. These data indicate that the COTI-2 and Erbitux® combination increases survival.

What is claimed is:

1. A method of treating endometrial cancer in a mammal in need thereof comprising administering a therapeutically effective amount of a compound comprising a compound of Formula I or IA:

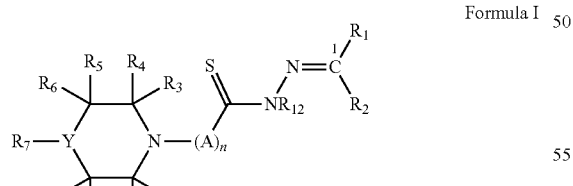

Formula I

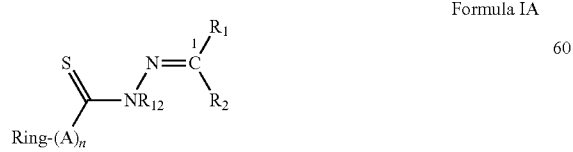

Formula IA a pharmaceutically-acceptable salt, hydrate, solvate, tautomer, optical isomer, and/or combination thereof;

wherein:
$R_1$ and $R_2$ together form a substituted or unsubstituted polycyclic ring comprising at least two ring systems, said at least two ring systems comprising a first ring system bonded to C1 and a second ring system fused to the first ring system, wherein:

the first ring system is a substituted or unsubstituted aromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted heteroaromatic group, the second ring system is a substituted or unsubstituted aromatic group, a substituted or unsubstituted heteroaromatic group, a substituted or unsubstituted carbocyclic group, or a substituted or unsubstituted heterocyclic group; or the first ring system is a substituted or unsubstituted saturated carbocyclic group, the second ring system is a substituted or unsubstituted aromatic group, a substituted or unsubstituted unsaturated carbocyclic group, a substituted or unsubstituted heterocyclic group, or a substituted or unsubstituted ring B:

Ring B wherein $X_1$ to $X_6$ are each independently selected from carbon or a heteroatom; or the first ring system is a substituted or unsubstituted unsaturated carbocyclic group, the second ring system is a substituted or unsubstituted aromatic group, a substituted or unsubstituted carbocyclic group, a substituted or unsubstituted heterocyclic group, or a substituted or unsubstituted ring B:

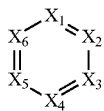

Ring B wherein $X_1$ to $X_6$ are each independently selected from carbon or a heteroatom; or the first ring system is a substituted or unsubstituted heterocyclic group, the second ring system is a substituted or unsubstituted heteroaromatic group, a substituted or unsubstituted carbocyclic group, or a substituted or unsubstituted heterocyclic group; and $R_3$ to $R_{11}$ are each independently selected from H, a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic;

$R_{12}$ is selected from H or a hydrocarbyl group;

Y is selected from a heteroatom;

Ring is selected from a substituted or unsubstituted thiomorpholinyl group, a substituted or unsubstituted morpholinyl group, or a substituted or unsubstituted piperidinyl group, wherein the nitrogen in the Ring is bonded to A;

A is selected from a substituted or unsubstituted hydrocarbon group, a substituted or unsubstituted heterogeneous group, a substituted or unsubstituted carbocyclic group, a substituted or unsubstituted heterocyclic group, substituted or unsubstituted aromatic, or a substituted or unsubstituted heteroaromatic; and n is 0 or 1.

2. The method according to claim 1, wherein the cancer is characterized by a KRAS mutation.

3. The method according to claim 1, further comprising simultaneously or sequentially administering an anti-cancer agent in combination with the compound.

4. The method according to claim 3, wherein the combination produces a synergistic therapeutic effect as compared to sole administration of either the anti-cancer agent or the compound.

5. The method according to claim 4, wherein the anti-cancer agent is an mTOR-Raptor complex inhibitor.

6. The method according to claim 4, wherein the anticancer agent is a cytotoxic agent.

7. The method according to claim 4, wherein the anti-cancer agent is selected from the group consisting of cisplatin, rapamycin, tecrolimus, temsirolimus, paclitaxel, erlotinib, cetuximab, doxorubicin, and combinations thereof.

8. The method according to claim 4, wherein the dose of the anti-cancer agent is selected to lower overall toxicity as compared to administration of the anti-cancer agent alone in an amount sufficient to achieve the same treatment effect on cancerous cells.

9. The method according to claim 4, wherein the dose of at least one of the anti-cancer agent or the compound is selected to increase the overall treatment effect on cancerous cells as compared to administration of the anti-cancer agent alone in an amount producing the same toxicity.

* * * * *